(12) United States Patent
Wang et al.

(10) Patent No.: US 8,741,884 B2
(45) Date of Patent: *Jun. 3, 2014

(54) COMPOUNDS FOR THE TREATMENT OF HEPATITIS C

(75) Inventors: Tao Wang, Farmington, CT (US); Zhiwei Yin, Glastonbury, CT (US); Zhongxing Zhang, Madison, CT (US); Annapurna Pendri, South Glastonbury, CT (US); Guo Li, Wallingford, CT (US); Samuel Gerritz, Gullford, CT (US); Weixu Zhai, Middletown, CT (US); Paul Michael Scola, Glastonbury, CT (US); Li-Qiang Sun, Glastonbury, CT (US); Eric Mull, Gullford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 271 days.

This patent is subject to a terminal disclaimer.

(21) Appl. No.: 13/086,704

(22) Filed: Apr. 14, 2011

(65) Prior Publication Data

US 2012/0093767 A1 Apr. 19, 2012

Related U.S. Application Data

(60) Provisional application No. 61/331,037, filed on May 4, 2010.

(51) Int. Cl.
*A61K 31/33* (2006.01)
*C07D 487/00* (2006.01)

(52) U.S. Cl.
USPC .................. 514/183; 540/471; 540/472

(58) Field of Classification Search
None
See application file for complete search history.

(56) References Cited

U.S. PATENT DOCUMENTS

| 4,816,064 A | 3/1989 | Konno et al. |
|---|---|---|
| 7,163,943 B2 | 1/2007 | Timmer et al. |
| 7,169,785 B2 | 1/2007 | Timmer et al. |
| 2009/0286778 A1 | 11/2009 | Combs et al. |
| 2011/0086858 A1 | 4/2011 | Wang et al. |

FOREIGN PATENT DOCUMENTS

| WO | WO 2004/026881 | 4/2004 |
|---|---|---|
| WO | WO 2004/089286 | 10/2004 |
| WO | WO 2008/057209 | 5/2008 |
| WO | WO 2009/091388 | 7/2009 |
| WO | WO 2009/132202 | 10/2009 |
| WO | WO 2010/118367 | 10/2010 |

OTHER PUBLICATIONS

U.S. Appl. No. 13/086,036, filed Apr. 13, 2011, Wang et al.

*Primary Examiner* — Noble Jarrell
(74) *Attorney, Agent, or Firm* — James Epperson

(57) ABSTRACT

The disclosure provides compounds of formula I, including pharmaceutically acceptable salts, as well as compositions and methods of using the compounds. The compounds have activity against hepatitis C virus (HCV) and may be useful in treating those infected with HCV.

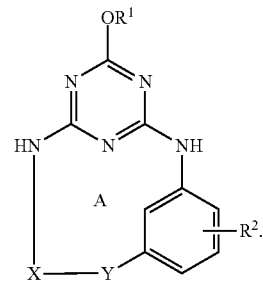

15 Claims, No Drawings

COMPOUNDS FOR THE TREATMENT OF HEPATITIS C

CROSS REFERENCE TO RELATED APPLICATIONS

This patent application claims the benefit of U.S. provisional patent application No. 61/331,037 filed May 4, 2010.

BACKGROUND OF THE INVENTION

The disclosure generally relates to the novel compounds of formula I including pharmaceutically acceptable salts, which have activity against hepatitis C virus (HCV) and are useful in treating those infected with HCV. The disclosure also relates to compositions and methods of using these compounds.

Hepatitis C virus (HCV) chronically infects an estimated 170 million people worldwide, with 3 to 4 million infected individuals in the United States alone (Boyer, N. and Marcellin, P. J. *Hepatology.* 2000, 32:98-112; Alter, M. J., et al. *Engl. J. Med.* 1999, 341:556-562). Prior to the mid 1990s, transfusion with infected blood products was the main route of HCV transmission. Following the introduction of blood screening methods, transmission via injection drug use became the primary risk factor. Chronic infection often leads to the development of severe liver complications, including fibrosis, cirrhosis, and hepatocellular carcinoma. HCV infection is also the leading cause of orthotopic liver transplantation in the United States. The degree to which disease progression is related to viral and cellular factors is not completely understood.

Considerable heterogeneity is found within the nucleotide and encoded amino acid sequence of the HCV genome (Simmonds, P. *J. Gen. Virology.* 2004, 85:3173-3188). Based on this sequence diversity, six major genotypes and multiple associated subtypes have been described. The genotypes of HCV differ in their worldwide distribution, and the clinical significance of the genetic heterogeneity of HCV remains elusive despite numerous studies of the possible effect of genotypes on pathogenesis and therapy.

Medical treatment for HCV is limited by the lack of a vaccine or approved therapies that specifically target the virus. Currently, patients undergo treatment with a combination of parenterally administered pegylated alpha-interferon and oral ribavirin. Genotype 1 HCV is the most difficult to treat and elimination of the virus (sustained virologic response) is achieved for only approximately 50% of patients (Fried, M. W. et al. *N. Engl. J. Med.* 2002, 347:975-982; Zeumzem, S. *Nature Clinical Practice.* 2008, 5:610-622). This poor treatment response, combined with often severe side effects induced by therapy, highlight a need for improved antiviral drugs with better efficacy and safety profiles.

HCV is a member of the Flaviviridae family of viruses with a single-stranded positive-sense RNA genome. Following infection of host cells, the 9.6 Kb genome is translated into a polyprotein precursor of approximately 3,000 amino acids (reviewed in Lindenbach, B. D. and Rice, C. M. *Nature.* 2005, 436:933-938; Moradpour, D, Penin, F., and Rice, C. M. *Nature Reviews.* 2007, 5:453-463). Post-translational processing by both cellular and viral proteases results in the generation of at least 10 separate viral proteins. The structural proteins (which by definition are found in mature virions) include core, E1, E2, and possibly p7, and originate from the amino-terminal region of the polyprotein. The core protein assembles into the viral nucleocapsid. The E1 and E2 glycoproteins form heterodimers that are found within the lipid envelope surrounding the viral particles, and mediate host cell receptor binding and entry of the virus into cells. It is unclear if p7 is a structural protein, and its role in replication has yet to be defined. However p7 is believed to form an ion channel in cellular membranes, preventing acidification of intracellular compartments in which virions are assembled, and it has been shown to be essential for viral replication and assembly. The nonstructural proteins NS2, NS3, NS4A, NS4B, NS5A, and NS5B are produced through maturational cleavages of the carboxy-terminal region of the polyprotein. NS2 along with the amino terminus of NS3 form the NS2-3 metalloprotease which cleaves at the N52-NS3 junction. Additionally, NS2 is involved in assembly and egress of nascent virions. The NS3 protein contains both a serine protease in its amino-terminal region, and a nucleotide-dependent RNA helicase in its carboxy-terminal region. NS3 forms a heterodimer with the NS4A protein, constituting the active protease which mediates cleavages of the polyprotein downstream of NS3, both in cis, at the NS3-NS4A cleavage site, and in trans, for the remaining NS4A-NS4B, NS4B-NS5A, NS5A-NS5B sites. The complex formation of the NS3 protein with NS4A seems necessary to the processing events, enhancing the proteolytic efficiency at all of the sites. The NS3 protein also exhibits nucleoside triphosphatase and RNA helicase activities. The NS4B protein has been shown to be important for localization of HCV proteins into replication complexes in altered membranous structures within the cell. NS5B encodes an RNA-dependent RNA polymerase that is involved in the replication of HCV.

Subgenomic HCV replicons, containing the untranslated regions 5' and 3' to the coding sequence fused to the nonstructural proteins or the full-length polyprotein, are competent for translation, viral protein expression, and replication within cultured cells (Lohmann, V. et al. *Science.* 1999, 285:110-113; Moradpour, D, Penin, F., and Rice, C. M. *Nature Reviews.* 2007, 5:453-463). The replicon system has proven valuable for the identification of inhibitors targeting the nonstructural proteins associated with these functions. However, only limited subsets of HCV genotypes have been used to generate functional replicons.

Other systems have been used to study the biology of the HCV structural proteins that mediate the entry into host cells. For example, virus-like-particles made in recombinant baculovirus-infected cells with the HCV core, E1 and E2 proteins have also been used to study the function of the HCV E1 and E2 proteins (Barth, H., et al. *J. Biol. Chem.* 2003, 278:41003-41012). In addition, pseudotyping systems where the E1 and E2 glycoproteins are used to functionally replace the glycoproteins of retroviruses have been developed (Bartosch, B., Dubuisson, J. and Cosset, F.-L. *J. Exp. Med.* 2003, 197:633-642; Hsu, M. et al. *Proc. Natl. Acad. Sci. USA.* 2003, 100: 7271-7276). These systems yield HCV pseudoparticles that bind to and enter host cells in a manner which is believed to be analogous to the natural virus, thus making them a convenient tool to study the viral entry steps as well as to identify inhibitors block this process.

Recently, a full-length genotype 2a HCV clone, JFH1, was isolated and demonstrated the ability to replicate in vitro. Through repeated passage and adaptation in cell culture increased titers of infectious virus were produced (Lindenbach, B. D., et al. *Science.* 2005, 309:623-626; Wakita, T. et al. *Nature Med.* 2005, 11:791-796). In contrast to the HCV replicon or pseudotyping systems, the infectious virus is useful for studying the complete HCV replication cycle, including identifying inhibitors of not only the replication proteins, but those involved in early steps in virus infection (entry and uncoating) and production of progeny viruses (genome packaging, nucleocapsid assembly, virion envelopment and egress).

Triazines have been disclosed. See WO 2009/091388 and US 2009/0286778.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

One aspect of the invention is a compound of formula I

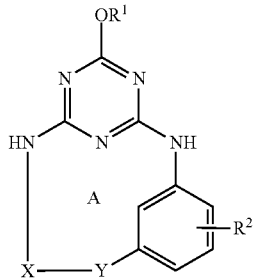

where
$R^1$ is alkyl, hydroxyalkyl, alkoxyalkyl, haloalkyl, cycloalkyl, hydroxycycloalkyl, alkoxycycloalkyl, halocycloalkyl, cycloalkenyl, benzyl, indanyl, or alkylcarbonyl;
$R^2$ is hydrogen, halo, cyano, alkyl, haloalkyl, alkoxy, haloalkoxy, $CO_2R^6$, or $CON(R^7)(R^8)$;
$R^3$ is hydrogen, alkyl, alkylcarbonyl, alkoxycarbonyl, aminocarbonyl, alkylaminocarbonyl, or dialkyaminocarbonyl;
$R^4$ is hydrogen or alkyl;
$R^5$ is hydrogen, alkyl, (amino)alkyl, (alkylamino)alkyl, or (dialkylamino)alkyl;
$R^6$ is hydrogen, alkyl, or benzyl;
$R^7$ is hydrogen, alkyl, pyrrolidinonyl, piperidinonyl, homopiperazinonyl, $(R^9)$alkyl, (Q)alkyl, $((R^9)$alkyl)-Q-alkyl, $(R^9)(R^9)$alkyl, or $(R^9)(Q)$alkyl;
or $R^7$ is pyrrolidinonyl, piperidinonyl, homopiperazinonyl, or

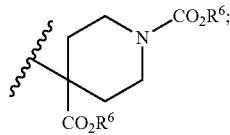

$R^8$ is hydrogen or alkyl;
or $R^7$ and $R^8$ taken together with the nitrogen to which they are attached is azetidinyl, pyrrolidinyl, piperidinyl, piperazinyl, or morpholinyl, and is substituted with 0-2 substituents selected from alkyl, $(CO_2R^6)$alkyl, $CO_2R^6$, $CON(R^{10})(R^{10})$, and $N(R^{10})CO_2R^6$;
or $R^7$ and $R^8$ taken together with the nitrogen to which they are attached is a spiro [3-7.3-7] bicyclic ring system where the bicyclic ring system contains 0-1 additional nitrogens, and is substituted with 0-2 substituents selected from alkyl, $(CO_2R^6)$alkyl, $CO_2R^6$, $CON(R^{10})$ $(R^{11})$, and $N(R^{10})CO_2R^6$;

$R^9$ is $CO_2R^6$, $C(O)(N(R^{10})(R^{11}))$, $C(=NR^{12})(N(R^{10})(R^{11}))$, $CON(R^{10})SO_2R^{13}$, $N(R^{10})(R^{11})$, $N(R^{10})COR^6$, $N(R^{10})COPh$, $N(R^{10})CO_2R^6$, $N(R^{10})C(O)(N(R^{10})(R^{11}))$, $N(R^{10})C(=NR^{12})(N(R^{10})(R^{11}))$, or $(R^{13})SO_2$;
$R^{10}$ is hydrogen or alkyl;
$R^{11}$ is hydrogen or alkyl;
or $N(R^{10})(R^{11})$ taken together with the nitrogen to which they are attached is azetidinyl, pyrrolidinyl, piperidinyl, piperazinyl, or morpholinyl
$R^{12}$ is hydrogen, alkyl, or phenyl;
$R^{13}$ is alkyl, cycloalkyl, or phenyl;
Q is cycloalkyl, phenyl, tetrahydrofuranyl, tetrahydropyranyl, azetidinyl, pyrrolidinyl, piperidinyl, piperazinyl, or morpholinyl, and is substituted with 0-2 $R^9$ substituents;
X is an alkylene or alkenylene chain containing 0-6 groups selected from the group consisting of O, $NR^3$, S, $S(O)$, $S(O_2)$, $C(O)O$, $C(O)NR^4$, $OC(O)NR^4$, $NR^4C(O)NR^4$, $NR^4C(NR^{12})NR^4$, and Z, provided that O, $NR^3$, S, $S(O)$, $S(O_2)$, $C(O)O$, $C(O)NR^4$, $OC(O)NR^4$, $NR^4C(O)NR^4$, and $NR^4C(NR^{12})NR^4$ do not directly bond to each other or to NH or X, such that ring A is 13-24 membered; and where the alkylene or alkenylene chain is substituted with 0-6 substituents selected from the group consisting of alkyl, alkylidinyl, hydroxy, alkoxy, and phenyl where the phenyl substituent is further substituted with 0-4 cyano, halo, alkyl, haloalkyl, alkoxy, or haloalkoxy substituents;
Y is $CH_2$, O, $CO_2$, or $C(O)NR^5$; and
Z is $C_{3-7}$ cycloalkylene or phenylene;
or a pharmaceutically acceptable salt thereof.

Another aspect of the invention is a compound of formula I where
$R^1$ is alkyl, hydroxyalkyl, alkoxyalkyl, haloalkyl, cycloalkyl, hydroxycycloalkyl, alkoxycycloalkyl, halocycloalkyl, cycloalkenyl, benzyl, indanyl, or alkylcarbonyl;
$R^2$ is hydrogen, halo, cyano, alkyl, haloalkyl, alkoxy, haloalkoxy, $CO_2R^6$, or $CON(R^7)(R^8)$;
$R^3$ is hydrogen, alkyl, alkylcarbonyl, alkoxycarbonyl, aminocarbonyl, alkylaminocarbonyl, or dialkyaminocarbonyl;
$R^4$ is hydrogen or alkyl;
$R^5$ is hydrogen, alkyl, (amino)alkyl, (alkylamino)alkyl, or (dialkylamino)alkyl;
$R^6$ is hydrogen or alkyl;
$R^7$ is hydrogen, alkyl, $(R^9)$alkyl, (Q)alkyl, $((R^9)$alkyl)-Q-alkyl, $(R^9)(R^9)$alkyl, or $(R^9)(Q)$alkyl;
$R^8$ is hydrogen or alkyl;
or $R^7$ and $R^8$ taken together with the nitrogen to which they are attached is azetidinyl, pyrrolidinyl, piperidinyl, piperazinyl, or morpholinyl, and is substituted with 0-2 substituents selected from alkyl, $(CO_2R^6)$alkyl, $CO_2R^6$, $CON(R^{10})$ $(R^{10})$, and $N(R^{10})CO_2R^6$;
or $R^7$ and $R^8$ taken together with the nitrogen to which they are attached is a spiro [3-7.3-7] bicyclic ring system where the bicylic ring system contains 0-1 additional nitrogens, and is substituted with 0-2 substituents selected from alkyl, $(CO_2R^6)$alkyl, $CO_2R^6$, $CON(R^{10})(R^{11})$, and $N(R^{10})CO_2R^6$;
$R^9$ is $CO_2R^6$, $C(=NR^{12})(N(R^{10})(R^{11}))$, $CON(R^{10})SO_2R^{13}$, $N(R^{10})(R^{11})$, or $N(R^{10})CO_2R^6$;
$R^{10}$ is hydrogen or alkyl;
$R^{11}$ is hydrogen or alkyl;
or $N(R^{10})(R^{11})$ taken together with the nitrogen to which they are attached is azetidinyl, pyrrolidinyl, piperidinyl, piperazinyl, or morpholinyl
$R^{12}$ is hydrogen, alkyl, or phenyl;
$R^{13}$ is alkyl, cycloalkyl, or phenyl;

Q is cycloalkyl, tetrahydrofuranyl, tetrahydropyranyl, azetidinyl, pyrrolidinyl, piperidinyl, piperazinyl, or morpholinyl, and is substituted with 0-2 $R^9$ substituents;

X is an alkylene or alkenylene chain containing 0-4 groups selected from the group consisting of O, $NR^3$, S, S(O), S(O$_2$), C(O)O, C(O)$NR^4$, OC(O)$NR^4$, $NR^4$C(O)$NR^4$, $NR^4$C($NR^{12}$)$NR^4$, and Z, provided that O, $NR^3$, S, S(O), S(O$_2$), C(O)O, C(O)$NR^4$, OC(O)$NR^4$, $NR^4$C(O)$NR^4$, and $NR^4$C($NR^{12}$)$NR^4$ do not directly bond to each other or to NH or X, such that ring A is 13-24 membered; and where the alkylene or alkenylene chain is substituted with 0-3 substituents selected from the group consisting of alkyl, alkylidinyl, hydroxy, alkoxy, and phenyl where the phenyl substituent is further substituted with 0-4 cyano, halo, alkyl, haloalkyl, alkoxy, or haloalkoxy substituents;

Y is CH$_2$, O, CO$_2$, or C(O)$NR^5$; and

Z is C$_{3-7}$ cycloalkylene or phenylene;

or a pharmaceutically acceptable salt thereof.

Another aspect of the invention is a compound of formula I where $R^1$ is haloalkyl; $R^2$ is hydrogen, CO$_2R^6$, or CON($R^7$)($R^8$); $R^3$ is hydrogen or alkylcarbonyl; $R^4$ is hydrogen or alkyl; $R^5$ is hydrogen or alkyl; $R^6$ is hydrogen or alkyl; Q is cycloalkyl, pyrrolidinyl, or piperidinyl, and is substituted with 0-2 $R^9$ substituents; ring A is 21-23 membered; Y is O or CON$R^5$; and Z is phenylene; or a pharmaceutically acceptable salt thereof.

Another aspect of the invention is a compound of formula I where $R^1$ is trifluoroethyl; $R^2$ is hydrogen, CO$_2R^6$, or CON($R^7$)($R^8$); $R^3$ is hydrogen or alkylcarbonyl; $R^4$ is hydrogen or alkyl; $R^5$ is hydrogen or alkyl; $R^6$ is hydrogen or alkyl; Q is cyclopropyl, pyrrolidinyl, or piperidinyl, and is substituted with 0-2 $R^9$ substituents; Y is O; and Z is phenylene; or a pharmaceutically acceptable salt thereof.

Another aspect of the invention is a compound of formula I where $R^1$ is trifluoroethyl.

Another aspect of the invention is a compound of formula I where $R^2$ is CON($R^7$)($R^8$).

Another aspect of the invention is a compound of formula I where $R^7$ is ($R^9$)alkyl, (Q)alkyl, (($R^9$)alkyl)-Q-alkyl, ($R^9$)($R^9$)alkyl, or ($R^9$)(Q)alkyl; and $R^8$ is hydrogen.

Another aspect of the invention is a compound of formula I where $R^7$ and $R^8$ taken together with the nitrogen to which they are attached is pyrrolidinyl or piperidinyl, and is substituted with 0-2 substituents selected from alkyl, (CO$_2R^6$)alkyl, CO$_2R^6$, CON($R^{10}$)($R^{10}$) and N($R^{10}$)CO$_2R^6$.

Another aspect of the invention is a compound of formula I where $R^7$ and $R^8$ taken together with the nitrogen to which they are attached is a spiro[5.5] bicyclic ring system where the bicylic ring system contains 0-1 additional nitrogens, and is substituted with 0-2 substituents selected from alkyl, (CO$_2R^6$)alkyl, CO$_2R^6$, CON($R^{10}$)($R^{11}$), and N($R^{10}$)CO$_2R^6$.

Another aspect of the invention is a compound of formula I where Y is O.

Another aspect of the invention is a compound of formula I where Z is phenylene.

Any scope of any variable, including $R^1$, $R^2$, $R^3$, $R^4$, $R^5$, $R^6$, $R^7$, $R^8$, $R^9$, $R^{10}$, $R1^1$, $R^{12}$, $R^{13}$, Q, X, Y, and Z, can be used independently with the scope of any other instance of a variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Alkylene" means a straight or branched divalent alkyl group composed of 1 to 6 carbons. "Alkenylene" means a straight or branched divalent alkyl group composed of 2 to 6 carbons with at least one double bond. For ring A, X is an alkylene or alkenylene chain with sufficient carbons and optionally other defined groups to form a 13-24 membered ring. "Cycloalkylene" means a divalent cycloalkane moiety composed of 3 to 7 carbons and includes gem-divalency (for example 1,1-cyclopropanediyl) as well as non-gem-divalency (for example, 1,4-cyclohexanediyl). "Alkylidinyl" means a divalent alkene substituent where the divalency occurs on the same carbon of the alkene. Phenylene means a divalent benzene ring. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The substituents described above may be attached at any suitable point of attachment unless otherwise specified. However, it is understood that the compounds encompassed by the present invention are those that are chemically stable as understood by those skilled in the art. Additionally, the compounds encompassed by the present disclosure are those that are suitably stable for use as a pharmaceutical agent.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the structures below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Infection assays. HCV pseudoparticles, produced using standardized methodology (Bartosch, B., Dubuisson, J. and Cosset, F.-L. *J. Exp. Med.* 2003, 197:633-642) were made via a liposome-based transfection procedure of 293T cells with plasmids expressing the murine leukemia virus capsid and polymerase proteins, an MLV genome encoding the luciferase reporter gene, and envelope glycoproteins from either HCV or vesicular stomatitis virus (VSV). The genotype 1a HCV E1 and E2 envelope coding sequences were derived from the H77C isolate (GenBank accession number AF009606). Media containing pseudoparticles was collected 3 days following transfection, filtered, and stored at −20° C. as a viral stock. Infections were performed in 384-well plates by mixing pseudovirus with $1\times10^4$ Huh7 cells/well in the presence or absence of test inhibitors, followed by incubation at 37° C. Luciferase activity, reflecting the degree of entry of the pseudoparticles into host cells, was measured 2 days after infection. The specificity of the compounds for inhibiting HCV was determined by evaluating inhibition of VSV pseudoparticle infection.

Compounds and data analysis. Test compounds were serially diluted 3-fold in dimethyl sulfoxide (DMSO) to give a final concentration range in the assay of 50.0 μM to 0.04 μM. Maximum activity (100% of control) and background were derived from control wells containing DMSO but no inhibitor or from uninfected wells, respectively. The individual signals in each of the compound test wells were then divided by the averaged control values after background subtraction and multiplied by 100% to determine percent activity. Assays were performed in duplicate and average $EC_{50}$ values (reflecting the concentration at which 50% inhibition of virus replication was achieved) were calculated. Compound $EC_{50}$ data is expressed as A:=0.10-100 nM; B=100-1000 nM; C=1000-50000 nM). Representative data for compounds are reported in Table 1.

TABLE 1

| Example | $EC_{50}$ (nM) | $EC_{50}$ (nM) |
|---|---|---|
| 1001 | C | |
| 1002 | C | |
| 1003 | C | |
| 1004 | C | |
| 1005 | C | |
| 1006 | C | |
| 1007 | C | 9842 |
| 1008 | A | |
| 1009 | A | |
| 1010 | A | 5.14 |
| 1011 | A | |
| 1012 | A | |
| 1013 | A | |
| 1014 | C | |
| 1015 | C | 3057 |
| 1016 | C | |
| 1017 | B | |
| 1018 | C | 5645.00 |
| 1019 | B | |
| 1020 | C | |
| 1022 | A | |
| 1101 | A | |
| 1102 | A | |
| 1103 | C | |
| 1104 | B | |
| 1105 | A | 49.08 |
| 1106 | A | |
| 1107 | A | |
| 1109 | B | |
| 1131 | B | |
| 1132 | C | |
| 1133 | B | |
| 1151 | A | |
| 1152 | A | |
| 1153 | B | |
| 1201 | A | |
| 1202 | A | |
| 1301 | B | |
| 1302 | C | |
| 1303 | B | |
| 1304 | A | |
| 1305 | A | |
| 1306 | A | |
| 1307 | A | |
| 1308 | A | |
| 1309 | B | |
| 1310 | A | |
| 1313 | A | |
| 1314 | A | |
| 1317 | A | |
| 1319 | A | |
| 1320 | A | |
| 1321 | A | |
| 1322 | A | |
| 1323 | A | |
| 1324 | A | |
| 1325 | A | |
| 1402 | A | |
| 1403 | A | |
| 1404 | A | |
| 1405 | A | |
| 1406 | A | |
| 1407 | A | |
| 1408 | A | |
| 1409 | A | |
| 1410 | B | |
| 1411 | A | |
| 1412 | A | 24.78 |
| 1413 | A | |
| 1501 | A | |
| 1502 | A | |
| 1503 | A | |
| 1504 | A | |
| 1551 | A | |
| 1552 | A | |
| 1553 | A | |
| 1554 | A | 20.57 |
| 1555 | B | |
| 1556 | B | 101.30 |
| 1557 | B | |
| 1558 | A | |
| 1559 | A | |
| 1560 | A | |
| 1561 | A | |
| 1562 | A | 28.70 |
| 1602 | A | |
| 1603 | A | |
| 1604 | A | |
| 1605 | A | 23.04 |
| 1606 | A | |
| 1607 | A | |
| 1608 | A | 56.17 |
| 1612 | A | |
| 1613 | A | |
| 1700 | A | |
| 1701 | A | |
| 1702 | A | |
| 1706 | A | |
| 1707 | A | |
| 1711 | A | |
| 1801 | B | |

TABLE 1-continued

| Example | EC$_{50}$ (nM) | EC$_{50}$ (nM) |
|---|---|---|
| 1802 | A | |
| 1803 | C | |
| 1804 | B | 239.20 |
| 1806 | B | |
| 1807 | C | |
| 2001 | A | |
| 2003 | A | |
| 2004 | A | |
| 2005 | A | |
| 2006 | A | |
| 2007 | B | 159 |
| 2008 | A | |
| 2009 | A | 18.0 |
| 3001 | A | |
| 3002 | A | |
| 3003 | A | |
| 3004 | A | |
| 3005 | A | |
| 3006 | A | |
| 3007 | A | |
| 3008 | A | 5.36 |
| 3009 | A | |
| 3010 | A | |
| 3011 | A | |
| 3012 | A | |
| 3013 | A | |
| 3014 | A | |
| 3015 | A | |
| 3016 | A | |
| 3017 | A | |
| 3018 | A | |
| 3019 | A | 10.22 |
| 3020 | A | |
| 3021 | A | |
| 3022 | A | |
| 3023 | A | |
| 3024 | B | |
| 3025 | A | |
| 4001 | C | 42610.00 |
| 5001 | B | 409.20 |
| 5002 | A | |

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
| --- | --- | --- |
| Omega IFN | IFN-ω | Intarcia Therapeutics |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |

TABLE 2-continued

| Brand Name | Type of Inhibitor or Target | Source Company |
| --- | --- | --- |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/SciClone Pharmaceuticals Inc, San Mateo, CA |
| Levovirin | IMPDH inhibitor | Ribapharm Inc., Costa Mesa, CA |
| Viramidine | Ribavirin Prodrug | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | Immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| Batabulin (T67) | β-tubulin inhibitor | Tularik Inc., South San Francisco, CA |
| Merimepodib (VX-497) | IMPDH inhibitor | Vertex Pharmaceuticals Inc., Cambridge, MA |
| Telaprevir | NS3 serine protease | Vertex Pharmaceuticals |

TABLE 2-continued

| Brand Name | Type of Inhibitor or Target | Source Company |
|---|---|---|
| (VX-950, LY-570310) | inhibitor | Inc., Cambridge, MA/ Eli Lilly and Co. Inc., Indianapolis, IN |
| Omniferon | natural IFN-α | Viragen Inc., Plantation, FL |
| XTL-6865 (XTL-002) | monoclonal antibody | XTL Biopharmaceuticals Ltd., Rehovot, Isreal |
| HCV-796 | NS5B Replicase Inhibitor | Wyeth/Viropharma |
| NM-283 | NS5B Replicase Inhibitor | Idenix/Novartis |
| GL-59728 | NS5B Replicase Inhibitor | Gene Labs/Novartis |
| GL-60667 | NS5B Replicase Inhibitor | Gene Labs/Novartis |
| 2'C MeA | NS5B Replicase Inhibitor | Gilead |
| PSI 6130 | NS5B Replicase Inhibitor | Roche |
| R1626 | NS5B Replicase Inhibitor | Roche |
| SCH 503034 | serine protease inhibitor | Schering Plough |
| NIM811 | Cyclophilin Inhibitor | Novartis |
| Suvus | Methylene blue | Bioenvision |
| Multiferon | Long lasting IFN | Viragen/Valentis |
| Actilon (CPG10101) | TLR9 agonist | Coley |
| Interferon-β | Interferon-β-1a | Serono |
| Zadaxin | Immunomodulator | Sciclone |
| Pyrazolopyrimidine compounds and salts From WO-2005047288 26 May 2005 | HCV Inhibitors | Arrow Therapeutics Ltd. |
| 2'C Methyl adenosine | NS5B Replicase Inhibitor | Merck |
| GS-9132 (ACH-806) | HCV Inhibitor | Achillion/Gilead |

SYNTHETIC METHODS

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "cc" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

LC/MS Method (i.e., compound identification). All Liquid Chromatography (LC) data were recorded on a Shimadzu LC-10AS or LC-20AS liquid chromatograph using a SPD-10AV or SPD-20A UV-Vis detector and Mass Spectrometry (MS) data were determined with a Micromass Platform for LC in electrospray mode.

HPLC Method (i.e., compound isolation). Compounds purified by preparative HPLC were diluted in methanol (1.2 mL) and purified using a Shimadzu LC-8A or LC-10A automated preparative HPLC system.

Synthesis of Compound 1001

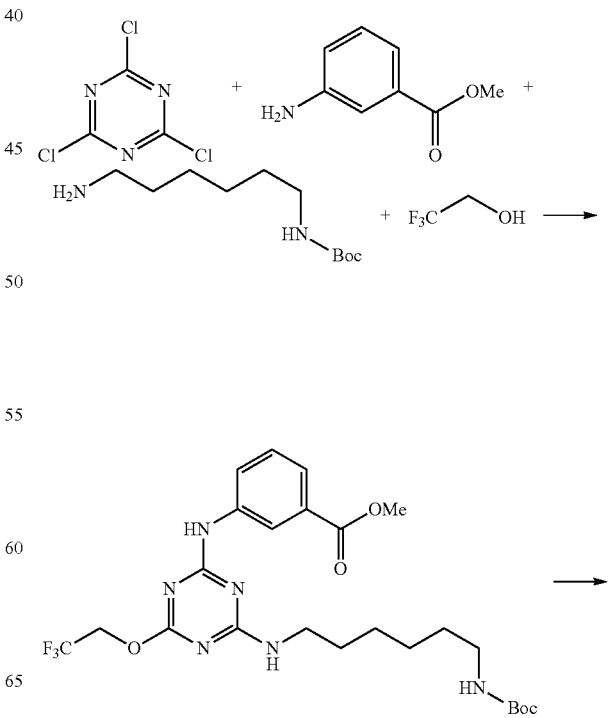

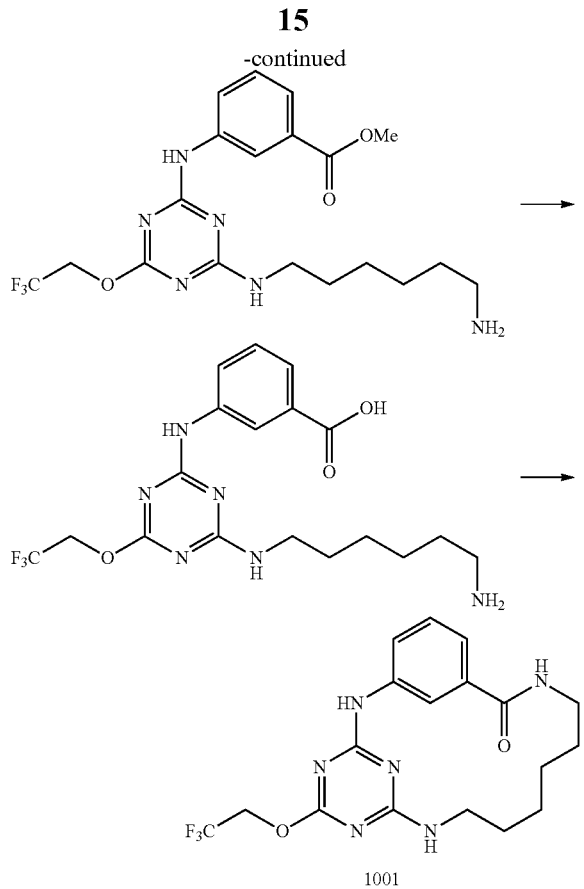

1001

Step 1, preparation of methyl 3-(4-(6-(tert-butoxycarbonylamino)hexylamino)-6-(2,2,2-trifluoroethoxy)-1,3,5-triazin-2-ylamino)benzoate: First, iPr₂NEt (10 mL) was added into the solution of 2,4,6-trichloro-1,3,5-triazine (5 g) and methyl 3-aminobenzoate (4.1 g) in dioxane at room temperature. The reaction mixture was stirred at room temperature for 6 hours. Solvent was removed under vacuum to offer crude methyl 3-(4,6-dichloro-1,3,5-triazin-2-ylamino)benzoate compound with N-ethyl-N-isopropylpropan-2-amine (1:1) hydrochloride which was used without any purification. Then, Pr₂NEt (2 mL) was added into the solution of crude methyl 3-(4,6-dichloro-1,3,5-triazin-2-ylamino)benzoate compound with N-ethyl-N-isopropylpropan-2-amine (1:1) hydrochloride (600 mg) and tert-butyl 6-aminohexylcarbamate (279 mg) in THF at room temperature. The reaction mixture was stirred at room temperature for 16 hours. Solvent was removed under vacuum to offer crude methyl 3-(4-(6-(tert-butoxycarbonylamino)hexylamino)-6-chloro-1,3,5-triazin-2-ylamino)benzoate compound with N-ethyl-N-isopropylpropan-2-amine (1:2) dihydrochloride which was used as is. Finally, NaH (300 mg) was added into the solution of crude methyl 3-(4-(6-(tert-butoxycarbonylamino)hexylamino)-6-chloro-1,3,5-triazin-2-ylamino)benzoate compound with N-ethyl-N-isopropylpropan-2-amine (1:2) dihydrochloride (1.05 g) and 2,2,2-trifluoroethanol (646 mg) in THF. After stirring at room temperature for 16 hours, the reaction was quenched with NaHCO₃ and aqueous phase was extracted with EtOAc. The combined organic layer was dried over MgSO₄, filtered and concentrated to offer a crude methyl 3-(4-(6-(tert-butoxycarbonylamino)hexylamino)-6-(2,2,2-trifluoroethoxy)-1,3,5-triazin-2-ylamino)benzoate which was used in the further step without purification.

| methyl 3-(4-(6-(tert-butoxycarbonylamino)hexylamino)-6-(2,2,2-trifluoroethoxy)-1,3,5-triazin-2-ylamino)benzoate | |
|---|---|
| MS (M + H)⁺ Calcd. | 543.3 |
| MS (M + H)⁺ Observ. | 543.2 |
| Retention Time | 2.60 minutes |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 3 min |
| Flow Rate | 5 mL/min |
| Wavelength | 220 |
| Solvent Pair | ACN:Water:Ammonium Actetate |
| Column | Phenomenex Luna 4.6 × 50 mm S10 |

Step 2, preparation of methyl 3-(4-(6-aminohexylamino)-6-(2,2,2-trifluoroethoxy)-1,3,5-triazin-2-ylamino)benzoate: methyl 3-(4-(6-(tert-butoxycarbonylamino)hexylamino)-6-(2,2,2-trifluoroethoxy)-1,3,5-triazin-2-ylamino)benzoate (500 mg) was dissolved in TFA (2 mL) and CH₂Cl₂ (30 mL) at room temperature. After 16 hours, reaction showed formation of methyl 3-(4-(6-aminohexylamino)-6-(2,2,2-trifluoroethoxy)-1,3,5-triazin-2-ylamino)benzoate. After removal of solvents, the residue used as is in the next step.

| methyl 3-(4-(6-aminohexylamino)-6-(2,2,2-trifluoroethoxy)-1,3,5-triazin-2-ylamino)benzoate | |
|---|---|
| MS (M + H)⁺ Calcd. | 443.2 |
| MS (M + H)⁺ Observ. | 443.2 |
| Retention Time | 2.22 minutes |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 3 min |
| Flow Rate | 5 mL/min |
| Wavelength | 220 |
| Solvent Pair | ACN:Water:Ammonium Actetate |
| Column | Phenomenex Luna 4.6 × 50 mm S10 |

Step 3, preparation of 3-(4-(6-aminohexylamino)-6-(2,2,2-trifluoroethoxy)-1,3,5-triazin-2-ylamino)benzoic acid: To a mixture of methyl 3-(4-(6-aminohexylamino)-6-(2,2,2-trifluoroethoxy)-1,3,5-triazin-2-ylamino)benzoate (1.0 g) in MeOH (10 mL) was added a solution of K₂CO₃ (0.312 g) in water (5 mL). The mixture was stirred at room temperature for 16 hours, before the mixture was neutralized with 1N HCl to pH3. All solvents were then removed under vacuum. The residue was diluted with 100 mL of MeOH, followed by filtration to remove solid. The filtrate was concentrated and purified by preparative HPLC to give 3-(4-(6-aminohexylamino)-6-(2,2,2-trifluoroethoxy)-1,3,5-triazin-2-ylamino)benzoic acid (50 mg).

| 3-(4-(6-aminohexylamino)-6-(2,2,2-trifluoroethoxy)-1,3,5-triazin-2-ylamino)benzoic acid | |
|---|---|
| MS (M + H)+ Calcd. | 429.2 |
| MS (M + H)+ Observ. | 428.9 |
| Retention Time | 2.28 minutes |
| | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 5 mL/min |
| Wavelength | 220 |
| Solvent Pair | Water-Methanol-TFA |
| Column | PHENOMENEX-LUNA 3.0 × 50 mm S10 |

Step 4, preparation of Compound 1001: To a solution of 3-(4-(6-aminohexylamino)-6-(2,2,2-trifluoroethoxy)-1,3,5-triazin-2-ylamino)benzoic acid (12 mg) and 2-(1H-benzotriazol-1-yl)-1,1,3,3-tetramethyluronium tetrafluoroborate (9 mg) in DMF (5 mL) was added iPr$_2$NEt (10 μL). The mixture was stirred at room temperature for 16 hours, before DMF was removed under vacuum. The residue was purified by preparative HPLC to give Compound 1001 (4 mg).

| Compound 1001 | |
|---|---|
| MS (M + H)+ Calcd. | 411.2 |
| MS (M + H)+ Observ. | 410.9 |
| Retention Time | 2.37 minutes |
| | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 5 mL/min |
| Wavelength | 220 |
| Solvent Pair | Water-Methanol-TFA |
| Column | PHENOMENEX-LUNA 3.0 × 50 mm S10 |
| | NMR |
| $^1$H (500 MHz, DMSO-D6)δ ppm | 9.82 (s, 1H), 8.74 (s, 1H), 8.29 (m, 1H), 7.81 (m, 1H), 7.32 (m, 2H), 7.21 (m, 1H)), 4.95 (m, 2H), 1.62-1.36 (m, 12H) |

Synthesis of Compound 1002

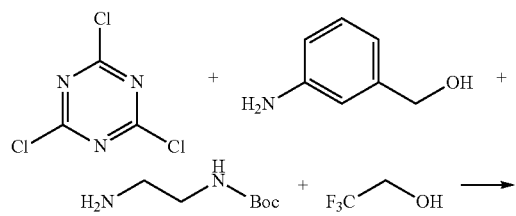

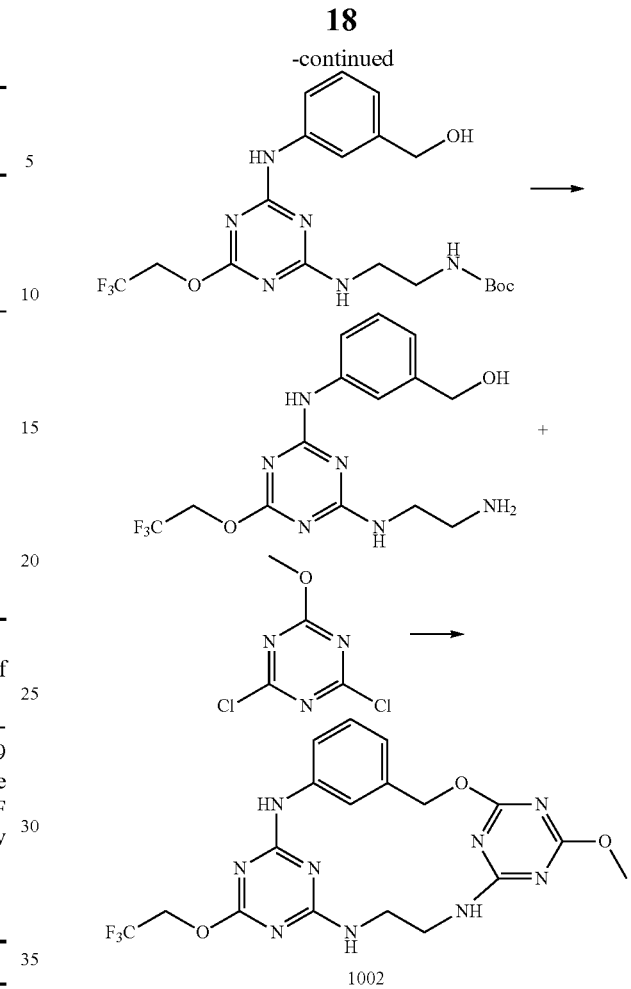

1002

Step 1, preparation of tert-butyl 2-(4-(3-(hydroxymethyl)phenylamino)-6-(2,2,2-trifluoroethoxy)-1,3,5-triazin-2-ylamino)ethylcarbamate: First, iPr$_2$NEt (25 mL) was added into the solution of 2,4,6-trichloro-1,3,5-triazine (10 g) and (3-aminophenyl)methanol (6.7 g) in THF (200 mL) at room temperature. The reaction mixture was stirred at room temperature for 16 hours. Solvents were removed under vacuum to offer crude (3-(4,6-dichloro-1,3,5-triazin-2-ylamino)phenyl)methanol compound with N-ethyl-N-isopropylpropan-2-amine (1:1) hydrochloride which was used without any purification. Then, Pr$_2$NEt (5 mL) was added into the solution of crude (3-(4,6-dichloro-1,3,5-triazin-2-ylamino)phenyl)methanol compound with N-ethyl-N-isopropylpropan-2-amine (1:1) hydrochloride (2 g) and tert-butyl 2-aminoethylcarbamate (734 mg) in THF at room temperature. The reaction mixture was stirred at room temperature for 16 hours. Solvent was removed under vacuum to offer crude tert-butyl 2-(4-chloro-6-(3-(hydroxymethyl)phenylamino)-1,3,5-triazin-2-ylamino)ethylcarbamate compound with N-ethyl-N-isopropylpropan-2-amine (1:2) dihydrochloride which was used as is. Finally, NaH (1 g) was added into the solution of crude tert-butyl 2-(4-chloro-6-(3-(hydroxymethyl)phenylamino)-1,3,5-triazin-2-ylamino)ethylcarbamate compound with N-ethyl-N-isopropylpropan-2-amine (1:2) dihydrochloride (1.8 g) and 2,2,2-trifluoroethanol (2.3 g) in THF. After stirring at room temperature for 16 hours, the reaction was quenched with NaHCO$_3$ and aqueous phase was extracted with EtOAc. The combined organic layer was dried over MgSO$_4$, filtered and concentrated to offer a crude tert-butyl 2-(4-(3-(hydroxymethyl)phenylamino)-6-(2,2,2-trifluoroethoxy)-1,3,5-triazin-2-ylamino)ethylcarbamate which was used in the further step without purification.

| tert-butyl 2-(4-(3-(hydroxymethyl)phenylamino)-6-(2,2,2-trifluoroethoxy)-1,3,5-triazin-2-ylamino)ethylcarbamate | |
|---|---|
| MS (M + H)+ Calcd. | 459.2 |
| MS (M + H)+ Observ. | 459.2 |
| Retention Time | 1.98 minutes |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 3 min |
| Flow Rate | 5 mL/min |
| Wavelength | 220 |
| Solvent Pair | ACN:Water:Ammonium Actetate |
| Column | Phenomenex Luna 4.6 × 50 mm S10 |

Step 2, preparation of (3-(4-(2-aminoethylamino)-6-(2,2,2-trifluoroethoxy)-1,3,5-triazin-2-ylamino)phenyl)methanol: tert-butyl 2-(4-(3-(hydroxymethyl)phenylamino)-6-(2,2,2-trifluoroethoxy)-1,3,5-triazin-2-ylamino) ethylcarbamate (1 g) was dissolved in TFA (2 mL) and $CH_2Cl_2$ (30 mL) at room temperature. After 16 hours, reaction showed formation of (3-(4-(2-aminoethylamino)-6-(2,2,2-trifluoroethoxy)-1,3,5-triazin-2-ylamino)phenyl)methanol. After removal of solvents, the residue was used as is in the next step.

| (3-(4-(2-aminoethylamino)-6-(2,2,2-trifluoroethoxy)-1,3,5-triazin-2-ylamino)phenyl)methanol | |
|---|---|
| MS (M + H)+ Calcd. | 359.1 |
| MS (M + H)+ Observ. | 359.1 |
| Retention Time | 1.57 minutes |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 3 min |
| Flow Rate | 5 mL/min |
| Wavelength | 220 |
| Solvent Pair | ACN:Water:Ammonium Actetate |
| Column | Phenomenex Luna 4.6 × 50 mm S10 |

Step 3, preparation of Compound 1002: To a solution of (3-(4-(2-aminoethylamino)-6-(2,2,2-trifluoroethoxy)-1,3,5-triazin-2-ylamino)phenyl)methanol (30 mg) in THF (20 mL) was added 2,4-dichloro-6-methoxy-1,3,5-triazine (16.6 mg) and $iPr_2NEt$ (0.073 mL). The mixture was stirred at room temperature for 48 hours before all the solvents were removed under vacuum. The residue was purified by preparative HPLC to give Compound 1002 (5 mg).

| Compound 1002 | |
|---|---|
| MS (M + H)+ Calcd. | 466.2 |
| MS (M + H)+ Observ. | 466.1 |
| Retention Time | 1.31 minutes |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 5 mL/min |
| Wavelength | 220 |
| Solvent Pair | ACN:Water:Ammonium Actetate |
| Column | PHENOMENEX-LUNA 3.0 × 50 mm S10 |
| NMR | |
| $^1$H (500 MHz, DMSO-D6)δ ppm | 9.67 (s, 1H), 8.25 (s, 1H), 8.00 (m, 1H), 7.87 (m, 1H), 7.30 (t, 1H, J = 8 Hz), 7.13 (d, 1H, J = 8 Hz), 7.01 (d, 1H, J = 8 Hz), 5.32 (s, 2H), 4.95 (m, 2H), 3.77 (s, 3H), 3.52 (m, 2H), 3.38 (m, 2H) |

Synthesis of Compound 1003 and Compound 1004

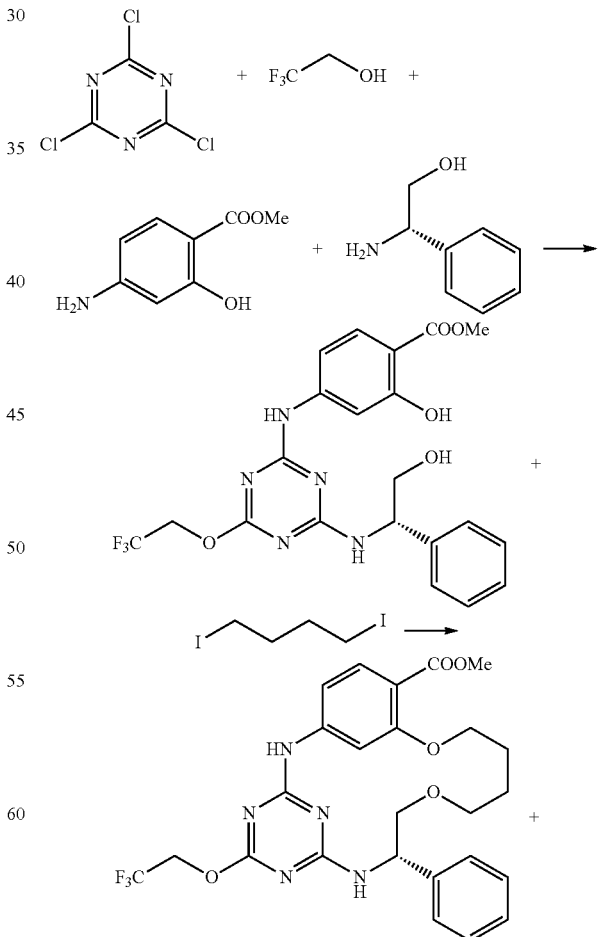

1003

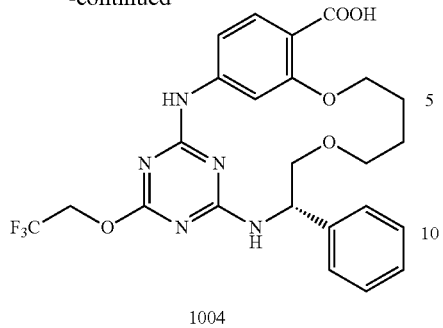

1004

Step 1, preparation of (S)-methyl 2-hydroxy-4-(4-(2-hydroxy-1-phenylethylamino)-6-(2,2,2-trifluoroethoxy)-1,3,5-triazin-2-ylamino)benzoate: iPr$_2$NEt (2 mL) was added into the solution of 2,4,6-trichloro-1,3,5-triazine (1 g) and 2,2,2-trifluoroethanol (542 mg) in THF (20 mL). The reaction was stirred at room temperature for 16 hours before methyl 4-amino-2-hydroxybenzoate (906 mg) and iPr$_2$NEt (2 mL) were added. The resulting mixture was stirred at room temperature for 16 hours. Then, (S)-2-amino-2-phenylethanol (744 mg) was added into the mixture. The reaction was carried out at room temperature for 16 hours, before it was quenched with water. The aqueous layer was extracted with EtOAc (3×20 mL). The combined organic layer was dried over Mg$_2$SO$_4$ and concentrated to offer a residue which was purified by silica gel chromatography.

| (S)-methyl 2-hydroxy-4-(4-(2-hydroxy-1-phenylethylamino)-6-(2,2,2-trifluoroethoxy)-1,3,5-triazin-2-ylamino)benzoate | |
|---|---|
| MS (M + H)$^+$ Calcd. | 480.1 |
| MS (M + H)$^+$ Observ. | 480.3 |
| Retention Time | 1.70 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3u |

Step 2, preparation of Compound 1003 and Compound 1004: NaH (20 mg) was added into the solution of (S)-methyl 2-hydroxy-4-(4-(2-hydroxy-1-phenylethylamino)-6-(2,2,2-trifluoroethoxy)-1,3,5-triazin-2-ylamino)benzoate (80 mg) and 1,4-diiodobutane (52 mg) in DMF (8 mL) and reaction was stirred room temperature for 16 hours. Solvents were removed under vacuum to offer a residue which was purified by preparative HPLC to give Compound 1003 (5 mg) and Compound 1004 (3 mg).

| Compound 1003 | |
|---|---|
| MS (M + H)$^+$ Calcd. | 534.2 |
| MS (M + H)$^+$ Observ. | 534.1 |
| Retention Time | 2.18 minutes |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 5 mL/min |
| Wavelength | 220 |
| Solvent Pair | Water-Methanol-TFA |
| Column | PHENOMENEX-LUNA 4.6 × 50 mm S10 |

| Compound 1004 | |
|---|---|
| MS (M + H)$^+$ Calcd. | 520.2 |
| MS (M + H)$^+$ Observ. | 520.1 |
| Retention Time | 2.13 minutes |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 5 mL/min |
| Wavelength | 220 |
| Solvent Pair | Water-Methanol-TFA |
| Column | PHENOMENEX-LUNA 4.6 × 50 mm S10 |

Synthesis of Compound 1005

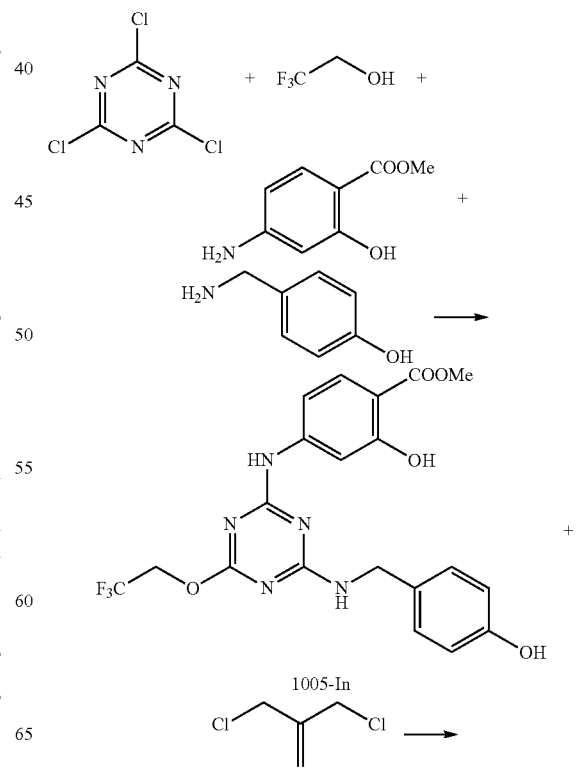

1005-In

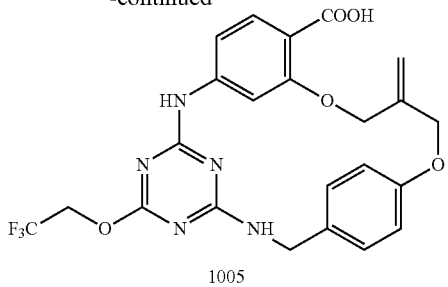

1005

Step 1, preparation of methyl 2-hydroxy-4-(4-(4-hydroxybenzylamino)-6-(2,2,2-trifluoroethoxy)-1,3,5-triazin-2-ylamino)benzoate: iPr$_2$NEt (2 mL) was added into the solution of 2,4,6-trichloro-1,3,5-triazine (1 g) and 2,2,2-trifluoroethanol (542 mg) in THF (20 mL). The reaction was stirred at room temperature for 16 hours before methyl 4-amino-2-hydroxybenzoate (906 mg) and iPr$_2$NEt (2 mL) were added. The resulting mixture was stirred at room temperature for 16 hours. Then, 4-(aminomethyl)phenol (668 mg) was added into the mixture. The reaction was carried out at room temperature for 16 hours, before it was quenched with water. The aqueous layer was extracted with EtOAc (3×20 mL). The combined organic layer was dried over Mg$_2$SO$_4$ and concentrated to offer a residue which was purified by silica gel chromatography to give methyl 2-hydroxy-4-(4-(4-hydroxybenzylamino)-6-(2,2,2-trifluoroethoxy)-1,3,5-triazin-2-ylamino)benzoate, Compound 1005-In.

| methyl 2-hydroxy-4-(4-(4-hydroxybenzylamino)-6-(2,2,2-trifluoroethoxy)-1,3,5-triazin-2-ylamino)benzoate | |
|---|---|
| MS (M + H)$^+$ Calcd. | 466.1 |
| MS (M + H)$^+$ Observ. | 466.3 |
| Retention Time | 1.81 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3u |

Step 2, preparation of Compound 1005: NaH (15 mg) was added into the solution of methyl 2-hydroxy-4-(4-(4-hydroxybenzylamino)-6-(2,2,2-trifluoroethoxy)-1,3,5-triazin-2-ylamino)benzoate (Compound 1005-In, 60 mg) and 3-chloro-2-(chloromethyl)prop-1-ene (16.2 mg) in DMF (6 mL) and reaction was stirred room temperature for 16 hours. Solvents were removed under vacuum to offer a residue which was purified by preparative HPLC to give Compound 1005 (8 mg).

| Compound 1005 | |
|---|---|
| MS (M + H)$^+$ Calcd. | 504.1 |
| MS (M + H)$^+$ Observ. | 504.1 |
| Retention Time | 2.26 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 5 mL/min |
| Wavelength | 220 |
| Solvent Pair | Water-Methanol-TFA |
| Column | PHENOMENEX-LUNA 4.6 × 50 mm S10 |

Synthesis of Compound 1006

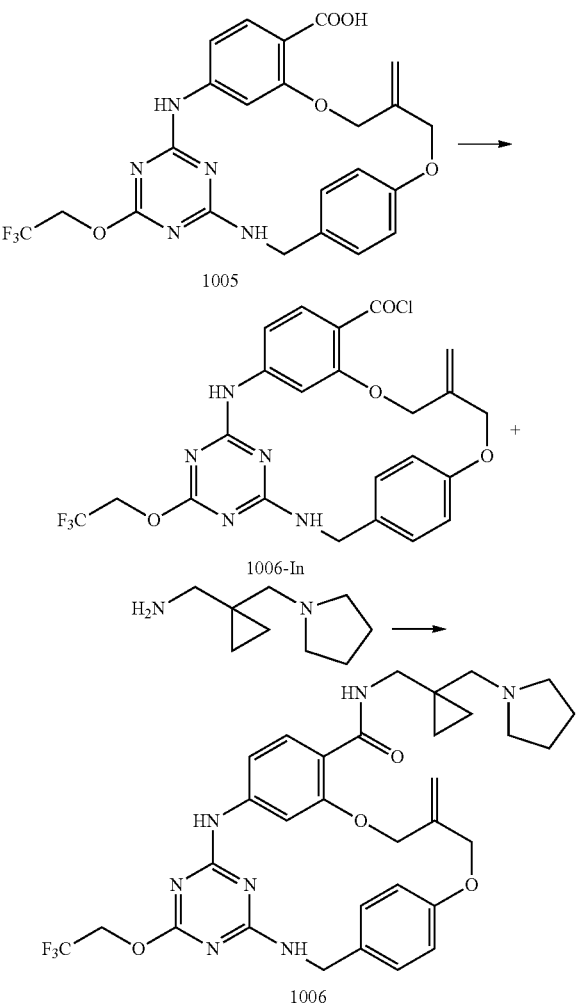

Step 1, preparation of Compound 1006-In: Compound 1005 (8 mg) and sulfurous dichloride (28 mg) were dissolved in dichloromethane (2 mL). The reaction mixture was heated at 50° C. for 6 hours. Removal of solvents under vacuum provided crude Compound 1006-In which was used in the next step without purification.

Step 2, preparation of Compound 1006: iPr$_2$NEt (1.98 mg) was added into the solution of crude Compound 1006-In (8 mg) and (1-(pyrrolidin-1-ylmethyl)cyclopropyl)methanamine (12 mg) in THF (1 mL). The reaction was stirred at room temperature for 16 hours. Solvents were removed under vacuum to offer a residue which was purified by preparative HPLC to give Compound 1006 (2 mg).

| | Compound 1006 |
|---|---|
| MS (M + H)+ Calcd. | 640.3 |
| MS (M + H)+ Observ. | 640.5 |
| Retention Time | 4.12 minutes |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3u |

| | Compound 1007 |
|---|---|
| MS (M + H)+ Calcd. | 580.2 |
| MS (M + H)+ Observ. | 580.1 |
| Retention Time | 2.16 min |
| | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 5 mL/min |
| Wavelength | 220 |
| Solvent Pair | Water-Methanol-TFA |
| Column | PHENOMENEX-LUNA 4.6 × 50 mm S10 |
| | NMR |
| $^1$H (500 MHz, CDCl$_3$)δ ppm | 7.77 (d, 1H, J = 8.5H), 7.15 (d, 2H, J = 8 Hz), 7.00 (m, 3H), 6.84 (dd, 1H, J = 8.5 Hz, J = 2 Hz), 4.50 (m, 2H), 4.44 (m, 2H), 4.39 (m, 2H), 3.97 (s, 3H), 3.87 (m, 2H), 3.78 (m, 2H), 3.73 (m, 2H), 3.47 (m, 2H), 3.39 (m, 2H), 3.06 (m, 2H) |

Synthesis of Compound 1007

Synthesis of Compound 1008

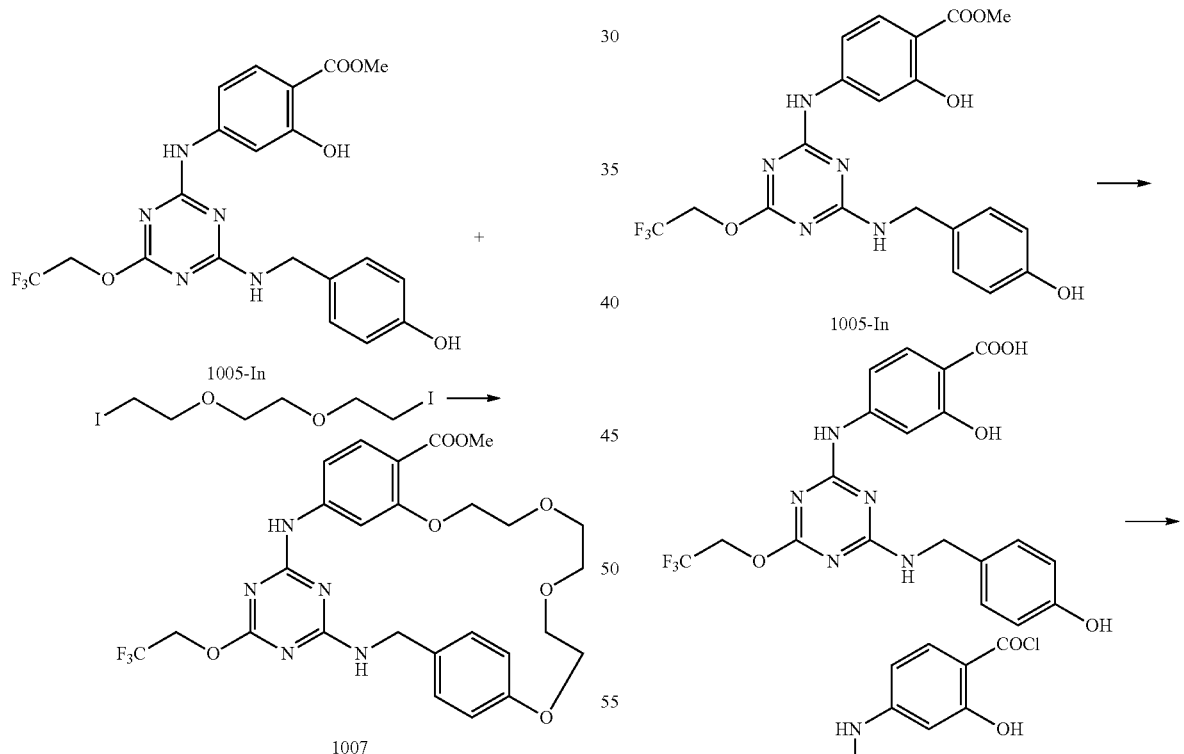

NaH (21 mg) was added into the solution of methyl 2-hydroxy-4-(4-(4-hydroxybenzylamino)-6-(2,2,2-trifluoroethoxy)-1,3,5-triazin-2-ylamino)benzoate (Compound 1005-In, 80 mg) and 1,2-bis(2-iodoethoxy)ethane (64 mg) in DMF (8 mL) and reaction was stirred room temperature for 4 hours before it was quenched by MeOH. Solvents were removed under vacuum to offer a residue which was purified by preparative HPLC to give Compound 1007 (2 mg).

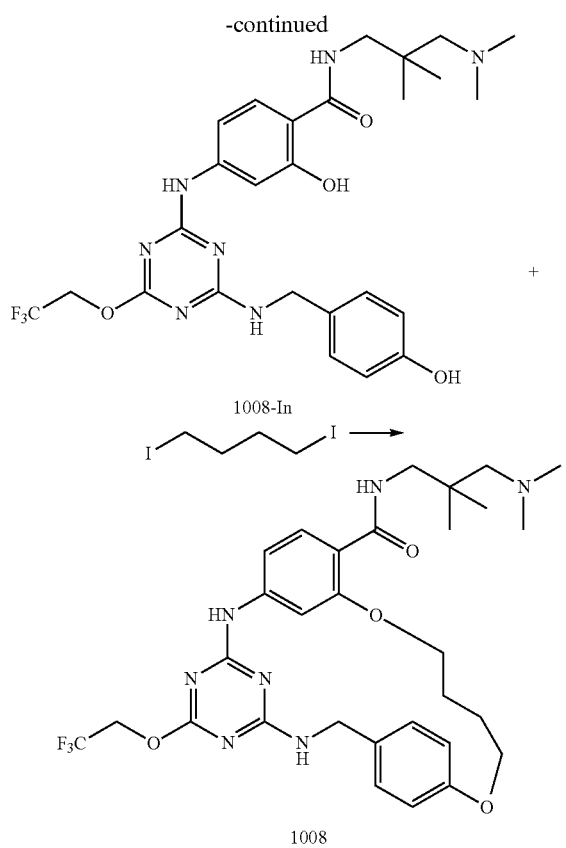

1008

Step 1, preparation of 2-hydroxy-4-(4-(4-hydroxybenzylamino)-6-(2,2,2-trifluoroethoxy)-1,3,5-triazin-2-ylamino)benzoic acid: $K_2CO_3$ (498 mg) was added into the solution of Compound 1005-In (558 mg) in water and MeOH (6 mL, v/v=1/1). The reaction was heated to 115° C. for 0.5 hour. Then 1N HCl was added dropwise to adjust acidity to pH2. Brown solid (2-hydroxy-4-(4-(4-hydroxybenzylamino)-6-(2,2,2-trifluoroethoxy)-1,3,5-triazin-2-ylamino)benzoic acid) was collected and dried under vacuum at 78° C. for 16 hours. The product was used in the next step without further purification.

Step 2, preparation of 2-hydroxy-4-(4-(4-hydroxybenzylamino)-6-(2,2,2-trifluoroethoxy)-1,3,5-triazin-2-ylamino)benzoyl chloride: 2-hydroxy-4-(4-(4-hydroxybenzylamino)-6-(2,2,2-trifluoroethoxy)-1,3,5-triazin-2-ylamino)benzoic acid (500 mg) in dichloromethane (3 mL) and sulfurous dichloride (1.98 g) were mixed together. The reaction mixture was heated to 115° C. for 4 hours. Removal of solvents under vacuum provided crude 2-hydroxy-4-(4-(4-hydroxybenzylamino)-6-(2,2,2-trifluoroethoxy)-1,3,5-triazin-2-ylamino)benzoyl chloride which was used in the next step without purification.

Step 3, preparation of N-(3-(dimethylamino)-2,2-dimethylpropyl)-2-hydroxy-4-(4-(4-hydroxybenzylamino)-6-(2,2,2-trifluoroethoxy)-1,3,5-triazin-2-ylamino)benzamide, Compound 1008-In: $iPr_2NEt$ (258 mg) was added into the solution of crude 2-hydroxy-4-(4-(4-hydroxybenzylamino)-6-(2,2,2-trifluoroethoxy)-1,3,5-triazin-2-ylamino)benzoyl chloride (470 mg) and (1-N1,N1,2,2-tetramethylpropane-1,3-diamine (130 mg) in DMF (2 mL). The reaction was stirred at room temperature for 4 hours. Solvents were removed under vacuum to offer a residue which was purified by preparative HPLC to give N-(3-(dimethylamino)-2,2-dimethylpropyl)-2-hydroxy-4-(4-(4-hydroxybenzylamino)-6-(2,2,2-trifluoroethoxy)-1,3,5-triazin-2-ylamino)benzamide, Compound 1008-I (300 mg).

| N-(3-(dimethylamino)-2,2-dimethylpropyl)-2-hydroxy-4-(4-(4-hydroxybenzylamino)-6-(2,2,2-trifluoroethoxy)-1,3,5-triazin-2-ylamino)benzamide, Compound 1008-I | |
|---|---|
| MS (M + H)+ Calcd. | 564.3 |
| MS (M + H)+ Observ. | 564.4 |
| Retention Time | 2.67 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3u |

Step 4, preparation of Compound 1008: $Cs_2CO_3$ (173 mg) was added into the solution of Compound 1008-In (60 mg) and 1,4-diiodobutane (33 mg) in THF (8 mL) and reaction was stirred room temperature for 16 hours. Solvents were removed under vacuum to offer a residue which was purified by preparative HPLC to give Compound 1008 (2.4 mg).

| Compound 1008 | |
|---|---|
| MS (M + H)+ Calcd. | 618.3 |
| MS (M + H)+ Observ. | 618.1 |
| Retention Time | 1.48 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 5 mL/min |
| Wavelength | 220 |
| Solvent Pair | Water-Methanol-TFA |
| Column | PHENOMENEX-LUNA 4.6 × 50 mm S10 |

Synthesis of Compound 1009

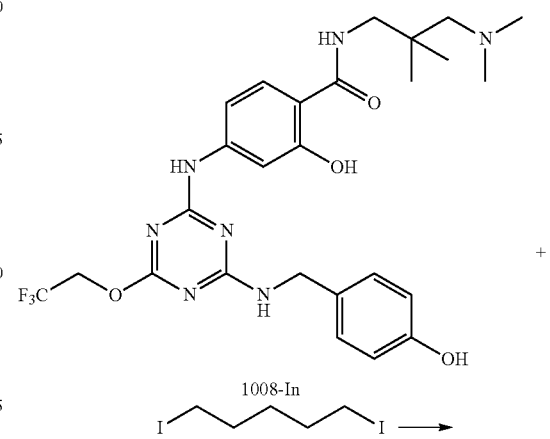

-continued

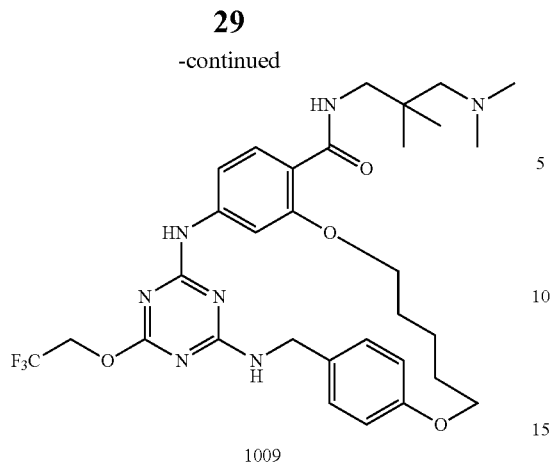

1009

Cs$_2$CO$_3$ (139 mg) was added into the solution of Compound 1008-In (80 mg) and 1,5-diiodopentane (46 mg) in DMF (2 mL) and reaction was heated to 70° C. for 16 hours. Solvents were removed under vacuum to offer a residue which was purified by preparative HPLC to give Compound 1009 (3.7 mg).

| | Compound 1009 |
|---|---|
| MS (M + H)$^+$ Calcd. | 632.3 |
| MS (M + H)$^+$ Observ. | 632.2 |
| Retention Time | 1.46 min |
| | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 5 mL/min |
| Wavelength | 220 |
| Solvent Pair | Water-Methanol-TFA |
| Column | PHENOMENEX-LUNA 4.6 × 50 mm S10 |

Synthesis of Compound 1010

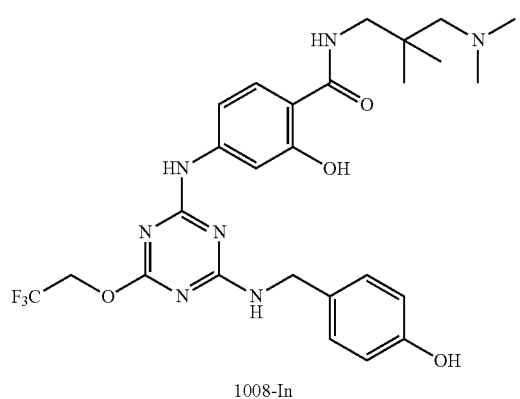

1008-In

+

-continued

I⟋⟋⟋⟋⟋⟋⟋⟋I →

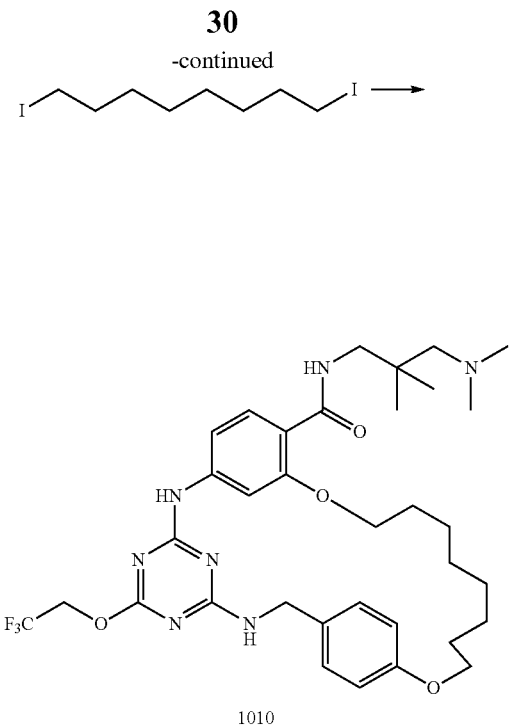

1010

Cs$_2$CO$_3$ (139 mg) was added into the solution of Compound 1008-In (80 mg) and 1,8-diiodooctane (52 mg) in DMF (2 mL) and reaction was heated to 70° C. for 16 hours. Solvents were removed under vacuum to offer a residue which was purified by preparative HPLC to give Compound 1010 (7 mg).

| | Compound 1010 |
|---|---|
| MS (M + H)$^+$ Calcd. | 674.4 |
| MS (M + H)$^+$ Observ. | 674.3 |
| Retention Time | 1.95 min |
| | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 5 mL/min |
| Wavelength | 220 |
| Solvent Pair | Water-Methanol-TFA |
| Column | PHENOMENEX-LUNA 4.6 × 50 mm S10 |
| | NMR |
| $^1$H (500 MHz, CD$_3$OD)δ ppm | 8.30 (s, 1H), 7.91 (d, 1H, J = 8.5 Hz), 7.31 (d, 2H, J = 8.5 Hz), 6.95 (d, 2H, J = 8.5 Hz), 6.84 (dd, 1H, J = 8.5 Hz, J = 2 Hz), 4.90 (m, 2H), 4.72 (s, 2H), 4.26 (t, 1H, J = 5 Hz), 4.12 (t, 2H, J = 6.5 Hz), 3.66 (t, 1H, J = 6 Hz), 3.56 (t, 2H, J = 6.5 Hz), 3.43 (s, 2H), 3.01 (s, 2H), 2.99 (s, 6H), 1.80-1.20 (m, 12H), 1.15 (s, 6H) |

Synthesis of Compound 1011

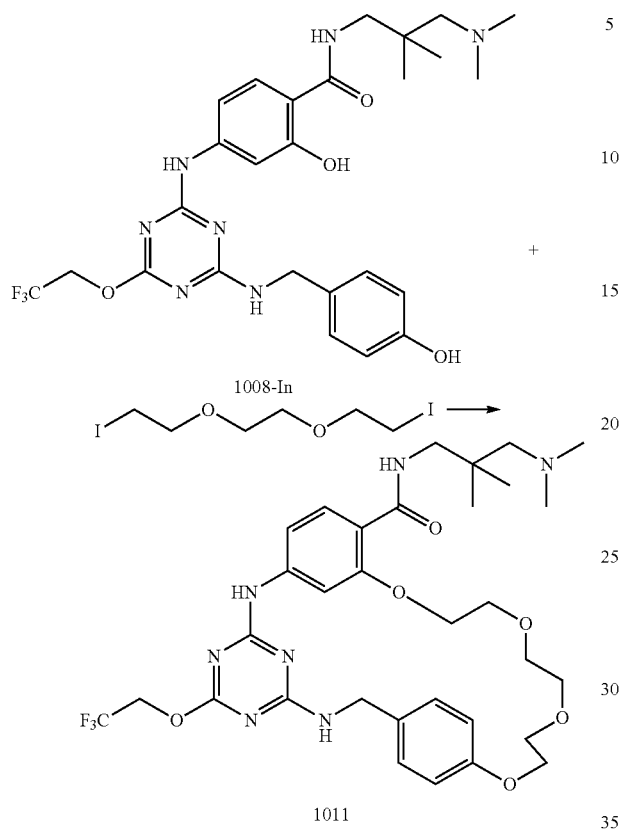

K$_2$CO$_3$ (37 mg) was added into the solution of Compound 1008-In (50 mg) and 1,2-bis(2-iodoethoxy)ethane (33 mg) in DMF (2 mL) and the reaction was stirred at room temperature for 16 hours. Solvents were removed under vacuum to offer a residue which was purified by preparative HPLC to give Compound 1011 (8 mg).

| | Compound 1011 |
|---|---|
| MS (M + H)$^+$ Calcd. | 678.3 |
| MS (M + H)$^+$ Observ. | 678.4 |
| Retention Time | 2.58 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3u |
| | NMR |
| $^1$H (500 MHz, CD$_3$OD)δ ppm | 8.66 (m, 1H), 8.22 (d, 1H, J = 2 Hz), 7.88 (d, 1H, J = 8.5 Hz), 7.25 (d, 2H, J = 8.5 Hz), 7.00 (d, 2H, J = 9 Hz), 6.80 (dd, 1H, J = 8.5 Hz, J = 2 Hz), 4.92 (m, 2H), 4.73 (s, 2H), 4.36 (t, 2H, J = 4 Hz), 3.80 (t, 2H, J = 4 Hz), 3.60 (m, 4H), 3.44 (m, 6H), 3.34 (s, 2H), 3.00 (s, 2H), 2.97 (s, 6H), 1.14 (s, 6H) |

Synthesis of Compound 1012

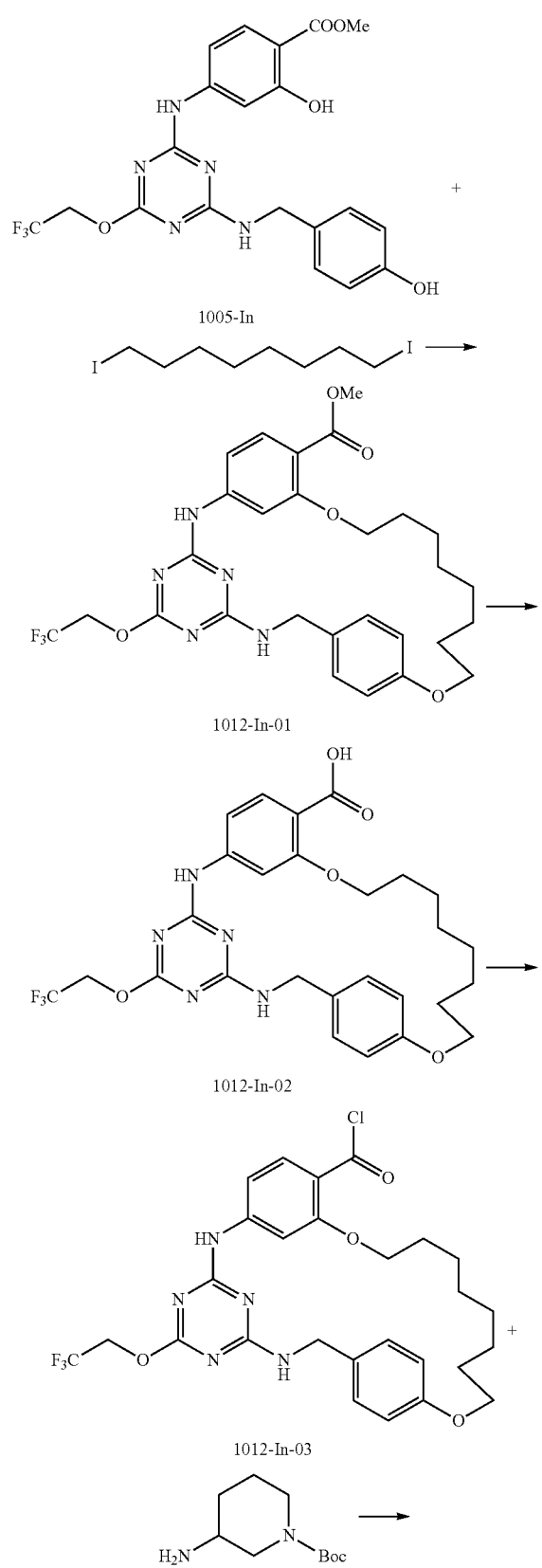

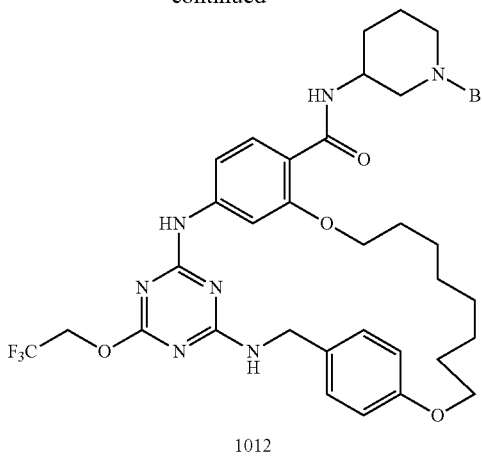

1012

Step 1, preparation of Compound 1012-In-01: Cs$_2$CO$_3$ (2.1 g) was added into the solution of Compound 1005-In (1 g) and 1,8-diiodooctane (786 mg) in DMF (10 mL) and the reaction was stirred at room temperature for 16 hours. After water (5 mL) was added, Compound 1012-In-01 precipitated out of solution. 650 mg of Compound 1012-In-01 was obtained after drying at 78° C. for 16 hours. It was used in the next step without further purification.

| Compound 1012-In-01 | |
|---|---|
| MS (M + H)$^+$ Calcd. | 576.2 |
| MS (M + H)$^+$ Observ. | 576.1 |
| Retention Time | 4.64 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3um |

Step 2, preparation of Compound 1012-In-02: K$_2$CO$_3$ (72 mg) was added into the solution of Compound 1012-In-01 (100 mg) in water and dioxane (8 mL, v/v=1/1). The reaction was heated to 70° C. for 16 hours. Then 1N HCl was added dropwise to adjust acidity to pH1. Aqueous phase was extracted with EtOAc (2×20 mL). The combined organic layer was dried over MgSO$_4$ and concentrated to give crude Compound 1012-In-02 (70 mg) which was used in the further reactions without purification.

| Compound 1012-In-02 | |
|---|---|
| MS (M + H)$^+$ Calcd. | 562.2 |
| MS (M + H)$^+$ Observ. | 562.3 |
| Retention Time | 3.33 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |

| Compound 1012-In-02 | |
|---|---|
| Flow Rate | 0.8 mL/min |
| Wavelength | 220 |
| Solvent Pair | ACN:Water:Ammonium Actetate |
| Column | Phenomenex LUNA C18, 50 × 2, 3u |

Step 3, preparation of Compound 1012-In-03: Compound 1012-In-02 (30 mg) in and sulfurous dichloride (300 mg) were mixed together. The reaction mixture was heated to 80° C. for 16 hours. Removal of solvents under vacuum provided crude Compound 1012-In-03 which was used in the next step without purification.

Step 4, preparation of Compound 1012: iPr$_2$NEt (67 mg) was added into the solution of crude Compound 1012-In-03 (100 mg) and tert-butyl 3-aminopiperidine-1-carboxylate (35 mg) in DMF (2 mL). The reaction was stirred at room temperature for 16 hours. Solvents were removed under vacuum to offer a residue which was purified by preparative HPLC to give Compound 1012 (15 mg).

| Compound 1012 | |
|---|---|
| MS (M + H)$^+$ Calcd. | 744.4 |
| MS (M + H)$^+$ Observ. | 744.4 |
| Retention Time | 4.12 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3u |

Synthesis of Compound 1013

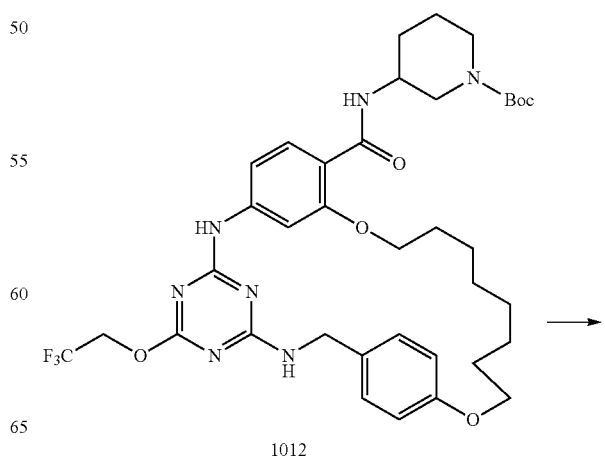

1012

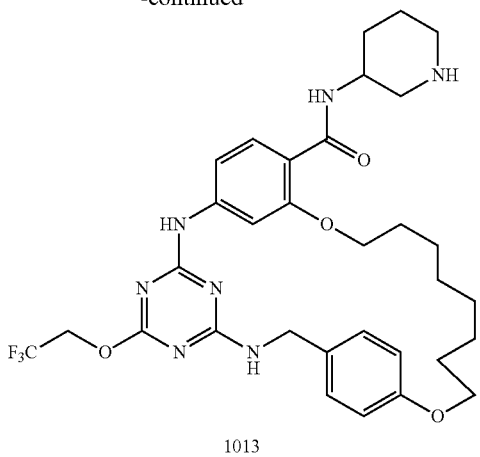

1013

Compound 1012 (10 mg) and TFA (0.016 mL) as dissolved in CH$_2$Cl$_2$ (1 mL at room temperature. After 16 hours, solvents were removed to give a residue which was purified by preparative HPLC to give Compound 1013 (5 mg).

| Compound 1013 | |
|---|---|
| MS (M + H)$^+$ Calcd. | 644.4 |
| MS (M + H)$^+$ Observ. | 644.4 |
| Retention Time | 3.08 min |

| Compound 1013 | |
|---|---|
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3u |
| NMR | |
| $^1$H (500 MHz, CD$_3$OD) δ ppm | 8.28 (d, 1H, J = 2 Hz), 7.87 (d, 1H, J = 8.5 Hz), 7.31 (d, 2H, J = 9 Hz), 6.96 (d, 2H, J = 8.5 Hz), 6.82 (dd, 1H, J = 8.5 Hz, J = 2 Hz), 5.51 (s, 1H), 4.80 (d, 1H, J = 15.5 Hz), 4.64 (d, 1H, J = 15.5 Hz), 4.26 (m, 2H), 3.58 (m, 2H), 3.00 (m, 1H), 2.91 (m, 1H), 2.20-0.70 (m, 24H) |

Synthesis of Compound 1014, Compound 1015 and Compound 1016

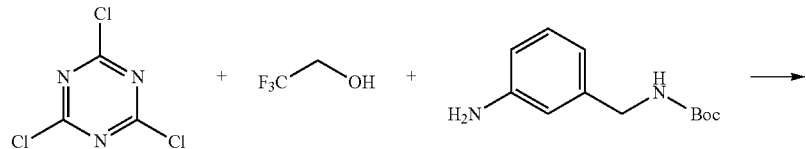

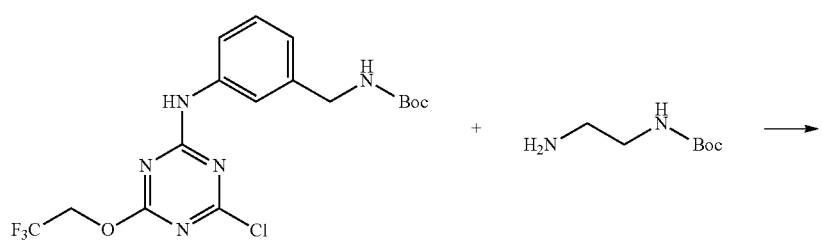

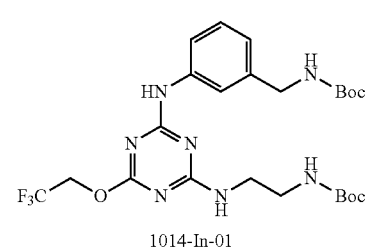
1014-In-01

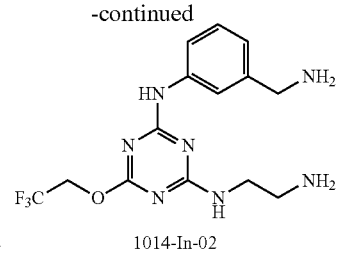
1014-In-02

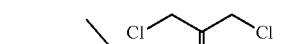

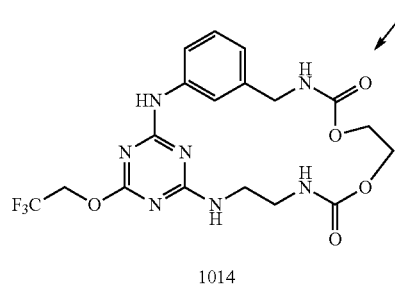
1014

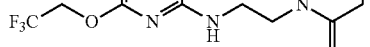

1015

1016

Step 1, preparation of tert-butyl 3-(4-chloro-6-(2,2,2-trifluoroethoxy)-1,3,5-triazin-2-ylamino)benzylcarbamate: In a dried round bottom flask, 2,4,6-trichloro-1,3,5-triazine (10 g) was dissolved in dried dichloromethane (800 mL). The reaction mixture was cooled at 0 to 5° C. and then iPr$_2$NEt (9.4 mL) and 2,2,2-trifluoroethanol (4.3 mL) were added. The mixture was stirred for 3 hours, followed by adding tert-butyl 3-aminobenzylcarbamate (9.5 g). The reaction was then stirred for another 16 hours before being quenched by water. Aqueous phase was extracted with dichloromethane. The solvents were removed under vacuum to give a residue which was purified by column chromatograph with dichloromethane to give tert-butyl 3-(4-chloro-6-(2,2,2-trifluoroethoxy)-1,3,5-triazin-2-ylamino)benzylcarbamate (10 g).

Step 2, preparation of Compound 1014-In-01: In a dried round bottom flask, tert-butyl 3-(4-chloro-6-(2,2,2-trifluoroethoxy)-1,3,5-triazin-2-ylamino)benzylcarbamate (10 g, 0.023 mol) was dissolved in dried DCM(250 mL). The reaction mixture was cooled at 0 to 5° C. and then DIPEA (4.8 mL) and tert-butyl 2-aminoethylcarbamate (4.4 g, 0.0277 mol) were added. The mixture was stirred at room temperature for 10 hours. The reaction was quenched with water and extracted with DCM. DCM was removed by evaporator. The desired product (5.3 g) was obtained by column chromatograph with DCM.

| Compound 1014-In-01 | |
|---|---|
| MS (M − H)$^+$ Calcd. | 556.2 |
| MS (M − H)$^+$ Observ. | 556.2 |
| Retention Time | 2.65 min |
| LC Condition | |
| Solvent A | 10 mM Ammonium Actetate |
| Solvent B | ACN |
| Gradient | Time: 0-3 min; % B: 40-95 |
| | Time: 3-6 min; % B: 95 |
| | Time: 6-6.5 min; % B: 95-40 |
| | Time: 6.5-8 min; % B: 40 |

| Compound 1014-In-01 | |
|---|---|
| Flow Rate | 1.5 mL/min |
| Solvent Pair | ACN:Water:Ammonium Actetate |
| Column | Atlantis dC18 (50 × 4.6 mm-5um) |
| NMR | |
| $^1$H (400 MHz, DMSO-d$_6$)δ ppm | 1.38 (s, 9H), 1.40 (s, 9H), 3.09-3.16 (m, 2H), 3.29-3.40 (m, 2H), 4.10-4.11 (d, 2H, J = 4 Hz,), 4.92-5.04 (m, 2H), 6.88-6.93 (m, 2H), 7.21-7.27 (m, 1H), 7.36-7.39 (m, 1H), 7.52 (m, 1H), 7.66 (b, 3H), 9.59-9.72 (d, 1H) |

Step 3, preparation of Compound 1014-In-02: Compound 1014-In-01 (3 g) was dissolved in dichloromethane (30 mL) and followed by adding TFA (3.32 mL). The mixture was stirred at room temperature for 2 hours. The solvent was removed under reduced pressure and the sticky oil was washed with Et$_2$O and dried under vacuum to provide crude Compound 1014-In-02 which was used in the next step without purification.

| Compound 1014-In-02 | |
|---|---|
| MS (M + H)$^+$ Calcd. | 358.2 |
| MS (M + H)$^+$ Observ. | 358.2 |
| Retention Time | 1.19 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 4 mL/min |
| Wavelength | 220 |
| Solvent Pair | ACN:Water:Ammonium Actetate |
| Column | Xbridge 4.6 × 50 mm C18 5um |

Step 4, preparation of Compound 1014, Compound 1015 and Compound 1016: To each of the reagents contained in 16×100 mm Wheaton tubes was added DMF (2 mL). A stock solution was prepared of the N2-(2-aminoethyl)-N4-(3-(aminomethyl)phenyl)-6-(2,2,2-trifluoroethoxy)-1,3,5-triazine-2,4-diamine (Compound 1014-In-02) compound with 2 eq. of TFA (2.014 g) in 156 mls DMF. iPr$_2$NEt (4 mL) to this stock solution. To each of the reagents was added 6 mL of the N2-(2-aminoethyl)-N4-(3-(aminomethyl)phenyl)-6-(2,2,2-trifluoroethoxy)-1,3,5-triazine-2,4-diamine (Compound 1014-In-02) solution. Vials were covered and allowed to shake at room temp for 18 hours. All reactions were heated to 90° C. for 6 hours using a Haake B7 Temperature controller and allowed to cool to room temperature afterwards. Solvents were removed under nitrogen flow at 35° C. using a Zymark TurboVap Evaporator. 1.0 mL of DMF was added to each reaction vial. The mixtures were shook well to allow all the materials dissolve. Solutions were transferred to a 96 well filter plate collecting into a 96 well deep well plate using a vacuum manifold. Each reaction vial was rinsed with 0.4 mL of DMF and transferred to the filter plate. The products were isolated by preparative HPLC. Samples were dried using Genevac HT-24 with the below conditions. Fractions were combined using DMF as the transfer solvents.

Prep HPLC Condition for Parallel Synthesis
Chromeleon 6.70 spl LC software
HP 1100 quarternary pump for analytical
Varian prostar binary pump with 50 mL/min head for prep
Dionex UVD340U UV spectrometer
Sedex 75 ELS detector
Thermo-Finnigen MSQ Surveyor Plus mass spectrometer
Column—Waters Xbridge 19×250 mm 10 um C18
Mobile Phase—A=Water; B=ACN; Modifier=10 mM NH4OAc
Method—

| Time | B % | Flow |
|---|---|---|
| _0.00' | _10 | 20.0 |
| _4.00' | _95 | 20.0 |
| 24.00' | _95 | 20.0 |
| 27.00' | _95 | 20.0 |
| 27.50' | _10 | 20.0 |
| 29.00 | _.10_' | 20.0 |
| _._' | — | _.— |
| _._' | — | _.— |

ELSD Triggered Collection
Analytical LC/MS for Parallel Synthesis
MassLynx 4.0 SP4 LC-MS software
CTC-Leap HTS-PAL autosampler
Agilent 1100 binary pump
Agilent 1100 photodiode array
Polymer Lab 2100 ELS detector (Evap. Temp.=45° C., Neb. Temp.=35° C.)
Waters ZQ with ESCi mass spectrometer
Column—Waters Xbridge 4.6×100 mm 5 um C18
Mobile Phase—A=Water; B=ACN; Modifier=10 mM NH4OAc
Method—

| Time | B % | Flow |
|---|---|---|
| _0.00' | _10 | _1.0 |
| _6.00' | _95 | _1.0 |
| _7.50' | _95 | _1.0 |
| _8.00' | _10 | _1.0 |
| _10.00' | _10 | _1.0 |
| —.—' | — | —.— |
| —.—' | — | —.— |
| —.—' | — | —.— |

Detector—UV—220 nm
Detector—MS-ESI Pos
Genevac Conditions (Post Prep)
  GeneVac Program 1—ACN-H$_2$O-Buffer in 16×100 TT & AL blocks: Temp=45 C, 0.3 h @ 175 to 40 bar, 1.7 h @ 40 bar, defrost, 6 h @ 8 bar, 6 h @ Full Vac, defrost.
Genevac Conditions (Fractions)
  GeneVac Program 2—DMF with AL blocks or Heat Transfer Plates: Temp=45 C, 16 h @ Full Vac, defrost.

| Compound 1014 | |
|---|---|
| MS (M + H)$^+$ Calcd. | 472.2 |
| MS (M + H)$^+$ Observ. | 472.1 |
| Retention Time | 4.35 min |

| Compound 1015 | |
|---|---|
| MS (M + H)$^+$ Calcd. | 456.2 |
| MS (M + H)$^+$ Observ. | 456.2 |
| Retention Time | 3.84 min |

| Compound 1016 | |
|---|---|
| MS (M + H)$^+$ Calcd. | 410.2 |
| MS (M + H)$^+$ Observ. | 410.2 |
| Retention Time | 4.03 min |

The following analogues were prepared according to the process of synthesis of Compound 1012.

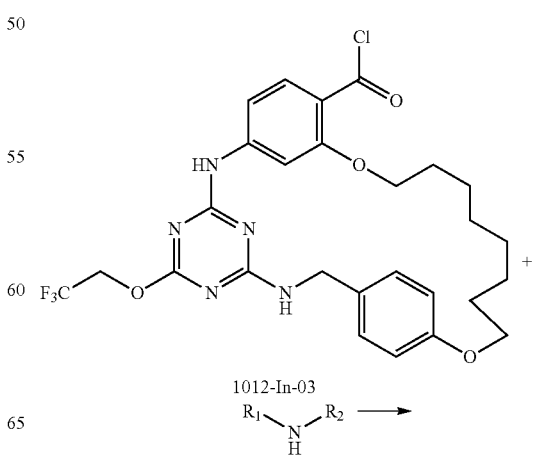

-continued

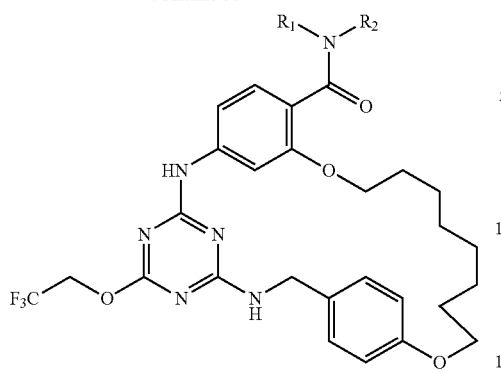

---
Compound 1017
---

Amine Used 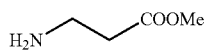

Product 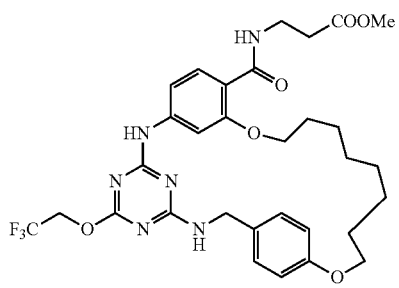 [SMILES: COC(=O)CCNC(=O)c1ccc2cc1OCCCCCCCCOc1ccc(cc1)CNc1nc(nc(OCC(F)(F)F)n1)N2]

| | |
|---|---|
| MS (M + H)+ Calcd. | 647.3 |
| MS (M + H)+ Observ. | 647.2 |
| Retention Time | 4.80 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 X 50 mm 3 um |

---
Compound 1018
---

Amine Used 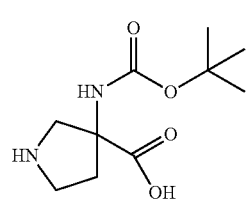 [SMILES: CC(C)(C)OC(=O)NC1(C(=O)O)CCNC1]

-continued

Product 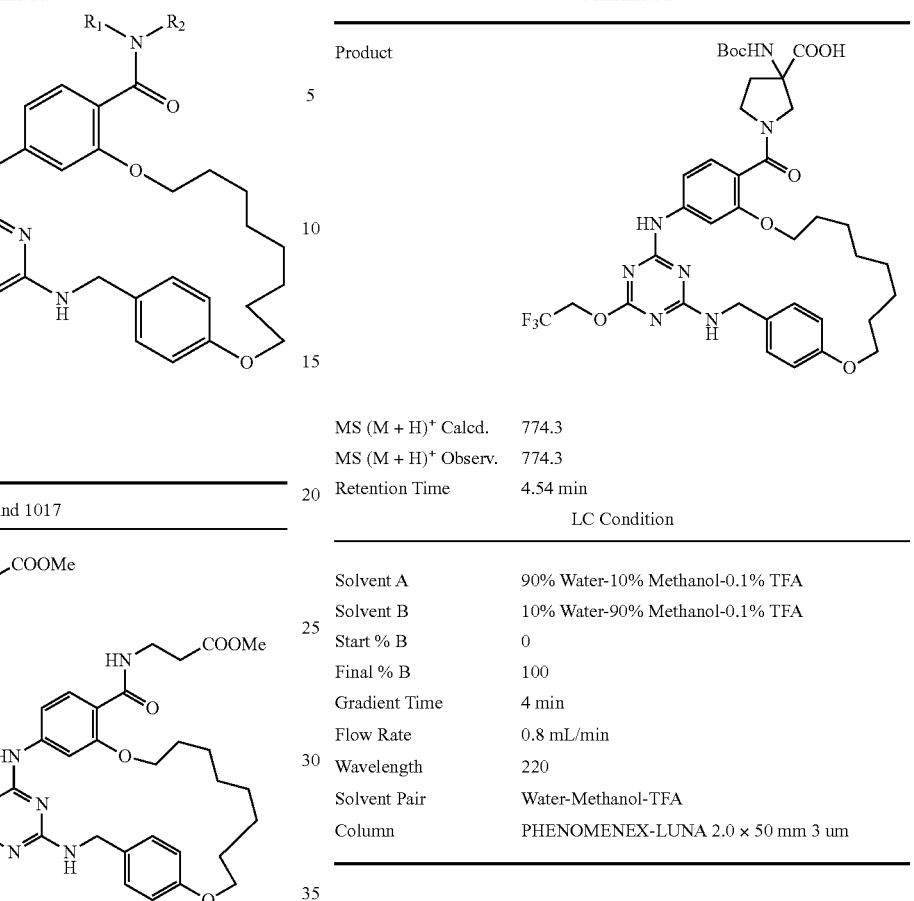

| | |
|---|---|
| MS (M + H)+ Calcd. | 774.3 |
| MS (M + H)+ Observ. | 774.3 |
| Retention Time | 4.54 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Preparation of Compound 1019, 1020, 1021 and 1022

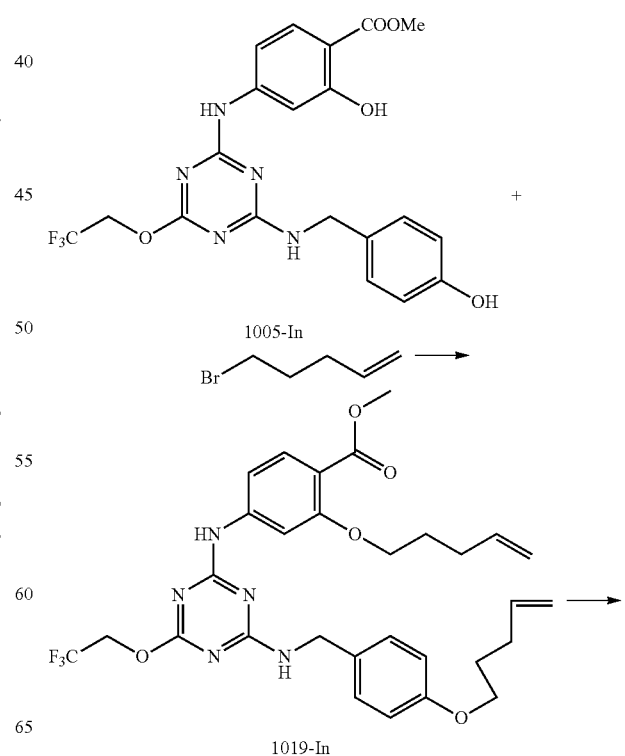

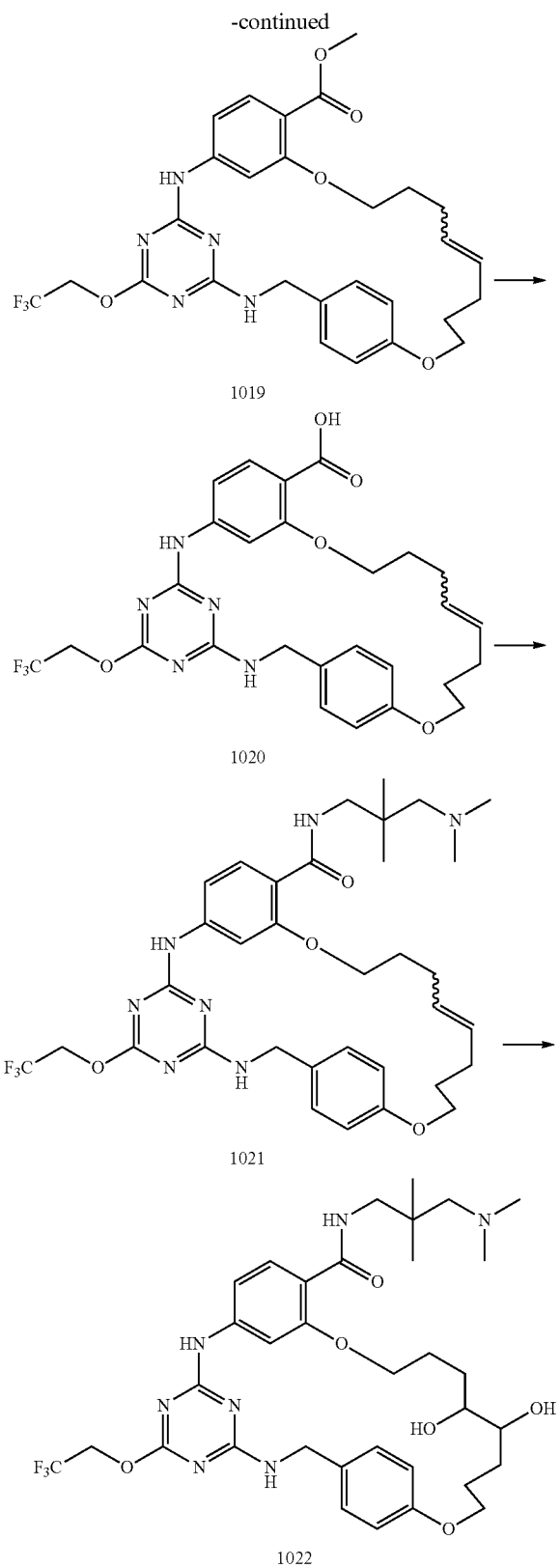

give a residue which was purified by silica gel chromatography to afford 1.0 g of Compound 1019-In.

| Compound 1019-In | |
|---|---|
| MS (M + H)⁺ Calcd. | 602.3 |
| MS (M + H)⁺ Observ. | 602.1 |
| Retention Time | 4.88 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Step 2: To a solution of Compound 1019-In (0.15 g) in DCE (20 mL) in a sealed tube, was added Grubbs Catalyst 2nd Generation (0.02 g, 0.024) under notrogen. The sealed tube was heated at 85° C. for 16 hours, before 50 mL of EtOAc was added. The solution was washed with water (2×20 mL), brine (10 mL), and dried over MgSO₄. Concentration under vacuum provided a residue which was purified by preparative HPLC to give Compound 1019 (30 mg).

| Compound 1019 | |
|---|---|
| MS (M + H)⁺ Calcd. | 574.2 |
| MS (M + H)⁺ Observ. | 574.1 |
| Retention Time | 4.73 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Step 3: LiOH (3.8 mg) was added into the solution of Compound 1019 (30 mg) in water and THF (2 mL, v/v=1/1). The reaction was heated to 115° C. for 16 hours. Then 1N HCl was added dropwise to adjust acidity to pH2. Aqueous phase was extracted with EtOAc (2×20 mL). The combined organic layer was dried over MgSO₄ and concentrated to give a residue which was purified by preparative HPLC to afford Compound 1020 (20 mg).

| Compound 1020 | |
|---|---|
| MS (M + H)⁺ Calcd. | 560.2 |
| MS (M + H)⁺ Observ. | 560.1 |
| Retention Time | 4.71 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |

Step 1: Cs₂CO₃ (4.20 g) and 5-bromopent-1-ene (1.28 g) were added into a solution of Compound 1005-In (2.0 g) in DMF (100 mL). The reaction was stirred at room temperature for 3 days. Then, solvents were removed under vacuum to

45
-continued

Compound 1020

| | |
|---|---|
| Solvent Pair | Water-Methanol-TFA |
| Column | PHENOMENEX-LUNA 2.0 × 50 mm 3 um |

Step 4: iPr$_2$NEt (14 mg) was added into a solution of 1020 (20 mg), N1,N1,2,2-tetramethylpropane-1,3-diamine (5.59 mg) and TBTU (15 mg) in DMF (1 mL) at room temperature. The reaction was stirred for 16 hours at room temperature. Compound 1021 (3 mg) was isolated by preparative HPLC.

Compound 1021

| | |
|---|---|
| MS (M + H)$^+$ Calcd. | 672.3 |
| MS (M + H)$^+$ Observ. | 672.2 |
| Retention Time | 4.29 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Step 5: Osmium Tetraoxide (catalytic amount) was added into a solution of Compound 1021 (3 mg) in dichloromethane (1 mL). The reaction was stirred at room temperature for 16 hours, before being quenched by saturated solution of Na2SO3 (10 mL). The aqueous layer was extracted with EtOAc (3×10 mL). The combined organic phase was dried over MgSO$_4$ and concentrated under vacuum to give the crude product which was purified by preparative HPLC to afford Compound 1022 (2.5 mg).

Compound 1022

| | |
|---|---|
| MS (M + H)$^+$ Calcd. | 706.3 |
| MS (M + H)$^+$ Observ. | 706.5 |
| Retention Time | 2.75 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3u |

46

The following general procedure was applied to synthesize compounds of Formula 1:

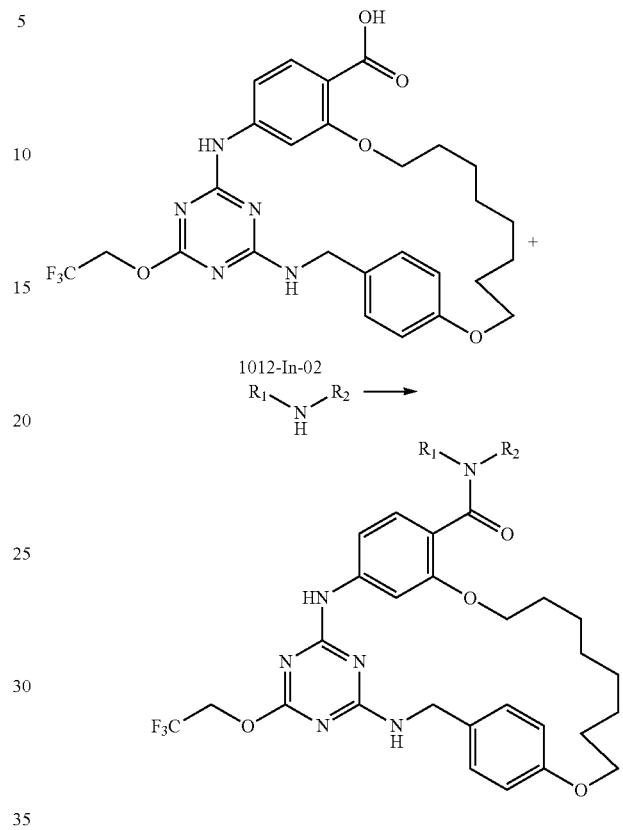

iPr$_2$NEt or Et$_3$N (1-20 eq.) was added into a solution of 1012-In-2 (1 eq.), amine (1-1.5 eq.) and TBTU (1-2 eq.) in DMF or THF at room temperature. The reaction was stirred for 16-72 hours at room temperature or increased temperature from 40° C. to 115° C., before quenched with sodium bicarbonate. The aqueous layer was extracted with EtOAc. The combined organic phase was dried over Mg$_2$SO$_4$ and concentrated under vacuum to give a crude product, which was purified by preparative HPLC.

Compound 1101

| | |
|---|---|
| Amine Used | H$_2$N~~~O~~~O~~~ |
| Product | (structure) |

47

-continued

| | |
|---|---|
| MS (M + H)+ Calcd. | 661.3 |
| MS (M + H)+ Observ. | 661.2 |
| Retention Time | 4.78 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Compound 1102

Amine Used

Product

| | |
|---|---|
| MS (M + H)+ Calcd. | 698.4 |
| MS (M + H)+ Observ. | 698.3 |
| Retention Time | 4.23 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Compound 1103

Amine Used

48

-continued

Product

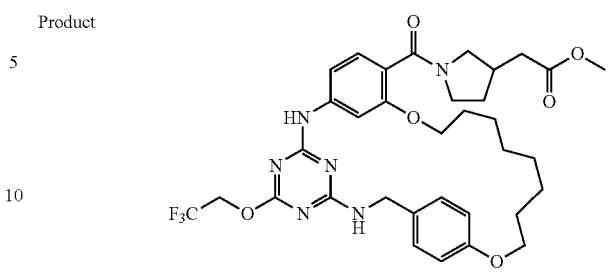

| | |
|---|---|
| MS (M + H)+ Calcd. | 687.3 |
| MS (M + H)+ Observ. | 687.2 |
| Retention Time | 4.65 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Compound 1104

Amine Used

Product

| | |
|---|---|
| MS (M + H)+ Calcd. | 633.3 |
| MS (M + H)+ Observ. | 633.2 |
| Retention Time | 4.87 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

| Compound 1105 | |
|---|---|
| Amine Used | 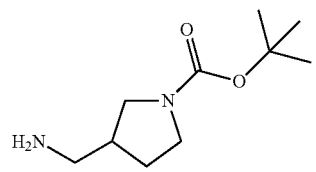 |
| Product | 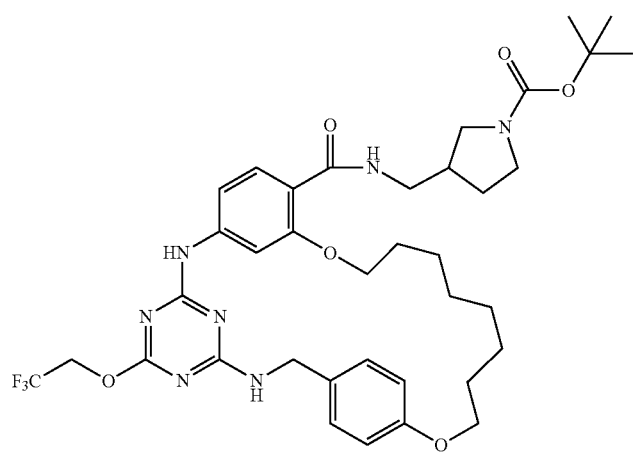 [SMILES: CC(C)(C)OC(=O)N1CCC(CNC(=O)c2ccc3cc2OCCCCCCCCOc2ccc(cc2)CNc2nc(nc(OCC(F)(F)F)n2)N3)C1] |
| MS (M + H)+ Calcd. | 744.4 |
| MS (M + H)+ Observ. | 744.5 |
| Retention Time | 4.96 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |
| Compound 1106 | |
|---|---|
| Amine Used | 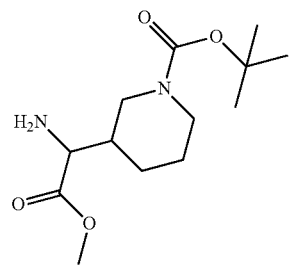 [SMILES: COC(=O)C(N)C1CCCN(C(=O)OC(C)(C)C)C1] |

-continued

Product

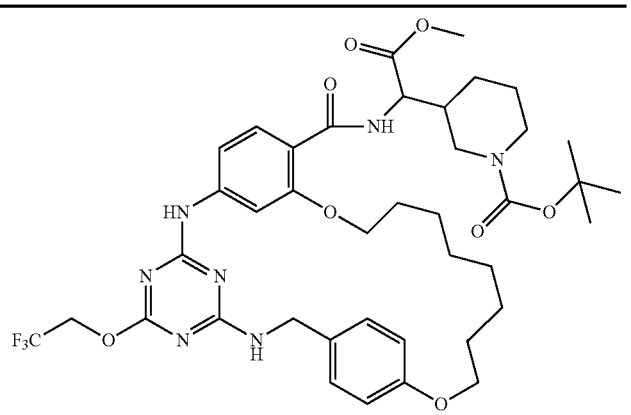

| | |
|---|---|
| MS (M + H)+ Calcd. | 816.4 |
| MS (M + H)+ Observ. | 816.3 |
| Retention Time | 4.93 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Compound 1107

Amine Used

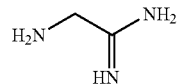

Product

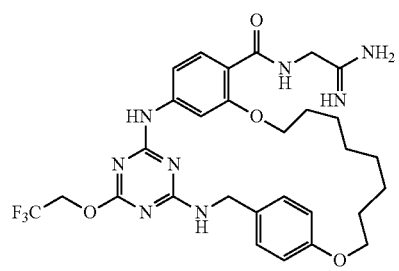 [SMILES: N=C(N)CNC(=O)c1ccc2cc1OCCCCCCCCOc1ccc(cc1)CNc1nc(nc(OCC(F)(F)F)n1)N2]

| | |
|---|---|
| MS (M + H)+ Calcd. | 617.3 |
| MS (M + H)+ Observ. | 617.1 |
| Retention Time | 4.28 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Compound 1109

Amine Used

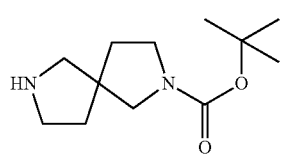 [SMILES: CC(C)(C)OC(=O)N1CCC2(CCNC2)C1]

-continued

Product

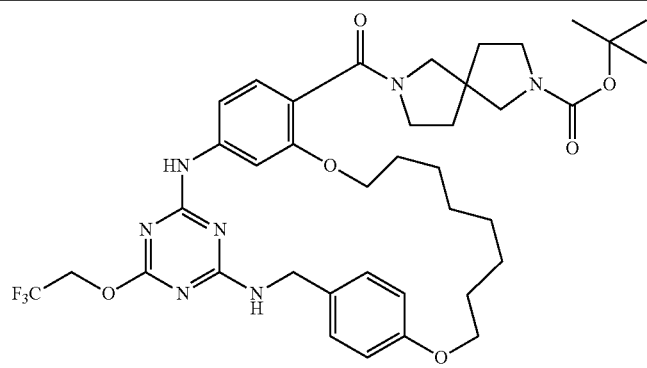

| | |
|---|---|
| MS (M + H)+ Calcd. | 770.4 |
| MS (M + H)+ Observ. | 770.3 |
| Retention Time | 4.88 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

General Procedure of Hydrolysis of Ester: LiOH, NaOH, KOH, $Li_2CO_3$, $Na_2CO_3$ or $K_2CO_3$ was added into the solution of the starting material in water and THF or acetone or methanol (v/v=1/1). The reaction was carried out at room temperature to 115° C. for 5 minutes to 16 hours. Then 1N HCl was added dropwise to adjust acidity to pH2. Aqueous phase was extracted with EtOAc. The combined organic layer was dried over $MgSO_4$ and concentrated to give a residue which was purified by preparative HPLC to provide the desired product. A specific example is the synthesis of Compound 1131.

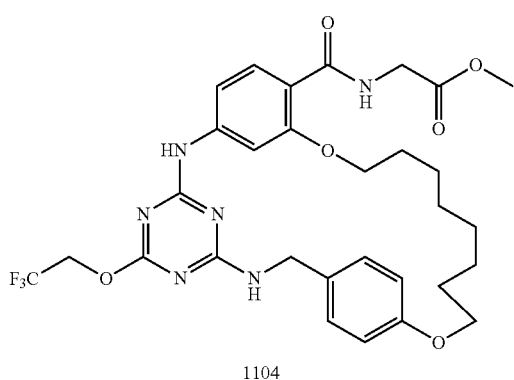

1104

-continued

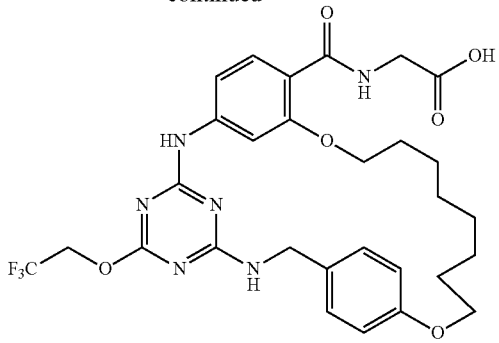

1131

LiOH (2.3 mg) was added into the solution of Compound 1104 (20 mg) in water and THF (2 mL, v/v=1/1). The reaction was heated to 115° C. for 5 minutes to 16 hours. Then 1N HCl was added dropwise to adjust acidity to pH2. Aqueous phase was extracted with EtOAc (2×20 mL). The combined organic layer was dried over $MgSO_4$ and concentrated to give a residue which was purified by preparative HPLC to provide Compound 1131.

| Compound 1131 | |
|---|---|
| MS (M + H)+ Calcd. | 619.2 |
| MS (M + H)+ Observ. | 619.1 |
| Retention Time | 4.65 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |

| Compound 1131 | |
|---|---|
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1132

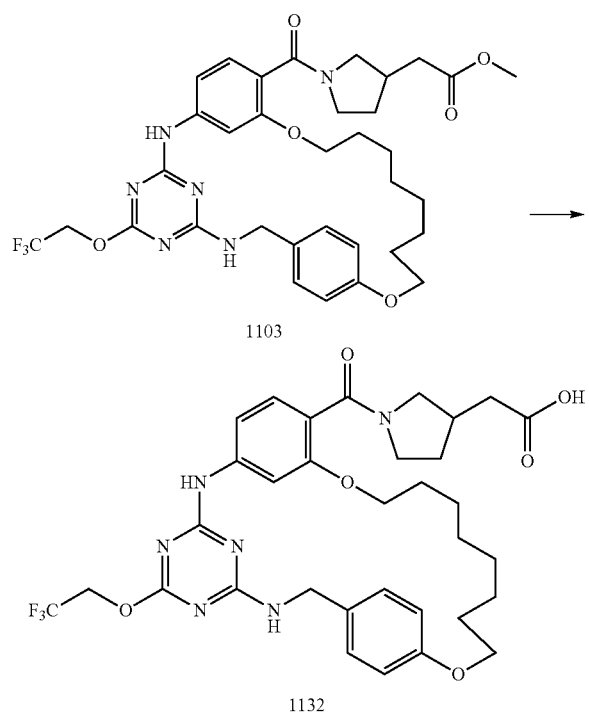

By following the general procedure of hydrolysis of ester exemplified by the preparation of Compound 1131, using Compound 1103 as the starting material, it led to the formation of Compound 1132.

| Compound 1132 | |
|---|---|
| MS (M + H)+ Calcd. | 673.3 |
| MS (M + H)+ Observ. | 673.1 |
| Retention Time | 4.59 min |
| | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1133

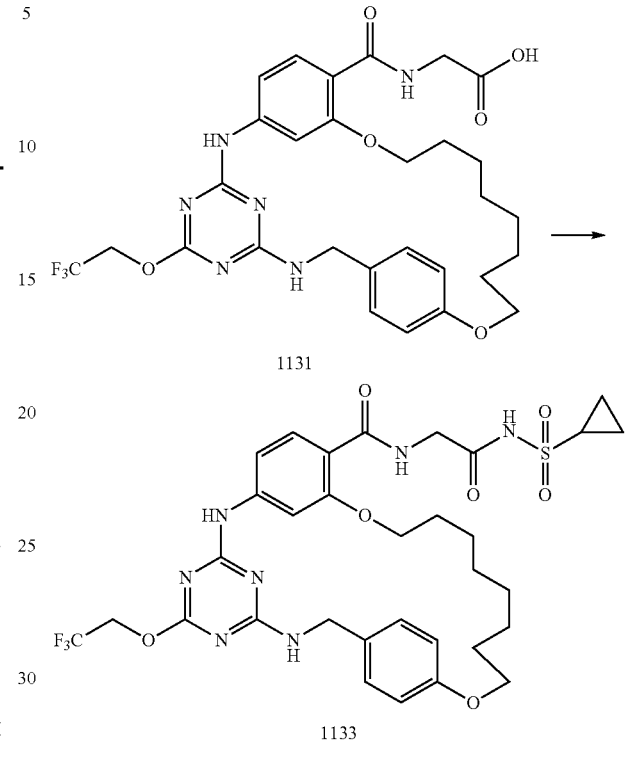

iPr$_2$NEt (8.8 mg) was added into a solution of Compound 1131 (14 mg), cyclopropanesulfonamide (3.6 mg) and TBTU (8.7 mg) in DMF (1 mL) at room temperature. The reaction was stirred at room temperature for 16 hours. Removal of solvents under vacuum gave a residue which was purified by preparative HPLC to provide Compound 1133 (2 mg).

| Compound 1133 | |
|---|---|
| MS (M + H)+ Calcd. | 722.3 |
| MS (M + H)+ Observ. | 722.1 |
| Retention Time | 4.72 min |
| | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

General Procedure of Removal Boc Protecting Group: TFA was mixed with the starting material or added into a solution of the starting material in dichloromethane at room temperature. The reaction was stirred at room temperature for 5 minutes to 16 hours. Removal of solvents under vacuum gave a residue which was purified by preparative HPLC to provide the desired Product. A specific example is the synthesis of Compound 1151.

Synthesis of Compound 1152

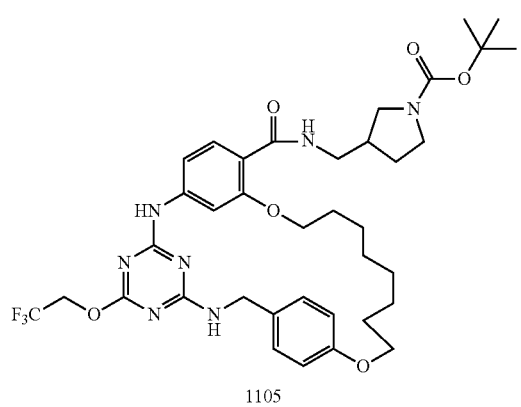

1105

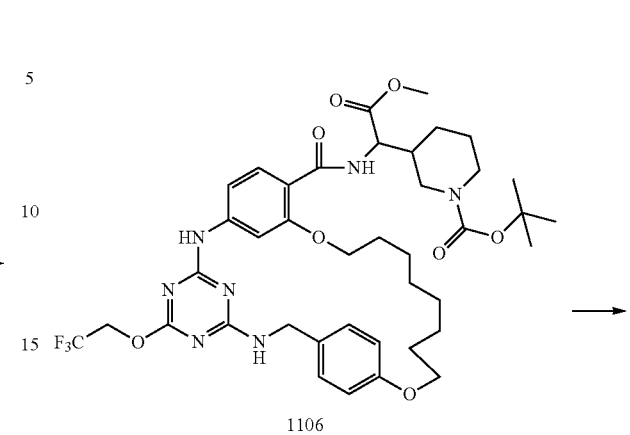

1106

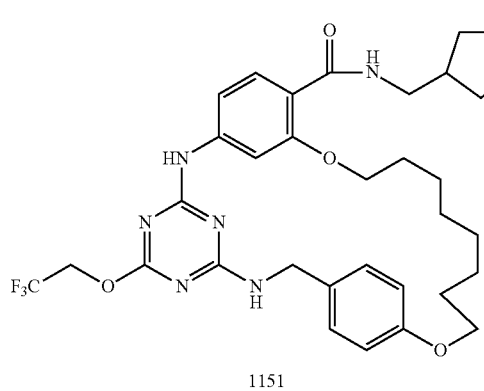

1151

1152

TFA (0.021 mL) was added into a solution of Compound 1105 (20 mg) in dichloromethane (2 mL) at room temperature. The reaction was stirred at room temperature for 16 hours. Removal of solvents under vacuum gave a residue which was purified by preparative HPLC to provide Compound 1151.

By following the general procedure examplified by the preparation of Compound 1151, using Compound 1106 as the starting material, it led to the formation of Compound 1152.

| Compound 1151 | |
|---|---|
| MS (M + H)+ Calcd. | 644.3 |
| MS (M + H)+ Observ. | 644.2 |
| Retention Time | 4.21 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

| Compound 1152 | |
|---|---|
| MS (M + H)+ Calcd. | 716.3 |
| MS (M + H)+ Observ. | 716.2 |
| Retention Time | 4.50 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1153

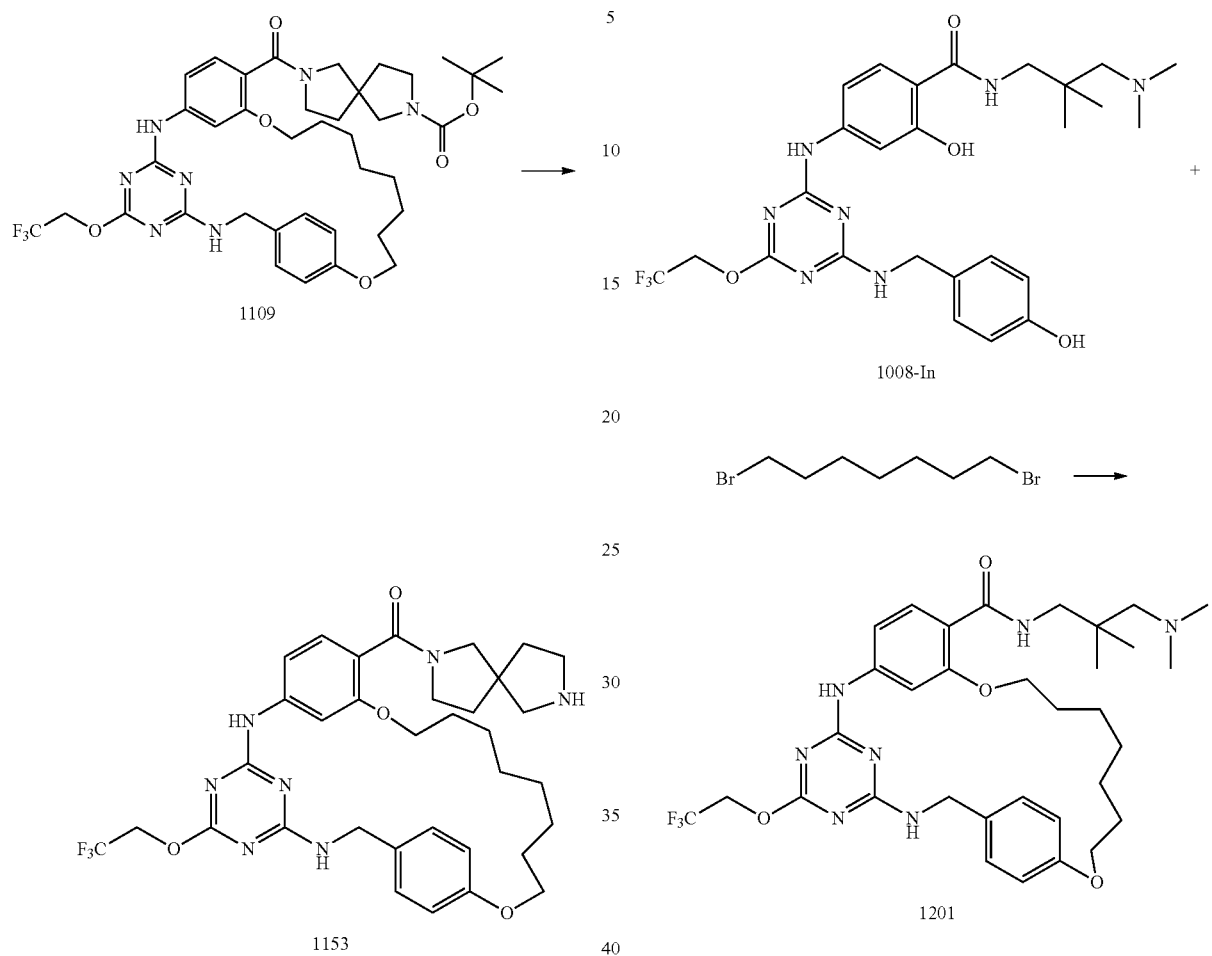

1109

1153

By following the general procedure examplified by the preparation of Compound 1151, using Compound 1109 as the starting material, it led to the formation of Compound 1153.

|  | Compound 1153 |
| --- | --- |
| MS (M + H)+ Calcd. | 670.3 |
| MS (M + H)+ Observ. | 670.2 |
| Retention Time | 4.24 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1201

1008-In

1201

By following the same procedure for the preparation of Compound 1009, using 1,7-dibromoheptane as alkylating agent, it led to the formation of Compound 1201.

|  | Compound 1201 |
| --- | --- |
| MS (M + H)+ Calcd. | 660.3 |
| MS (M + H)+ Observ. | 660.2 |
| Retention Time | 4.00 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

61
Synthesis of Compound 1202

62
Synthesis of Compound 1301

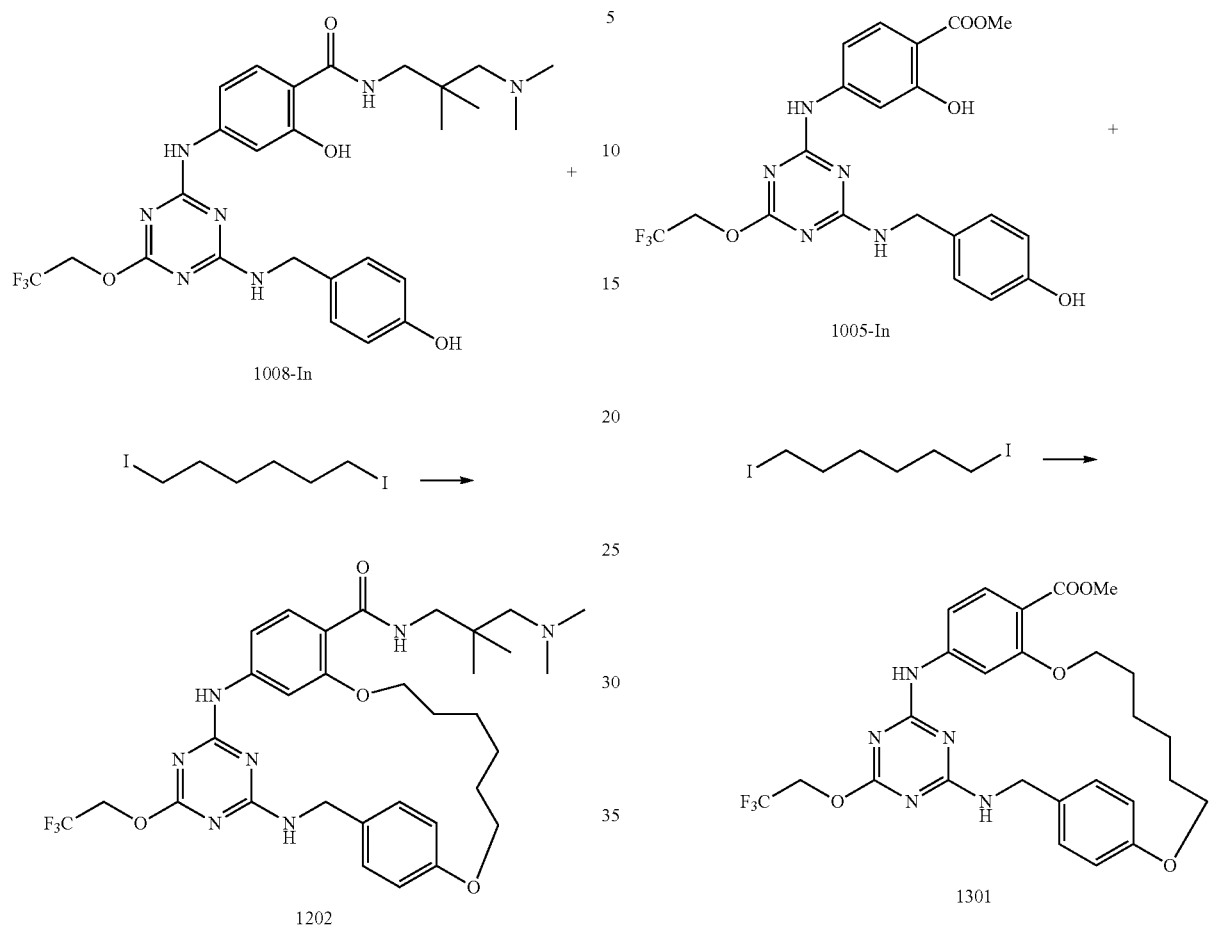

By following the same procedure for the preparation of Compound 1009, using 1,6-diiodohexane as alkylating agent, it led to the formation of Compound 1202.

By following the same procedure for the preparation of Compound 1007, using 1,6-diiodohexane as alkylating agent, it led to the formation of Compound 1301.

| | Compound 1202 |
|---|---|
| MS (M + H)+ Calcd. | 646.3 |
| MS (M + H)+ Observ. | 646.2 |
| Retention Time | 3.79 min |
| | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

| | Compound 1301 |
|---|---|
| MS (M + H)+ Calcd. | 548.2 |
| MS (M + H)+ Observ. | 548.0 |
| Retention Time | 4.60 min |
| | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1302

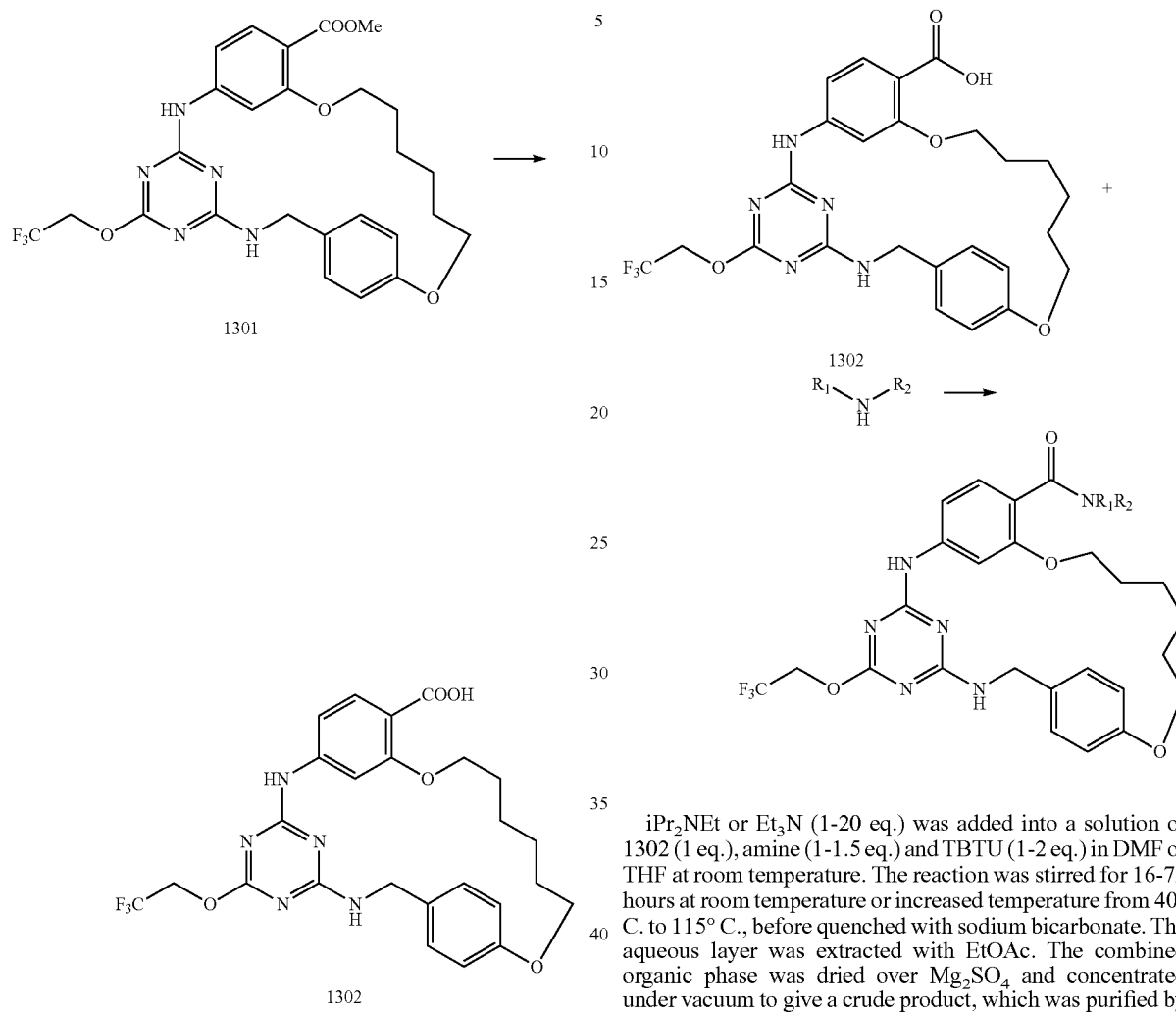

By following the same procedure for the preparation of Compound 1012-In-02, using Compound 1301 as the starting material, it led to the formation of Compound 1302.

| Compound 1302 | |
|---|---|
| MS (M + H)$^+$ Calcd. | 534.2 |
| MS (M + H)$^+$ Observ. | 534.0 |
| Retention Time | 4.50 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

The following general procedure was applied to synthesize compounds of Formula 1:

iPr$_2$NEt or Et$_3$N (1-20 eq.) was added into a solution of 1302 (1 eq.), amine (1-1.5 eq.) and TBTU (1-2 eq.) in DMF or THF at room temperature. The reaction was stirred for 16-72 hours at room temperature or increased temperature from 40° C. to 115° C., before quenched with sodium bicarbonate. The aqueous layer was extracted with EtOAc. The combined organic phase was dried over Mg$_2$SO$_4$ and concentrated under vacuum to give a crude product, which was purified by preparative HPLC.

| Compound 1303 | |
|---|---|
| Amine Used | |
| Product | |
| MS (M + H)$^+$ Calcd. | 619.2 |
| MS (M + H)$^+$ Observ. | 619.2 |
| Retention Time | 4.60 min |

-continued

| LC Condition | |
|---|---|
| Solvent A | 90% Water-10% Methanol-0.1% TFA |
| Solvent B | 10% Water-90% Methanol-0.1% TFA |
| Start % B | 0 |
| Final % B | 100 |

| | |
|---|---|
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Compound 1304

Amine Used

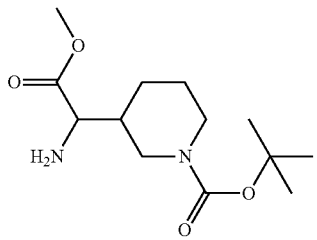 [SMILES: COC(=O)C(N)C1CCCN(C(=O)OC(C)(C)C)C1]

Product

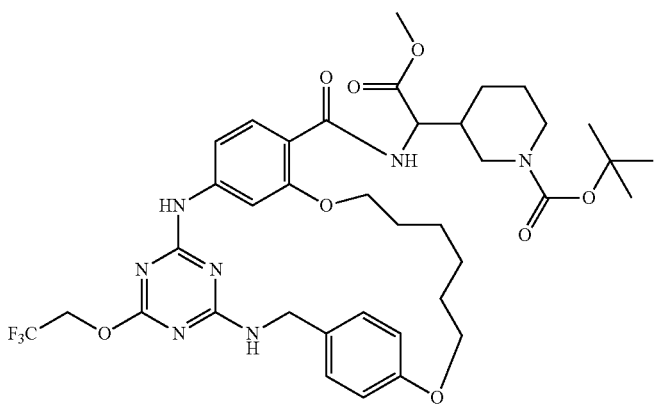 [SMILES: COC(=O)C(NC(=O)c1ccc2cc1OCCCCCCOc1ccc(cc1)CNc1nc(nc(OCC(F)(F)F)n1)N2)C1CCCN(C(=O)OC(C)(C)C)C1]

| | |
|---|---|
| MS (M + H)+ Calcd. | 788.4 |
| MS (M + H)+ Observ. | 788.2 |
| Retention Time | 4.87 min |

| LC Condition | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Compound 1305

Amine Used

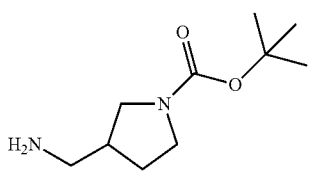

-continued

Product

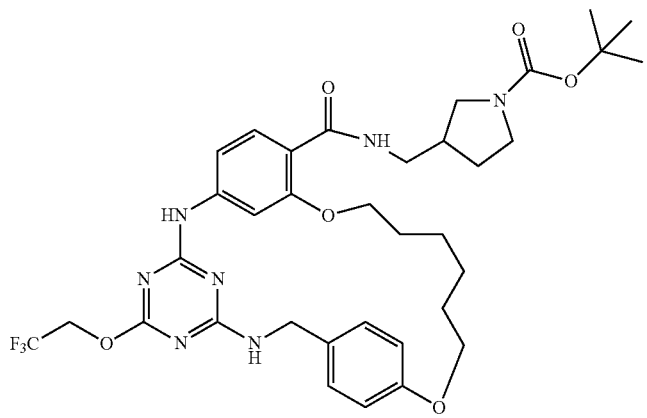 [SMILES: CC(C)(C)OC(=O)N1CCC(CNC(=O)c2ccc3cc2OCCCCCCOc2ccc(cc2)CNc2nc(nc(OCC(F)(F)F)n2)N3)C1]

| | |
|---|---|
| MS (M + H)+ Calcd. | 716.3 |
| MS (M + H)+ Observ. | 716.1 |
| Retention Time | 4.83 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Compound 1306

Amine Used

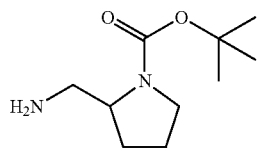

Product

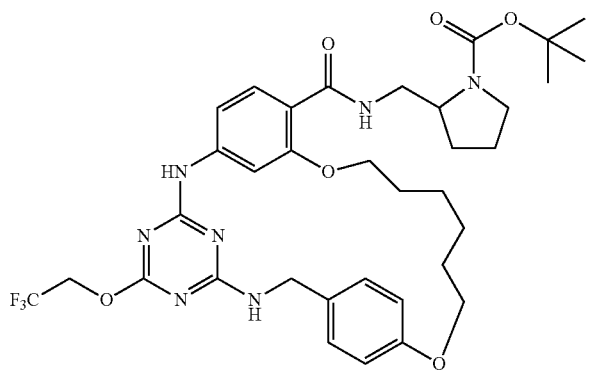 [SMILES: CC(C)(C)OC(=O)N1CCCC1CNC(=O)c1ccc2cc1OCCCCCCOc1ccc(cc1)CNc1nc(nc(OCC(F)(F)F)n1)N2]

| | |
|---|---|
| MS (M + H)+ Calcd. | 716.3 |
| MS (M + H)+ Observ. | 716.2 |
| Retention Time | 4.97 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |

| | -continued |
|---|---|
| Flow Rate | 0.8 mL/min |
| Wavelength | 220 |
| Solvent Pair | Water-Methanol-TFA |
| Column | PHENOMENEX-LUNA 2.0 × 50 mm 3 um |

Compound 1307

| | |
|---|---|
| Amine Used | 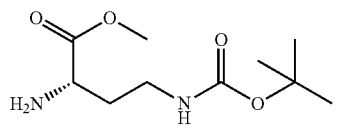 [SMILES: COC(=O)[C@@H](N)CCNC(=O)OC(C)(C)C] |
| Product | 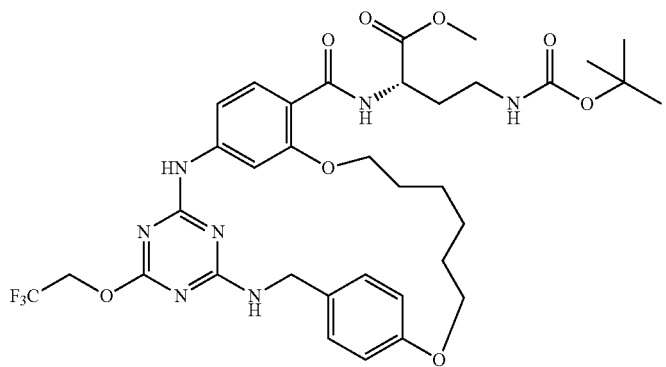 [SMILES: COC(=O)[C@H](CCNC(=O)OC(C)(C)C)NC(=O)c1ccc2cc1OCCCCCCOc1ccc(cc1)CNc1nc(nc(OCC(F)(F)F)n1)N2] |
| MS (M + H)+ Calcd. | 748.3 |
| MS (M + H)+ Observ. | 748.2 |
| Retention Time | 4.87 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Compound 1308

Amine Used

Product

| | | |
|---|---|---|
| MS (M + H)+ Calcd. | 774.3 | |
| MS (M + H)+ Observ. | 774.3 | |
| Retention Time | 4.85 min | |
| LC Condition | | |
| Solvent A | 90% Water-10% Methanol-0.1% TFA | |
| Solvent B | 10% Water-90% Methanol-0.1% TFA | |
| Start % B | 0 | |
| Final % B | 100 | |
| Gradient Time | 4 min | |
| Flow Rate | 0.8 mL/min | |
| Wavelength | 220 | |
| Solvent Pair | Water-Methanol-TFA | |
| Column | PHENOMENEX-LUNA 2.0 × 50 mm 3 um | |

Compound 1309

Amine Used

Product

| | |
|---|---|
| MS (M + H)+ Calcd. | 734.3 |
| MS (M + H)+ Observ. | 734.2 |
| Retention Time | 4.91 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

| Compound 1310 | |
|---|---|
| Amine Used | 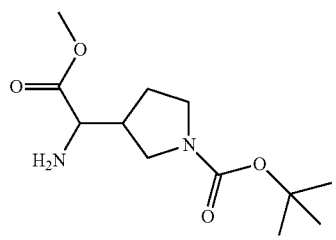 [SMILES: COC(=O)C(N)C1CCN(C(=O)OC(C)(C)C)C1] |
| Product | 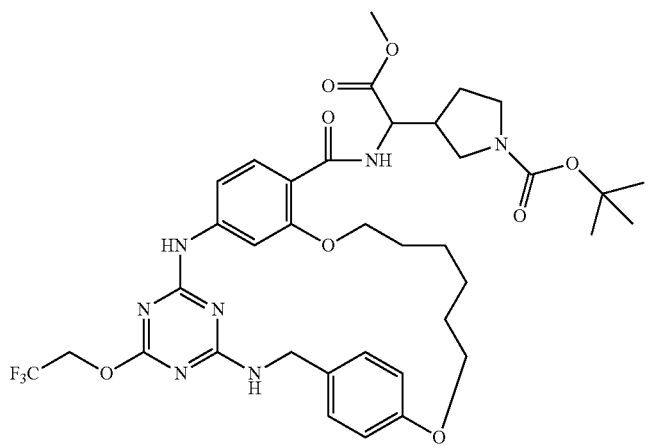 [SMILES: COC(=O)C(NC(=O)c1ccc2cc1OCCCCCCOc1ccc(cc1)CNc1nc(nc(OCC(F)(F)F)n1)N2)C1CCN(C(=O)OC(C)(C)C)C1] |
| MS (M + H)⁺ Calcd. | 774.3 |
| MS (M + H)⁺ Observ. | 774.5 |
| Retention Time | 3.68 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3u |
| Compound 1313 | |
|---|---|
| Amine Used | 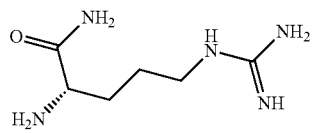 [SMILES: N=C(N)NCCC[C@H](N)C(N)=O] |

-continued

| Product | 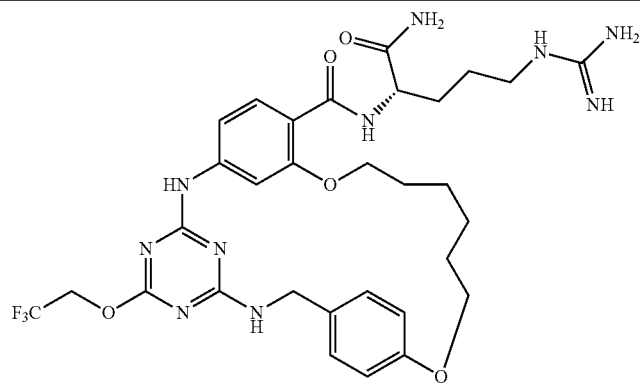 |
|---|---|

MS (M + H)+ Calcd.   689.3
MS (M + H)+ Observ.  689.2
Retention Time       3.67 min LC Condition Solvent A        90% Water-10% Methanol-0.1% TFA
Solvent B        10% Water-90% Methanol-0.1% TFA
Start % B        0
Final % B        100
Gradient Time    4 min
Flow Rate        0.8 mL/min
Wavelength       220
Solvent Pair     Water-Methanol-TFA
Column           PHENOMENEX-LUNA 2.0 × 50 mm 3 um

30

Compound 1314

| Amine Used | 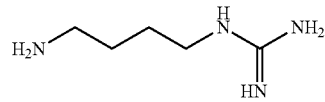 |
|---|---|
| Product | 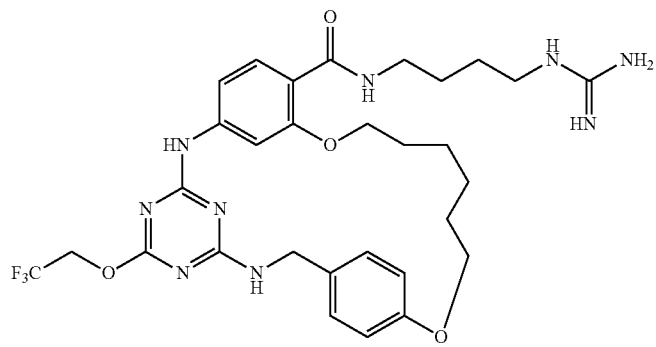 [SMILES: N=C(N)NCCCCNC(=O)c1ccc2cc1OCCCCCCOc1ccc(cc1)CNc1nc(nc(OCC(F)(F)F)n1)N2] |

MS (M + H)+ Calcd.   646.3
MS (M + H)+ Observ.  646.2
Retention Time       3.83 min LC Condition Solvent A        90% Water-10% Methanol-0.1% TFA
Solvent B        10% Water-90% Methanol-0.1% TFA
Start % B        0
Final % B        100
Gradient Time    4 min
Flow Rate        0.8 mL/min
Wavelength       220
Solvent Pair     Water-Methanol-TFA
Column           PHENOMENEX-LUNA 2.0 × 50 mm 3 um

| Compound 1317 | |
|---|---|
| Amine Used | 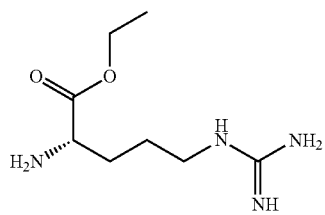 |
| Product | 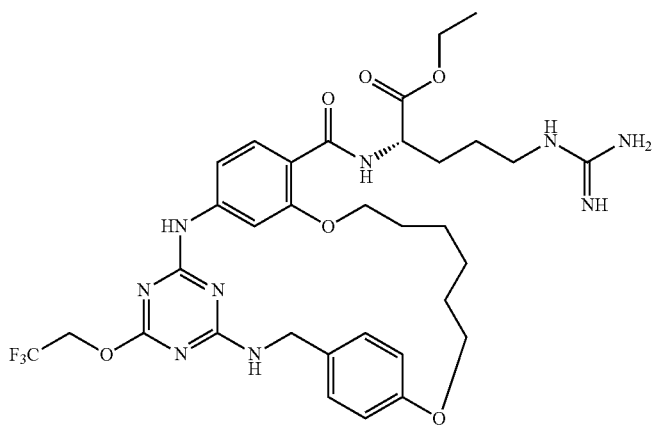 [SMILES: CCOC(=O)[C@H](CCCNC(=N)N)NC(=O)c1ccc2cc1OCCCCCCOc1ccc(cc1)CNc1nc(nc(OCC(F)(F)F)n1)N2] |
| MS (M + H)+ Calcd. | 718.3 |
| MS (M + H)+ Observ. | 718.3 |
| Retention Time | 4.00 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |
| Compound 1319 | |
|---|---|
| Amine Used | 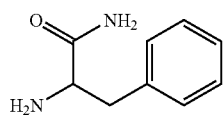 |
| Product | 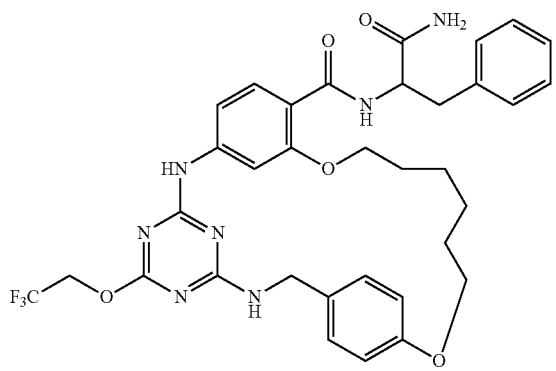 [SMILES: NC(=O)C(Cc1ccccc1)NC(=O)c1ccc2cc1OCCCCCCOc1ccc(cc1)CNc1nc(nc(OCC(F)(F)F)n1)N2] |

-continued

| | |
|---|---|
| MS (M + H)+ Calcd. | 680.3 |
| MS (M + H)+ Observ. | 680.2 |
| Retention Time | 4.68 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Compound 1320

Amine Used

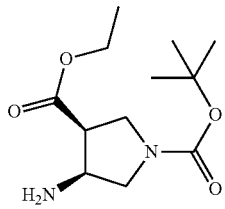 [SMILES: CCOC(=O)[C@H]1CN(C(=O)OC(C)(C)C)C[C@H]1N]

Product

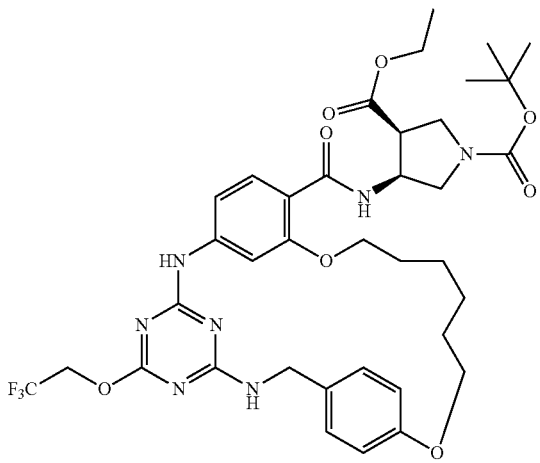 [SMILES: CCOC(=O)[C@H]1CN(C(=O)OC(C)(C)C)C[C@H]1NC(=O)c1ccc2cc1OCCCCCCOc1ccc(cc1)CNc1nc(nc(OCC(F)(F)F)n1)N2]

| | |
|---|---|
| MS (M + H)+ Calcd. | 774.3 |
| MS (M + H)+ Observ. | 774.3 |
| Retention Time | 4.53 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

| Compound 1321 | |
|---|---|
| Amine Used | 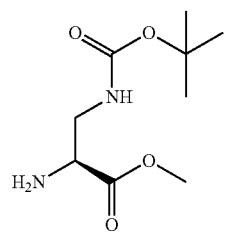 |
| Product | 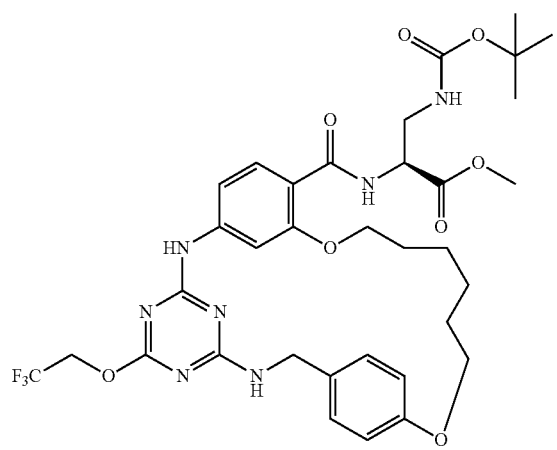 [SMILES: COC(=O)[C@H](CNC(=O)OC(C)(C)C)NC(=O)c1ccc2cc1OCCCCCCOc1ccc(cc1)CNc1nc(nc(OCC(F)(F)F)n1)N2] |
| MS (M + H)+ Calcd. | 734.3 |
| MS (M + H)+ Observ. | 734.2 |
| Retention Time | 4.41 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |
| Compound 1322 | |
|---|---|
| Amine Used | 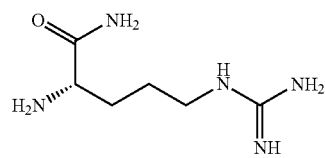 [SMILES: N=C(N)NCCC[C@H](N)C(N)=O] |

| | |
|---|---|
| Product | 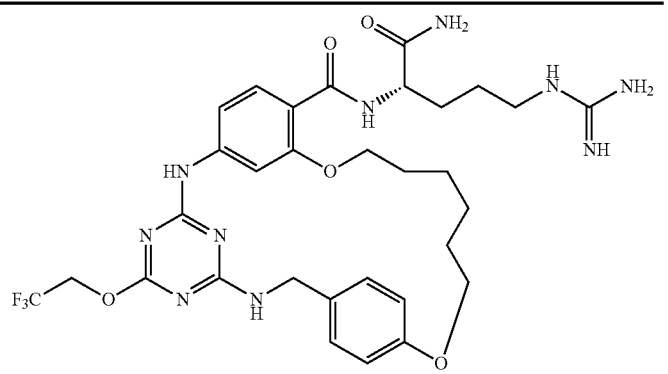 |
| MS (M + H)+ Calcd. | 689.3 |
| MS (M + H)+ Observ. | 689.2 |
| Retention Time | 3.53 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

| Compound 1323 | |
|---|---|
| Amine Used | 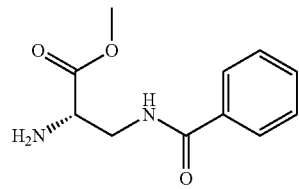 [SMILES: COC(=O)[C@@H](N)CNC(=O)c1ccccc1] |
| Product | 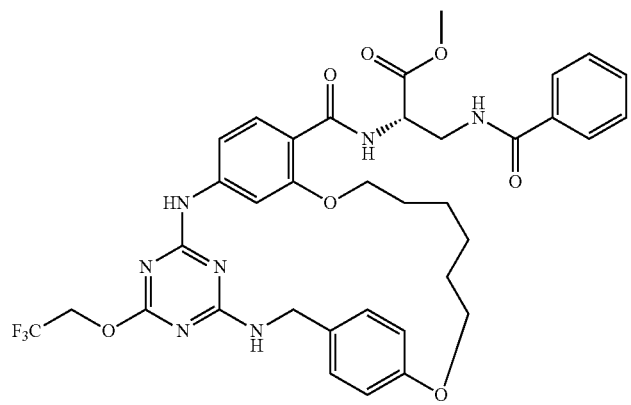 [SMILES: COC(=O)[C@H](CNC(=O)c1ccccc1)NC(=O)c1ccc2cc1OCCCCCCOc1ccc(cc1)CNc1nc(nc(OCC(F)(F)F)n1)N2] |
| MS (M + H)+ Calcd. | 738.3 |
| MS (M + H)+ Observ. | 738.2 |
| Retention Time | 4.39 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |

| | |
|---|---|
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Compound 1324

Amine Used:

[Structure: 3-amino-pyrrolidin-2-one]

Product:

[Structure of Compound 1324]

| | |
|---|---|
| MS (M + H)+ Calcd. | 616.2 |
| MS (M + H)+ Observ. | 616.2 |
| Retention Time | 4.18 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Compound 1325

Amine Used:

[Structure of Boc-protected amino acid tert-butyl ester]

Product:

[Structure of Compound 1325]

| | |
|---|---|
| MS (M + H)+ Calcd. | 790.4 |
| MS (M + H)+ Observ. | 790.4 |
| Retention Time | 4.78 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |

| | |
|---|---|
| Wavelength | 220 |
| Solvent Pair | Water-Methanol-TFA |
| Column | PHENOMENEX-LUNA 2.0 × 50 mm 3 um |

---

| Compound 1326 | |
|---|---|
| Amine Used | 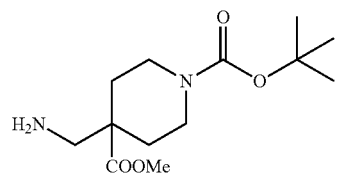 [SMILES: COC(=O)C1(CN)CCN(C(=O)OC(C)(C)C)CC1] |
| Product | 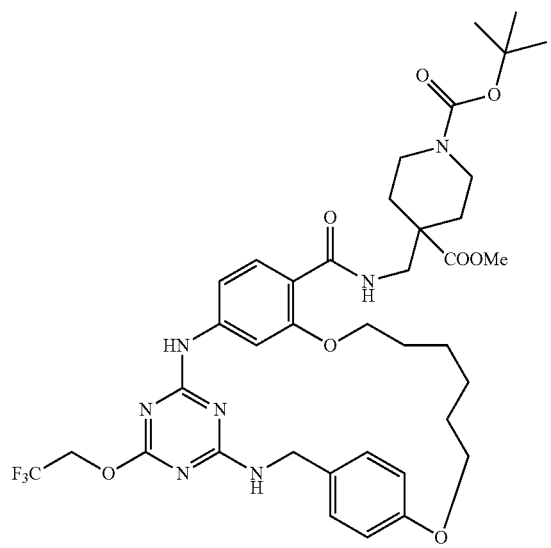 [SMILES: COC(=O)C1(CNC(=O)c2ccc3cc2OCCCCCCOc2ccc(cc2)CNc2nc(nc(OCC(F)(F)F)n2)N3)CCN(C(=O)OC(C)(C)C)CC1] |
| MS (M + H)+ Calcd. | 788.4 |
| MS (M + H)+ Observ. | 788.6 |
| Retention Time | 3.75 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3u |

Preparation of Intermediate 1401

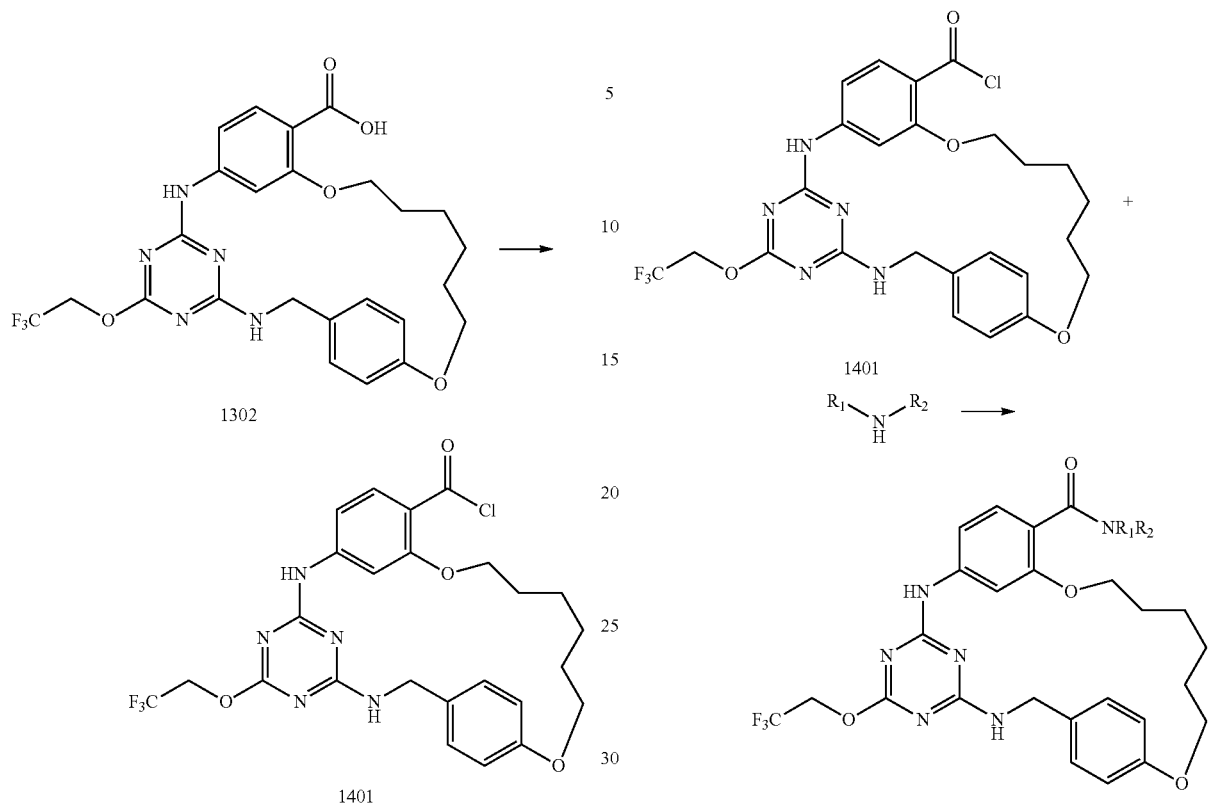

Compound 1302 (30 mg) in and sulfurous dichloride (300 mg) were mixed together. The reaction mixture was heated to 80° C. for 16 hours. Removal of solvents under vacuum provided crude Compound 1401 which was used in the next step without purification.

The following general procedure was applied to synthesize compounds of Formula 1:

iPr$_2$NEt or Et$_3$N (1-20 eq.) was added into a solution of 1401 (1 eq.) and amine (1-1.5 eq.) in DMF or THF at room temperature. The reaction was stirred for 16-72 hours at room temperature or increased temperature from 40° C. to 115° C., before quenched with sodium bicarbonate. The aqueous layer was extracted with EtOAc. The combined organic phase was dried over Mg$_2$SO$_4$ and concentrated under vacuum to give a crude product, which was purified by preparative HPLC.

| Compound 1402 | |
|---|---|
| Amine Used | 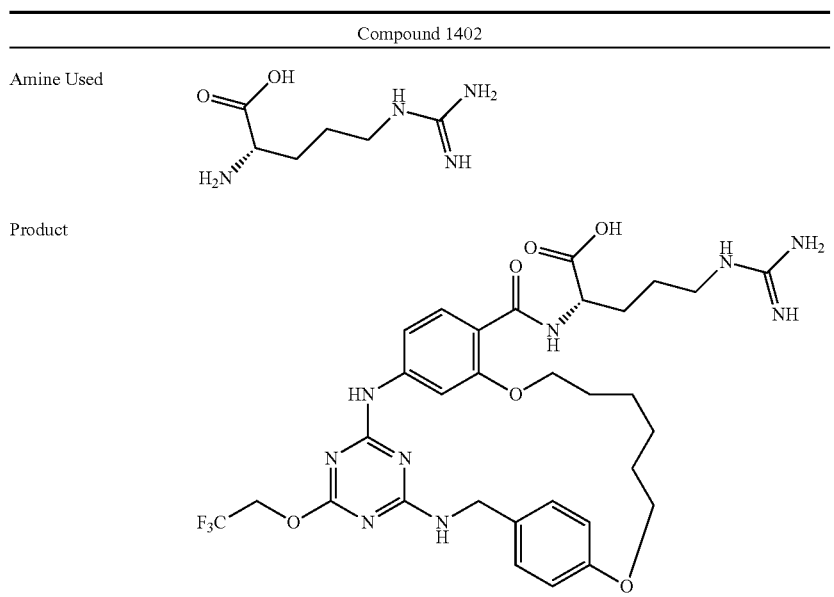 |
| Product | |

| | |
|---|---|
| MS (M + H)+ Calcd. | 690.3 |
| MS (M + H)+ Observ. | 690.3 |
| Retention Time | 3.84 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Compound 1403

| | |
|---|---|
| Amine Used | 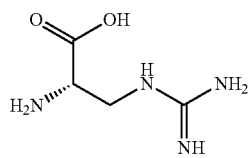 |
| Product | 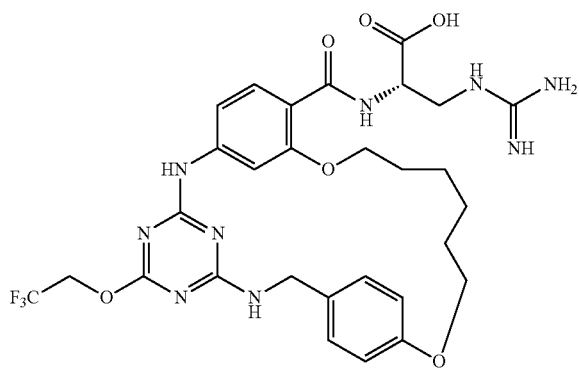 [SMILES: N=C(N)NC[C@H](NC(=O)c1ccc2cc1OCCCCCCOc1ccc(cc1)CNc1nc(nc(OCC(F)(F)F)n1)N2)C(=O)O] |
| MS (M + H)+ Calcd. | 662.3 |
| MS (M + H)+ Observ. | 662.2 |
| Retention Time | 3.87 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

| Compound 1404 | |
|---|---|
| Amine Used | 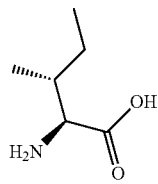 |
| Product | 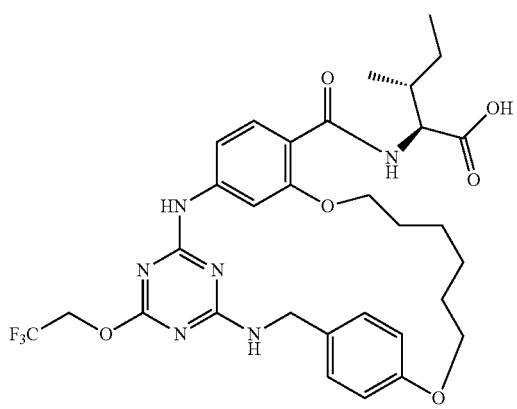 [SMILES: CC[C@@H](C)[C@H](NC(=O)c1ccc2cc1OCCCCCCOc1ccc(cc1)CNc1nc(nc(OCC(F)(F)F)n1)N2)C(=O)O] |
| MS (M + H)⁺ Calcd. | 647.3 |
| MS (M + H)⁺ Observ. | 647.2 |
| Retention Time | 4.75 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |
| Compound 1405 | |
|---|---|
| Amine Used | 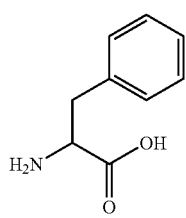 |

-continued

Product

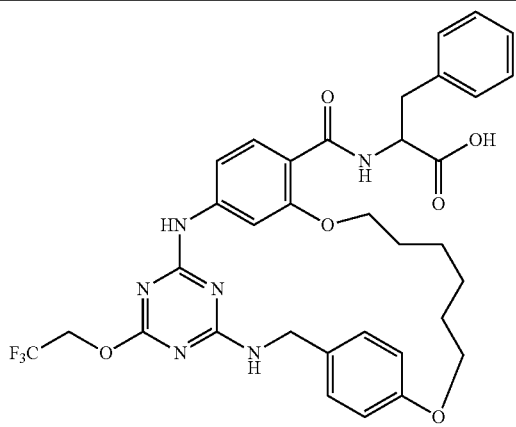

| | |
|---|---|
| MS (M + H)+ Calcd. | 681.3 |
| MS (M + H)+ Observ. | 681.2 |
| Retention Time | 4.69 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Compound 1406

Amine Used

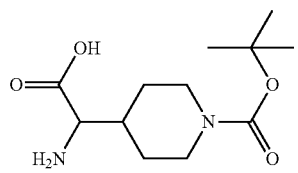

Product

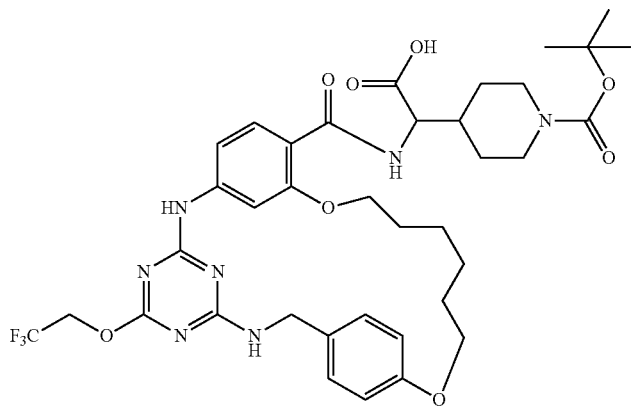 [SMILES: CC(C)(C)OC(=O)N1CCC(C(NC(=O)c2ccc3cc2OCCCCCCOc2ccc(cc2)CNc2nc(nc(OCC(F)(F)F)n2)N3)C(=O)O)CC1]

| | |
|---|---|
| MS (M + H)+ Calcd. | 774.3 |
| MS (M + H)+ Obser v. | 774.6 |
| Retention Time | 2.69 min |

LC Condition

| | |
|---|---|
| Solvent A | 5% ACN:95% Water:10 mM Ammonium Actetate |
| Solvent B | 95% ACN:5% Water:10 mM Ammonium Actetate |

| | |
|---|---|
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3 u |

Compound 1407

Amine Used

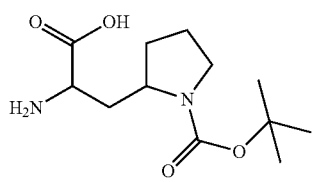 [SMILES: CC(C)(C)OC(=O)N1CCCC1CC(N)C(=O)O]

Product

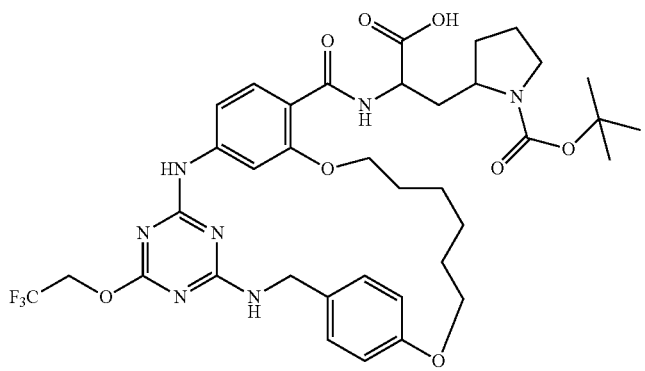 [SMILES: CC(C)(C)OC(=O)N1CCCC1CC(NC(=O)c1ccc2cc1OCCCCCCOc1ccc(cc1)CNc1nc(nc(OCC(F)(F)F)n1)N2)C(=O)O]

MS (M + H)⁺ Calcd. 774.3
MS (M + H)⁺ Observ. 774.6
Retention Time 2.75 min

LC Condition

| | |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3 u |

Compound 1408

Amine Used

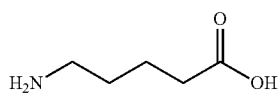

| | |
|---|---|
| Product | 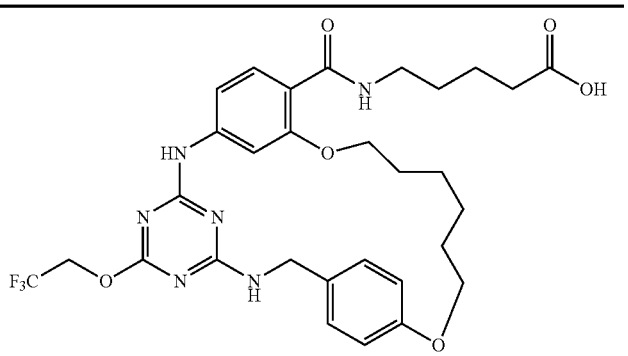 |

| | |
|---|---|
| MS (M + H)+ Calcd. | 633.3 |
| MS (M + H)+ Observ. | 633.1 |
| Retention Time | 4.70 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

| Compound 1409 | |
|---|---|
| Amine Used | 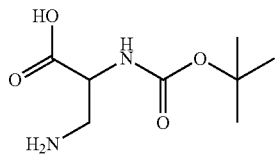 |
| Product | 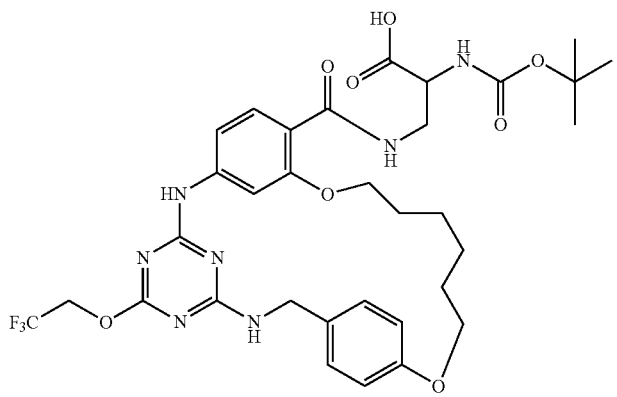 [SMILES: CC(C)(C)OC(=O)NC(CNC(=O)c1ccc2cc1OCCCCCCOc1ccc(cc1)CNc1nc(nc(OCC(F)(F)F)n1)N2)C(=O)O] |

| | |
|---|---|
| MS (M + H)+ Calcd. | 720.3 |
| MS (M + H)+ Observ. | 720.2 |
| Retention Time | 4.77 min |
| LC Condition | |
| Solvent A | 90% Water-10% Methanol-0.1% TFA |
| Solvent B | 10% Water -90% Methanol-0.1% TFA |
| Start % B | 0 |
| Final % B | 100 |
| Gradient Time | 4 min |
| Flow Rate | 0.8 mL/min |
| Wavelength | 220 |

| | |
|---|---|
| Solvent Pair | Water-Methanol-TFA |
| Column | PHENOMENEX-LUNA 2.0 × 50 mm 3 um |

| Compound 1410 | |
|---|---|
| Amine Used | 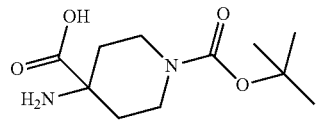 [SMILES: CC(C)(C)OC(=O)N1CCC(N)(C(=O)O)CC1] |
| Product | 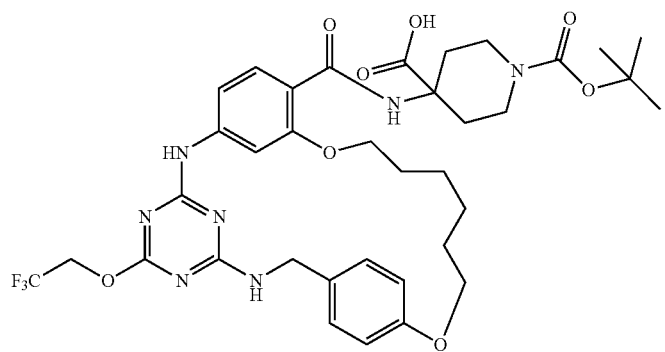 [SMILES: CC(C)(C)OC(=O)N1CCC(NC(=O)c2ccc3cc2OCCCCCCOc2ccc(cc2)CNc2nc(nc(OCC(F)(F)F)n2)N3)(C(=O)O)CC1] |
| MS (M + H)+ Calcd. | 760.3 |
| MS (M + H)+ Observ. | 760.4 |
| Retention Time | 2.77 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3 u |

| Compound 1411 | |
|---|---|
| Amine Used | 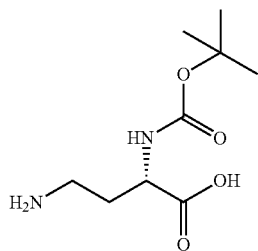 |
| Product | 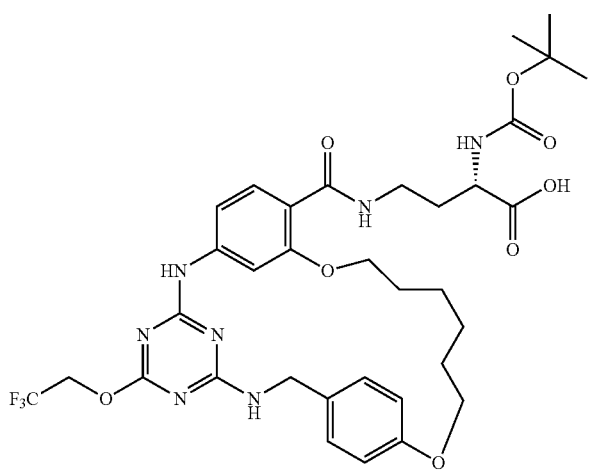 [SMILES: CC(C)(C)OC(=O)N[C@@H](CCNC(=O)c1ccc2cc1OCCCCCCOc1ccc(cc1)CNc1nc(nc(OCC(F)(F)F)n1)N2)C(=O)O] |
| MS (M + H)⁺ Calcd. | 734.3 |
| MS (M + H)⁺ Observ. | 734.2 |
| Retention Time | 4.82 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |
| Compound 1412 | |
|---|---|
| Amine Used | 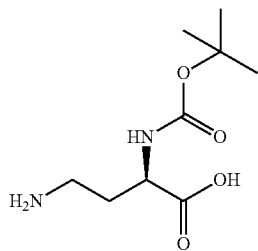 |

Product

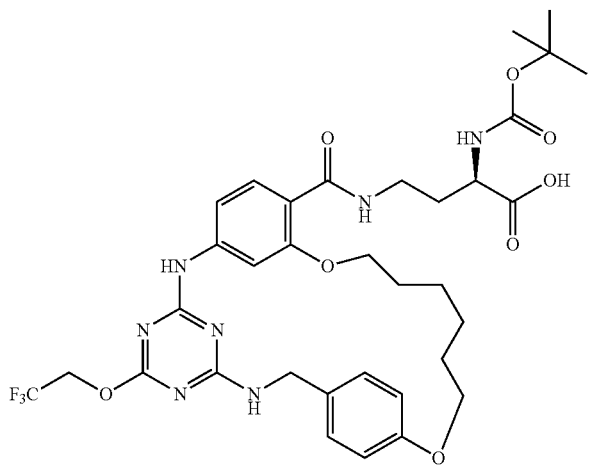 [SMILES: CC(C)(C)OC(=O)N[C@H](CCNC(=O)c1ccc2cc1OCCCCCCOc1ccc(cc1)CNc1nc(nc(OCC(F)(F)F)n1)N2)C(=O)O]

| | |
|---|---|
| MS (M + H)+ Calcd. | 734.3 |
| MS (M + H)+ Observ. | 734.2 |
| Retention Time | 4.82 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Compound 1413

Amine Used

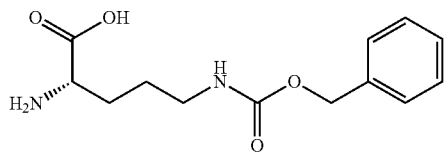 [SMILES: N[C@@H](CCCNC(=O)OCc1ccccc1)C(=O)O]

Product

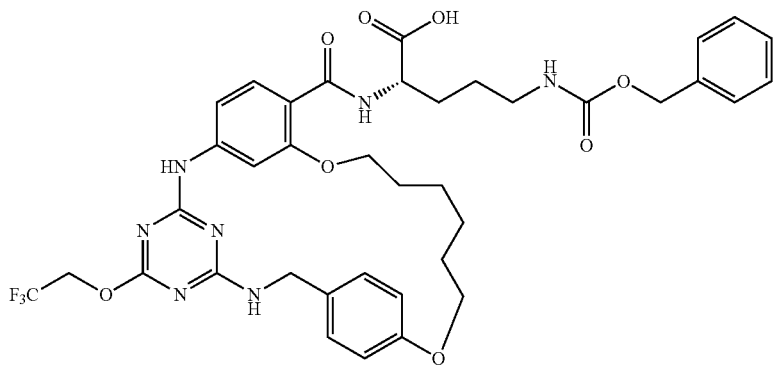 [SMILES: O=C(NCCC[C@H](NC(=O)c1ccc2cc1OCCCCCCOc1ccc(cc1)CNc1nc(nc(OCC(F)(F)F)n1)N2)C(=O)O)OCc1ccccc1]

| | |
|---|---|
| MS (M + H)+ Calcd. | 782.3 |
| MS (M + H)+ Observ. | 782.3 |
| Retention Time | 4.32 min |

LC Condition

| | |
|---|---|
| Solvent A | 90% Water-10% Methanol-0.1% TFA |
| Solvent B | 10% Water-90% Methanol-0.1% TFA |
| Start % B | 0 |

| | |
|---|---|
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1501

Synthesis of Compound 1502

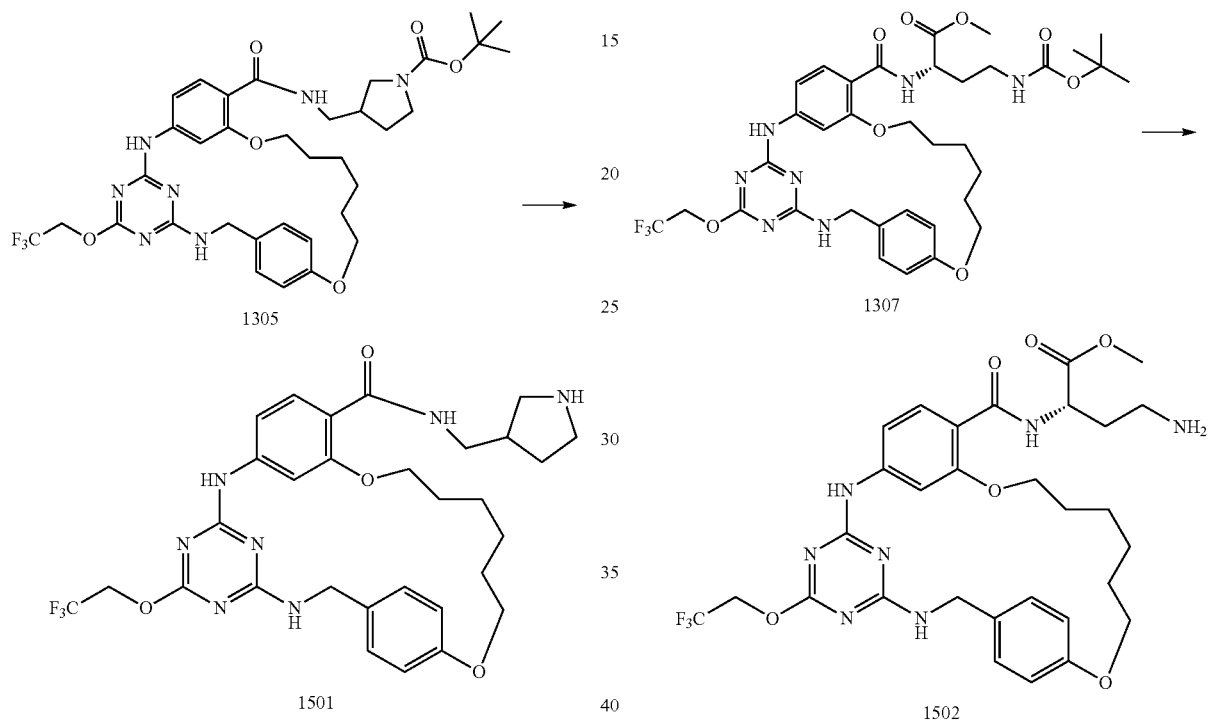

By following the general procedure examplified by the preparation of Compound 1151, using Compound 1305 as the starting material, it led to the formation of Compound 1501.

By following the general procedure examplified by the preparation of Compound 1151, using Compound 1307 as the starting material, it led to the formation of Compound 1502.

| Compound 1501 | |
|---|---|
| MS (M + H)+ Calcd. | 616.3 |
| MS (M + H)+ Observ. | 616.1 |
| Retention Time | 4.03 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

| Compound 1502 | |
|---|---|
| MS (M + H)+ Calcd. | 648.3 |
| MS (M + H)+ Observ. | 648.1 |
| Retention Time | 4.24 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1503

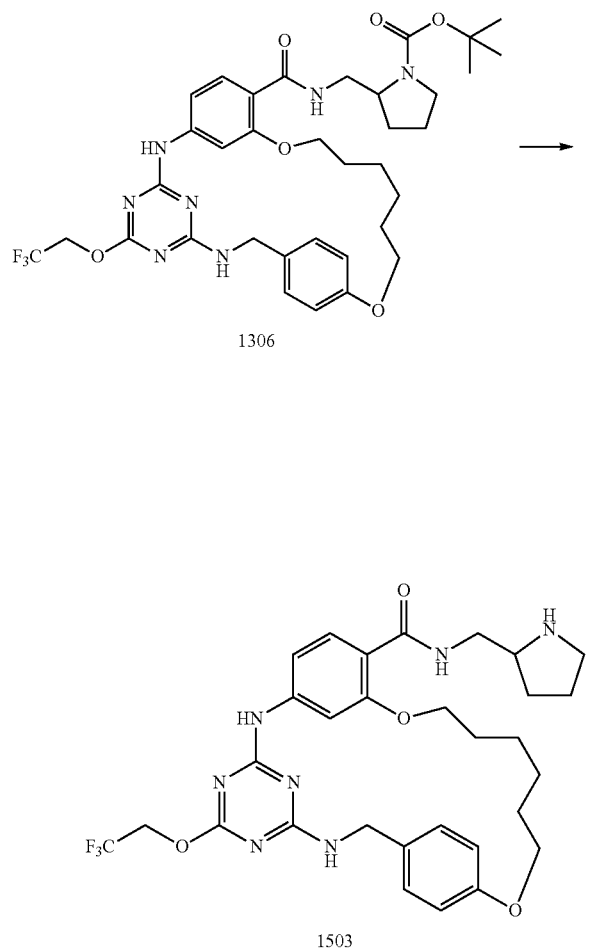

By following the general procedure examplified by the preparation of Compound 1151, using Compound 1306 as the starting material, it led to the formation of Compound 1503.

|  | Compound 1503 |
| --- | --- |
| MS (M + H)+ Calcd. | 616.3 |
| MS (M + H)+ Observ. | 616.1 |
| Retention Time | 4.12 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1504

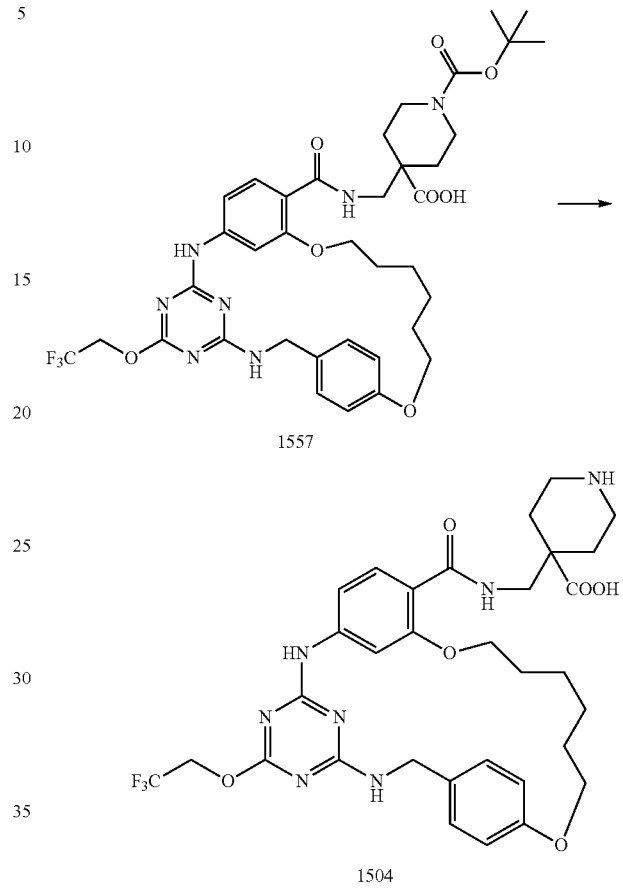

By following the general procedure examplified by the preparation of Compound 1151, using Compound 1306 as the starting material, it led to the formation of Compound 1503.

|  | Compound 1504 |
| --- | --- |
| MS (M + H)+ Calcd. | 674.3 |
| MS (M + H)+ Observ. | 674.3 |
| Retention Time | 3.77 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

111
Synthesis of Compound 1505

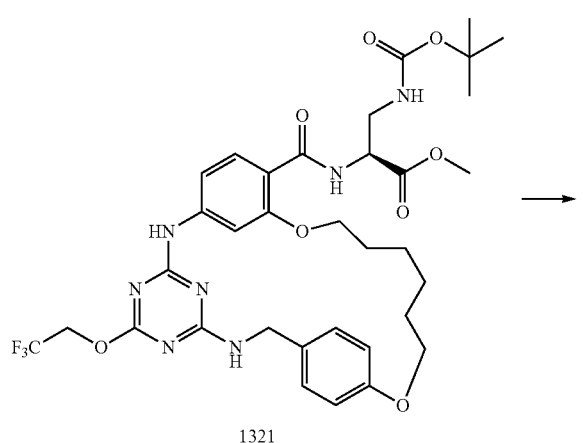

1321

1505

By following the general procedure examplified by the preparation of Compound 1151, using Compound 1321 as the starting material, it led to the formation of Compound 1505.

| Compound 1505 | |
|---|---|
| MS (M + H)+ Calcd. | 634.3 |
| MS (M + H)+ Observ. | 634.2 |
| Retention Time | 3.84 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

112
Synthesis of Compound 1551 and Compound 1552

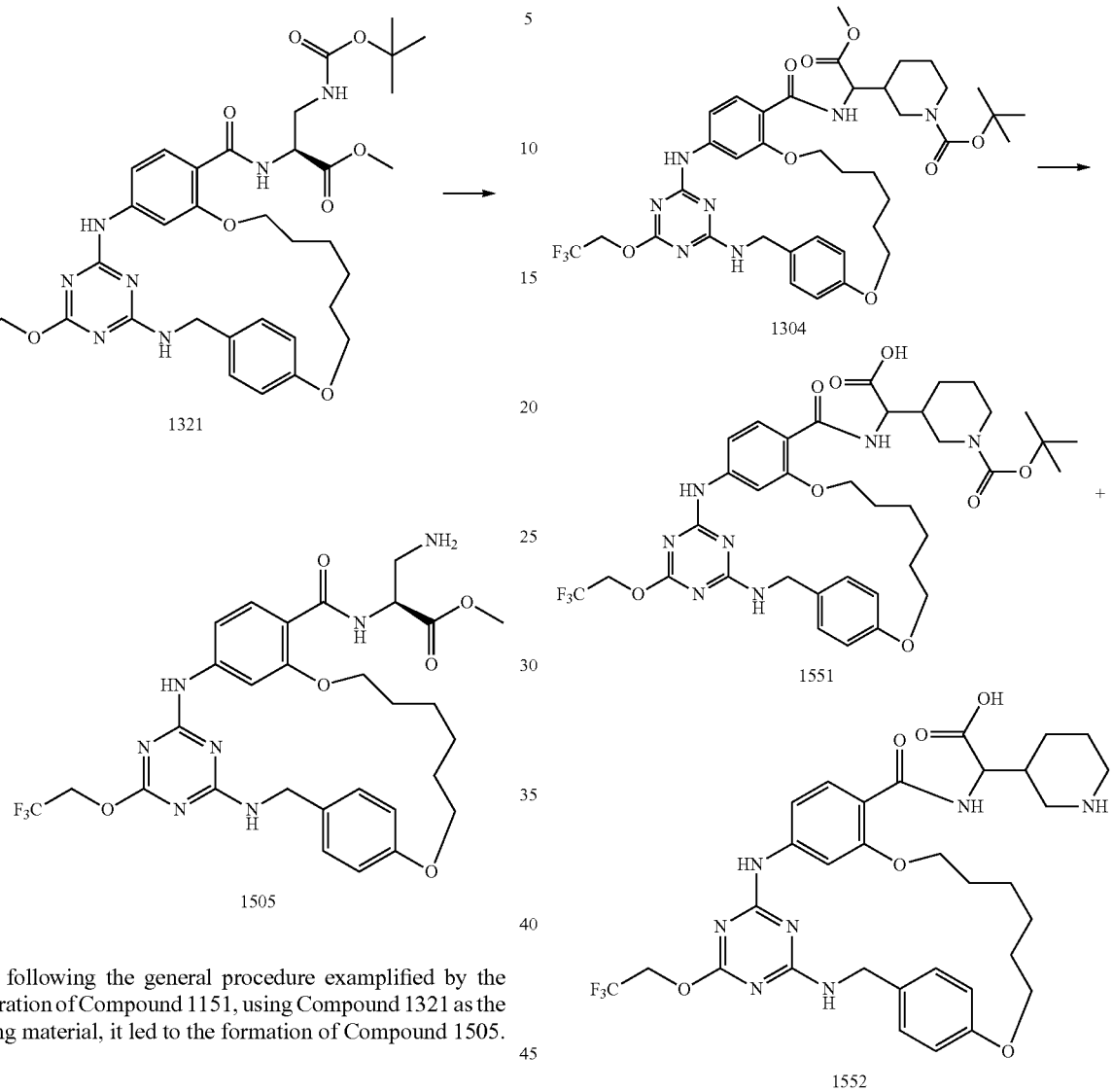

1304

1551

1552

By following the general procedure of hydrolysis of ester examplified by the preparation of Compound 1131, using Compound 1304 as the starting material, it led to the formation of Compound 1551 and Compound 1552.

| Compound 1551 | |
|---|---|
| MS (M + H)+ Calcd. | 774.3 |
| MS (M + H)+ Observ. | 774.2 |
| Retention Time | 4.75 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |

Compound 1551

| | |
|---|---|
| Solvent Pair | Water-Methanol-TFA |
| Column | PHENOMENEX-LUNA 2.0 × 50 mm 3 um |

Compound 1552

| | |
|---|---|
| MS (M + H)+ Calcd. | 674.3 |
| MS (M + H)+ Observ. | 674.2 |
| Retention Time | 3.99 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1553 and Compound 1554

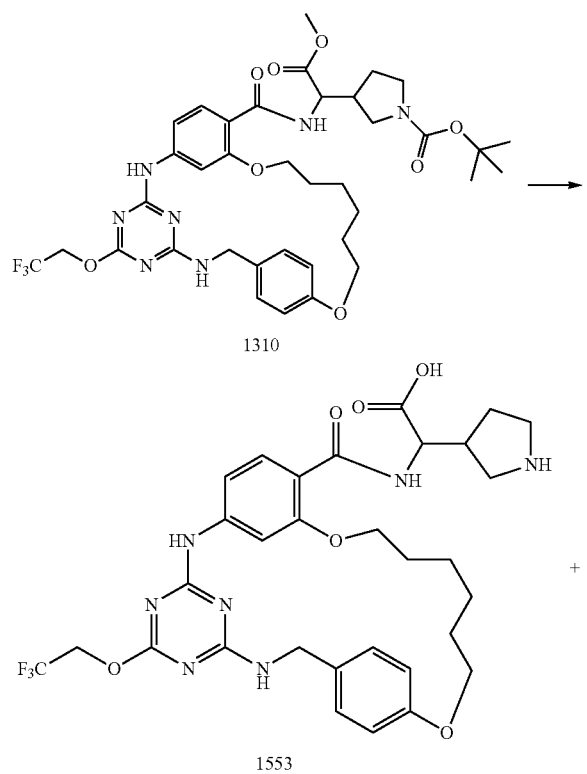

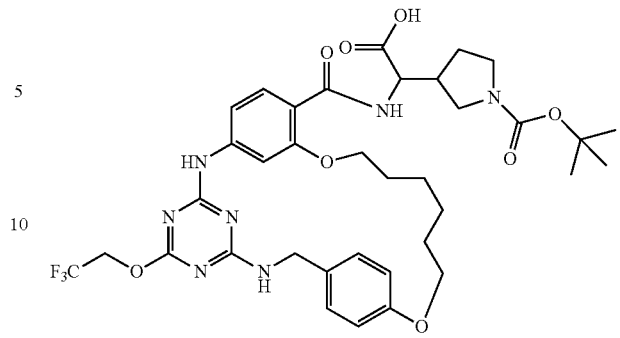

By following the general procedure of hydrolysis of ester examplified by the preparation of Compound 1131, using Compound 1310 as the starting material, it led to the formation of Compound 1553 and Compound 1554.

Compound 1553

| | |
|---|---|
| MS (M + H)+ Calcd. | 660.3 |
| MS (M + H)+ Observ. | 660.2 |
| Retention Time | 3.22 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Compound 1554

| | |
|---|---|
| MS (M + H)+ Calcd. | 760.3 |
| MS (M + H)+ Observ. | 760.7 |
| Retention Time | 2.94 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3u |

Synthesis of Compound 1555 and Compound 1556

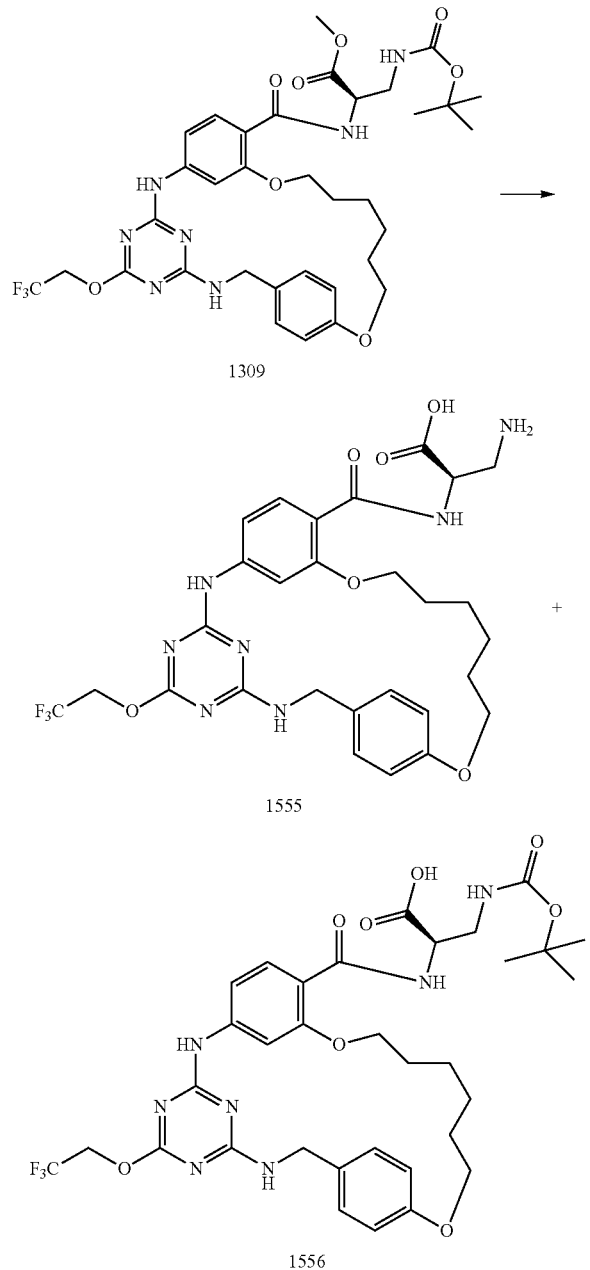

By following the general procedure of hydrolysis of ester exemplified by the preparation of Compound 1131, using Compound 1309 as the starting material, it led to the formation of Compound 1555 and Compound 1556.

| Compound 1555 | |
|---|---|
| MS (M + H)+ Calcd. | 620.2 |
| MS (M + H)+ Observ. | 620.1 |
| Retention Time | 3.65 min |

| Compound 1555 | |
|---|---|
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

| Compound 1556 | |
|---|---|
| MS (M + H)+ Calcd. | 720.3 |
| MS (M + H)+ Observ. | 720.5 |
| Retention Time | 2.58 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3u |

Synthesis of Compound 1557

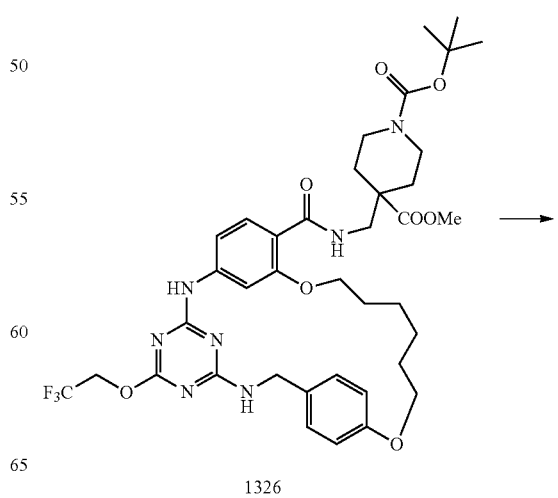

118

Synthesis of Compound 1558

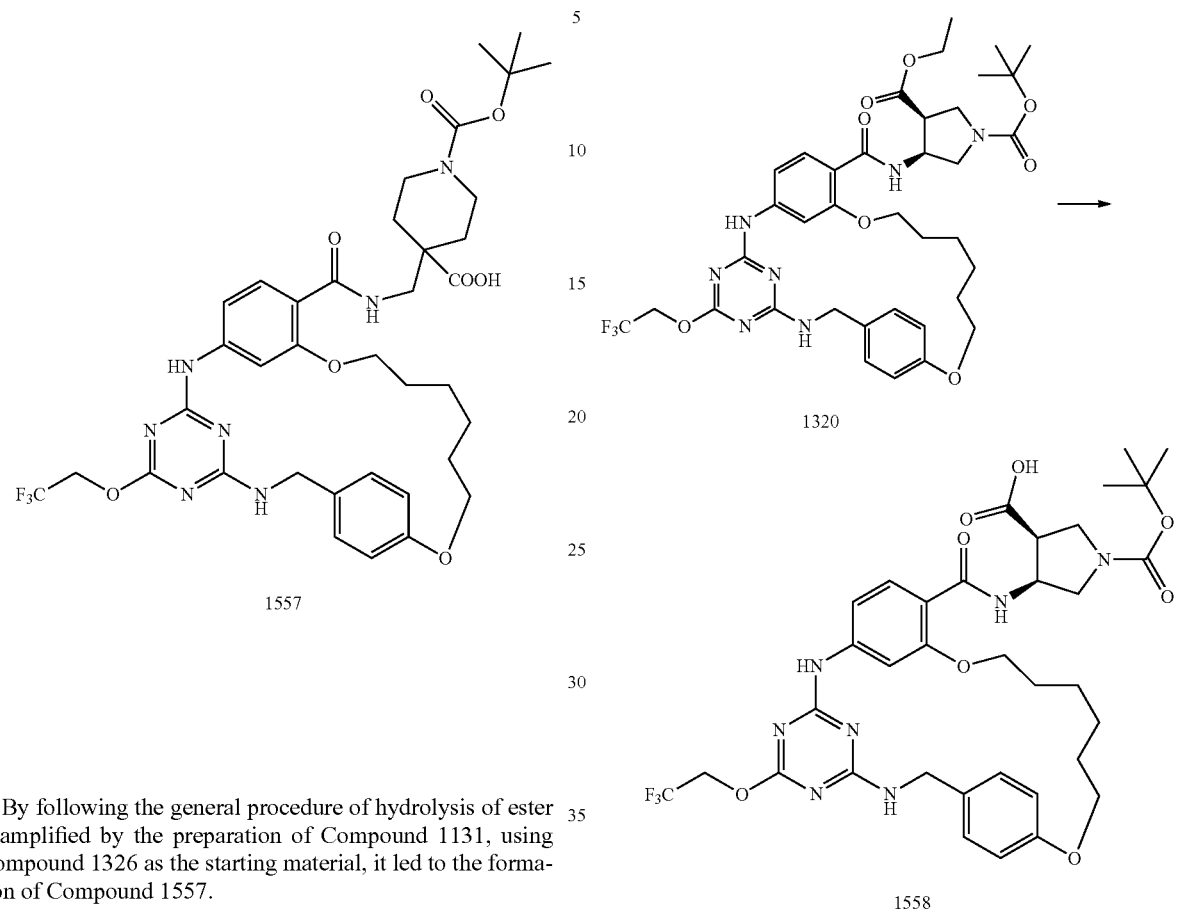

By following the general procedure of hydrolysis of ester examplified by the preparation of Compound 1131, using Compound 1326 as the starting material, it led to the formation of Compound 1557.

By following the general procedure of hydrolysis of ester examplified by the preparation of Compound 1131, using Compound 1320 as the starting material, it led to the formation of Compound 1558.

| Compound 1557 | |
|---|---|
| MS (M + H)⁺ Calcd. | 774.3 |
| MS (M + H)⁺ Observ. | 774.5 |
| Retention Time | 2.87 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3u |

| Compound 1558 | |
|---|---|
| MS (M + H)⁺ Calcd. | 746.3 |
| MS (M + H)⁺ Observ. | 746.3 |
| Retention Time | 4.47 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1559 and Compound 1560

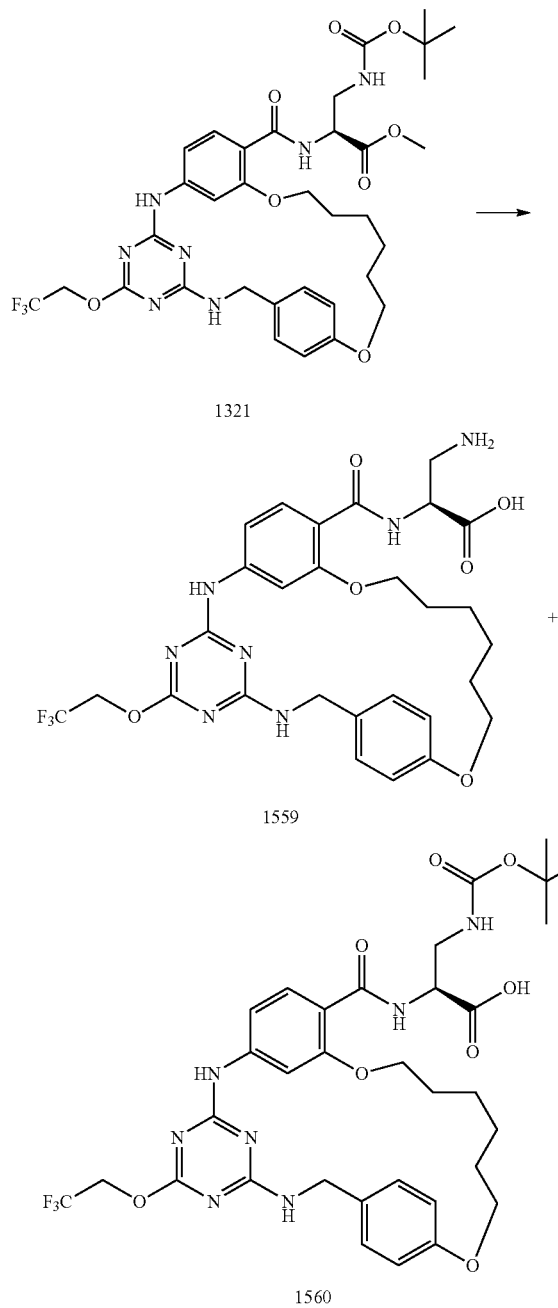

By following the general procedure of hydrolysis of ester exemplified by the preparation of Compound 1131, using Compound 1321 as the starting material, it led to the formation of Compound 1559 and Compound 1560.

| Compound 1559 | |
|---|---|
| MS (M + H)+ Calcd. | 620.2 |
| MS (M + H)+ Observ. | 620.2 |
| Retention Time | 3.71 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

| Compound 1560 | |
|---|---|
| MS (M + H)+ Calcd. | 720.3 |
| MS (M + H)+ Observ. | 720.3 |
| Retention Time | 4.26 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1561

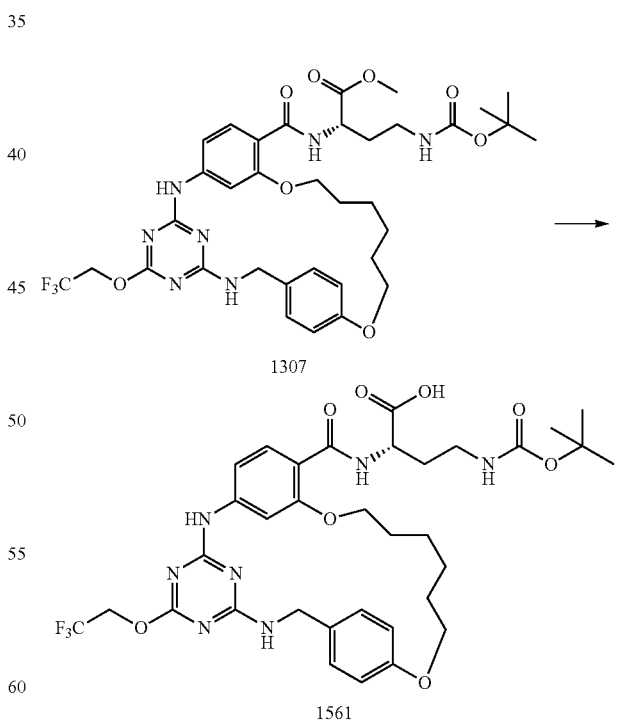

By following the general procedure of hydrolysis of ester exemplified by the preparation of Compound 1131, using Compound 1307 as the starting material, it led to the formation of Compound 1561.

| Compound 1561 | |
|---|---|
| MS (M + H)+ Calcd. | 734.3 |
| MS (M + H)+ Observ. | 734.5 |
| Retention Time | 2.68 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3u |

Synthesis of Compound 1562

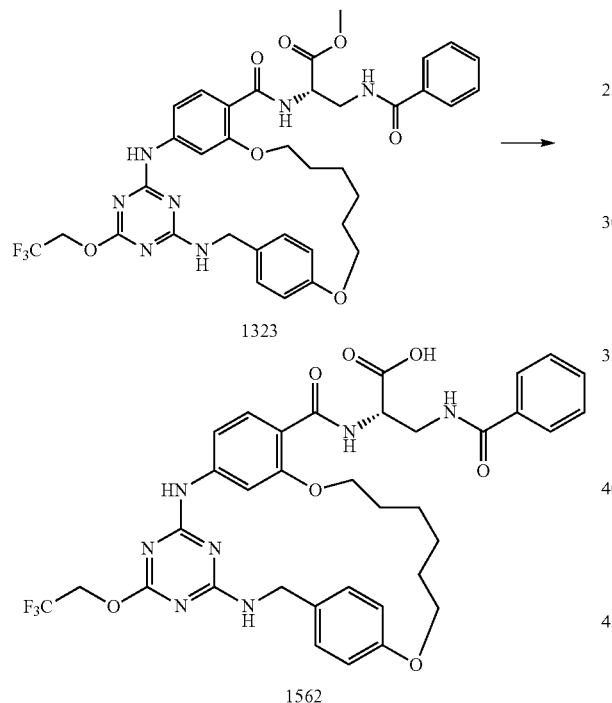

By following the general procedure of hydrolysis of ester exemplified by the preparation of Compound 1131, using Compound 1323 as the starting material, it led to the formation of Compound 1562.

| Compound 1562 | |
|---|---|
| MS (M + H)+ Calcd. | 724.3 |
| MS (M + H)+ Observ. | 724.4 |
| Retention Time | 2.48 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3u |

Synthesis of Compound 1600

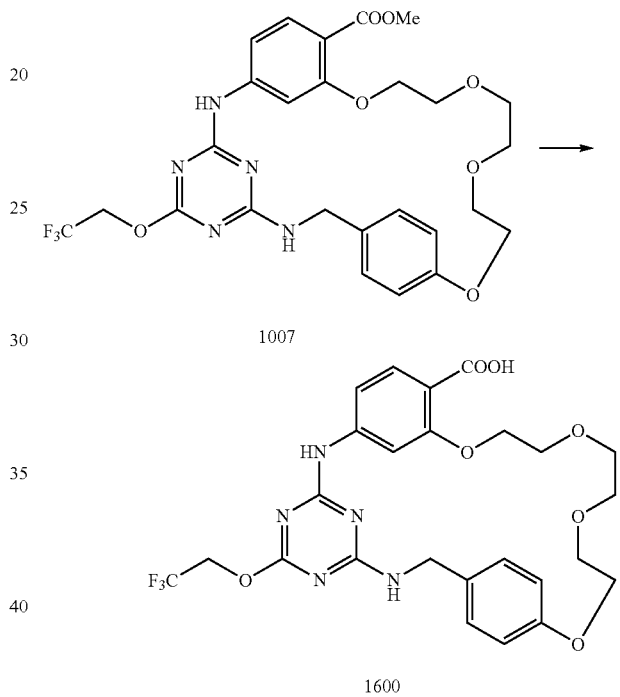

By following the general procedure of hydrolysis of ester exemplified by the preparation of Compound 1131, using Compound 1007 as the starting material, it led to the formation of Compound 1600.

| Compound 1600 | |
|---|---|
| MS (M + H)+ Calcd. | 566.2 |
| MS (M + H)+ Observ. | 566.0 |
| Retention Time | 4.31 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

The following general procedure was applied to synthesize compounds of Formula 1:

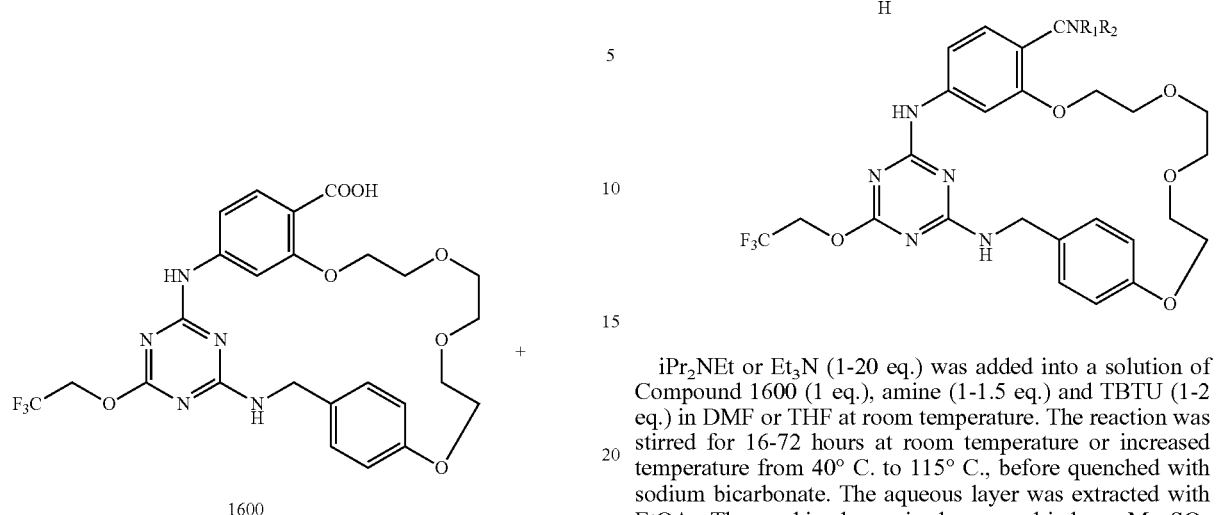

iPr$_2$NEt or Et$_3$N (1-20 eq.) was added into a solution of Compound 1600 (1 eq.), amine (1-1.5 eq.) and TBTU (1-2 eq.) in DMF or THF at room temperature. The reaction was stirred for 16-72 hours at room temperature or increased temperature from 40° C. to 115° C., before quenched with sodium bicarbonate. The aqueous layer was extracted with EtOAc. The combined organic phase was dried over Mg$_2$SO$_4$ and concentrated under vacuum to give a crude product, which was purified by preparative HPLC.

| Compound 1601 | |
|---|---|
| Amine Used | 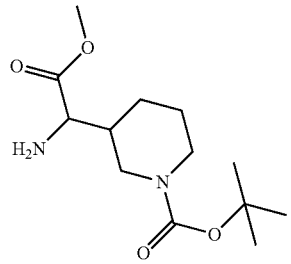 [SMILES: COC(=O)C(N)C1CCCN(C(=O)OC(C)(C)C)C1] |
| Product | 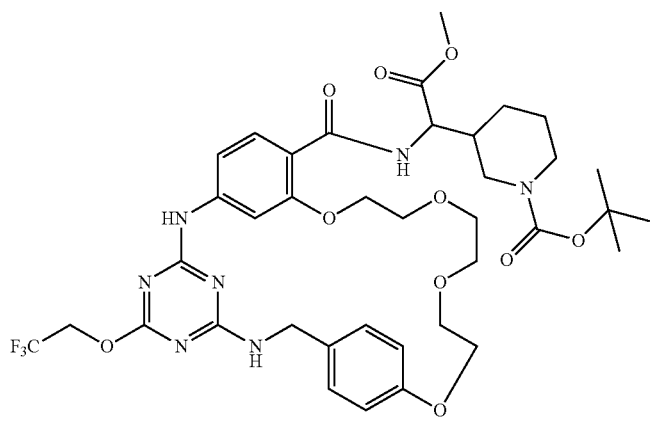 [SMILES: COC(=O)C(NC(=O)c1ccc2cc1OCCOCCOCCOc1ccc(cc1)CNc1nc(nc(OCC(F)(F)F)n1)N2)C1CCCN(C(=O)OC(C)(C)C)C1] |
| MS (M + H)$^+$ Calcd. | 820.3 |
| MS (M + H)$^+$ Observ. | 820.3 |
| Retention Time | 4.38 min |
| LC Condition | |
| Solvent A | 90% Water-10% Methanol-0.1% TFA |
| Solvent B | 10% Water-90% Methanol-0.1% TFA |

| | |
|---|---|
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Compound 1602

Amine Used

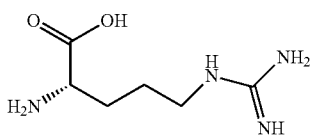 [SMILES: N=C(N)NCCC[C@H](N)C(=O)O]

Product

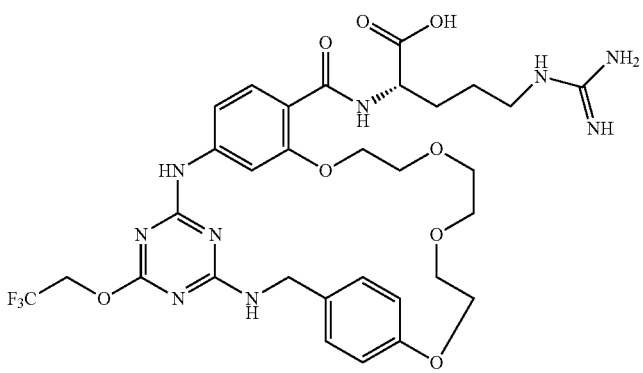 [SMILES: N=C(N)NCCC[C@H](NC(=O)c1ccc2cc1OCCOCCOCCOc1ccc(cc1)CNc1nc(nc(OCC(F)(F)F)n1)N2)C(=O)O]

| | |
|---|---|
| MS (M + H)+ Calcd. | 722.3 |
| MS (M + H)+ Observ. | 722.2 |
| Retention Time | 3.43 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Compound 1603

Amine Used

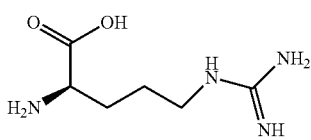 [SMILES: N=C(N)NCCC[C@@H](N)C(=O)O]

| | |
|---|---|
| Product | 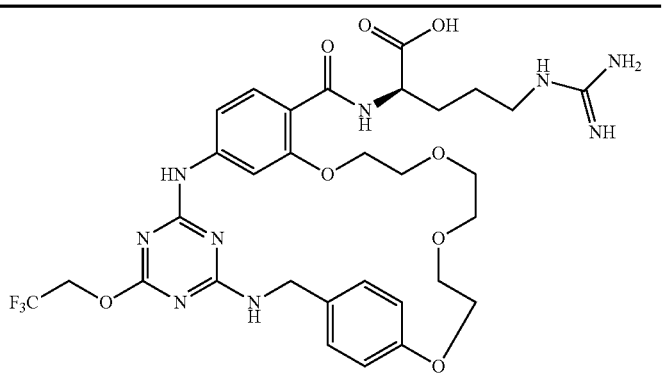 |
| MS (M + H)+ Calcd. | 722.3 |
| MS (M + H)+ Observ. | 722.2 |
| Retention Time | 3.43 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

---

Compound 1604

| | |
|---|---|
| Amine Used | 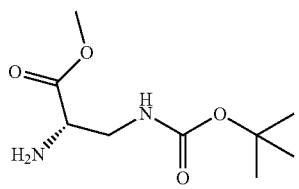 |
| Product | 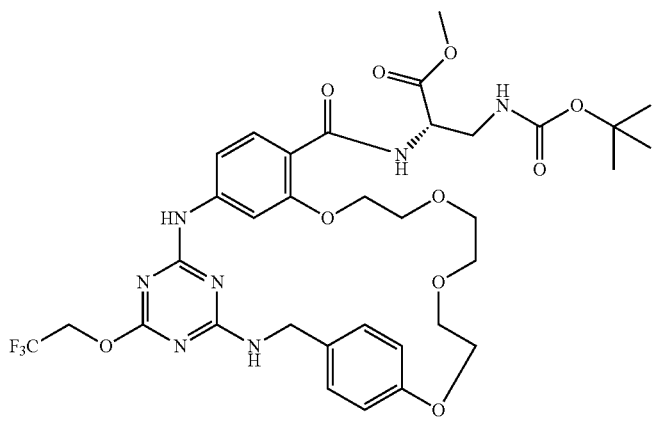 [SMILES: COC(=O)[C@H](CNC(=O)OC(C)(C)C)NC(=O)c1ccc2cc1OCCOCCOCCOc1ccc(cc1)CNc1nc(nc(OCC(F)(F)F)n1)N2] |
| MS (M + H)+ Calcd. | 766.3 |
| MS (M + H)+ Observ. | 766.3 |
| Retention Time | 4.27 min |

LC Condition

| | |
|---|---|
| Solvent A | 90% Water-10% Methanol-0.1% TFA |
| Solvent B | 10% Water-90% Methanol-0.1% TFA |
| Start % B | 0 |
| Final % B | 100 |

| | |
|---|---|
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1605

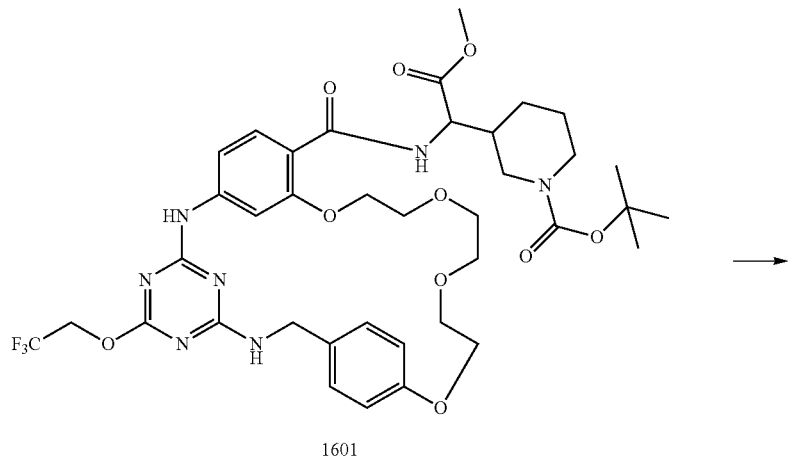

1601

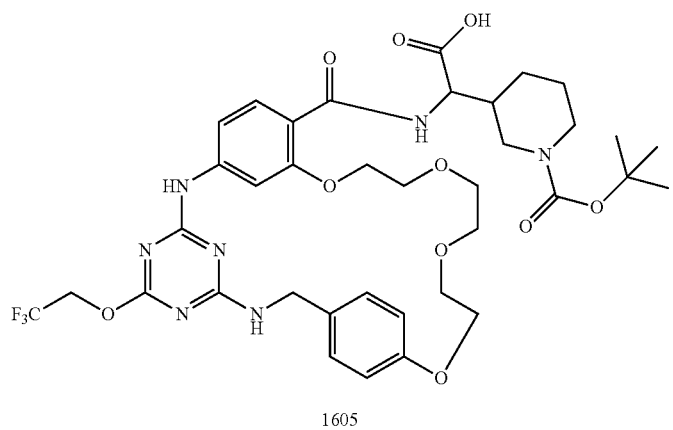

1605

By following the general procedure of hydrolysis of ester examplified by the preparation of Compound 1131, using Compound 1601 as the starting material, it led to the formation of Compound 1605.

| Compound 1605 | |
|---|---|
| MS (M + H)+ Calcd. | 806.3 |
| MS (M + H)+ Observ. | 806.5 |
| Retention Time | 2.64 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3u |

131
Synthesis of Compound 1606

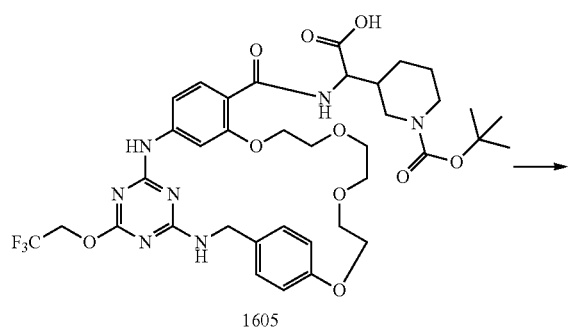
1605

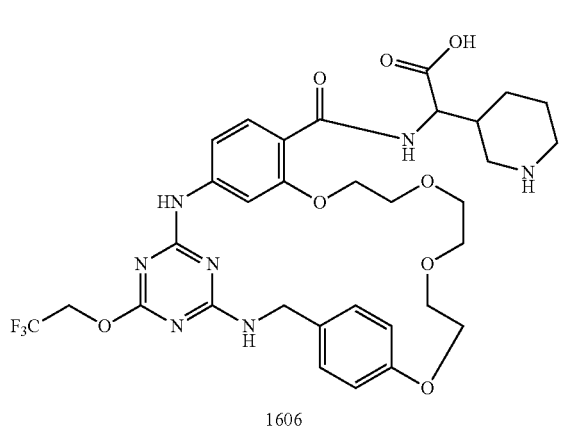
1606

By following the general procedure examplified by the preparation of Compound 1151, using Compound 1605 as the starting material, it led to the formation of Compound 1606.

| Compound 1606 | |
| --- | --- |
| MS (M + H)⁺ Calcd. | 706.3 |
| MS (M + H)⁺ Observ. | 706.4 |
| Retention Time | 2.19 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3u |

132
Synthesis of Compound 1607

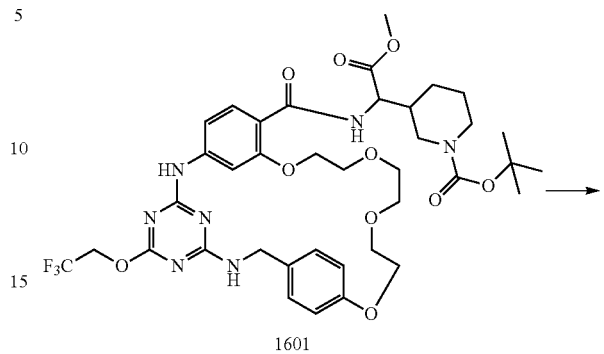
1601

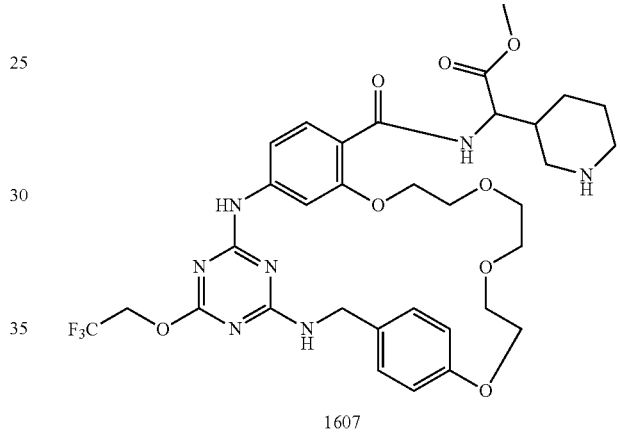
1607

By following the general procedure examplified by the preparation of Compound 1151, using Compound 1601 as the starting material, it led to the formation of Compound 1607.

| Compound 1607 | |
| --- | --- |
| MS (M + H)⁺ Calcd. | 720.3 |
| MS (M + H)⁺ Observ. | 720.4 |
| Retention Time | 2.50 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3u |

Synthesis of Compound 1608

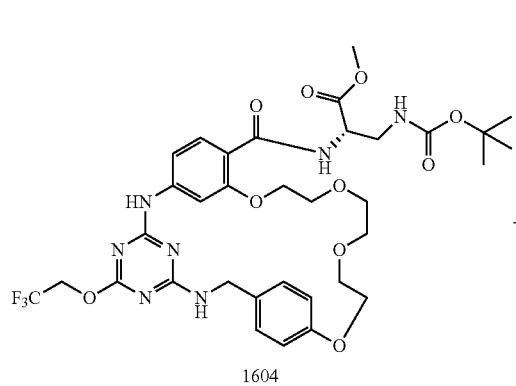

1604

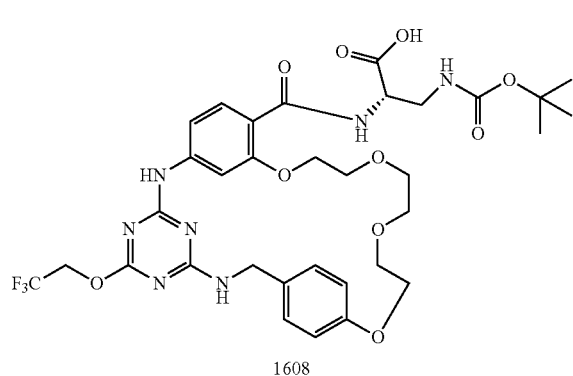

1608

By following the general procedure of hydrolysis of ester exemplified by the preparation of Compound 1131, using Compound 1604 as the starting material, it led to the formation of Compound 1608.

| Compound 1608 | |
|---|---|
| MS (M + H)+ Calcd. | 752.3 |
| MS (M + H)+ Observ. | 752.6 |
| Retention Time | 2.39 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3u |

Preparation of Intermediate 1609-In

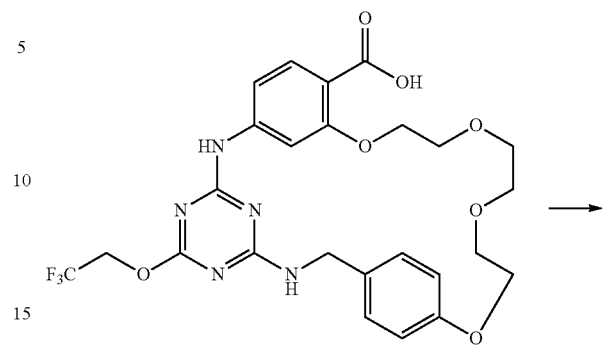

1600

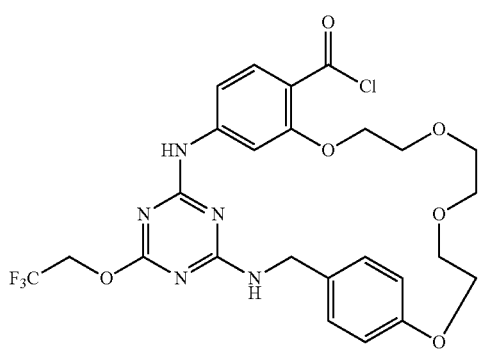

1609-In

Step 1: Compound 1600 (20 mg) in and sulfurous dichloride (63 mg) were mixed together. The reaction mixture was heated to 60° C. for 6 hours. Removal of solvents under vacuum provided crude Compound 1609-In which was used in the next step without purification.

Synthesis of Compound 1611, Compound 1612 and Compound 1613

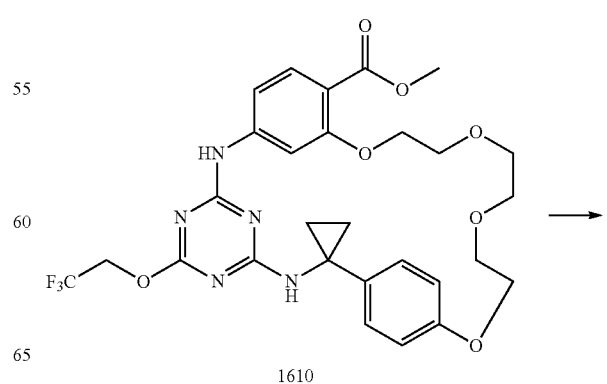

1610

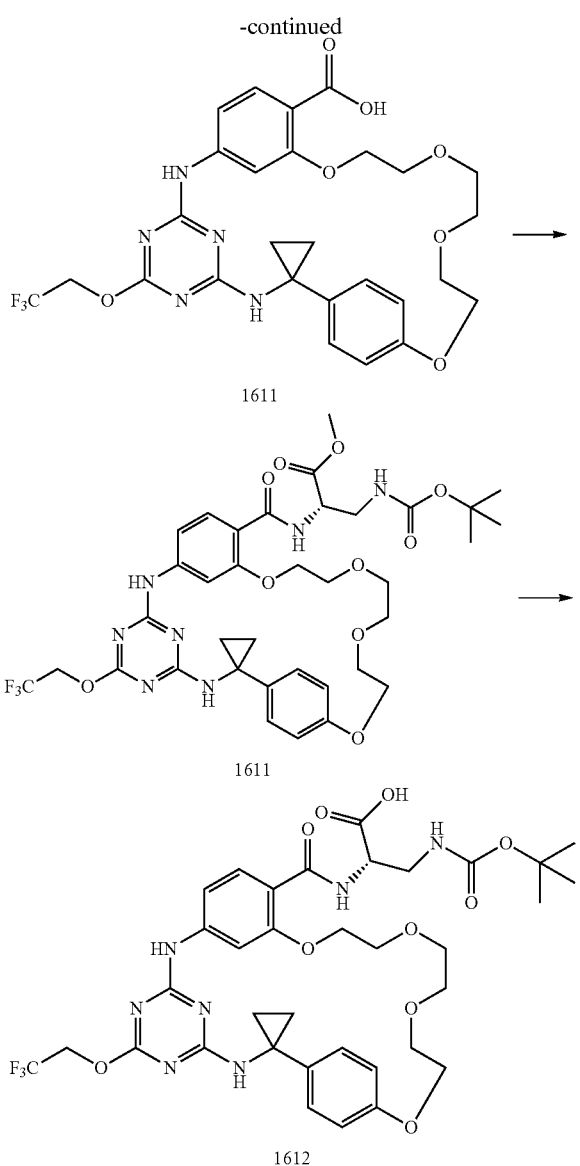

Step 1: By following the general procedure of hydrolysis of ester exemplified by the preparation of Compound 1131, using Compound 1610 as the starting material, it led to the formation of Compound 1611.

| | Compound 1611 |
|---|---|
| MS (M + H)+ Calcd. | 592.2 |
| MS (M + H)+ Observ. | 592.1 |
| Retention Time | 4.02 min |
| | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Step 2: By following the same procedure of the preparation of Compound 1604, using Compound 1611 as the starting material, it led to the formation of Compound 1612.

| | Compound 1612 |
|---|---|
| MS (M + H)+ Calcd. | 792.3 |
| MS (M + H)+ Observ. | 792.3 |
| Retention Time | 4.32 min |
| | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Step 3: By following the general procedure of hydrolysis of ester exemplified by the preparation of Compound 1131, using Compound 1612 as the starting material, it led to the formation of Compound 1613.

| | Compound 1613 |
|---|---|
| MS (M + H)+ Calcd. | 778.3 |
| MS (M + H)+ Observ. | 778.3 |
| Retention Time | 4.17 min |
| | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1700

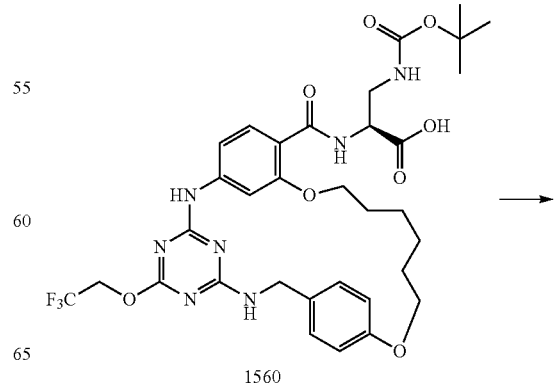

1560

-continued

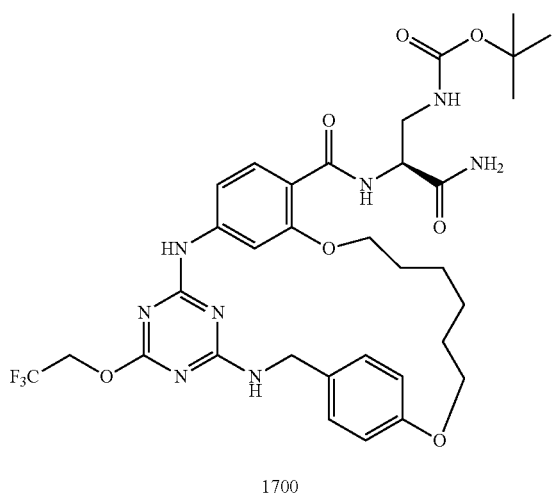

1700

NH₃ gas was blowed into a solution of iPr₂NEt (2.2 mg), Compound 1560 (6 mg), and TBTU (3.5 mg) in DMF (1 mL) at room temperature for 5 minutes and the reaction was stirred for 4 hours at room temperature. Compound 1700 was isolated by preparative HPLC.

| Compound 1700 | |
|---|---|
| MS (M + H)⁺ Calcd. | 719.3 |
| MS (M + H)⁺ Observ. | 719.3 |
| Retention Time | 4.30 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1701

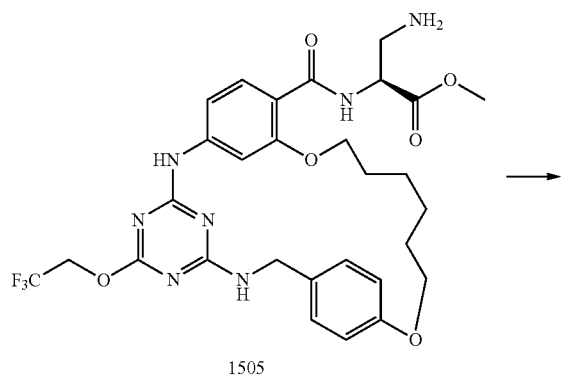

1505

-continued

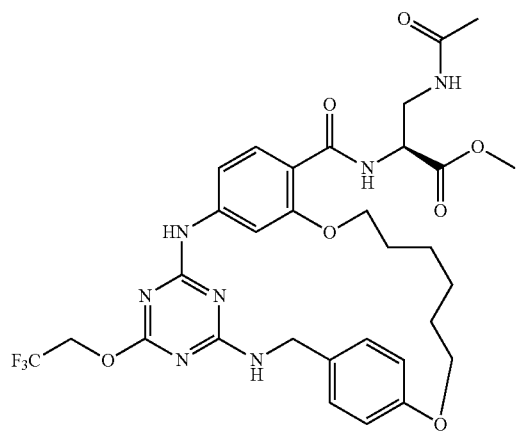

1701

Acetyl chloride (3.7 mg) was added into a solution of iPr₂NEt (12 mg) and Compound 1505 (30 mg) in DMF (1 mL) at room temperature and the reaction was stirred for 1 hour at room temperature. Compound 1701 was isolated by preparative HPLC.

| Compound 1701 | |
|---|---|
| MS (M + H)⁺ Calcd. | 676.3 |
| MS (M + H)⁺ Observ. | 676.2 |
| Retention Time | 4.22 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1702

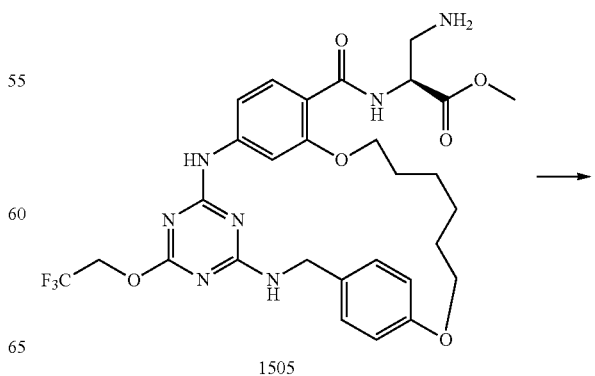

1505

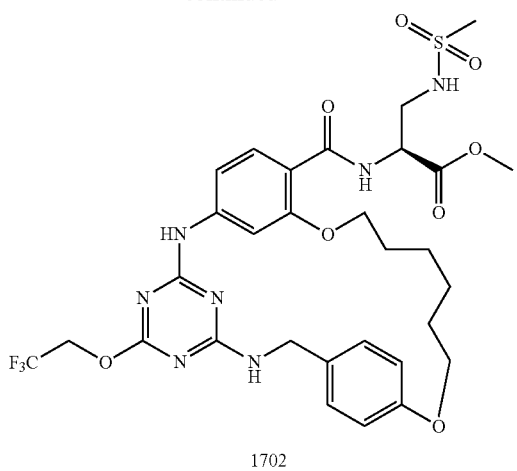

1702

Methanesulfonyl chloride (5.4 mg) was added into a solution of iPr$_2$NEt (12 mg) and Compound 1505 (30 mg) in DMF (1 mL) at room temperature and the reaction was stirred for 1 hour at room temperature. Compound 1702 was isolated by preparative HPLC.

| Compound 1702 | |
|---|---|
| MS (M + H)$^+$ Calcd. | 712.2 |
| MS (M + H)$^+$ Observ. | 712.1 |
| Retention Time | 4.18 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1706

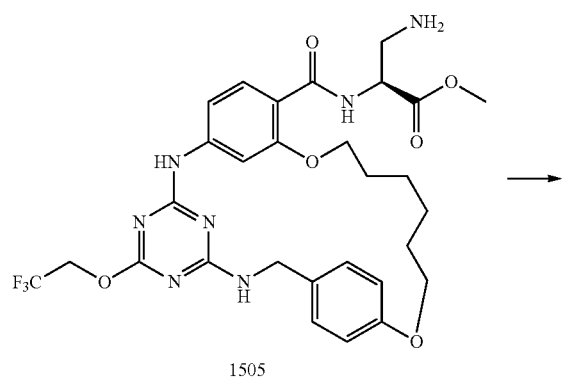

1505

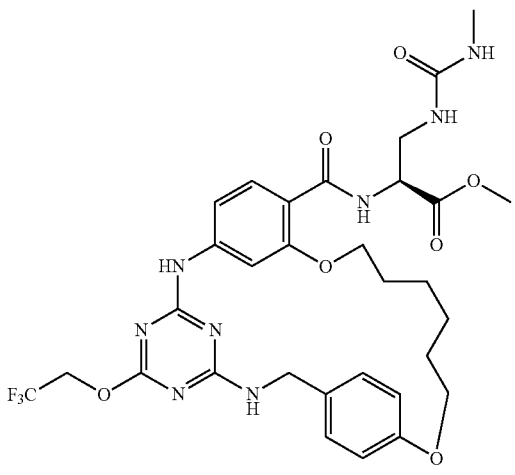

1706

Methylcarbamic chloride (7.1 mg) was added into a solution of iPr$_2$NEt (16 mg) and Compound 1505 (40 mg) in DMF (1 mL) at room temperature and the reaction was stirred for 4 hours at room temperature. Compound 1706 was isolated by preparative HPLC.

| Compound 1706 | |
|---|---|
| MS (M + H)$^+$ Calcd. | 691.3 |
| MS (M + H)$^+$ Observ. | 691.2 |
| Retention Time | 4.25 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

141

Synthesis of Compound 1707

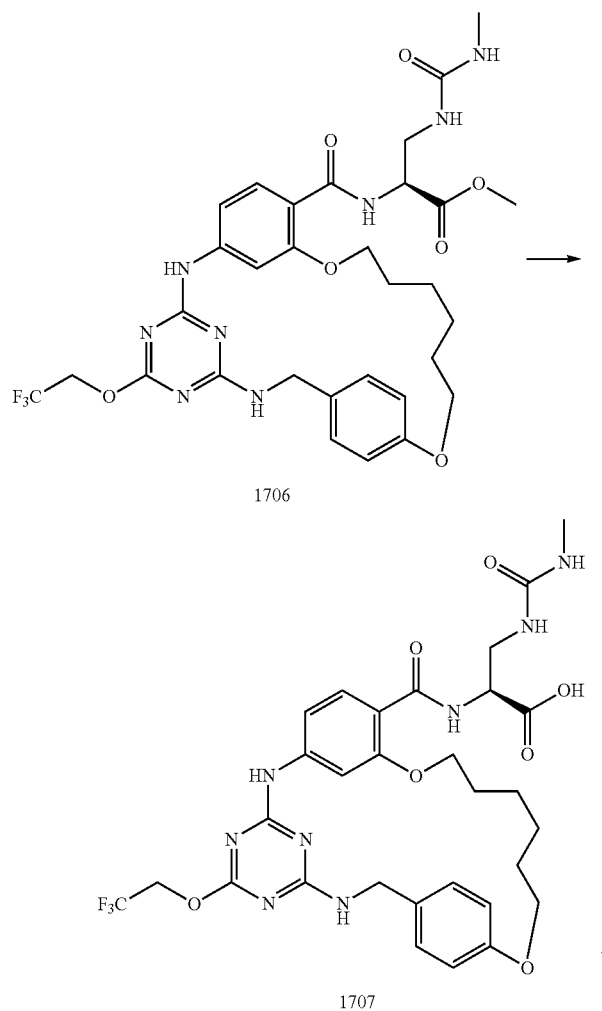

1706

1707

By following the general procedure of hydrolysis of ester exemplified by the preparation of Compound 1131, using Compound 1706 as the starting material, it led to the formation of Compound 1707.

| Compound 1707 | |
|---|---|
| MS (M + H)+ Calcd. | 677.3 |
| MS (M + H)+ Observ. | 677.3 |
| Retention Time | 2.14 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3 u |

142

Synthesis of Compound 1711

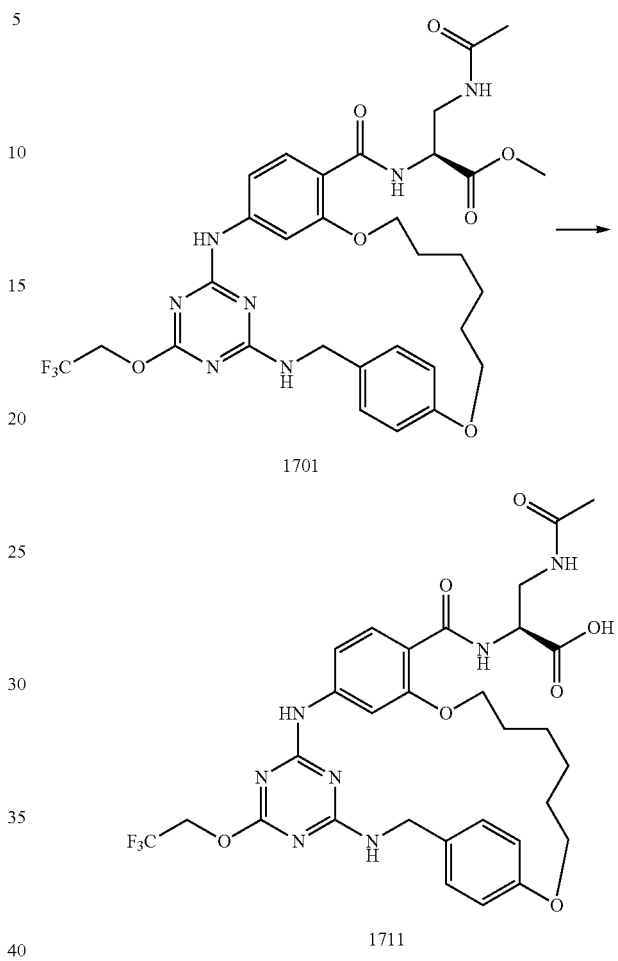

1701

1711

By following the general procedure of hydrolysis of ester exemplified by the preparation of Compound 1131, using Compound 1701 as the starting material, it led to the formation of Compound 1711.

| Compound 1711 | |
|---|---|
| MS (M + H)+ Calcd. | 705.3 |
| MS (M + H)+ Observ. | 705.4 |
| Retention Time | 2.25 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3 u |

Synthesis of Compound 1801

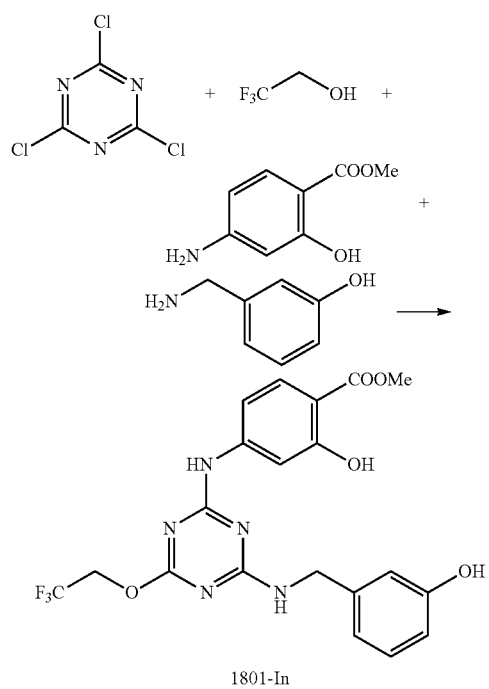

1801-In

Stage 1: By following the same procedure of synthesis of Compound 1005-In using 3-(aminomethyl)phenol instead of 4-(aminomethyl)phenol, it led to the formation of Compound 1801-In.

|  | Compound 1801-In |
|---|---|
| MS (M + H)+ Calcd. | 466.1 |
| MS (M + H)+ Observ. | 466.0 |
| Retention Time | 3.39 min |
|  | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Stage 2: To a suspension of Compound 1801-In (200 mg) and Cs$_2$CO$_3$ (560 mg) in DMF (50 mL) was added 1,4-diiodobutane (133 mg). The mixture was stirred at room temperature for 16 hours. DMF was removed under vacuum. The residue was diluted with EtOAc (200 mL) and washed with water (50 mL), brine (50 mL), dried over MgSO$_4$ and concentrated. The residue was purified by prep HPLC to give Compound 1801.

|  | Compound 1801 |
|---|---|
| MS (M + H)+ Calcd. | 520.2 |
| MS (M + H)+ Observ. | 520.0 |
| Retention Time | 3.58 min |
|  | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Synthesis of Compound 1802

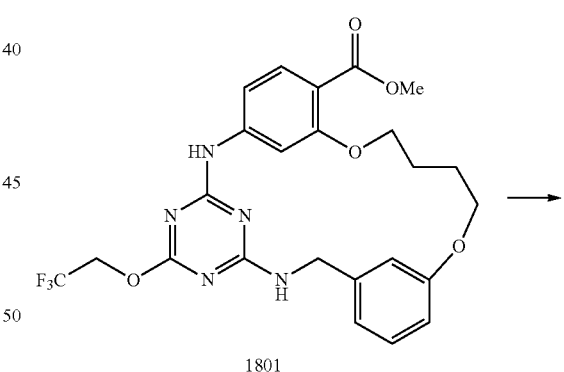

1801

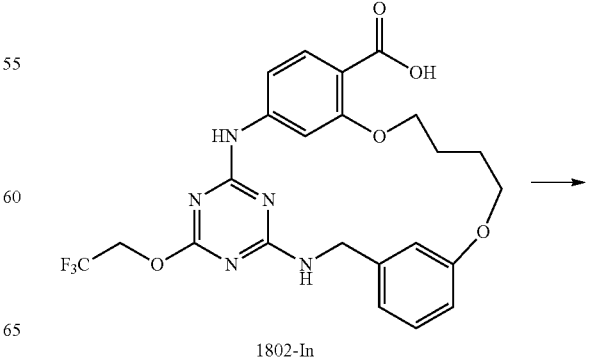

1802-In

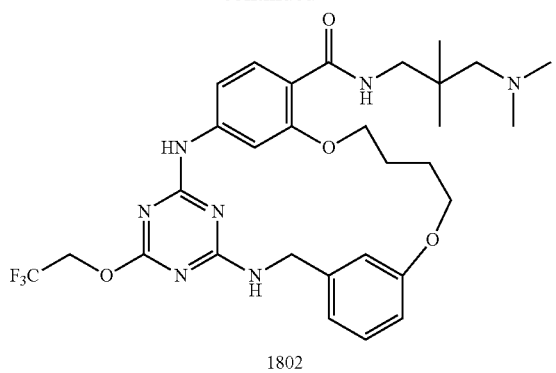

1802

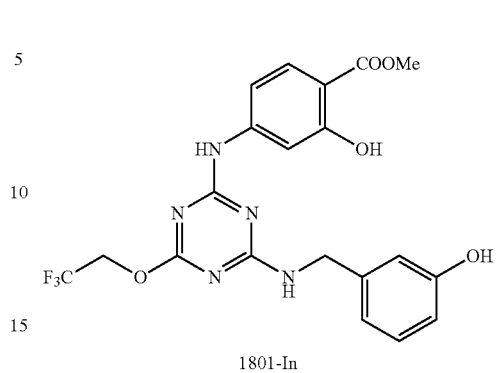

1801-In

Step 1: A suspension of Compound 1801 (12 mg) and K₂CO₃ (16 mg) in acetone (1 mL)/water (1 mL) was heated at 100° C. for 6 hours. After cooling to room temperature, the mixture was acidified to pH=3. All solvents was removed under vacuum. The residue was used in the next step without further purification.

| | Compound 1802-In |
|---|---|
| MS (M + H)⁺ Calcd. | 506.2 |
| MS (M + H)⁺ Observ. | 506.0 |
| Retention Time | 3.56 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Step 2: To a solution of Compound 1802-In (8 mg) and TBTU (7.62 mg) in DMF (2 mL) was added N1,N1,2,2-tetramethylpropane-1,3-diamine (6.18) and DIPEA (0.011 mL). After stirring at room temperature for 4 hours, the mixture was purified by preparative HPLC to give Compound 1802.

| | Compound 1802 |
|---|---|
| MS (M + H)⁺ Calcd. | 618.3 |
| MS (M + H)⁺ Observ. | 618.4 |
| Retention Time | 1.76 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Synthesis of Compound 1803

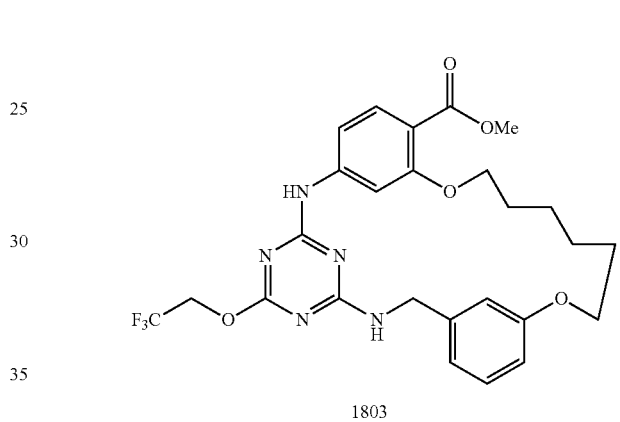

1803

By following the same procedure of synthesis of Compound 1801 using 1,6-diiodohexane instead of 1,4-diiodobutane, it led to the formation of Compound 1803.

| | Compound 1803 |
|---|---|
| MS (M + H)⁺ Calcd. | 548.2 |
| MS (M + H)⁺ Observ. | 548.3 |
| Retention Time | 2.90 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3 u |

147

Synthesis of Compound 1804

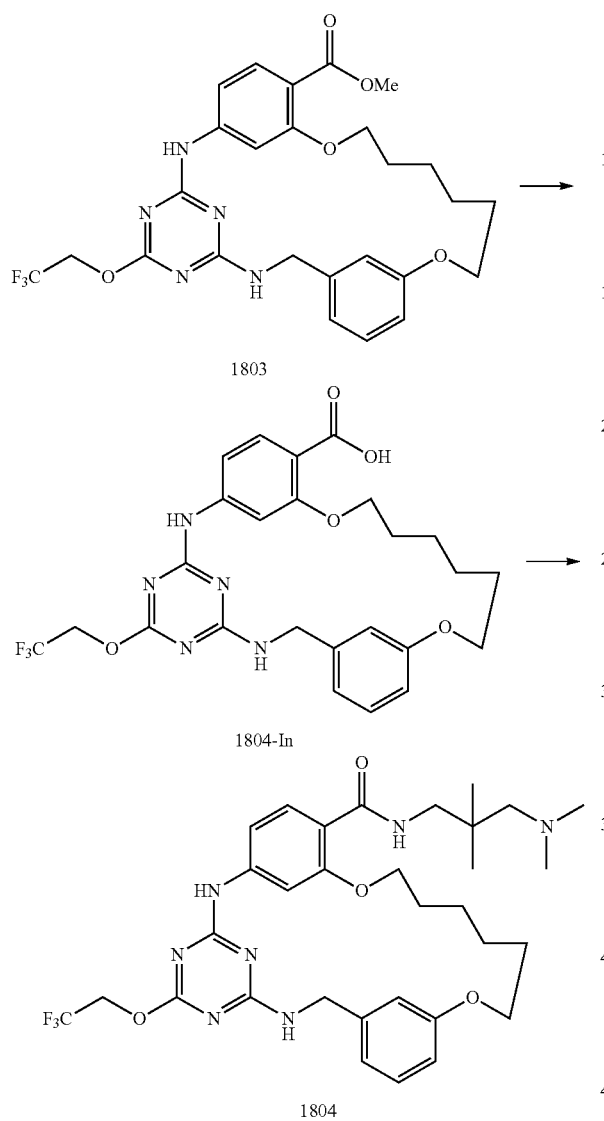

By following the same procedure of synthesis of Compound 1802 using Compound 1803 as the starting material, it led to the formation of Compound 1804.

| Compound 1804 | |
|---|---|
| MS (M + H)+ Calcd. | 646.3 |
| MS (M + H)+ Observ. | 646.5 |
| Retention Time | 3.72 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |

148

| Compound 1804 | |
|---|---|
| Solvent Pair | ACN:Water:Ammonium Actetate |
| Column | Phenomenex LUNA C18, 50 × 2, 3 u |

Synthesis of Compound 1805

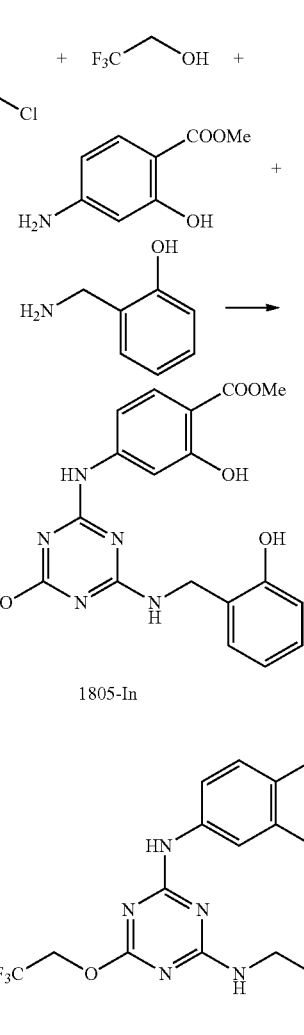

Stage 1: By following the same procedure of syntheis of Compound 1005-In using 2-(aminomethyl)phenol instead of 4-(aminomethyl)phenol, it led to the formation of Compound 1805-In.

| Compound 1805-In | |
|---|---|
| MS (M + H)+ Calcd. | 466.1 |
| MS (M + H)+ Observ. | 466.0 |
| Retention Time | 3.79 min |

-continued

| Compound 1805-In | |
|---|---|
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

Stage 2: To a suspension of Compound 1805-In (100 mg) and $Cs_2CO_3$ (280 mg) in DMF (50 mL) was added 1,4-diiodohexane (72.6 mg). The mixture was stirred at room temperature for 16 hours. DMF was removed under vacuum. The residue was diluted with EtOAc (200 mL) and washed with water (50 mL), brine (50 mL), dried over $MgSO_4$ and concentrated. The residue was purified by prep HPLC to give Compound 1805.

| Compound 1805 | |
|---|---|
| MS (M + H)+ Calcd. | 548.2 |
| MS (M + H)+ Observ. | 548.3 |
| Retention Time | 3.24 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3 u |

Synthesis of Compound 1806

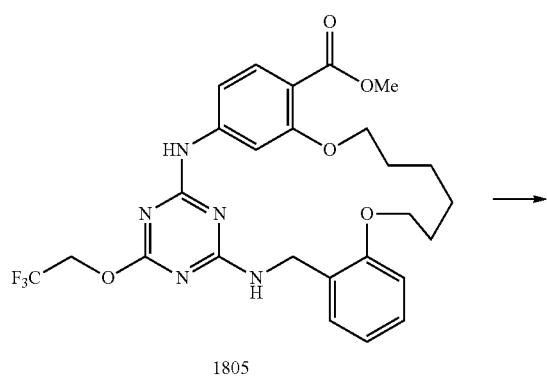

1805

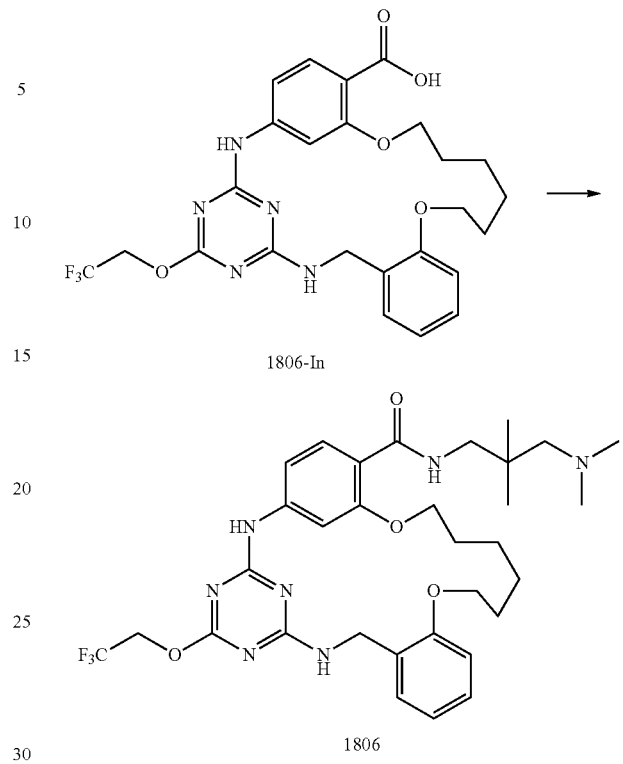

1806-In

1806

By following the same procedure of synthesis of Compound 1802 using Compound 1805 as the starting material, it led to the formation of Compound 1806.

| Compound 1806 | |
|---|---|
| MS (M + H)+ Calcd. | 646.3 |
| MS (M + H)+ Observ. | 646.5 |
| Retention Time | 4.00 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3 u |

Synthesis of Compound 1807

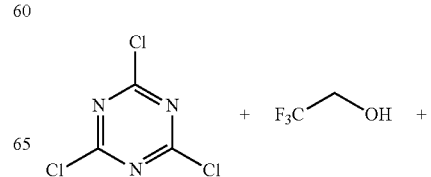

151

-continued

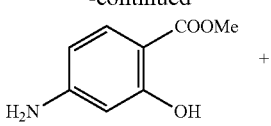

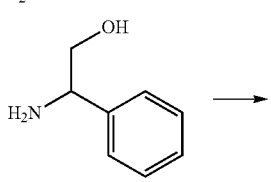

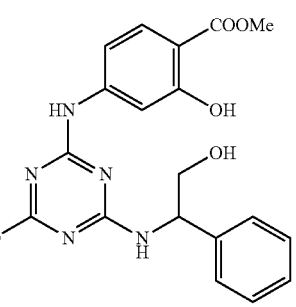

1807-In-01

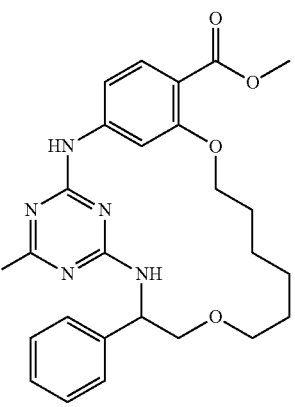

1807-In-02

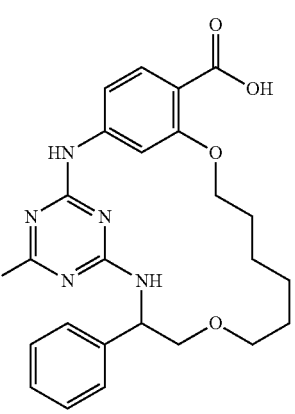

1807-In-03

152

-continued

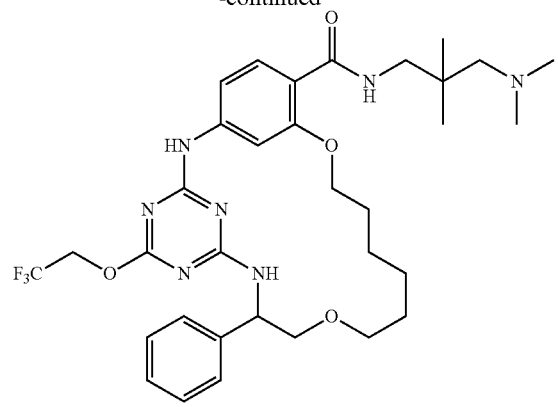

1807

Stage 1: By following the same procedure of synthesis of Compound 1005-In using 2-amino-2-phenylethanol instead of 4-(aminomethyl)phenol, it led to the formation of Compound 1807-In-01.

| | Compound 1807-In-01 |
|---|---|
| MS (M + H)+ Calcd. | 480.1 |
| MS (M + H)+ Observ. | 480.2 |
| Retention Time | 2.37 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3 u |

Stage 2: By following the same procedure of synthesis of Compound 1805 using Compound 1807-In-01 as the starting material, it led to the formation of Compound 1807-In-02.

| | Compound 1807-In-02 |
|---|---|
| MS (M + H)+ Calcd. | 562.2 |
| MS (M + H)+ Observ. | 562.3 |
| Retention Time | 3.91 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3 u |

Stage 3: By following the same procedure of synthesis of Compound 1806 using Compound 1807-In-02 as the starting material, it led to the formation of Compound 1807.

| Compound 1807 | |
|---|---|
| MS (M + H)+ Calcd. | 660.3 |
| MS (M + H)+ Observ. | 660.2 |
| Retention Time | 2.97 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |
The next section describes the synthesis of 2000 series compounds.
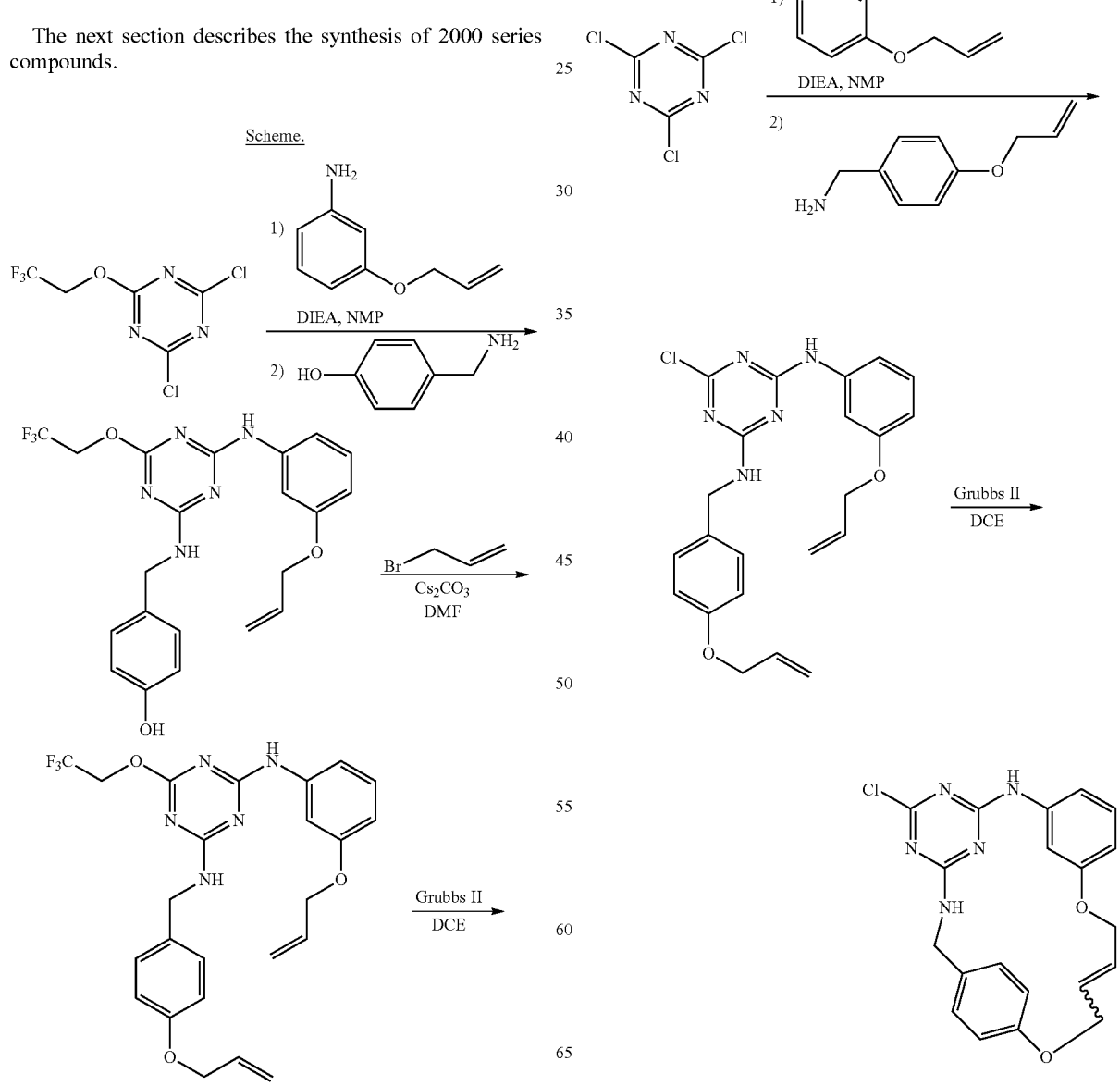

Scheme.
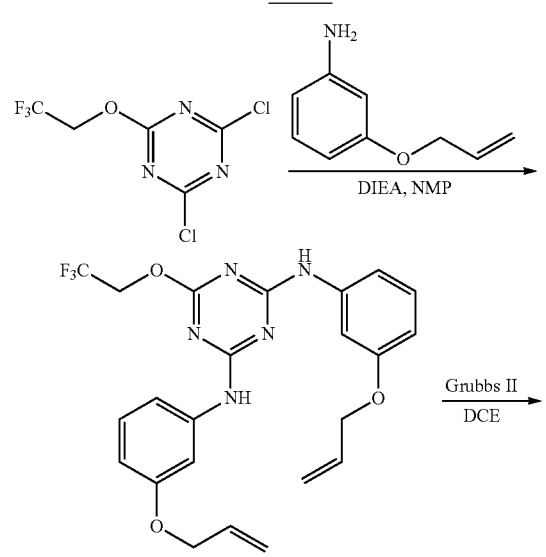
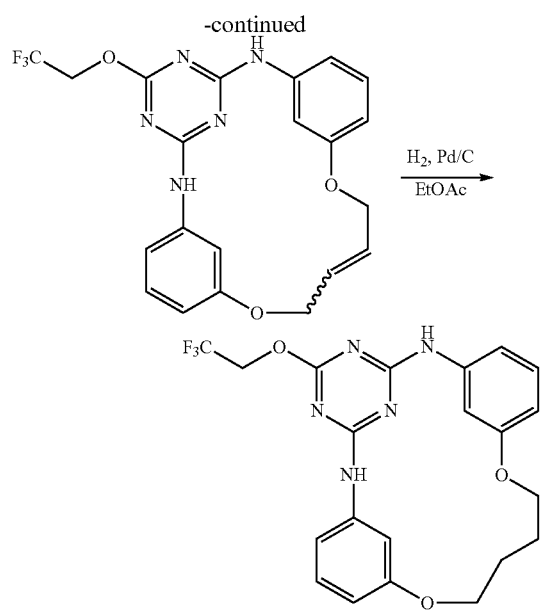
Scheme:
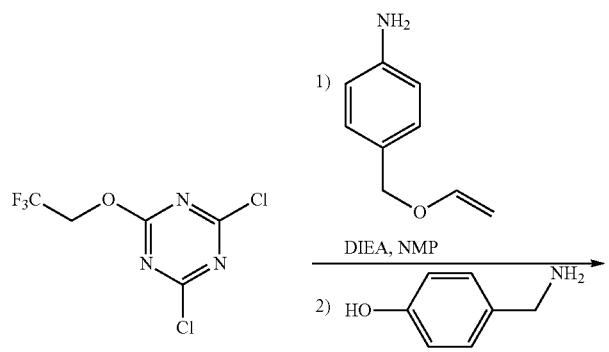
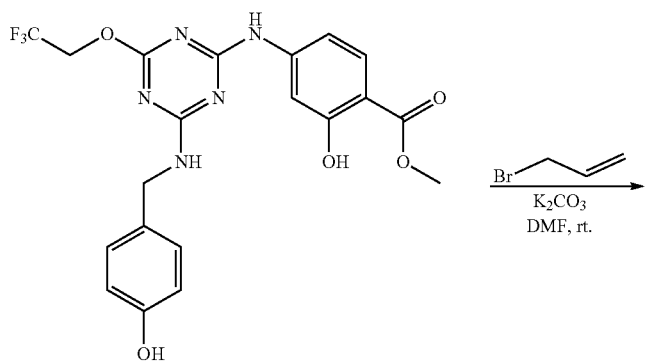

-continued
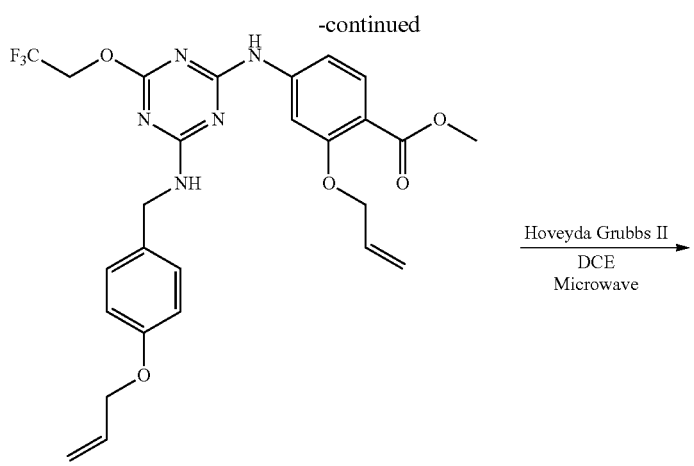
Hoveyda Grubbs II
―――――――→
DCE
Microwave
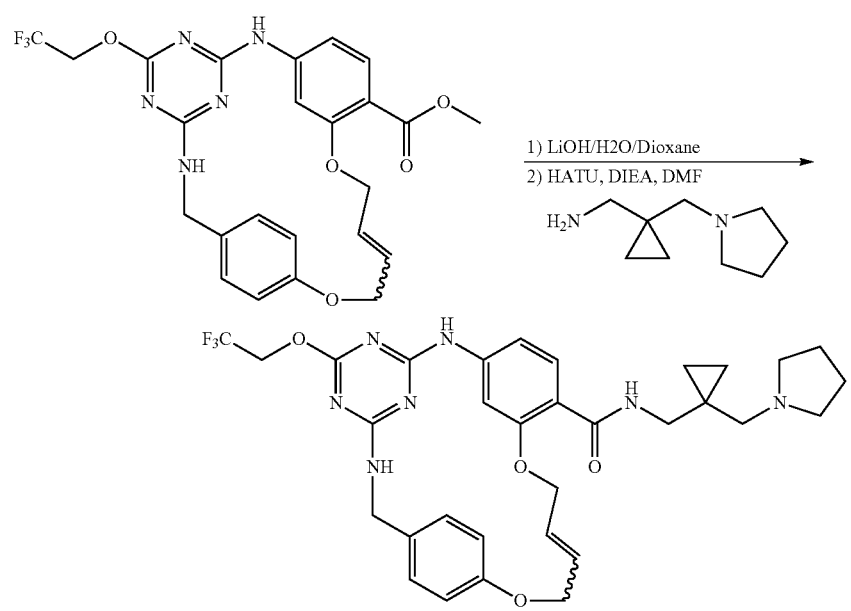
1) LiOH/H2O/Dioxane
―――――――――→
2) HATU, DIEA, DMF
Scheme.
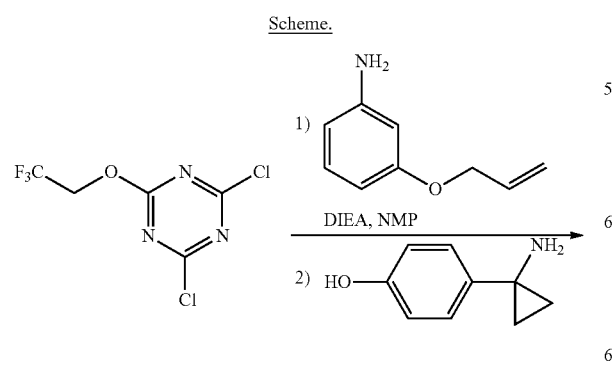
DIEA, NMP
―――――――→
-continued
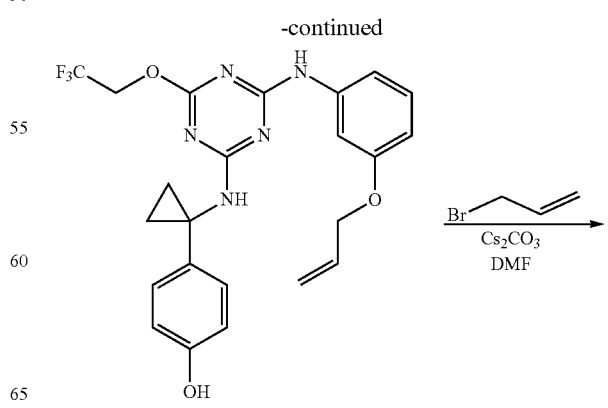
Br⌒⌒
―――――→
Cs2CO3
DMF

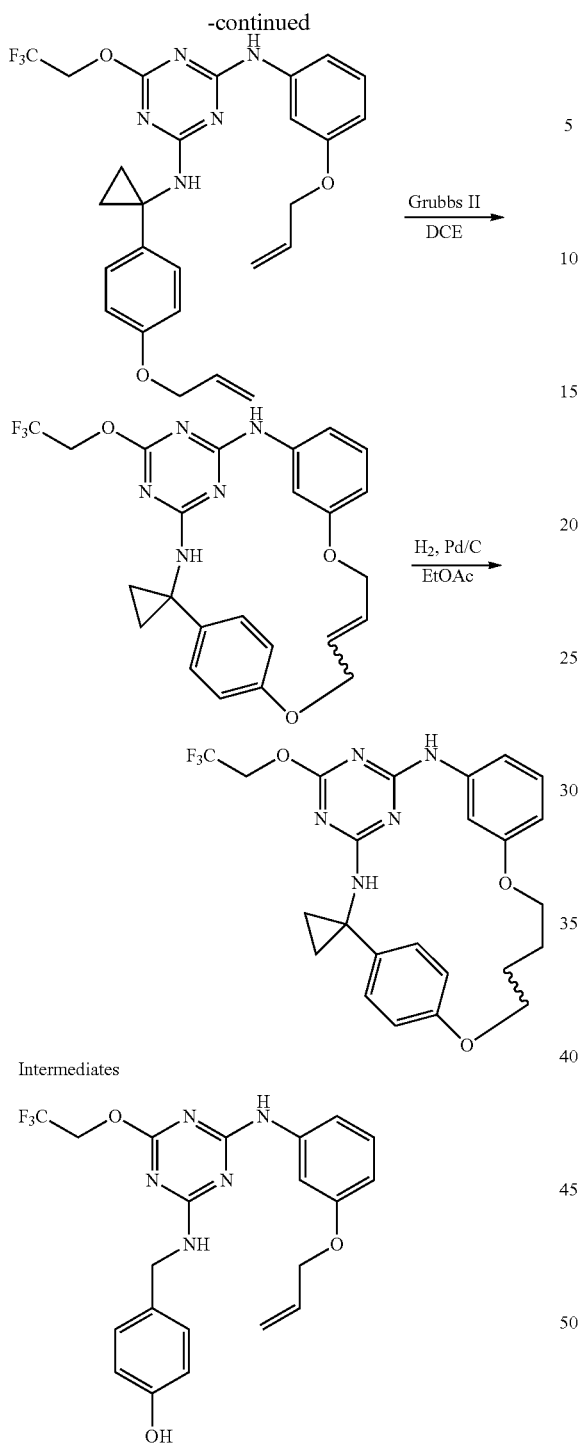

Intermediates 4-((4-(3-(allyloxy)phenylamino)-6-(2,2,2-trifluoroethoxy)-1,3,5-triazin-2-ylamino)-methyl)phenol, TFA salt. To a 0.1 M solution of 2,4-dichloro-6-(2,2,2-trifluoroethoxy)-1,3,5-triazine in N-methylpyrrolidine (8 ml, 0.8 mmol) was added 3-(allyloxy)aniline (119 mg, 0.8 mmol) and diisopropylethylamine (DIEA) (0.28 ml, 1.6 mmol) at room temperature. The resulting mixture was stirred at room temperature for ½ hr. and the completion of the reaction was monitored by LC/MS. 4-(Aminomethyl)phenol (99 mg, 0.8 mmol) was added, followed by diisopropylethylamine (DIEA) (0.28 ml, 1.6 mmol). The reaction mixture was stirred at room temperature for 16 hrs. The reaction mixture was purified by preparative HPLC to afford 169 mg (37.6%) of the title compound as TFA salt. 1H NMR (500 MHz, MeOD) δ ppm 4.41-4.52 (m, 2 H), 4.57 (s, 2 H), 4.89-4.97 (m, 2 H), 5.18-5.49 (m, 2 H), 5.93-6.14 (m, 1 H), 6.68 (dd, J=8.09, 1.98 Hz, 1 H), 6.76 (d, J=8.55 Hz, 2 H), 7.10 (d, J=7.63 Hz, 1 H), 7.16-7.27 (m, 3 H), 7.33-7.58 (m, 1 H).

| 4-((4-(3-(allyloxy)phenylamino)-6-(2,2,2-trifluoroethoxy)-1,3,5-triazin-2-ylamino)methyl)phenol, TFA salt | |
|---|---|
| MS (M + H)+ Calcd. | 448 |
| MS (M + H)+ Observ. | 447.96 |
| Retention Time | 2.562 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

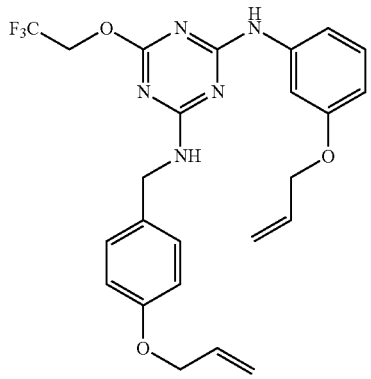 [SMILES: C=CCOc1ccc(CNc2nc(Nc3cccc(OCC=C)c3)nc(OCC(F)(F)F)n2)cc1]

N2-(4-(allyloxy)benzyl)-N4-(3-(allyloxy)phenyl)-6-(2,2,2-trifluoroethoxy)-1,3,5-triazine-2,4-diamine, TFA salt. To a solution of 4-((4-(3-(allyloxy)phenylamino)-6-(2,2,2-trifluoroethoxy)-1,3,5-triazin-2-ylamino)methyl)phenol, TFA (145 mg, 0.258 mmol) in DMF (5 ml) was added cesium carbonate (252 mg, 0.775 mmol). The mixture was stirred at 45° C. for 20 mins. 3-Bromoprop-1-ene (46.9 mg, 0.387 mmol) was added and the resulting mixture was stirred at room temperature for 72 hrs. The completion of the reaction was monitored by LC/MS. Purification of the reaction mixture by preparative HPLC gave 55 mg (35.4%) of the title compound as TFA salt. 1H NMR (400 MHz, DMSO-$d_6$) δ ppm 4.28-4.62 (m, 6 H), 4.86-5.11 (m, 2 H), 5.16-5.32 (m, 2 H), 5.32-5.59 (m, 2 H), 5.95-6.18 (m, 2 H), 6.52-6.70 (m, 1 H), 6.80-7.03 (m, 2 H), 7.08-7.38 (m, 4 H), 7.47 (br. s., 1 H), 8.27 (br. s., 1 H), 9.47-9.88 (m, 1 H).

| N2-(4-(allyloxy)benzyl)-N4-(3-(allyloxy)phenyl)-6-(2,2,2-trifluoroethoxy)-1,3,5-triazine-2,4-diamine, TFA salt. | |
|---|---|
| MS (M + H)+ Calcd. | 488 |
| MS (M + H)+ Observ. | 488.05 |
| Retention Time | 2.908 min |

N2-(4-(allyloxy)benzyl)-N4-(3-(allyloxy)phenyl)-6-(2,2,2-trifluoroethoxy)-1,3,5-triazine-2,4-diamine, TFA salt.

| LC Condition | |
|---|---|
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

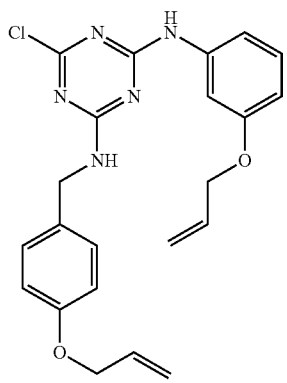 [SMILES: C=CCOc1ccc(CNc2nc(Cl)nc(Nc3cccc(OCC=C)c3)n2)cc1]

N2-(4-(allyloxy)benzyl)-N4-(3-(allyloxy)phenyl)-6-chloro-1,3,5-triazine-2,4-diamine, TFA salt. A solution of 2,4,6-trichloro-1,3,5-triazine (184 mg, 0.998 mmol) in NMP (6 ml) was cooled down to 0° C. At 0° C. 3-(allyloxy)aniline (149 mg, 0.998 mmol)) was added followed by N,N-Diisopropylethylamine (387 mg, 2.99 mmol). The resulting mixture was stirred at 0° C. for 3 hrs and the completion of the reaction was monitored by LC/MS. (4-(allyloxy)phenyl)methanamine, TFA (277 mg, 0.998 mmol) and N,N-Diisopropylethylamine (387 mg, 2.99 mmol) were added. The reaction mixture was stirred at room temperature for 16 hrs. The reaction mixture was purified by preparative HPLC to afford 150 mg (35.5%) of the title compound as TFA salt. 1H NMR (500 MHz, MeOD) δ ppm 4.41-4.63 (m, 6 H), 5.19-5.30 (m, 2 H), 5.32-5.47 (m, 2 H), 5.96-6.13 (m, 2 H), 6.62-6.71 (m, 1 H), 6.87-6.95 (m, 2 H), 7.04-7.22 (m, 2 H), 7.25-7.34 (m, 2 H), 7.47 (s, 1 H).

N2-(4-(allyloxy)benzyl)-N4-(3-(allyloxy)phenyl)-6-chloro-1,3,5-triazine-2,4-diamine, TFA salt.

| | |
|---|---|
| MS (M + H)+ Calcd. | 424 |
| MS (M + H)+ Observ. | 423.99 |
| Retention Time | 2.821 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |

N2-(4-(allyloxy)benzyl)-N4-(3-(allyloxy)phenyl)-6-chloro-1,3,5-triazine-2,4-diamine, TFA salt.

| | |
|---|---|
| Solvent Pair | methanol:Water:TFA |
| Column | Phenomenex Luna 3 × 50 mm S10 |

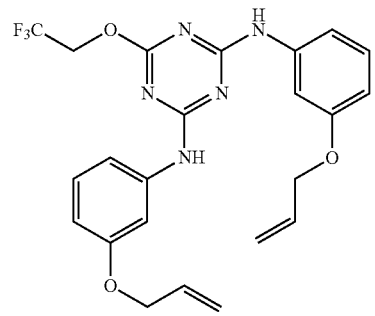 [SMILES: C=CCOc1cccc(Nc2nc(Nc3cccc(OCC=C)c3)nc(OCC(F)(F)F)n2)c1]

N2,N4-bis(3-(allyloxy)phenyl)-6-(2,2,2-trifluoroethoxy)-1,3,5-triazine-2,4-diamine, TFA salt. To a 0.1 M solution of 2,4-dichloro-6-(2,2,2-trifluoroethoxy)-1,3,5-triazine in N-methylpyrrolidine (8 ml, 0.8 mmol) was added 3-(allyloxy)aniline (239 mg, 1.6 mmol) and diisopropylethylamine (DIEA) (0.559 ml, 3.2 mmol) at room temperature. The resulting mixture was stirred at 40° C. for 70 hrs. The reaction mixture was purified by preparative HPLC to afford 158 mg (33.6%) of the title compound as TFA salt. 1H NMR (500 MHz, DMSO-d6) δ ppm 4.42-4.63 (m, 4 H), 5.04 (q, J=8.85 Hz, 2 H), 5.26 (d, J=10.68 Hz, 2 H), 5.39 (d, J=16.79 Hz, 2 H), 5.95-6.11 (m, 2 H), 6.65 (dd, J=8.85, 2.44 Hz, 2 H), 7.10-7.50 (m, 6 H), 9.71-9.96 (m, 2 H).

N2,N4-bis(3-(allyloxy)phenyl)-6-(2,2,2-trifluoroethoxy)-1,3,5-triazine-2,4-diamine, TFA salt.

| | |
|---|---|
| MS (M + H)+ Calcd. | 474 |
| MS (M + H)+ Observ. | 474.06 |
| Retention Time | 2.067 min |
| LC Condition | |
| Solvent A | 5% MeOH:95% Water:10 mM Ammonium Acetate |
| Solvent B | 95% MeOH:5% Water:10 mM Ammonium Acetate |
| Start % B | 0 |
| Final % B | 100 |
| Gradient Time | 2 min |
| Flow Rate | 4 mL/min |
| Wavelength | 220 |
| Solvent Pair | MeOH:Water:Ammonium Acetate |
| Column | Phenomenex Luna 3 × 50 mm S10 |

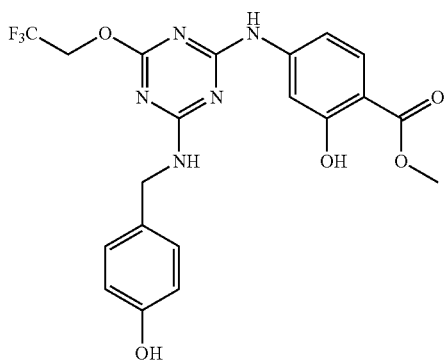 [SMILES: COC(=O)c1ccc(Nc2nc(NCc3ccc(O)cc3)nc(OCC(F)(F)F)n2)cc1O]

Methyl 2-hydroxy-4-(4-(4-hydroxybenzylamino)-6-(2,2,2-trifluoroethoxy)-1,3,5-triazin-2-ylamino)benzoate, TFA salt. To a 0.1 M solution of 2,4-dichloro-6-(2,2,2-trifluoroethoxy)-1,3,5-triazine in N-methylpyrrolidine (10 ml, 1.0 mmol) was added methyl 4-amino-2-hydroxybenzoate (167 mg, 1.000 mmol), followed by DIEA (0.35 ml, 2.00 mmol) at room temperature. The resulting mixture was stirred at room temperature for ½ hr. and the completion of the reaction was monitored by LC/MS. 4-(Aminomethyl)phenol (123 mg, 1.0 mmol) was added, followed by diisopropylethylamine (DIEA) (0.35 ml, 2.0 mmol). The reaction mixture was stirred at room temperature for 16 hrs. The reaction mixture was purified by preparative HPLC to afford 208 mg (35.9%) of the title compound as TFA salt. 1H NMR (400 MHz, DMSO-$d_6$) δ ppm 3.91 (s, 3 H), 4.44 (dd, J=14.81, 6.27 Hz, 2 H), 4.84-5.08 (m, 2 H), 6.63-6.83 (m, 2 H), 7.03-7.37 (m, 3 H), 7.44-7.87 (m, 2 H), 8.40 (br. s., 1 H), 9.26 (s, 1 H), 9.78-10.27 (m, 1 H), 10.69 (d, J=8.78 Hz, 1 H).

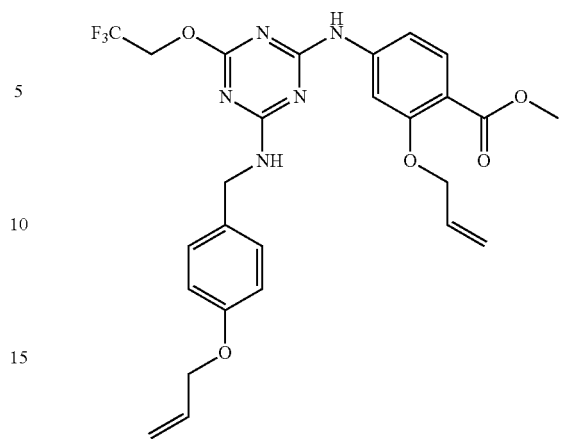

Methyl 2-(allyloxy)-4-(4-(4-(allyloxy)benzylamino)-6-(2,2,2-trifluoroethoxy)-1,3,5-triazin-2-ylamino)benzoate, TFA salt. To a solution of methyl 2-hydroxy-4-(4-(4-hydroxybenzylamino)-6-(2,2,2-trifluoroethoxy)-1,3,5-triazin-2-ylamino)benzoate, TFA (180 mg, 0.311 mmol) in DMF (4 ml) was added potassium carbonate (129 mg, 0.932 mmol). The mixture was stirred at 45° C. for 20 mins. 3-Bromoprop-1-ene (113 mg, 0.932 mmol) was added and the resulting mixture was stirred at room temperature for 7 hrs. The completion of the reaction was monitored by LC/MS. Purification of the reaction mixture by preparative HPLC gave 104 mg (50.8%) of the title compound as TFA salt. 1H NMR (500 MHz, MeOD) δ ppm 3.85 (s, 3 H), 4.36-4.60 (m, 4 H), 4.65 (s, 2 H), 4.93-5.05 (m, 2 H), 5.14-5.67 (m, 4 H), 6.11-6.03 (m, 2 H), 6.79-6.99 (m, 2 H), 7.16 (d, J=9.46 Hz, 1 H), 7.24-7.41 (m, 2 H), 7.59-7.86 (m, 2 H).

| Methyl 2-hydroxy-4-(4-(4-hydroxybenzylamino)-6-(2,2,2-trifluoroethoxy)-1,3,5-triazin-2-ylamino)benzoate, TFA salt. | |
|---|---|
| MS (M + H)+ Calcd. | 466 |
| MS (M + H)+ Observ. | 465.99 |
| Retention Time | 2.528 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

| Methyl 2-(allyloxy)-4-(4-(4-(allyloxy)benzylamino)-6-(2,2,2-trifluoroethoxy)-1,3,5-triazin-2-ylamino)benzoate, TFA salt. | |
|---|---|
| MS (M + H)+ Calcd. | 546 |
| MS (M + H)+ Observ. | 545.91 |
| Retention Time | 2.868 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

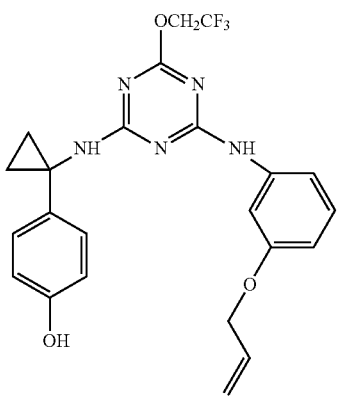

4-(1-(4-(3-(allyloxy)phenylamino)-6-(2,2,2-trifluoroethoxy)-1,3,5-triazin-2-ylamino)cyclopropyl)phenol, TFA salt. To a 0.15 M solution of 2,4-dichloro-6-(2,2,2-trifluoroethoxy)-1,3,5-triazine in N-methylpyrrolidine (6 ml, 0.9 mmol) was added 3-(allyloxy)aniline (134 mg, 0.9 mmol) and diisopropylethylamine (DIEA) (349 mg, 2.7 mmol) at room temperature. The resulting mixture was stirred at room temperature for 18 h. The reaction mixture was purified by preparative HPLC to afford 167 mg (39%) of the title compound as TFA salt. 1H NMR (500 MHz, DMSO-$d_6$) δ ppm 1.27 (m, 4H), 4.15-4.17 (m, 2H), 4.41-4.6 (m, 4 H), 5.27-5.42 (m, 2 H), 6.07 (s, 1 H), 6.66-6.68 (m, 3 H), 7.10-7.16 (m, 4 H).

| 4-(1-(4-(3-(allyloxy)phenylamino)-6-(2,2,2-trifluoroethoxy)-1,3,5-triazin-2-ylamino)cyclopropyl)phenol, TFA salt. | |
|---|---|
| MS (M + H)+ Calcd. | 473.45 |
| MS (M + H)+ Observ. | 474.25 |
| Retention Time | 2.527 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

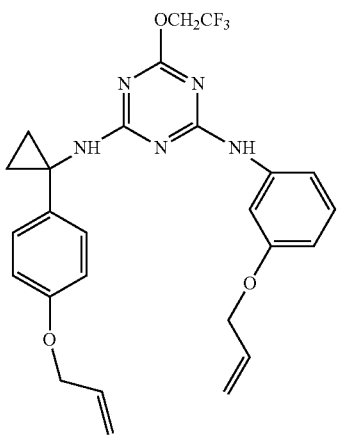

N2-(3-(allyloxy)phenyl)-N4-(1-(4-(allyloxy)phenyl)cyclopropyl)-6-(2,2,2-trifluoroethoxy)-1,3,5-triazine-2,4-diamine TFA salt. To a 0.1 M solution of 2,4-dichloro-6-(2,2,2-trifluoroethoxy)-1,3,5-triazine in N-methylpyrrolidine (10 ml, 1.0 mmol) was added methyl 4-amino-2-hydroxybenzoate (167 mg, 1.000 mmol), followed by DIEA (0.35 ml, 2.00 mmol) at room temperature. The resulting mixture was stirred at room temperature for ½ hr. and the completion of the reaction was monitored by LC/MS. 4-(Aminomethyl)phenol (123 mg, 1.0 mmol) was added, followed by diisopropylethylamine (DIEA) (0.35 ml, 2.0 mmol). The reaction mixture was stirred at room temperature for 16 hrs. The reaction mixture was purified by preparative HPLC to afford 208 mg (35.9%) of the title compound as TFA salt. 1H NMR (400 MHz, DMSO-$d_6$) δ ppm 1.31 (s, 4H), 4.41-4.57 (m, 4 H), 4.7-4.95 (m, 4H) 5.26-5.4 (m, 4H), 6.01 (s, 1H), 6.63-6.83 (m, 2 H), 7.03-7.37 (m, 3 H), 7.44-7.87 (m, 2 H).

| N2-(3-(allyloxy)phenyl)-N4-(1-(4-(allyloxy)phenyl)cyclopropyl)-6-(2,2,2-trifluoroethoxy)-1,3,5-triazine-2,4-diamine TFA salt | |
|---|---|
| MS (M + H)+ Calcd. | 513.51 |
| MS (M + H)+ Observ. | 514.66 |
| Retention Time | 2.88 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

Example 2001

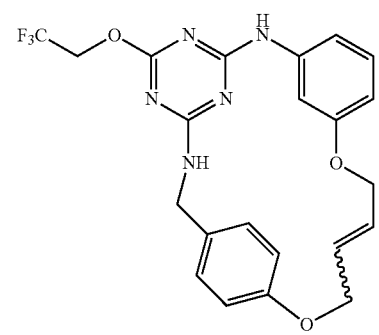 [SMILES: FC(F)(F)COc1nc2nc(n1)Nc1cccc(c1)OCC=CCOc1ccc(cc1)CN2]

To a solution of N2-(4-(allyloxy)benzyl)-N4-(3-(allyloxy)phenyl)-6-(2,2,2-trifluoroethoxy)-1,3,5-triazine-2,4-diamine (38 mg, 0.078 mmol) in DCE (40 ml) in a sealed tube, nitrogen was bubbled in for ½ hr. Under nitrogen GrubbsII catalyst (10 mg, 0.03 mmol) was added. The reaction mixture was sealed and stirred at 80° C. for 5 hrs. The solvent was evaporated and the residue was purified by preparative HPLC to afford 8 mg (17.9%) of the above compound as TFA salt. Preparative HPLC condition: Phenomenex Luna C18 30×100 mm S10, 30 to 100% B over 18 minute gradient, 6 minute hold time, A=10% methanol 90% water 0.1% TFA, B=90% methanol 10% water 0.1% TFA. Flow rate: 35 ml/min. 1H NMR (500 MHz, MeOD) δ ppm 4.29 (s, 2 H), 4.56-4.72 (m, 4 H), 4.93-5.01 (m, 2 H), 5.64-5.87 (m, 2 H), 6.49 (d, J=8.85 Hz, 2 H), 6.67 (s, 1 H), 6.78-6.92 (m, 3 H), 7.02-7.15 (m, 1 H), 7.34-7.36 (m, 1 H).

| Example 2001 | |
|---|---|
| MS (M + H)+ Calcd. | 460 |
| MS (M + H)+ Observ. | 459.94 |
| Retention Time | 1.840 min |
| LC Condition | |
| Solvent A | 5% MeOH:95% Water:10 mM Ammonium Acetate |
| Solvent B | 95% MeOH:5% Water:10 mM Ammonium Acetate |
| Start % B | 0 |
| Final % B | 100 |
| Gradient Time | 2 min |
| Flow Rate | 4 mL/min |
| Wavelength | 220 |
| Solvent Pair | MeOH:Water:Ammonium Acetate |
| Column | Phenomenex Luna 3 × 50 mm S10 |

Example 2002

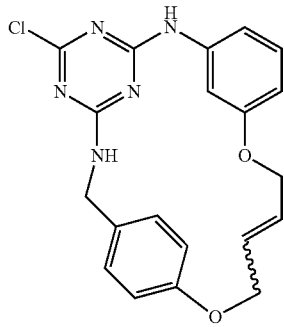 [SMILES: Clc1nc2nc(n1)Nc1cccc(c1)OCC=CCOc1ccc(cc1)CN2]

The above compound was prepared as a TFA salt from N2-(4-(allyloxy)benzyl)-N4-(3-(allyloxy)phenyl)-6-chloro-1,3,5-triazine-2,4-diamine, TFA salt by analogy to Example 2001. 1H NMR (500 MHz, MeOD) δ ppm 4.25 (s, 2 H), 4.60-4.65 (m, 4 H), 5.70-5.81 (m, 2 H), 6.47-6.51 (m, 2 H), 6.67 (s, 1 H), 6.76-6.80 (m, 1 H), 6.86 (d, J=8.55 Hz, 2 H), 7.04-7.08 (m, 1 H), 7.29-7.32 (m, 1 H).

| Example 2002 | |
|---|---|
| MS (M + H)+ Calcd. | 396 |
| MS (M + H)+ Observ. | 396.15 |
| Retention Time | 2.180 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

Example 2003

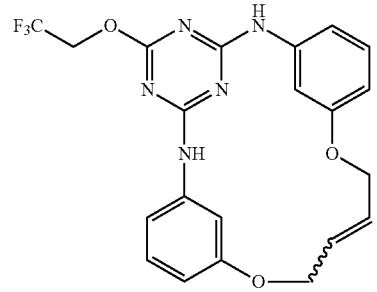 [SMILES: FC(F)(F)COc1nc2nc(n1)Nc1cccc(c1)OCC=CCOc1cccc(c1)N2]

The above compound was prepared as a TFA salt from N2,N4-bis(3-(allyloxy)-phenyl)-6-(2,2,2-trifluoroethoxy)-1,3,5-triazine-2,4-diamine, TFA salt by analogy to Example 2001. 1H NMR (500 MHz, MeOD) δ ppm 4.72 (d, J=2.14 Hz, 4 H), 4.91-4.99 (m, 2 H), 5.78 (t, J=2.29 Hz, 2 H), 6.59-6.78 (m, 4 H), 7.21 (t, J=8.24 Hz, 2 H), 7.68 (t, J=2.29 Hz, 2 H).

| Example 2003 | |
|---|---|
| MS (M + H)+ Calcd. | 446 |
| MS (M + H)+ Observ. | 446.00 |
| Retention Time | 2.730 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

Example 2004

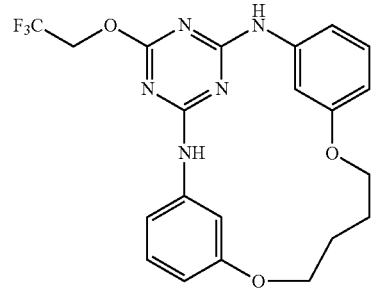

To a solution of example 2003 (20 mg, 0.036 mmol) in ethyl acetate (10 ml) was added 10% palladium on carbon (5 mg, 0.047 mmol). The reaction mixture was stirred under hydrogen balloon at room temperature for 5 h. The reaction mixture was filtered through a pad of celite. The solvent was evaporated and the residue was purified by preparative HPLC to afford 15 mg (74.7%) of the above compound as TFA salt. Preparative HPLC condition: Phenomenex Luna C18 30×100 mm S10, 30 to 100% B over 18 minute gradient, 6 minute hold time, A=10% methanol 90% water 0.1% TFA, B=90% methanol 10% water 0.1% TFA. Flow rate: 35 ml/min.

1H NMR (500 MHz, MeOD) δ ppm 2.00 (dt, J=5.57, 2.86 Hz, 4 H), 4.13-4.28 (m, 4 H), 4.91-4.99 (m, 2 H), 6.59-6.75 (m, 4 H), 7.14-7.28 (m, 2 H), 7.79-7.80 (m, 2 H).

| Example 2004 | |
|---|---|
| MS (M + H)⁺ Calcd. | 448 |
| MS (M + H)⁺ Observ. | 447.95 |
| Retention Time | 2.753 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

Example 2005

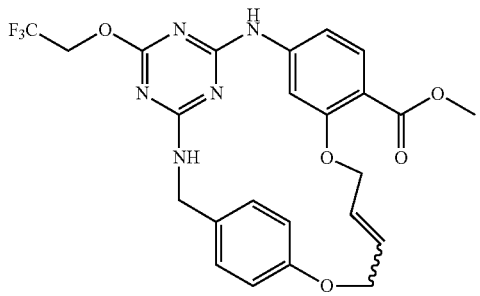 [SMILES: COC(=O)c1ccc2cc1OCC=CCOc1ccc(cc1)CNc1nc(nc(OCC(F)(F)F)n1)N2]

To a solution of methyl 2-(allyloxy)-4-(4-(4-(allyloxy) benzylamino)-6-(2,2,2-trifluoroethoxy)-1,3,5-triazin-2-ylamino)benzoate, TFA (45 mg, 0.068 mmol) in DCE (10 ml) in a 20 ml microwave tube, nitrogen was bubbled in for ½ hr. Under nitrogen Hoveyda GrubbsII catalyst (6 mg, 0.007 mmol) was added. The reaction mixture was heated by microwave at 130° C. for 15 mins. The solvent was evaporated and the residue was purified by preparative HPLC to afford 9 mg (20.9%) of the above compound as TFA salt. Preparative HPLC condition: Phenomenex Luna C18 30×100 mm S10, 15 to 75% B over 12 minute gradient, 8 minute hold time, A=10% methanol 90% water 0.1% TFA, B=90% methanol 10% water 0.1% TFA. Flow rate: 35 ml/min. 1H NMR (500 MHz, MeOD) δ ppm 3.95 (s, 3 H), 4.28 (s, 2 H), 4.60 (d, J=5.49 Hz, 2 H), 4.69 (d, J=6.71 Hz, 2 H), 4.85-4.91 (m, 2 H), 5.60-5.70 (m, 1 H), 5.79-5.90 (m, 1 H), 6.43 (d, J=8.55 Hz, 2 H), 6.76 (s, 1 H), 6.85 (d, J=8.55 Hz, 2 H), 7.32-7.34 (m, 1 H), 7.86 (dd, 1 H).

| Example 2005 | |
|---|---|
| MS (M + H)⁺ Calcd. | 518 |
| MS (M + H)⁺ Observ. | 517.84 |
| Retention Time | 2.322 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

Example 2006

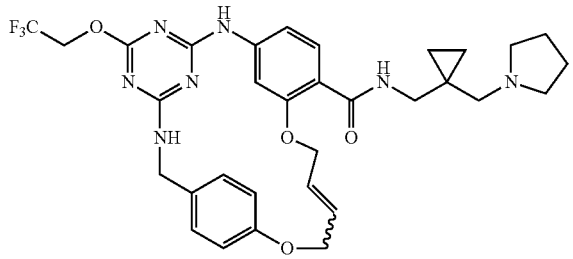 [SMILES: O=C(NCC1(CN2CCCC2)CC1)c1ccc2cc1OCC=CCOc1ccc(cc1)CNc1nc(nc(OCC(F)(F)F)n1)N2]

To a solution of example 2005 (8 mg, 0.013 mmol) in Dioxane (1 ml) was added 1N LiOH (0.5 ml, 0.5 mmol). The mixture was heated at 45° C. for 2 hrs and the completion of the reaction was monitored by LC/MS. The solvent was removed and the residue was dissolved in DMF (1 mL). (1-(pyrrolidin-1-ylmethyl)cyclopropyl)methanamine (4.00 mg, 0.026 mmol) was added followed by HATU (9.85 mg, 0.026 mmol) and DIEA (9.05 μL, 0.052 mmol). The reaction mixture as stirred at room temperature for 1 hr. The reaction mixture was purified by preparative HPLC to afford 7 mg (61.5%) of the above compound as TFA salt. Preparative HPLC condition: Phenomenex Luna C18 30×100 mm S10, 15 to 75% B over 14 minute gradient, 8 minute hold time, A=10% methanol 90% water 0.1% TFA, B=90% methanol 10% water 0.1% TFA. Flow rate: 35 ml/min. 1H NMR (500 MHz, MeOD) δ ppm 0.75-0.81 (m, 2 H), 0.88-0.95 (m, 2 H), 2.14-2.28 (m, 4 H), 3.18 (br. s., 4 H), 3.49-3.57 (m, 2 H), 3.80-3.90 (m, 2 H), 4.25 (s, 2 H), 4.60 (d, J=5.19 Hz, 2 H), 4.84-4.89 (m, 4 H), 5.70-5.89 (m, 2 H), 6.36 (d, J=8.55 Hz, 2 H), 6.76 (d, J=2.14 Hz, 1 H), 6.82 (d, J=8.85 Hz, 2 H), 7.43 (dd, J=8.55, 2.14 Hz, 1 H), 8.09 (d, 1 H).

| Example 2006 | |
|---|---|
| MS (M + H)⁺ Calcd. | 640 |
| MS (M + H)⁺ Observ. | 640.23 |
| Retention Time | 1.627 min |
| | LC Condition |
| Solvent A | 5% MeOH:95% Water:10 mM Ammonium Acetate |
| Solvent B | 95% MeOH:5% Water:10 mM Ammonium Acetate |
| Start % B | 0 |
| Final % B | 100 |
| Gradient Time | 2 min |
| Flow Rate | 4 mL/min |
| Wavelength | 220 |
| Solvent Pair | MeOH:Water:Ammonium Acetate |
| Column | Phenomenex Luna 3 × 50 mm S10 |

Example 2007

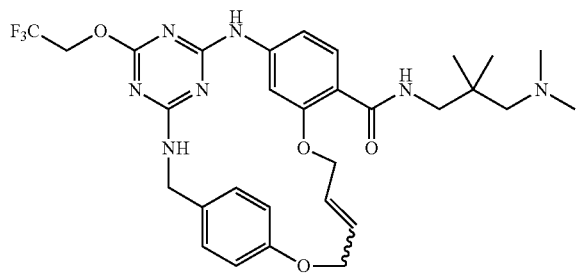 [SMILES: CN(C)CC(C)(C)CNC(=O)c1ccc2cc1OCC=CCOc1ccc(cc1)CNc1nc(nc(OCC(F)(F)F)n1)N2]

The above compound was prepared as a TFA salt by analogy to Example 2006. 1H NMR (500 MHz, MeOD) δ ppm 1.23 (s, 6 H), 3.06 (s, 6 H), 3.10 (s, 2 H), 3.55 (s, 2 H), 4.23 (s, 2 H), 4.61 (d, J=5.19 Hz, 2 H), 4.80-4.89 (m, 4 H), 5.71-5.91 (m, 2 H), 6.37 (d, J=8.85 Hz, 2 H), 6.73 (s, 1 H), 6.81 (d, J=8.55 Hz, 2 H), 7.42 (dd, J=8.55, 1.83 Hz, 1 H), 8.01 (d, 1 H).

| Example 2007 | |
|---|---|
| MS (M + H)+ Calcd. | 616 |
| MS (M + H)+ Observ. | 616.03 |
| Retention Time | 1.775 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 3 min |
| Flow Rate | 4 mL/min |
| Wavelength | 220 |
| Solvent Pair | methanol:Water:TFA |
| Column | Phenomenex Luna 3 × 50 mm S10 |

Example 2008

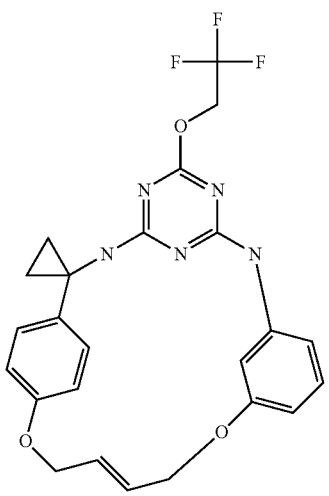 [SMILES: FC(F)(F)COc1nc2nc(n1)NC1(CC1)c1ccc(cc1)OC/C=C/COc1cccc(c1)N2]

To a solution of N2-(3-(allyloxy)phenyl)-N4-(1-(4-(allyloxy)phenyl)cyclopropyl)-6-(2,2,2-trifluoroethoxy)-1,3,5-triazine-2,4-diamine TFA (60 mg, 0.117 mmol) in DCE (100 ml) in a 200 ml vial, nitrogen was bubbled in for 1 hr. Under nitrogen Hoveyda Grubbsll catalyst (6 mg, 0.007 mmol) was added. The reaction mixture was heated by microwave at 70° C. for 18 h. The solvent was evaporated and the residue was purified by preparative HPLC to afford 9 mg (20.9%) of the above compound as TFA salt. Preparative HPLC condition: Phenomenex Luna C18 30×100 mm S10, 30 to 100% B over 15 minute gradient, 8 minute hold time, A=10% methanol 90% water 0.1% TFA, B=90% methanol 10% water 0.1% TFA. Flow rate: 35 ml/min. 1H NMR (500 MHz, MeOD) δ ppm 1.18 (m, 2H), 2.33 (m, 2H), 4.63 (d, J=5.49 Hz, 2 H), 4.69 (d, J=6.71 Hz, 2 H), 4.85-4.91 (m, 2 H), 5.60-5.70 (m, 1 H), 5.79-5.90 (m, 1 H), 6.43 (d, J=8.55 Hz, 2 H), 6.76 (s, 1 H), 6.8 (1H), 6.85 (d, J=8.55 Hz, 2 H), 7.09 (S, 1H), 7.32-7.34 (m, 1 H).

| Example 2008 | |
|---|---|
| MS (M + H)+ Calcd. | 486 |
| MS (M + H)+ Observ. | 486.24 |
| Retention Time | 2.545 min |
| | LC Condition |
| Solvent A | 10% MeOH:90% Water:0.1% TFA |
| Solvent B | 90% MeOH:10% Water:0.1% TFA |
| Start % B | 0 |
| Final % B | 100 |
| Gradient Time | 3 min |
| Flow Rate | 4 mL/min |
| Wavelength | 220 |
| Solvent Pair | MeOH:Water:0.1% TFA |
| Column | Phenomenex Luna 3.0 × 50 mm S10 |

Example 2009

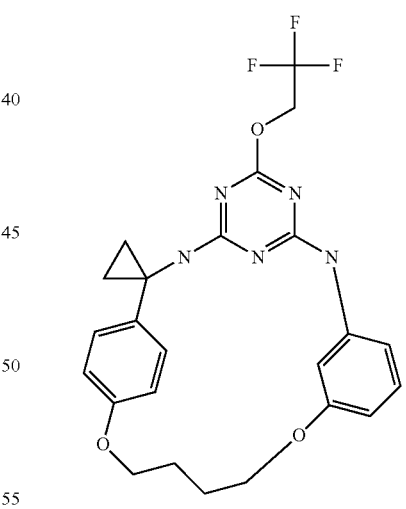

To a solution of example 2008 (5 mg, 0.010 mmol) in ethyl acetate (3 ml) was added 10% palladium on carbon (2 mg, 0.019 mmol). The reaction mixture was stirred under hydrogen balloon at room temperature for 5 h. The reaction mixture was filtered through a pad of celite. The solvent was evaporated and the residue was purified by preparative HPLC to afford 3 mg (47%) of the above compound as TFA salt. Preparative HPLC condition: Phenomenex Luna C18 30×100 mm S10, 30 to 100% B over 15 minute gradient, 6 minute hold time, A=10% methanol 90% water 0.1% TFA, B=90% methanol 10% water 0.1% TFA. Flow rate: 35 ml/min. 1H NMR (500 MHz, MeOD) δ ppm 1.22 (s, 4H), 1.84 (S,4H), 3.8 (m,2H), 4.13-4.28 (m, 2 H), 4.91-4.99 (m, 2 H), 6.56-6.57 (m, 2 H) 6.59-6.75 (m, 5 H), 7.15 (m, 1 H).

| Example 2009 | |
|---|---|
| MS (M + H)⁺ Calcd. | 487 |
| MS (M + H)⁺ Observ. | 488.3 |
| Retention Time | 1.922 min |
| LC Condition | |

| -continued | |
|---|---|
| Solvent A | 10% Acetonitrile:90% Water:0.1% TFA |
| Solvent B | 90% Acetonitrile:10% Water:0.1% TFA |
| Start % B | 0 |
| Final % B | 100 |
| Gradient Time | 2 min |
| Flow Rate | 1 mL/min |
| Wavelength | 220 |
| Solvent Pair | Acetonitrile:Water:0.1% TFA |
| Column | Phenomenex Luna 3 30 × 2, 3 u |

Procedures for the synthesis of 3000 series examples.

Scheme

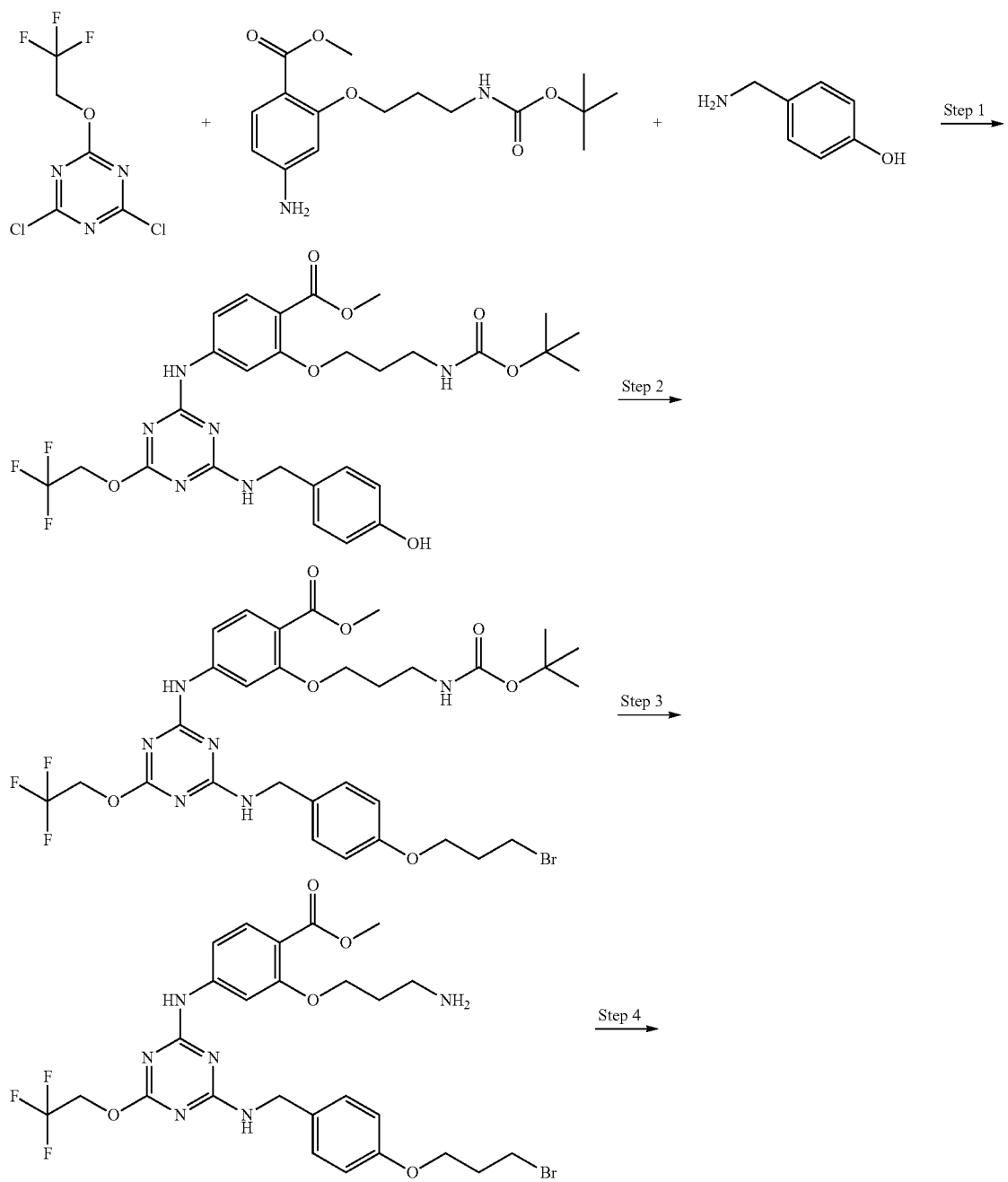

-continued
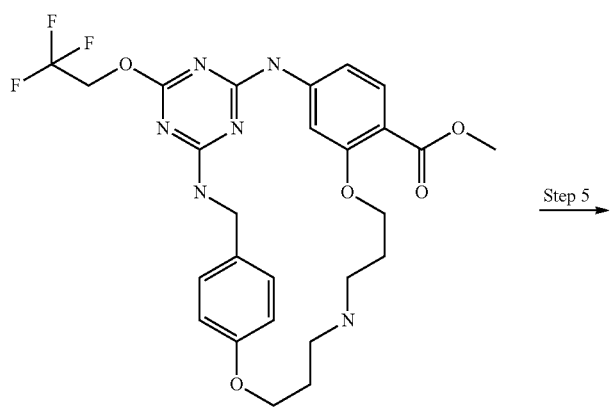
Step 5
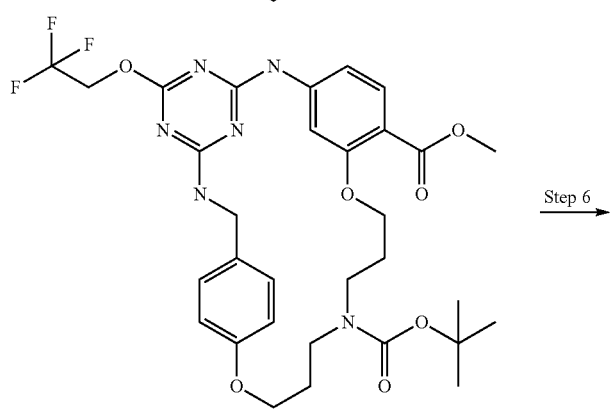
Step 6
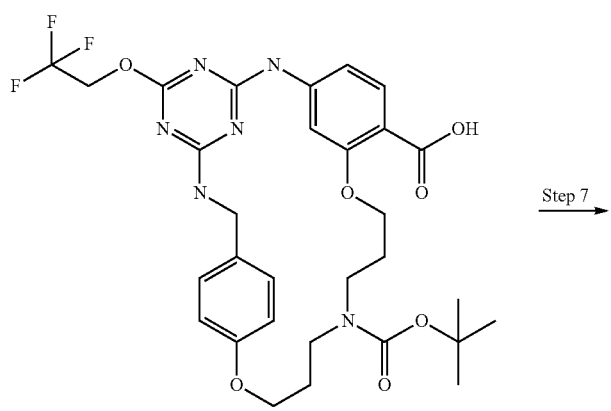
Step 7
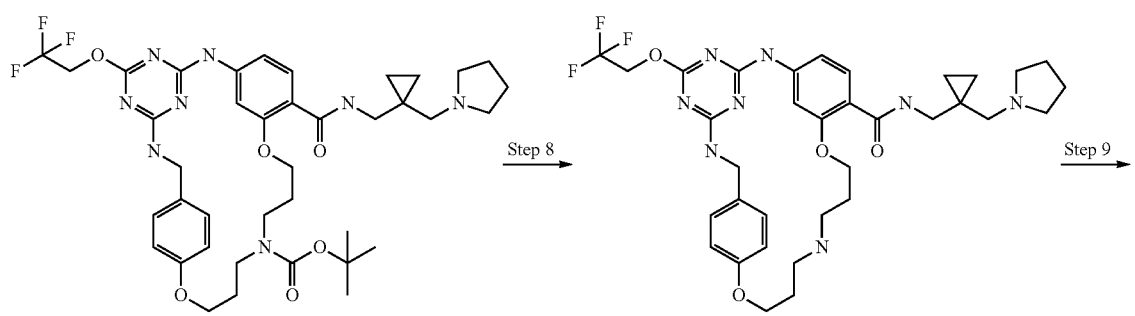
Step 8
Step 9
Step 10

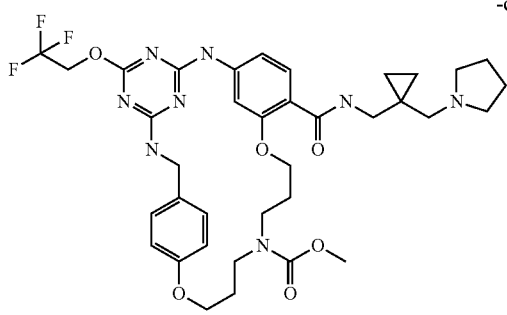
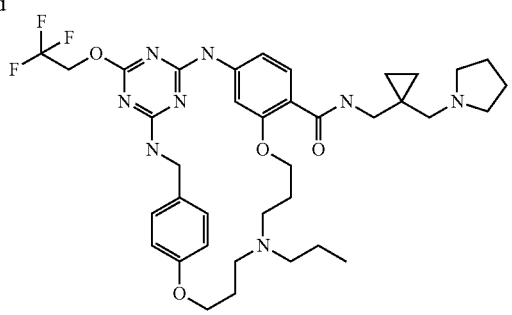

-continued

Step 1: To a solution of 2,4-dichloro-6-(2,2,2-trifluoroethoxy)-1,3,5-triazine (2.232 g, 9 mmol) and Hunig'sBase (3.14 mL, 18.00 mmol) in THF (20 mL) was added methyl 4-amino-2-(3-((tert-butoxycarbonyl)amino)propoxy)benzoate (2.92 g, 9.00 mmol). The resulting mixture was stirred for 16 h. The resulting solution will be used in the next step as it is. To the above solution was added Hunig'sBase (3.14 mL, 18.00 mmol) followed by 4-(aminomethyl)phenol (1.164 g, 9.45 mmol). The resulting mixture was refluxed for 1 h. The solvents were removed and purified by Biotage eluting with 50%-75% ethyl acetate in hexane to give 4.5 g of the desired product as a solid. MS m/z (M+ +H) 623.18.

Step 2: To a solution of methyl 2-(3-((tert-butoxycarbonyl)amino)propoxy)-4-((4-((4-hydroxybenzyl)amino)-6-(2,2,2-trifluoroethoxy)-1,3,5-triazin-2-yl)amino)benzoate (1.556 g, 2.5 mmol), 1,3-dibromopropane (1.009 g, 5.00 mmol), and 1,3-dibromopropane (1.009 g, 5.00 mmol) in acetone (50 mL) was added 1,3-dibromopropane (1.009 g, 5.00 mmol). The resulting solution was stirred for 16 h at reflux. After concentration, purification by Biotage eluting with 20-33% ethyl acetate in hexane to give 1300 mg of the desired product as a solid. MS m/z (M+ +H) 745.21.

Step 3: To a solution of methyl 4-((4-((4-(3-bromopropoxy)benzyl)amino)-6-(2,2,2-trifluoroethoxy)-1,3,5-triazin-2-yl)amino)-2-(3-((tert-butoxycarbonyl)amino)propoxy)benzoate (1.3 g, 1.748 mmol) in CH$_2$Cl$_2$ (10 mL) was added TFA (1.347 mL, 17.48 mmol). The resulting solution was stirred for 1 h. The solvents were removed and the residue was used as it was without any further purification. MS m/z (M+ +H) 645.11.

Step 4: To a solution of methyl 2-(3-aminopropoxy)-4-((4-((4-(3-bromopropoxy)benzyl)amino)-6-(2,2,2-trifluoroethoxy)-1,3,5-triazin-2-yl)amino)benzoate, TFA (1.136 g, 1.5 mmol) in vial in MeCN (15 mL) was added K$_2$CO$_3$ (0.829 g, 6.00 mmol). The resulting mixture was stirred in microwave at 130° C. for 1 h. After filtration washing with MeCN, the solvents were removed to give a crude product (840 mg) that will be used as it is. MS m/z (M+ +H) 563.12.

Step 5: To a solution of the Step 4 product (0.113 g, 0.2 mmol) in MeCN (10 mL) was added K$_2$CO$_3$ (0.111 g, 0.800 mmol) and BOC$_2$O (0.046 mL, 0.200 mmol). The resulting mixture was stirred for 16 h. After work up with ethyl acetate washing with water, the organic layer was dried over MgSO$_4$ and concentrated to give 90 mg of a crude product that will be used as it is. MS m/z (M+ +Na) 685.23.

Step 6: A mixture of the Step 5 product (440 mg, 0.664 mmol) and NaOH (531 mg, 13.28 mmol) in THF (10 mL) and Water (10.00 mL) was refluxed for 5 h. The THF was removed and neutralized with 1 N HCl, extracted with ethyl acetate, dried over MgSO$_4$, concentrated to give a 400 mg crude product that will be used as it is. MS m/z (M+ +Na) 671.21.

Step 7: To solution of the Step 6 product (350 mg, 0.540 mmol), Hunig'sBase (0.471 mL, 2.70 mmol) and (1-(pyrrolidin-1-ylmethyl)cyclopropyl)methanamine (125 mg, 0.809 mmol) in CH2Cl2 (8 mL) was added HATU (308 mg, 0.809 mmol). After stirring for 4 h and concentration, the mixture was purified by prep HPLC to give 60 mg of the desired product as TFA salt. MS m/z (M+ +H) 785.43.

Step 8: A solution of the Step 7 product (50 mg, 0.064 mmol), TFA (0.049 mL, 0.637 mmol) in CH$_2$Cl$_2$ (1 mL) was stirred for 0.5 h. After concentration, the residue was used in the next step as it is. MS m/z (M+ +H) 685.31.

Step 9: To a solution of the Step 8 product (10 mg, 0.015 mmol) and Hunig'sBase (0.026 mL, 0.146 mmol) in DMF (1 mL) was added dimethyl dicarbonate (5.87 mg, 0.044 mmol). The resulting mixture was stirred at rt for 5 min and quenched with MeOH. The solvents were removed and the residue was purified by prep HPLC to give 6 mg of the product as a FTA solid. MS m/z (M+ +H) 743.36.

Step 10: To a solution of the Step 8 product (7 mg, 10.22 μmol), acetic acid (0.614 mg, 10.22 μmol), and propionaldehyde (1.187 mg, 0.020 mmol) in MeOH (1 mL) added sodium cyanotrihydroborate (1.285 mg, 0.020 mmol). The resulting mixture was stirred for 3 h and purified by prep HPLC to give 5.4 mg of the desired product. MS m/z (M+ +H) 727.4.

TABLE 3
| Examples | Structures | Formula | MW | MS m/z (M + H) |
|---|---|---|---|---|
| 3001 | 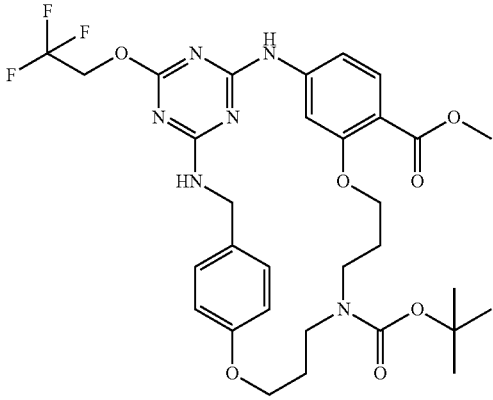 [SMILES: COC(=O)c1ccc2cc1OCCCN(C(=O)OC(C)(C)C)CCCOc1ccc(cc1)CNc1nc(nc(OCC(F)(F)F)n1)N2] | C31 H37 F3 N6 O7 | 662.66 | 685.18 (M + Na) |
| 3002 | 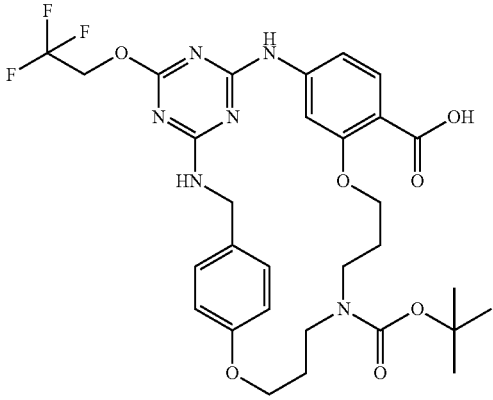 [SMILES: CC(C)(C)OC(=O)N1CCCOc2ccc(cc2)CNc2nc(nc(OCC(F)(F)F)n2)Nc2ccc(C(=O)O)c(c2)OCCC1] | C30 H35 F3 N6 O7 | 648.64 | 671.21 (M + Na) |
| 3003 | 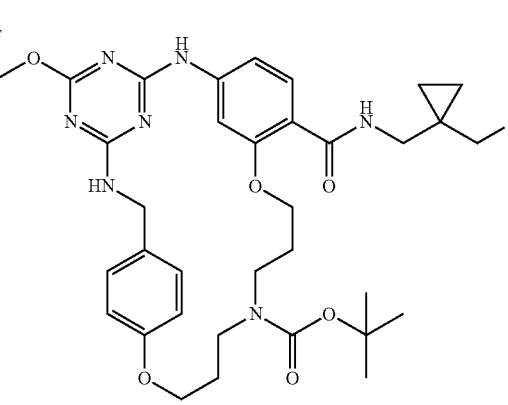 | C39 H51 F3 N8 O6 | 784.88 | 785.43 |

TABLE 3-continued

| Examples | Structures | Formula | MW | MS m/z (M + H) |
|---|---|---|---|---|
| 3004 | 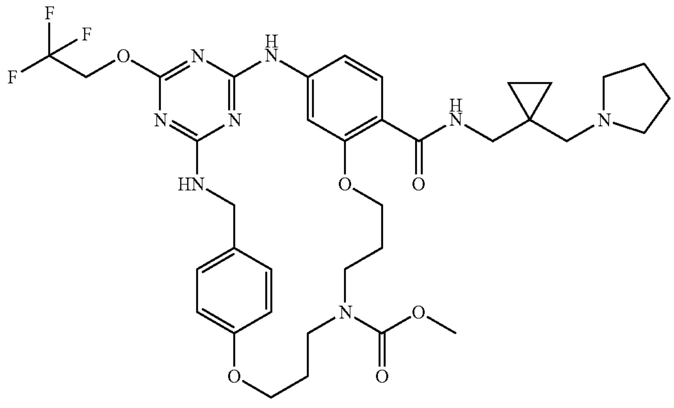 [SMILES: COC(=O)N1CCCOc2ccc(cc2)CNc2nc(nc(OCC(F)(F)F)n2)Nc2ccc(C(=O)NCC3(CN4CCCC4)CC3)c(c2)OCCC1] | C36 H45 F3 N8 O6 | 742.8 | 743.36 |
| 3005 | 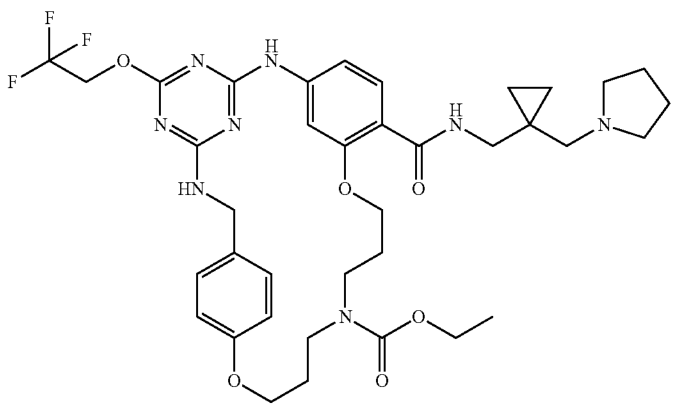 [SMILES: CCOC(=O)N1CCCOc2ccc(cc2)CNc2nc(nc(OCC(F)(F)F)n2)Nc2ccc(C(=O)NCC3(CN4CCCC4)CC3)c(c2)OCCC1] | C37 H47 F3 N8 O6 | 756.82 | 757.38 |
| 3006 | 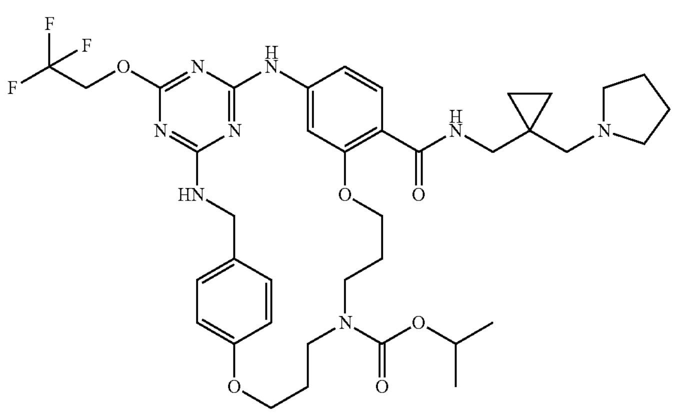 [SMILES: CC(C)OC(=O)N1CCCOc2ccc(cc2)CNc2nc(nc(OCC(F)(F)F)n2)Nc2ccc(C(=O)NCC3(CN4CCCC4)CC3)c(c2)OCCC1] | C38 H49 F3 N8 O6 | 770.85 | 771.41 |

TABLE 3-continued
| Examples | Structures | Formula | MW | MS m/z (M + H) |
|---|---|---|---|---|
| 3007 | 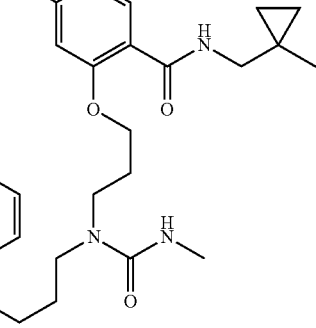 | C36 H46 F3 N9 O5 | 741.81 | 742.39 |
| 3008 | 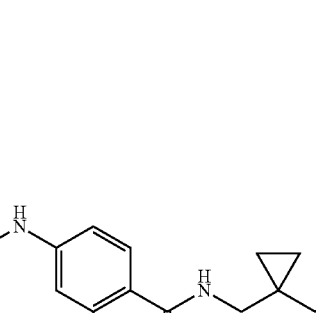 | C37 H48 F3 N9 O5 | 755.84 | 756.41 |
| 3009 | 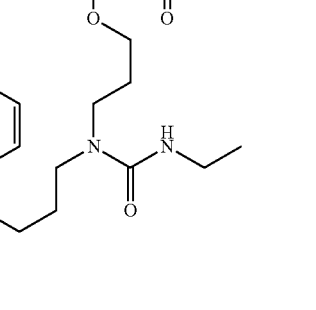 | C38 H50 F3 N9 O5 | 769.87 | 770.43 |

TABLE 3-continued
| Examples | Structures | Formula | MW | MS m/z (M + H) |
|---|---|---|---|---|
| 3010 | 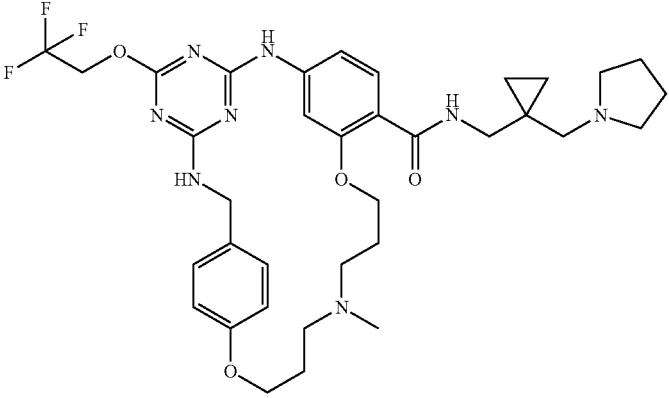 [SMILES: CN1CCCOc2ccc(cc2)CNc2nc(nc(OCC(F)(F)F)n2)Nc2ccc(C(=O)NCC3(CN4CCCC4)CC3)c(c2)OCCC1] | C35 H45 F3 N8 O4 | 698.79 | 669.3 |
| 3011 | 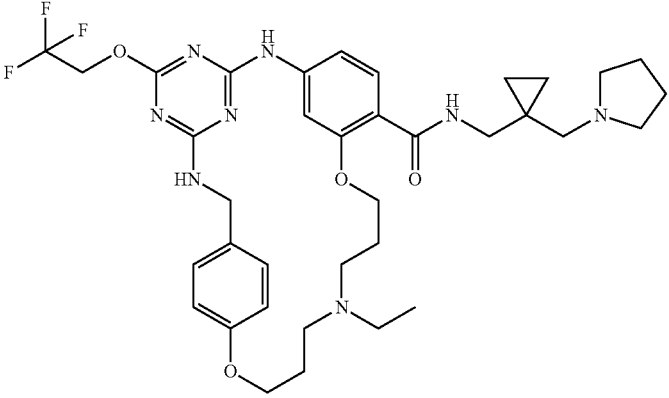 [SMILES: CCN1CCCOc2ccc(cc2)CNc2nc(nc(OCC(F)(F)F)n2)Nc2ccc(C(=O)NCC3(CN4CCCC4)CC3)c(c2)OCCC1] | C36 H47 F3 N8 O4 | 712.81 | 713.3 |
| 3012 | 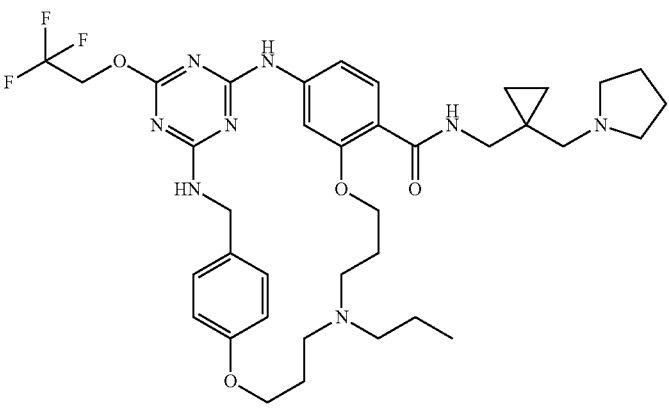 [SMILES: CCCN1CCCOc2ccc(cc2)CNc2nc(nc(OCC(F)(F)F)n2)Nc2ccc(C(=O)NCC3(CN4CCCC4)CC3)c(c2)OCCC1] | C37 H49 F3 N8 O4 | 726.84 | 727.4 |

TABLE 3-continued
| Examples | Structures | Formula | MW | MS m/z (M + H) |
|---|---|---|---|---|
| 3013 | 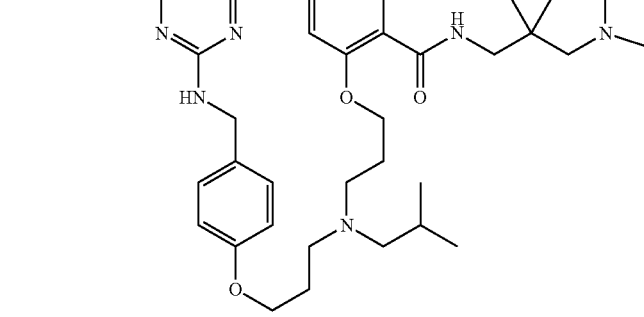 | C38 H51 F3 N8 O4 | 740.87 | 741.4 |
| 3014 | 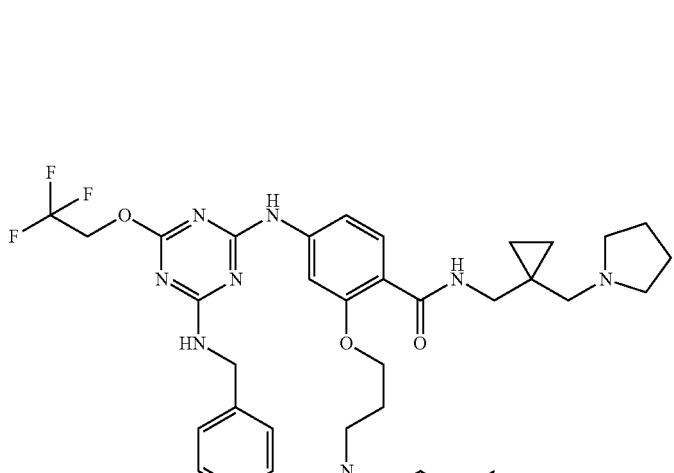 | C38 H51 F3 N8 O4 | 740.87 | 741.4 |
| 3015 | 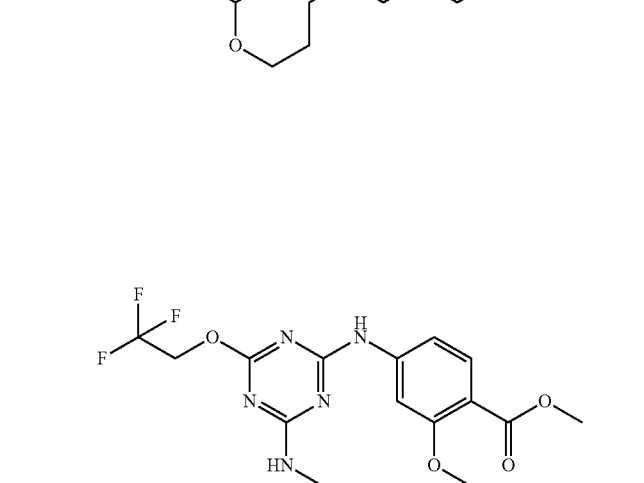 | C27 H31 F3 N6 O5 | 576.57 | 577.15 |

TABLE 3-continued

| Examples | Structures | Formula | MW | MS m/z (M + H) |
|---|---|---|---|---|
| 3016 | 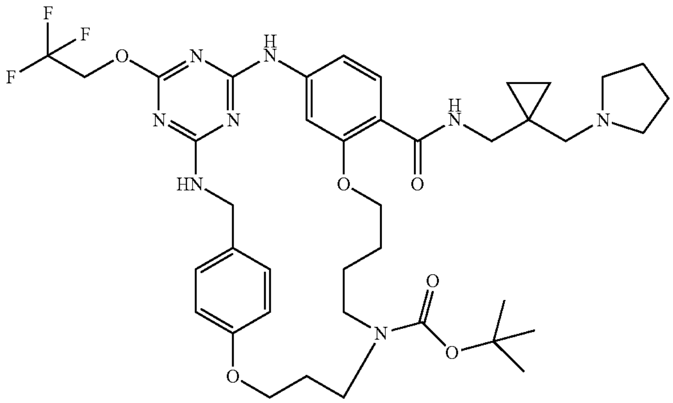 [SMILES: CC(C)(C)OC(=O)N1CCCCOc2cc(ccc2C(=O)NCC2(CN3CCCC3)CC2)Nc2nc(nc(OCC(F)(F)F)n2)NCc2ccc(cc2)OCCC1] | C40 H53 F3 N8 O6 | 798.9 | 799.39 |
| 3017 | 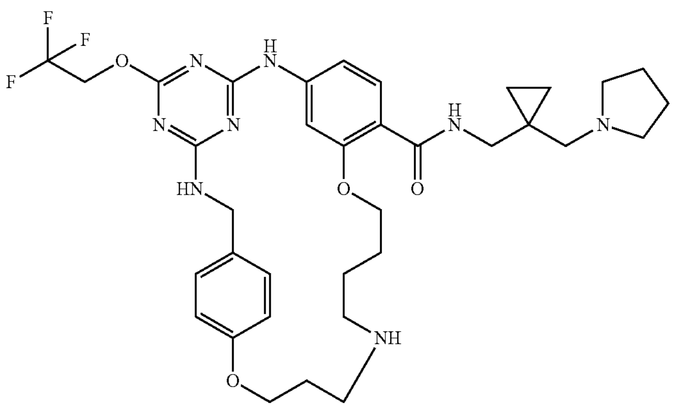 [SMILES: O=C(NCC1(CN2CCCC2)CC1)c1ccc2cc1OCCCCNCCCOc1ccc(cc1)CNc1nc(nc(OCC(F)(F)F)n1)N2] | C35 H45 F3 N8 O4 | 698.79 | 699.27 |
| 3018 | 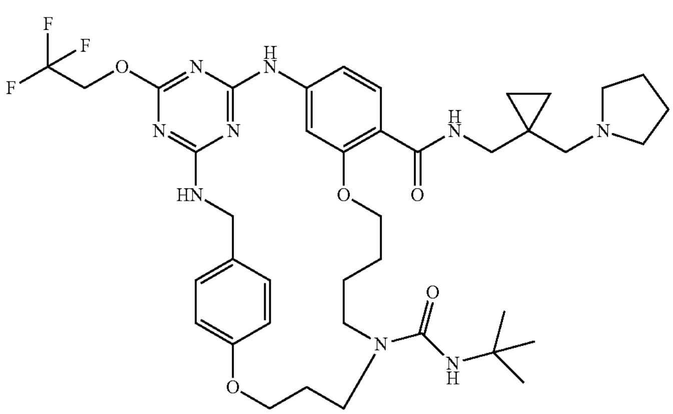 [SMILES: CC(C)(C)NC(=O)N1CCCCOc2cc(ccc2C(=O)NCC2(CN3CCCC3)CC2)Nc2nc(nc(OCC(F)(F)F)n2)NCc2ccc(cc2)OCCC1] | C40 H54 F3 N9 O5 | 797.92 | 798.35 |

TABLE 3-continued
| Examples | Structures | Formula | MW | MS m/z (M + H) |
|---|---|---|---|---|
| 3019 | 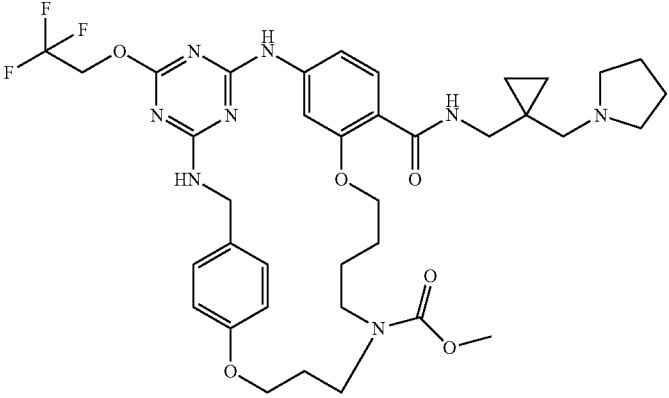 [SMILES: COC(=O)N1CCCCOc2cc(ccc2C(=O)NCC2(CN3CCCC3)CC2)Nc2nc(nc(OCC(F)(F)F)n2)NCc2ccc(cc2)OCCC1] | C37 H47 F3 N8 O6 | 756.82 | 757.38 |
| 3020 | 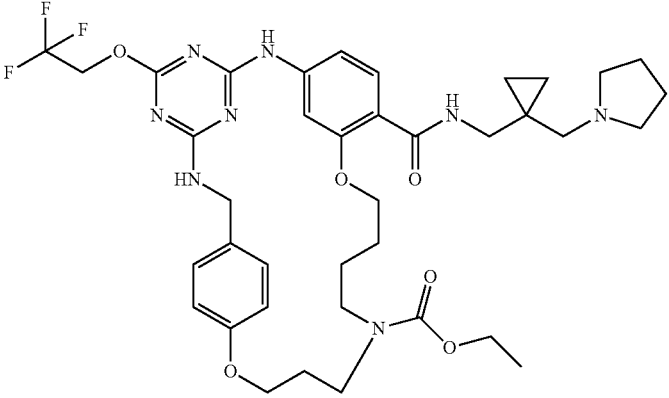 [SMILES: CCOC(=O)N1CCCCOc2cc(ccc2C(=O)NCC2(CN3CCCC3)CC2)Nc2nc(nc(OCC(F)(F)F)n2)NCc2ccc(cc2)OCCC1] | C38 H49 F3 N8 O6 | 770.85 | 771.4 |
| 3021 | 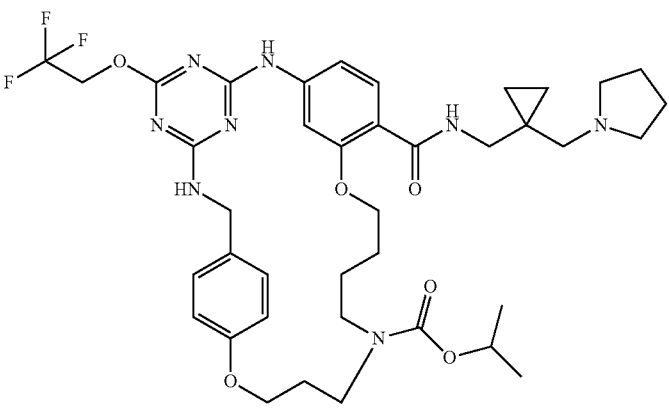 [SMILES: CC(C)OC(=O)N1CCCCOc2cc(ccc2C(=O)NCC2(CN3CCCC3)CC2)Nc2nc(nc(OCC(F)(F)F)n2)NCc2ccc(cc2)OCCC1] | C39 H51 F3 N8 O6 | 784.88 | 785.41 |

TABLE 3-continued
| Examples | Structures | Formula | MW | MS m/z (M + H) |
|---|---|---|---|---|
| 3022 | 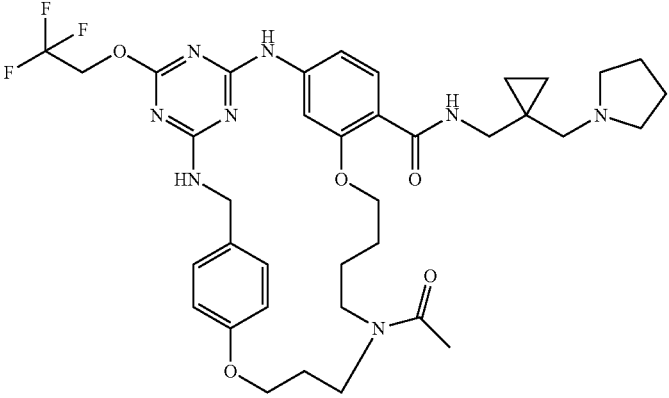 [SMILES: CC(=O)N1CCCCOc2cc(ccc2C(=O)NCC2(CN3CCCC3)CC2)Nc2nc(nc(OCC(F)(F)F)n2)NCc2ccc(cc2)OCCC1] | C37 H47 F3 N8 O5 | 740.82 | 741.36 |
| 3023 | 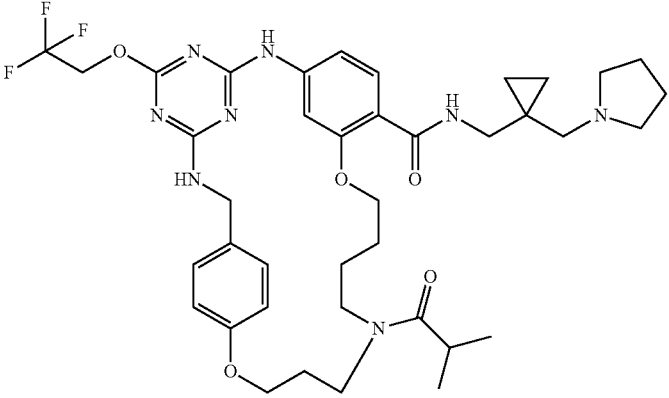 [SMILES: CC(C)C(=O)N1CCCCOc2cc(ccc2C(=O)NCC2(CN3CCCC3)CC2)Nc2nc(nc(OCC(F)(F)F)n2)NCc2ccc(cc2)OCCC1] | C39 H51 F3 N8 O5 | 768.88 | 769.4 |
| 3024 | 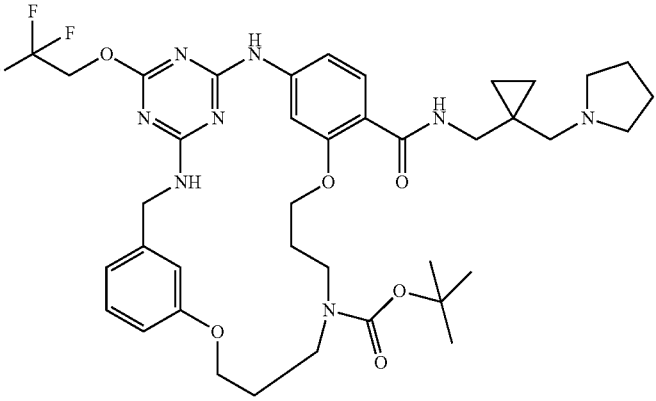 | C39 H51 F3 N8 O6 | 784.88 | 785.5 |

TABLE 3-continued
| Examples | Structures | Formula | MW | MS m/z (M + H) |
|---|---|---|---|---|
| 3025 | 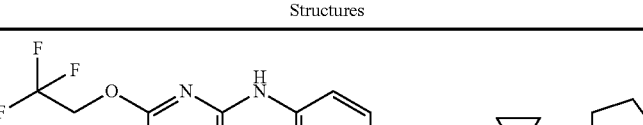 | C34 H43 F3 N8 O4 | 684.76 | 685.4 |
Series 4000
Example 4001
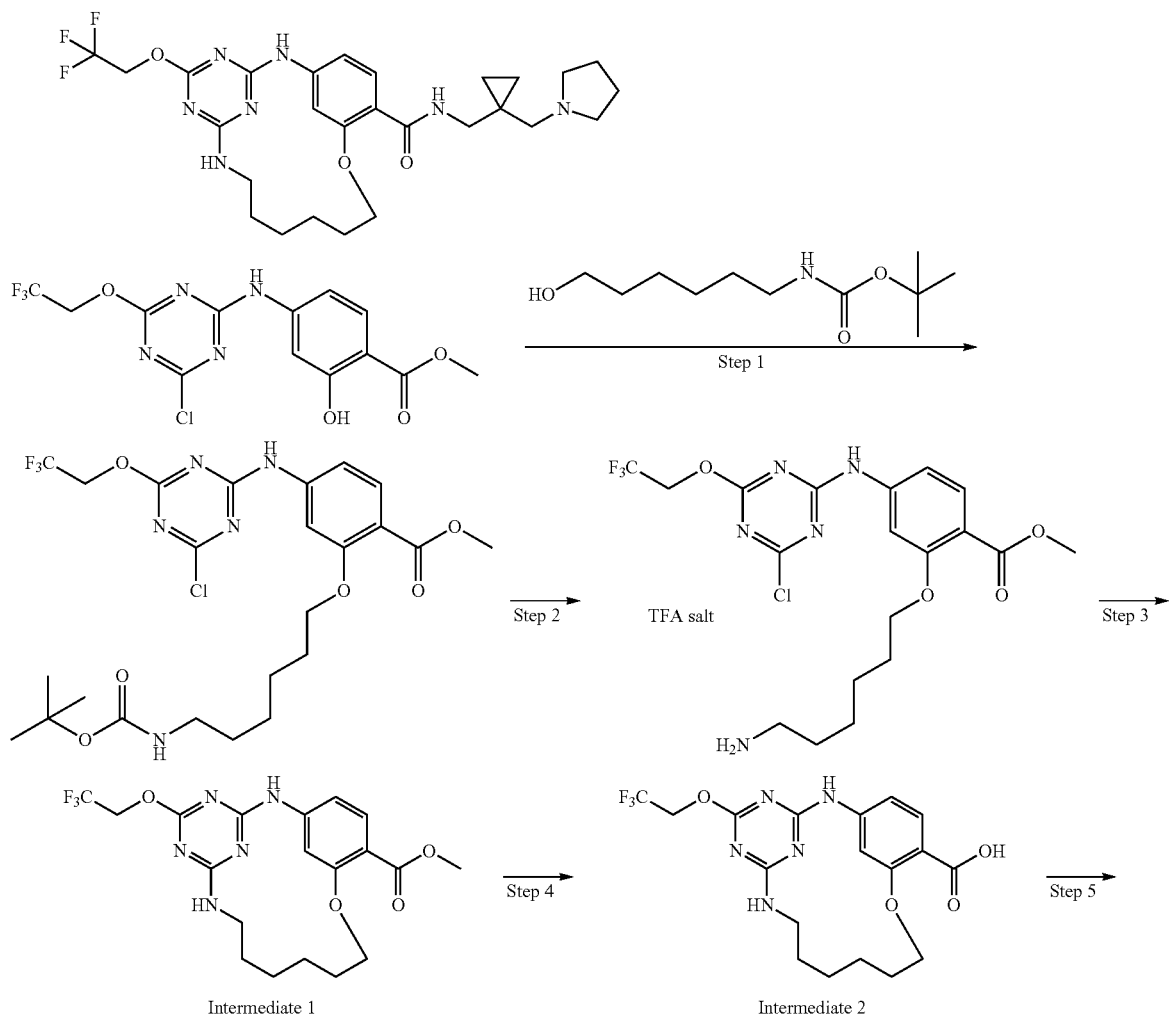
Intermediate 1
Intermediate 2

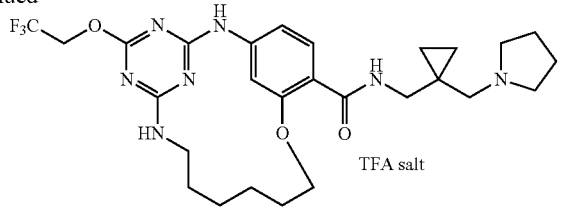

Example 4001

Step 1: methyl 4-(4-chloro-6-(2,2,2-trifluoroethoxy)-1,3,5-triazin-2-ylamino)-2-hydroxybenzoate (100 mg, 0.264 mmol), tert-butyl 6-hydroxyhexylcarbamate (68.9 mg, 0.317 mmol), Triphenylphosphine (139 mg, 0.528 mmol), were dissolved in DCM then DIAD (0.103 mL, 0.528 mmol) was added. The reaction was stirred for 16 h. The solvent was removed under vacuum and the crude product was purified by silica gel chromatography using 20% EtOAc/Hexanes. The product fractions were collected and the solvent was removed under vacuum to give 55 mg (36%) methyl 2-(6-(tert-butoxycarbonylamino)hexyloxy)-4-(4-chloro-6-(2,2,2-trifluoroethoxy)-1,3,5-triazin-2-ylamino)benzoate.

| methyl 2-(6-(tert-butoxycarbonylamino)hexyloxy)-4-(4-chloro-6-(2,2,2-trifluoroethoxy)-1,3,5-triazin-2-ylamino)benzoate | |
|---|---|
| MS (M + H)+ Calcd. | 578.2 |
| MS (M + H)+ Observ. | 578.1 |
| Retention Time | 1.19 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 2: methyl 2-(6-(tert-butoxycarbonylamino)hexyloxy)-4-(4-chloro-6-(2,2,2-trifluoroethoxy)-1,3,5-triazin-2-ylamino)benzoate (47 mg, 0.081 mmol) was dissolved in DCM (Volume: 2 mL) and Trifluoroacetic acid (500 μl) was added. The reaction was allowed to stir for 30 min. The solvent was removed under vacuum and methyl 2-(5-aminopentyloxy)-4-(4-chloro-6-(2,2,2-trifluoroethoxy)-1,3,5-triazin-2-ylamino)benzoate was carried to the next step without further purification.

Step 3: methyl 2-(6-aminohexyloxy)-4-(4-chloro-6-(2,2,2-trifluoroethoxy)-1,3,5-triazin-2-ylamino)benzoate, TFA (39 mg, 0.066 mmol) was dissolved in DCM (Volume: 20 mL) and Hunig'sBase (0.058 mL, 0.329 mmol) was added. The reaction was stirred for 16 h. The reaction mixture was concentrated under vacuum to give Intermediate 1 which was used in the next step without further purification.

| Intermediate 1 | |
|---|---|
| MS (M + H)+ Calcd. | 442.4 |
| MS (M + H)+ Observ. | 442.0 |
| Retention Time | 1.16 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 3: Intermediate 1 (50 mg, 0.113 mmol), was dissolved in THF (Ratio: 1.000, Volume: 1 mL) followed by the addition of LiOH (13.56 mg, 0.566 mmol) and Water (Ratio: 1.000, Volume: 1 mL). The reaction was headed to 65° C. for 2 h. The reaction was concentrated under vacuum and diluted 1N HCl. The solid that ppt out was collected and washed with water then dried to give 20 mg (41%) Intermediate 2.

| Intermediate 2 | |
|---|---|
| MS (M + H)+ Calcd. | 428.2 |
| MS (M + H)+ Observ. | 428.1 |
| Retention Time | 1.02 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 4: Intermediate 2 (20 mg, 0.047 mmol), (1-(pyrrolidin-1-ylmethyl)cyclopropyl)methanamine (8.66 mg, 0.056 mmol), HATU (26.7 mg, 0.070 mmol), and Hunig'sBase (0.041 mL, 0.234 mmol) were stirred in DMF (1 mL) for 16 h. The solvent was removed and the crude material was purified by rev. phase HPLC using a gradient of 20-80% ACN/water w/0.1% TFA modifier. The product fraction was collected and the solvent removed by speedvac to give 5 mg (15%) Example 4001 as the TFA salt. $^1$H NMR (400 MHz, CHLOROFORM-d) δ 8.77-8.66 (m, 1H), 7.90-7.79 (m, 1H), 6.89-6.78 (m, 2H), 4.57 (q, J=8.3 Hz, 2H), 4.10-3.95 (m, 2H), 3.92-3.79 (m, 2H), 3.58-3.42 (m, 4H), 3.08 (d, J=5.5 Hz, 2H), 3.02-2.88 (m, 2H), 2.33-2.22 (m, 2H), 2.20-2.10 (m, 3H), 1.83-1.58 (m, 10H), 1.16-1.06 (m, 2H), 0.69-0.59 (m, 2H).

| Example 4001 | |
|---|---|
| MS (M + H)+ Calcd. | 428.2 |
| MS (M + H)+ Observ. | 428.1 |
| Retention Time | 1.02 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |
Series 5000
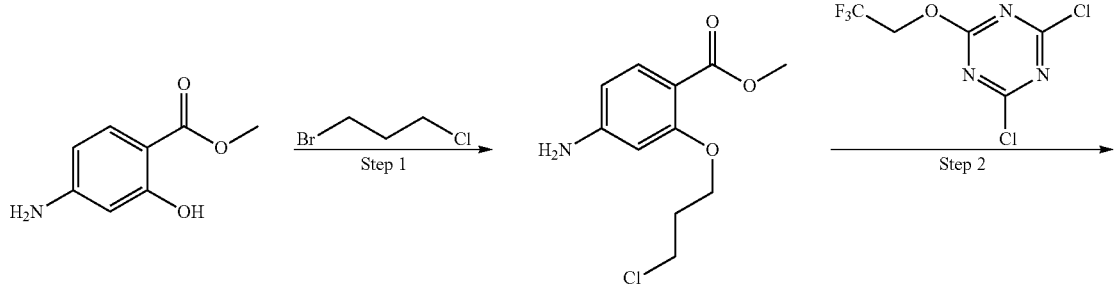
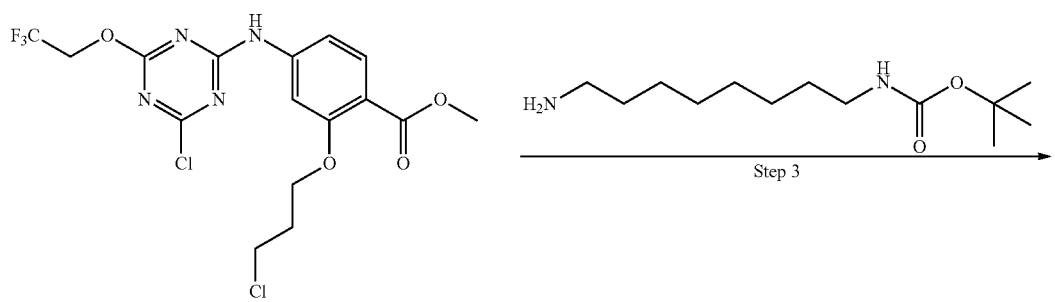
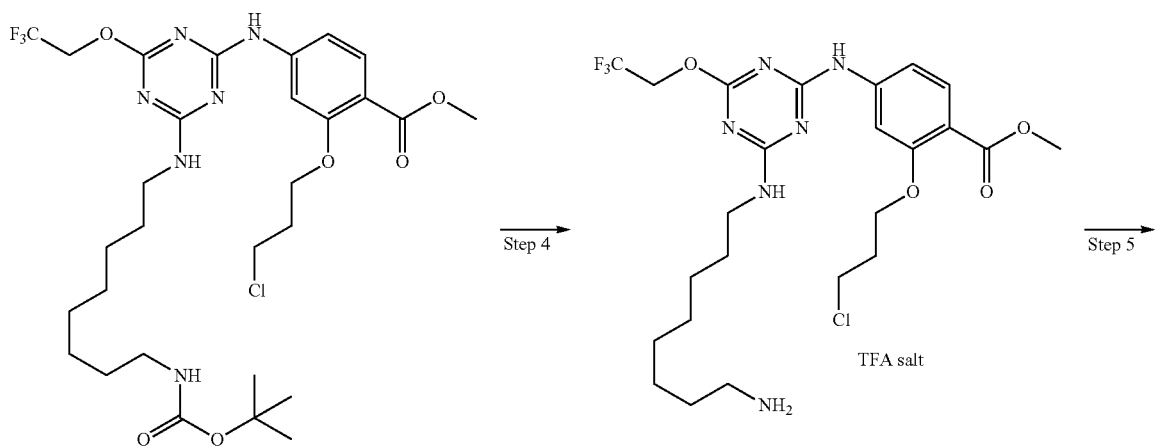

201
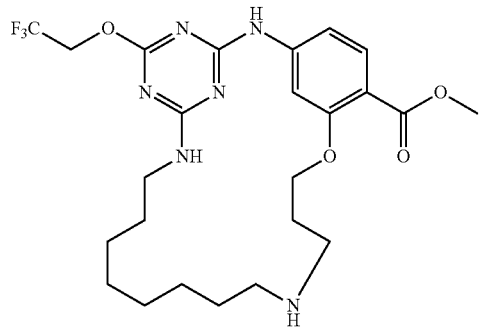
Intermediate 1
202
-continued
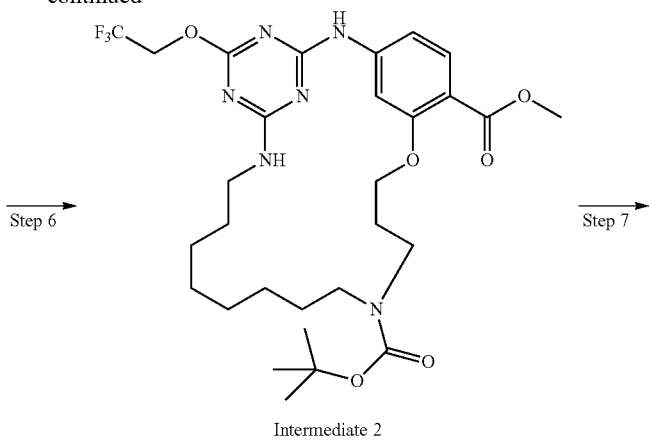
Intermediate 2
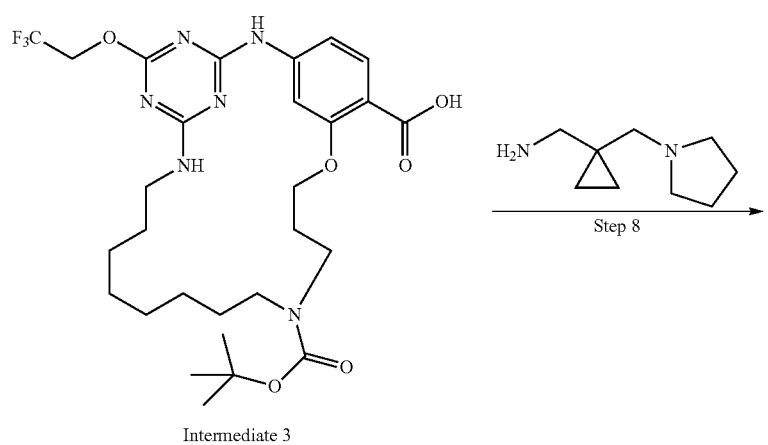
Intermediate 3
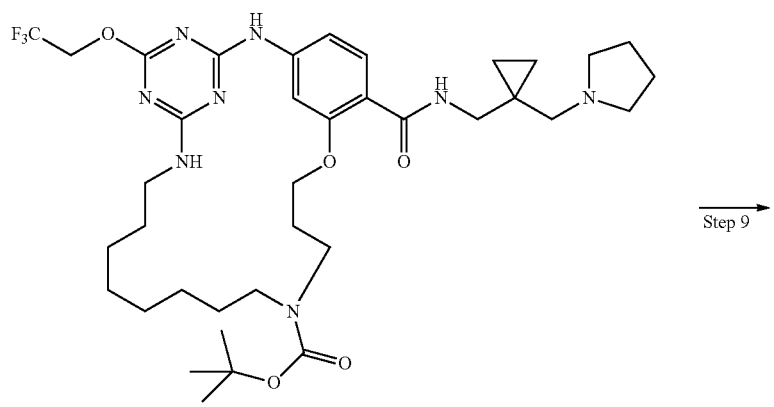
Example 5001
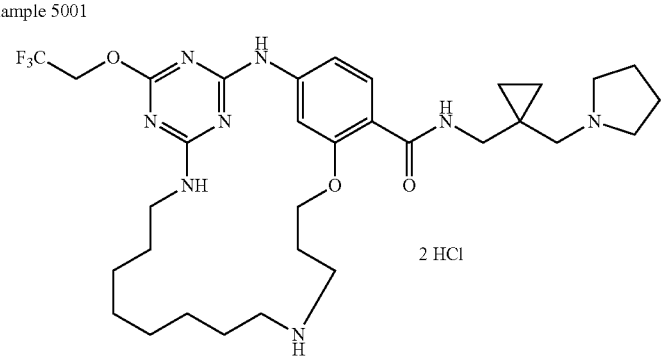
Example 5002

Step 1: To a solution of methyl 4-amino-2-hydroxybenzoate (500 mg, 2.99 mmol) and 1-bromo-3-chloropropane (0.294 mL, 2.99 mmol) in DMF (3 mL) was added CESIUM CARBONATE (1462 mg, 4.49 mmol). The resulting mixture was stirred at 60° C. for 6 hrs. The reaction mixture was poured into water, extracted with ethyl acetate, washed with brine, dried over MgSO4, concentrated. The crude product was purified by silica gel chromatography using a gradient of 20-50% EtOAc/Hexanes to give 686 mg (94%) methyl 4-amino-2-(3-chloropropoxy)benzoate.

| methyl 4-amino-2-(3-chloropropoxy)benzoate | |
|---|---|
| MS (M + H)$^+$ Calcd. | 244.1 |
| MS (M + H)$^+$ Observ. | 244.0 |
| Retention Time | 0.84 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 2: To a solution of 2,4-dichloro-6-(2,2,2-trifluoroethoxy)-1,3,5-triazine (770 mg, 2.79 mmol) in THF (10 mL) was added methyl 4-amino-2-(3-chloropropoxy)benzoate (681 mg, 2.79 mmol) and Hunig'sBase (1.464 mL, 8.38 mmol). The resulting mixture was stirred for 16 h. The reaction was diluted with DCM and water. The organic layer was collected and dried over sodium sulfate, and concentrated under vacuum. The crude product was purified by silica gel chromatography using 20-40% EtOAc/Hexanes. The product fractions were collected and concentrated under vacuum to give methyl 4-(4-chloro-6-(2,2,2-trifluoroethoxy)-1,3,5-triazin-2-ylamino)-2-(3-chloropropoxy)benzoate as a solid.

| methyl 4-(4-chloro-6-(2,2,2-trifluoroethoxy)-1,3,5-triazin-2-ylamino)-2-(3-chloropropoxy)benzoate | |
|---|---|
| MS (M + H)$^+$ Calcd. | 455.0 |
| MS (M + H)$^+$ Observ. | 455.0 |
| Retention Time | 1.09 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 3: To a solution of methyl 4-((4-chloro-6-(2,2,2-trifluoroethoxy)-1,3,5-triazin-2-yl)amino)-2-(3-chloropropoxy)benzoate (200 mg, 0.439 mmol) in THF (2 mL) was added tert-butyl (8-aminooctyl)carbamate (118 mg, 0.483 mmol) and Hunig'sBase (230 μl, 1.318 mmol). The resulting mixture was stirred for 16 h. The mixture was diluted with DCM and washed with water, then brine. The organic layer was collected, dried over sodium sulfate, and concentrated under vacuum. The crude product was purified by silica gel chromatography using a gradient of 20-40% EtOAc/hexanes. The product fractions were collected and the solvent removed under vacuum to give 208 mg (96%) methyl 4-(4-(8-(tert-butoxycarbonylamino)octylamino)-6-(2,2,2-trifluoroethoxy)-1,3,5-triazin-2-ylamino)-2-(3-chloropropoxy)benzoate.

| methyl 4-(4-(8-(tert-butoxycarbonylamino)octylamino)-6-(2,2,2-trifluoroethoxy)-1,3,5-triazin-2-ylamino)-2-(3-chloropropoxy)benzoate | |
|---|---|
| MS (M + H)$^+$ Calcd. | 663.3 |
| MS (M + H)$^+$ Observ. | 663.3 |
| Retention Time | 1.20 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 4: methyl 4-((4-((8-((tert-butoxycarbonyl)amino)octyl)amino)-6-(2,2,2-trifluoroethoxy)-1,3,5-triazin-2-yl)amino)-2-(3-chloropropoxy)benzoate (280 mg, 0.422 mmol) was dissolved in TFA (1 mL, 12.98 mmol) and DCM (2 mL). The reaction was stirred for 1 h. The solvent was removed under vacuum to give 286 mg (100%) methyl 4-(4-(8-aminooctylamino)-6-(2,2,2-trifluoroethoxy)-1,3,5-triazin-2-ylamino)-2-(3-chloropropoxy)benzoate, TFA which was used in the next step without further purification.

| methyl 4-(4-(8-aminooctylamino)-6-(2,2,2-trifluoroethoxy)-1,3,5-triazin-2-ylamino)-2-(3-chloropropoxy)benzoate, TFA | |
|---|---|
| MS (M + H)$^+$ Calcd. | 663.3 |
| MS (M + H)$^+$ Observ. | 663.3 |
| Retention Time | 1.20 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 5: methyl 4-((4-((8-aminooctyl)amino)-6-(2,2,2-trifluoroethoxy)-1,3,5-triazin-2-yl)amino)-2-(3-chloropropoxy)benzoate, TFA (0.286 g, 0.422 mmol) was dissolved in Acetonitrile (8.44 ml) and K$_2$CO$_3$ (0.175 g, 1.266 mmol) was added. The reaction was heated in the microwave at 150° C. for 1.5 h. DMF (2 mL) was added to the reaction to dissolve precipitated solid. The solution was decanted from the solid K$_2$CO$_3$ that remained. The solvent was removed under vacuum to give 222 mg crude Intermediate 1 which was used in the next step without further purification. LC/MS confirmation obtained.

| Intermediate 1 | |
|---|---|
| MS (M + H)+ Calcd. | 527.3 |
| MS (M + H)+ Observ. | 527.2 |
| Retention Time | 0.91 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 6: Intermediate 2 was prepared following the procedure reported for Example 3001 step 5.

| Intermediate 2 | |
|---|---|
| MS (M + H)+ Calcd. | 627.3 |
| MS (M + H)+ Observ. | 627.3 |
| Retention Time | 1.22 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 7: Intermediate 2 (46 mg, 0.073 mmol), was dissolved in THF (1 mL) followed by the addition of LiOH (8.79 mg, 0.367 mmol) and Water (1 mL). The reaction was headed to 65° C. for 6 h. The reaction was concentrated under vacuum and diluted 1N HCl. The solid that ppt out was collected and washed with water then dried to give crude intermediate 3.40 mg (89%).

| Intermediate 3 | |
|---|---|
| MS (M + H)+ Calcd. | 613.3 |
| MS (M + H)+ Observ. | 613.3 |
| Retention Time | 1.15 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 8: Intermediate 3 (40 mg, 0.065 mmol), (1-(pyrrolidin-1-ylmethyl)cyclopropyl)methanamine (12.09 mg, 0.078 mmol), HATU (37.2 mg, 0.098 mmol), and Hunig'sBase (0.057 mL, 0.326 mmol) were stirred in DMF (1 mL) for 16 h. The solvent was removed and the crude material was purified by reverse phase prep-HPLC using a gradient of 20-80% ACN/water w/0.1% TFA modifier. The product fraction was diluted with EtOAc, washed with saturated sodium bicarbonate solution, then brine. The organic layer was collected, dried over sodium sulfate, and concentrated under vacuum to give 30 mg (58%) Example 5001.

| Example 5001 | |
|---|---|
| MS (M + H)+ Calcd. | 749.4 |
| MS (M + H)+ Observ. | 749.5 |
| Retention Time | 1.09 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 9: Example 5001 (25 mg, 0.033 mmol) was dissolved in HCl 4 N in dioxane (1 ml, 32.9 mmol) and stirred for 1 h. The solvent was removed under vacuum to give 6 mg (24%) Example 5002 as a white solid.

| Example 5002 | |
|---|---|
| MS (M + H)+ Calcd. | 649.4 |
| MS (M + H)+ Observ. | 649.4 |
| Retention Time | 0.89 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of formula I

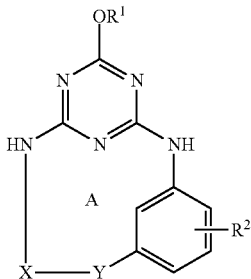

where
R$^1$ is alkyl, hydroxyalkyl, alkoxyalkyl, haloalkyl, cycloalkyl, hydroxycycloalkyl, alkoxycycloalkyl, halocycloalkyl, cycloalkenyl, benzyl, indanyl, or alkylcarbonyl;

R$^2$ is hydrogen, halo, cyano, alkyl, haloalkyl, alkoxy, haloalkoxy, CO$_2$R$^6$, or CON(R$^7$)(R$^8$);

R$^3$ is hydrogen, alkyl, alkylcarbonyl, alkoxycarbonyl, aminocarbonyl, alkylaminocarbonyl, or dialkyaminocarbonyl;

R$^4$ is hydrogen or alkyl;

R$^5$ is hydrogen, alkyl, (amino)alkyl, (alkylamino)alkyl, or (dialkylamino)alkyl;

R$^6$ is hydrogen, alkyl, or benzyl;

R$^7$ is hydrogen, alkyl, pyrrolidinonyl, piperidinonyl, homopiperazinonyl, (R$^9$)alkyl, (Q)alkyl, ((R$^9$)alkyl)-Q-alkyl, (R$^9$)(R$^9$)alkyl, or (R$^9$)(Q)alkyl;

or R$^7$ is pyrrolidinonyl, piperidinonyl, homopiperazinonyl, or

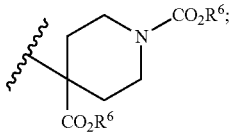

R$^8$ is hydrogen or alkyl;

or R$^7$ and R$^8$ taken together with the nitrogen to which they are attached is azetidinyl, pyrrolidinyl, piperidinyl, piperazinyl, or morpholinyl, and is substituted with 0-2 substituents selected from alkyl, (CO$_2$R$^6$)alkyl, CO$_2$R$^6$, CON(R$^{10}$)(R$^{10}$), and N(R$^{10}$)CO$_2$R$^6$;

or R$^7$ and R$^8$ taken together with the nitrogen to which they are attached is a spiro [3-7.3-7] bicyclic ring system where the bicylic ring system contains 0-1 additional nitrogens, and is substituted with 0-2 substituents selected from alkyl, (CO$_2$R$^6$)alkyl, CO$_2$R$^6$, CON(R$^{10}$)(R$^{11}$), and N(R$^{10}$)CO$_2$R$^6$;

R$^9$ is CO$_2$R$^6$, C(O)(N(R$^{10}$)(R11)), C(=NR$^{12}$)(N(R$^{10}$)(R$^{11}$)),CON(R$^{10}$)SO$_2$R$^{13}$,N(R$^{10}$)(R$^{11}$), N(R$^{10}$)COR$^6$,N(R$^{10}$)COPh, N(R$^{10}$)CO$_2$R$^6$,N(R$^{10}$)C(O)(N(R$^{10}$)(R$^{11}$)), N(R$^{10}$)C(=NR$^{12}$)(N(R$^{10}$)(R$^{11}$)), or (R$^{13}$)SO$_2$;

R$^{10}$ is hydrogen or alkyl;

R$^{11}$ is hydrogen or alkyl;

or N(R$^{10}$)(R$^{11}$) taken together with the nitrogen to which they are attached is azetidinyl, pyrrolidinyl, piperidinyl, piperazinyl, or morpholinyl R$^{12}$ is hydrogen, alkyl, or phenyl;

R$^{13}$ is alkyl, cycloalkyl, or phenyl;

Q is cycloalkyl, phenyl, tetrahydrofuranyl, tetrahydropyranyl, azetidinyl, pyrrolidinyl, piperidinyl, piperazinyl, or morpholinyl, and is substituted with 0-2 R$^9$ substituents;

X is an alkylene or alkenylene chain containing 0-6 groups selected from the group consisting of O, NR$^3$, S, S(O), S(O$_2$), C(O)O, C(O)NR$^4$, OC(O)NR$^4$, NR$^4$C(O)NR$^4$, NR$^4$C(NR$^{12}$)NR$^{4'}$, and Z, provided that O, NR$^3$, S, S(O), S(O$_2$), C(O)O, C(O)NR$^4$, OC(O)NR$^4$, NR$^4$C(O)NR$^4$, and NR$^4$C(NR$^{12}$)NR$^4$ do not directly bond to each other or to NH, such that ring A is 13-24 membered; and where the alkylene or alkenylene chain is substituted with 0-6 substituents selected from the group consisting of alkyl, alkylidinyl, hydroxy, alkoxy, and phenyl where the phenyl substituent is further substituted with 0-4 cyano, halo, alkyl, haloalkyl, alkoxy, or haloalkoxy substituents;

Y is CH$_2$, O, CO$_2$, or C(O)NR$^5$; and

Z is C$_{3-7}$ cycloalkylene or phenylene;

or a pharmaceutically acceptable salt therof.

2. A compound of formula I where
R$^1$ is alkyl, hydroxyalkyl, alkoxyalkyl, haloalkyl, cycloalkyl, hydroxycycloalkyl, alkoxycycloalkyl, halocycloalkyl, cycloalkenyl, benzyl, indanyl, or alkylcarbonyl;

R$^2$ is hydrogen, halo, cyano, alkyl, haloalkyl, alkoxy, haloalkoxy, CO$_2$R$^6$, or CON(R$^7$)(R$^8$);

R$^3$ is hydrogen, alkyl, alkylcarbonyl, alkoxycarbonyl, aminocarbonyl, alkylaminoearbonyl, or dialkyaminocarbonyl;

R$^4$ is hydrogen or alkyl;

R$^5$ is hydrogen, alkyl, (amino)alkyl, (alkylamino)alkyl, or (dialkylamino)alkyl;

R$^6$ is hydrogen or alkyl;

R$^7$ is hydrogen, alkyl, (R$^9$)alkyl, (Q)alkyl, ((R$^9$)alkyl)-Q-alkyl, (R$^9$)(R$^9$)alkyl, or (R$^9$)(Q)alkyl;

R$^8$ is hydrogen or alkyl;

or R$^7$ and R$^8$ taken together with the nitrogen to which they are attached is azetidinyl, pyrrolidinyl, piperidinyl, piperazinyl, or morpholinyl, and is substituted with 0-2 substituents selected from alkyl, (CO$_2$R$^6$)alkyl, CO$_2$R$^6$,)CON(R$^{10}$)(R$^{10}$), and N(R$^{10}$)CO$_2$R$^6$;

or R$^7$ and R$^8$ taken together with the nitrogen to which they are attached is a spiro [3-7.3-7] bicyclic ring system where the bicylic ring system contains 0-1 additional nitrogens, and is substituted with 0-2 substituents selected from alkyl, (CO$_2$R$^6$)alkyl, CO$_2$R$^6$,)CON(R$^{10}$)(R$^{11}$), and N(R$^{10}$)CO$_2$R$^6$;

R$^9$ is CO$_2$R$^6$,C(=NR$^{12}$)(N(R$^{10}$(R$^{11}$)), CON(R$^{10}$SO$_2$R$^{13}$,) N(R$^{10}$)(R$^{11}$), or N(R$^{10}$)CO$_2$R$^6$;

R$^{10}$ is hydrogen or alkyl;

R$^{11}$ is hydrogen or alkyl;

or N(R$^{10}$)(R$^{11}$) taken together with the nitrogen to which they are attached is azetidinyl, pyrrolidinyl, piperidinyl, piperazinyl, or morpholinyl R$^{12}$ is hydrogen, alkyl, or phenyl;

R$^{13}$ is alkyl, cycloalkyl, or phenyl;

Q is cycloalkyl, tetrahydrofuranyl, tetrahydropyranyl, azetidinyl, pyrrolidinyl, piperidinyl, piperazinyl, or morpholinyl, and is substituted with 0-2 R$^9$ substituents;

X is an alkylene or alkenylene chain containing 0-4 groups selected from the group consisting of O, NR$^3$, S, S(O), S(O$_2$), C(O)O, C(O)NR$^4$, OC(O)NR$^4$, NR$^4$C(O)NR$^4$, NR$^4$C(NR$^{12}$)NR$^{4'}$, and Z, provided that O, NR$^3$, S, S(O), S(O$_2$), C(O)O, C(O)NR$^4$, OC(O)NR$^4$, NR$^4$C(O)

$NR^4$, and $NR^4C(NR^{12})NR^4$ do not directly bond to each other or to NH, such that ring A is 13-24 membered; and where the alkylene or alkenylene chain is substituted with 0-3 substituents selected from the group consisting of alkyl, alkylidinyl, hydroxy, alkoxy, and phenyl where the phenyl substituent is further substituted with 0-4 cyano, halo, alkyl, haloalkyl, alkoxy, or haloalkoxy substituents;

Y is $CH_2$, O, $CO_2$, or $C(O)NR^5$; and

Z is $C_{3-7}$ cycloalkylene or phenylene;

or a pharmaceutically acceptable salt therof.

3. A compound of claim 2 where $R^1$ is haloalkyl; $R^2$ is hydrogen, $CO_2R^6$, or $CON(R^7)(R^8)$; $R^3$ is hydrogen or alkylcarbonyl; $R^4$ is hydrogen or alkyl; $R^5$ is hydrogen or alkyl; $R^6$ is hydrogen or alkyl; Q is cycloalkyl, pyrrolidinyl, or piperidinyl, and is substituted with 0-2 $R^9$ substituents; ring A is 21-23 membered; Y is O or $CONR^5$; and Z is phenylene; or a pharmaceutically acceptable salt therof.

4. A compound of claim 3 where $R^1$ is trifluoroethyl; $R^2$ is hydrogen, $CO_2R^6$, or $CON(R^7)(R^8)$; $R^3$ is hydrogen or alkylcarbonyl; $R^4$ is hydrogen or alkyl; $R^5$ is hydrogen or alkyl; $R^6$ is hydrogen or alkyl; Q is cyclopropyl, pyrrolidinyl, or piperidinyl, and is substituted with 0-2 $R^9$ substituents; Y is O; and Z is phenylene; or a pharmaceutically acceptable salt therof.

5. A compound of claim 4 where $R^7$ is $(R^9)$alkyl, (Q)alkyl, $((R^9)$alkyl)-Q-alkyl, $(R^9)(R^9)$alkyl, or $(R^9)(Q)$alkyl; and $R^8$ is hydrogen.

6. A compound of claim 4 where $R^7$ and $R^8$ taken together with the nitrogen to which they are attached is pyrrolidinyl or piperidinyl, and is substituted with 0-2 substituents selected from alkyl, $(CO_2R^6)$alkyl, $CO_2R^6$,)$CON(R^{10})(R^{10})$, and $N(R^{10})CO_2R^6$.

7. A compound of claim 4 where $R^7$ and $R^8$ taken together with the nitrogen to which they are attached is a spiro [5.5] bicyclic ring system where the bicylic ring system contains 0-1 additional nitrogens, and is substituted with 0-2 substituents selected from alkyl, $(CO_2R^6)$alkyl, $CO_2R^6$, $CON(R^{10})(R^{11})$, and $N(R^{10}) CO_2R^6$.

8. A compound of claim 1 where $R^1$ is trifluoroethyl.

9. A compound of claim 1 where $R^2$ is $CON(R^7)(R^8)$.

10. A compound of claim 1 where Y is O.

11. A compound of claim selected from the group consisting of

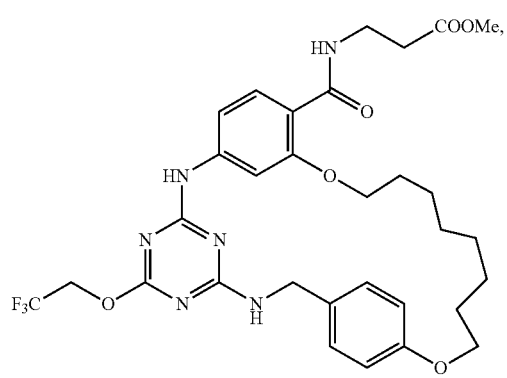

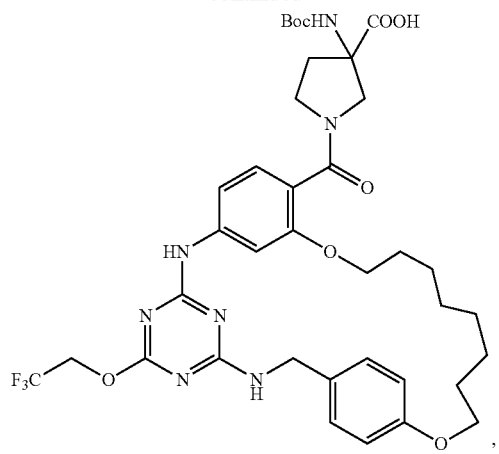

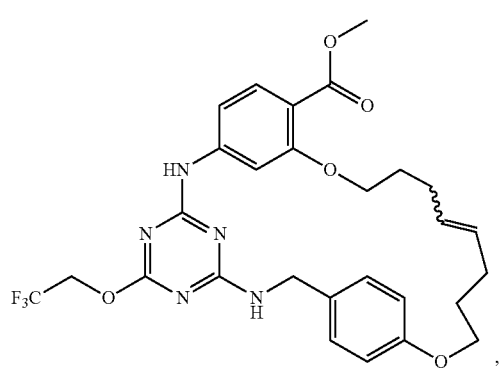

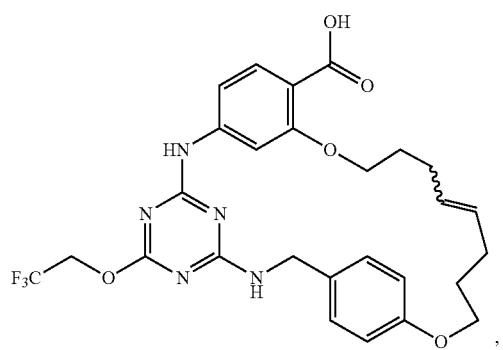

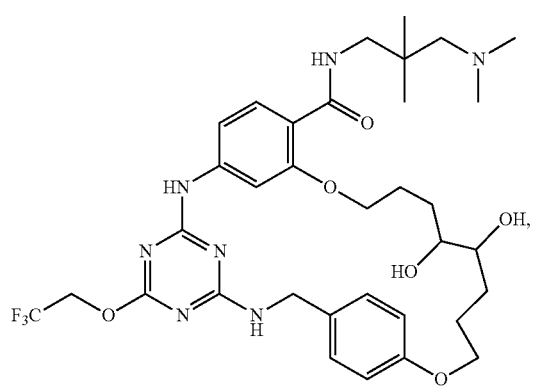

211
-continued
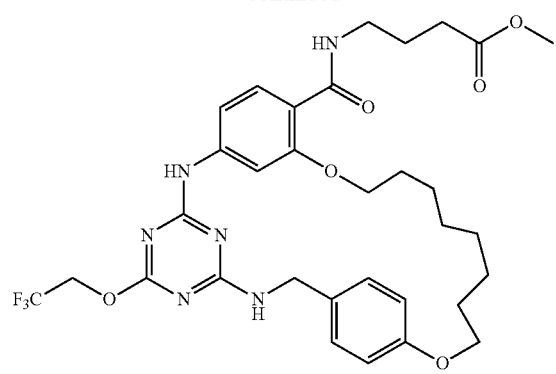
,
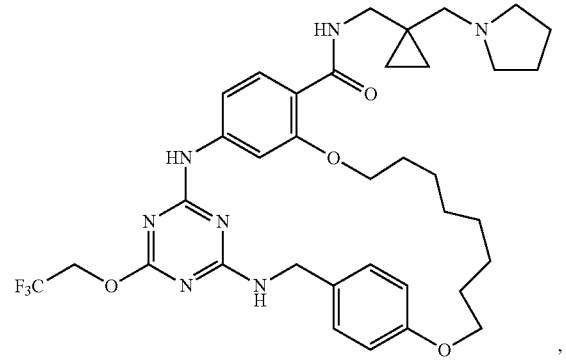
,
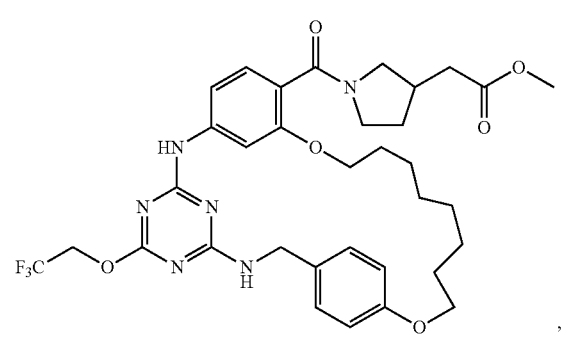
,
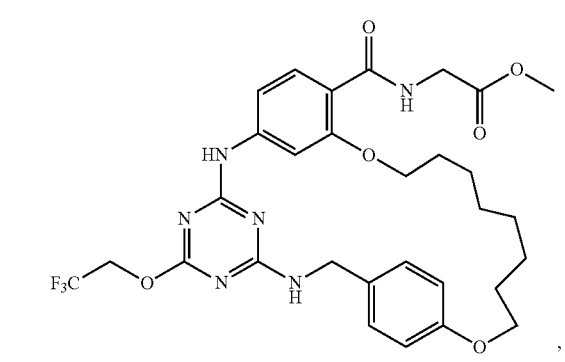
,
212
-continued
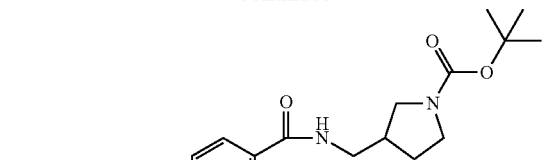
,
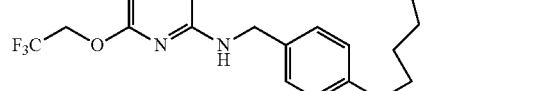
,
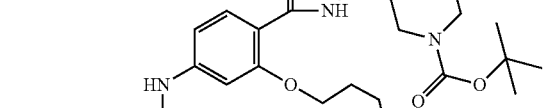
,
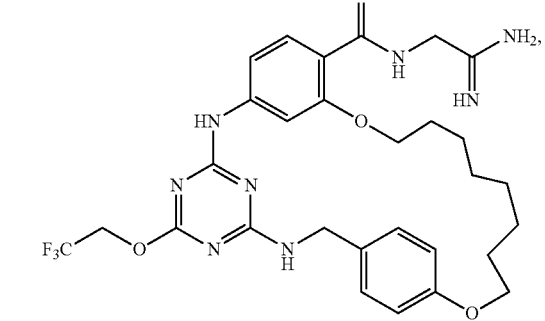
,
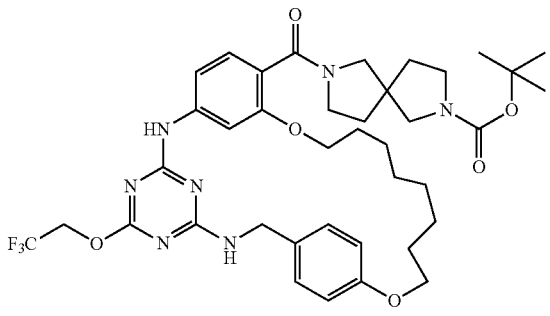
,
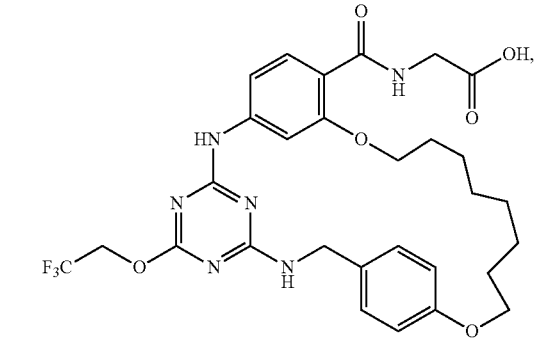

213
-continued
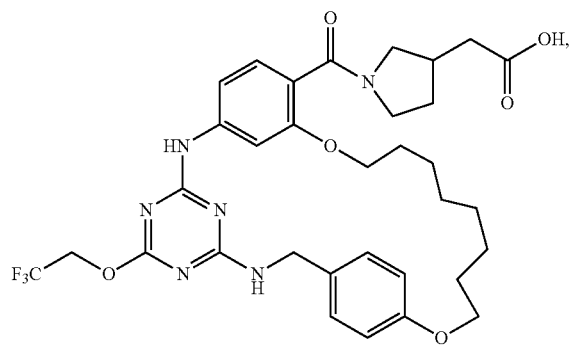
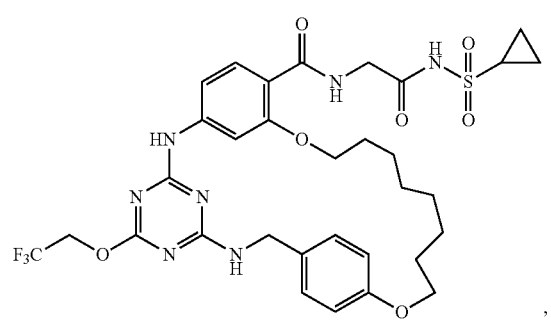
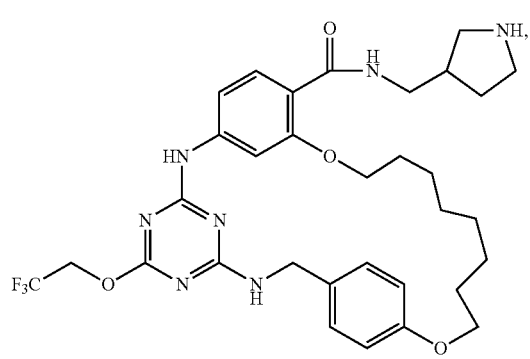
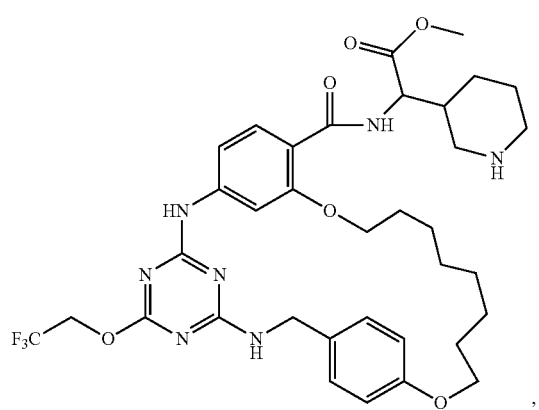
214
-continued
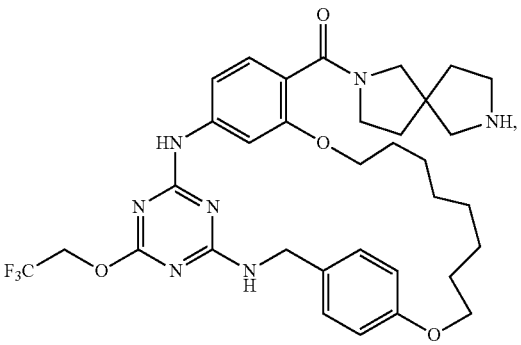
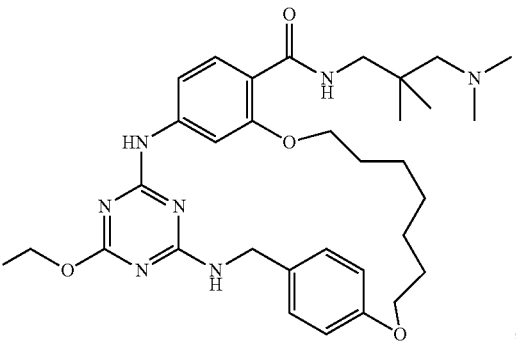
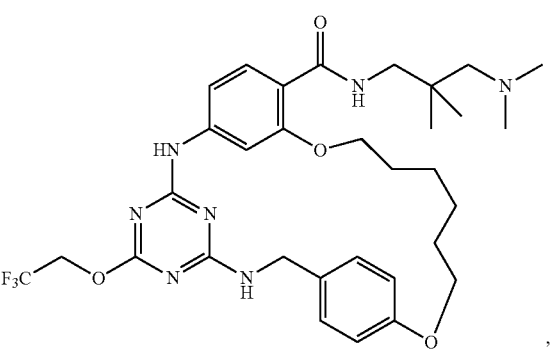
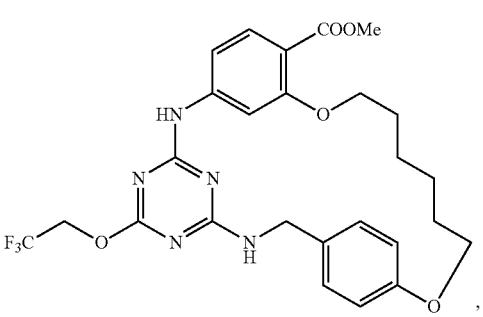
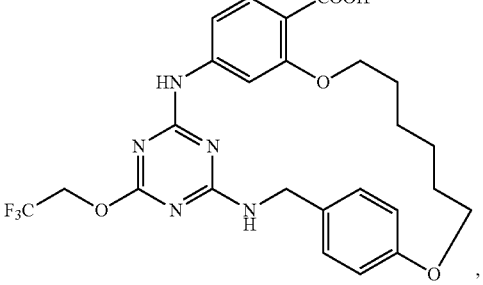

215
-continued
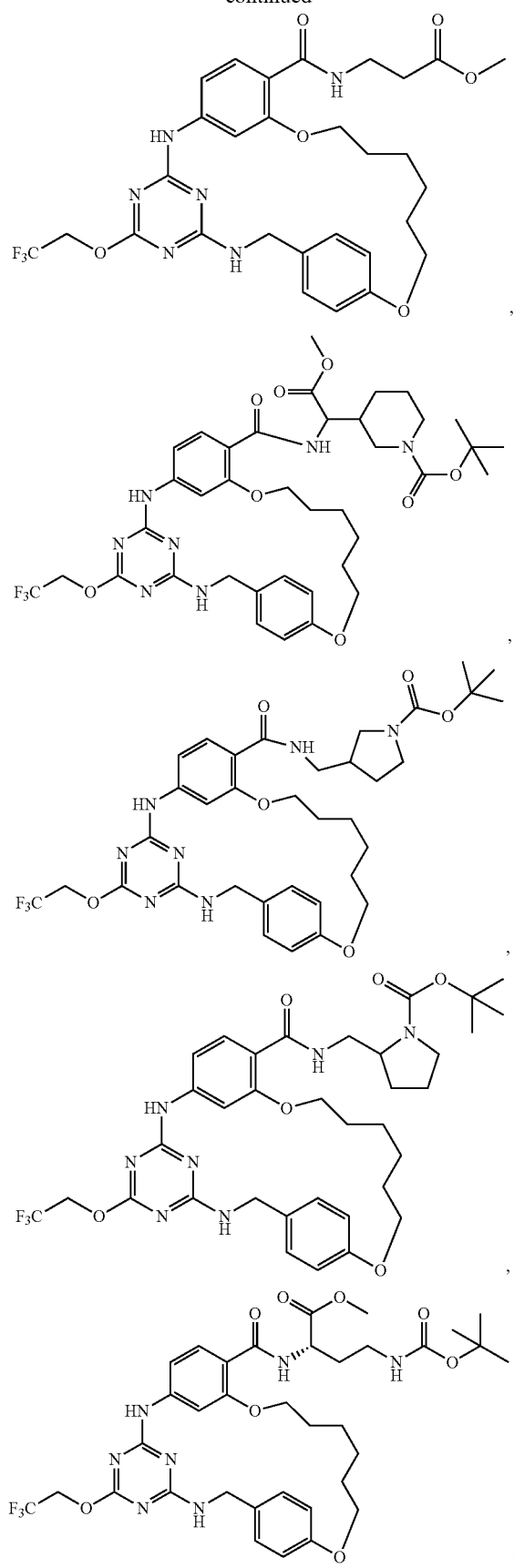
216
-continued
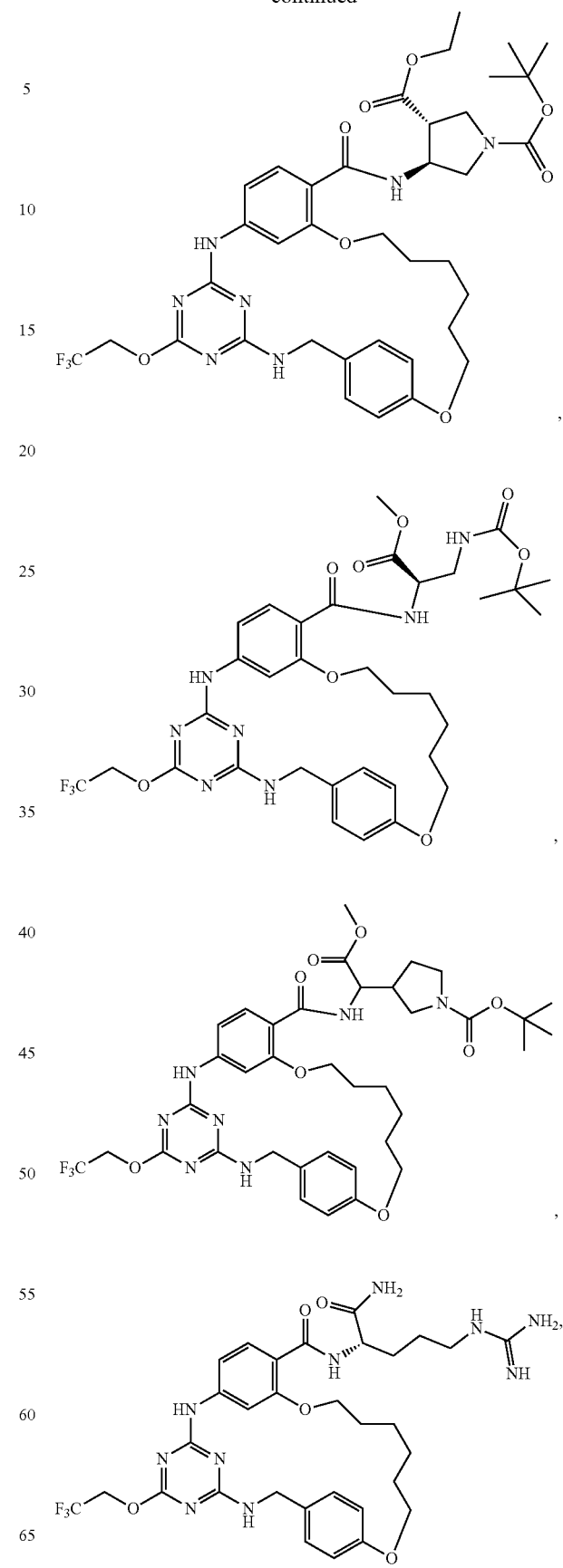

217
-continued
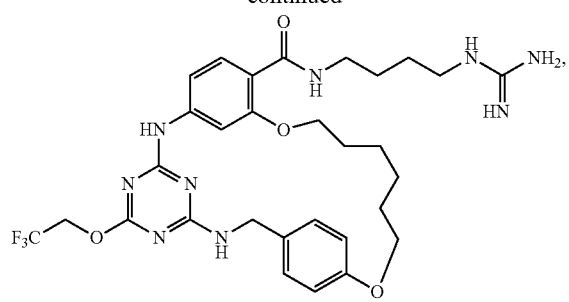
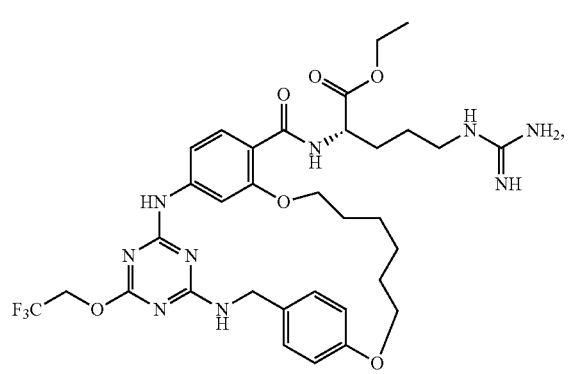
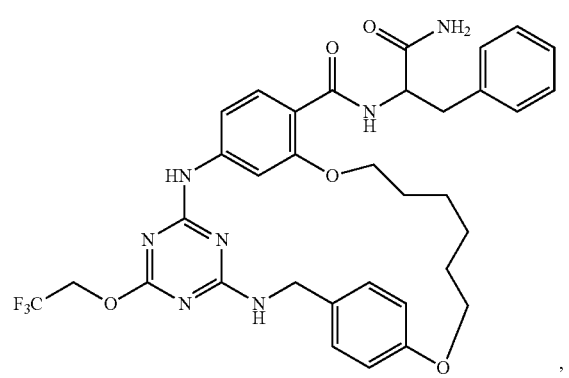
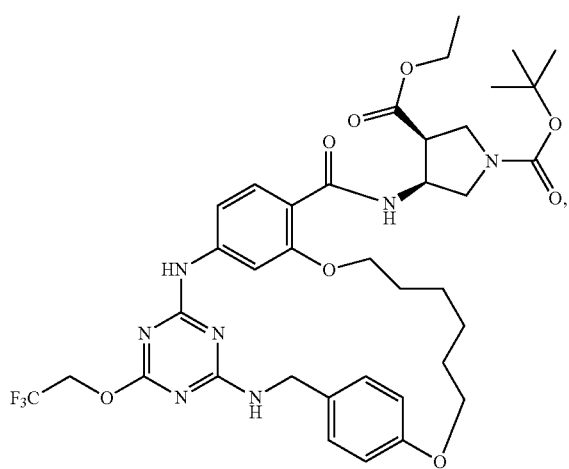
218
-continued
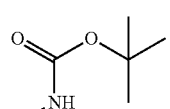

219
-continued
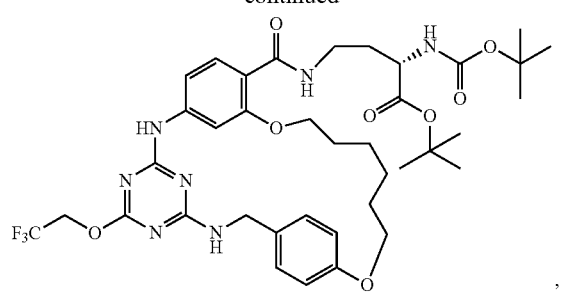
,
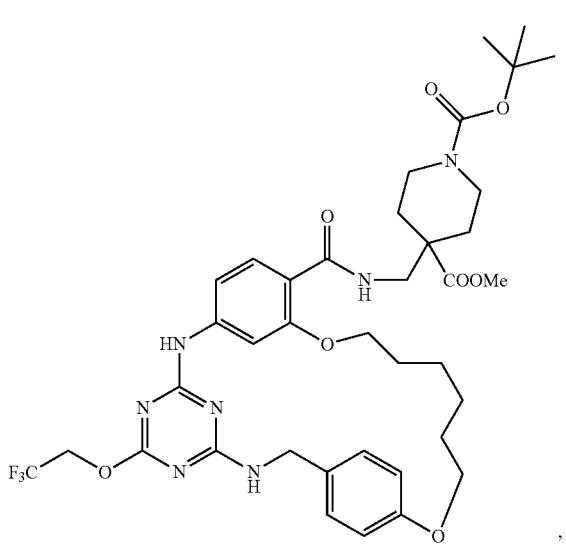
,
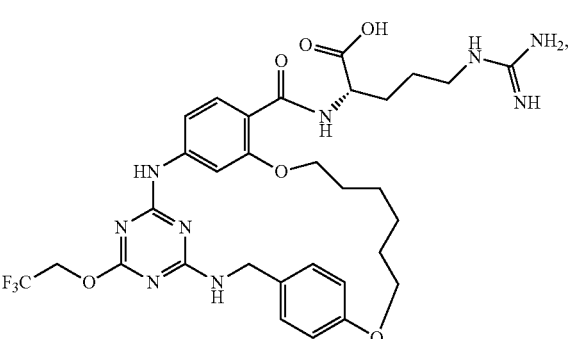
,
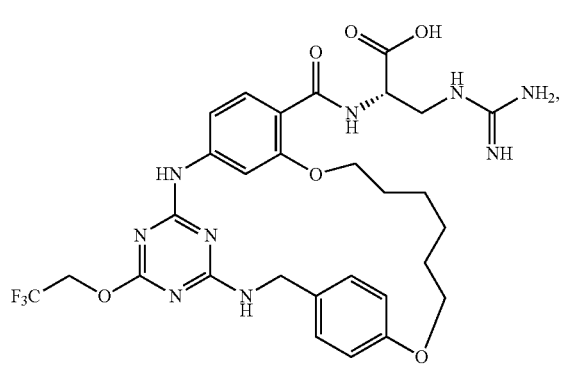
,
220
-continued
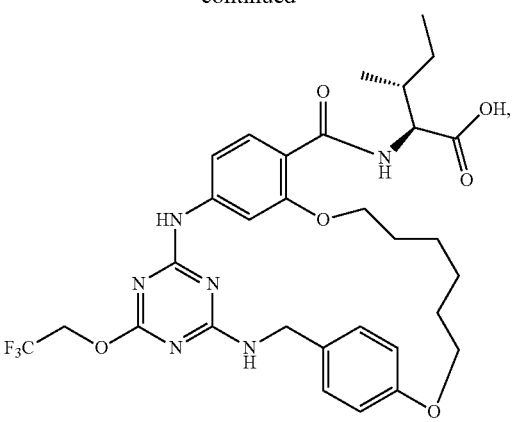
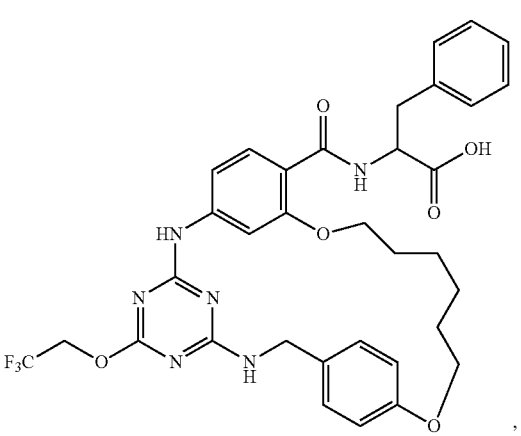
,
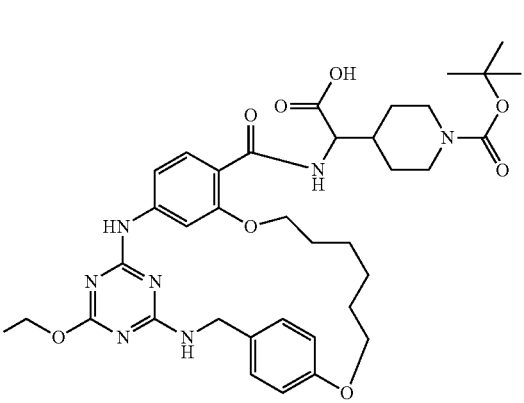
,
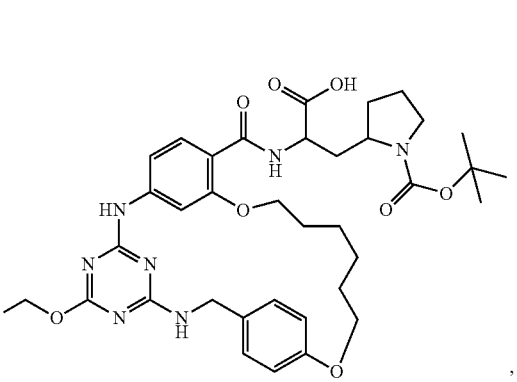
, 221
-continued
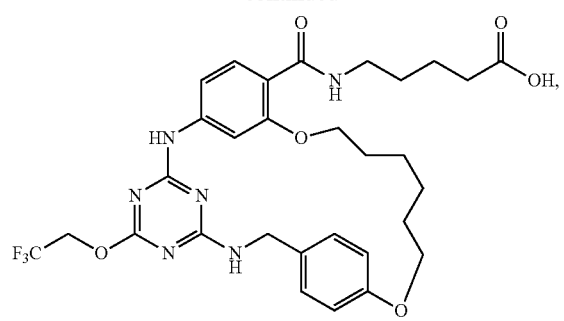
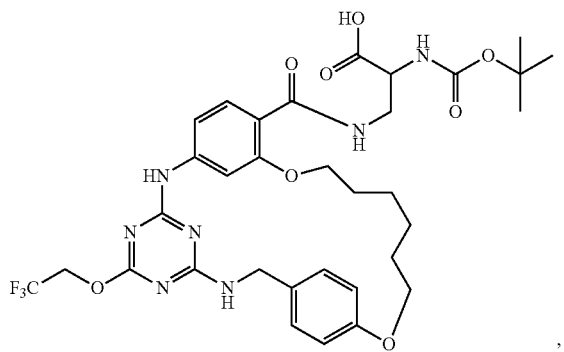
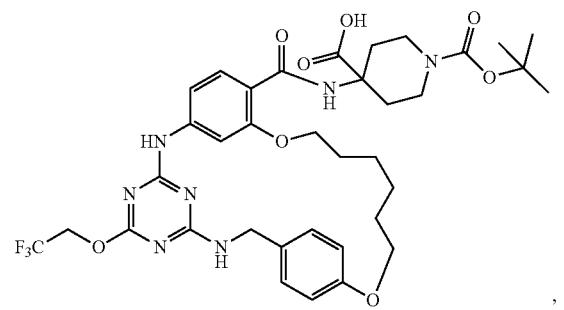
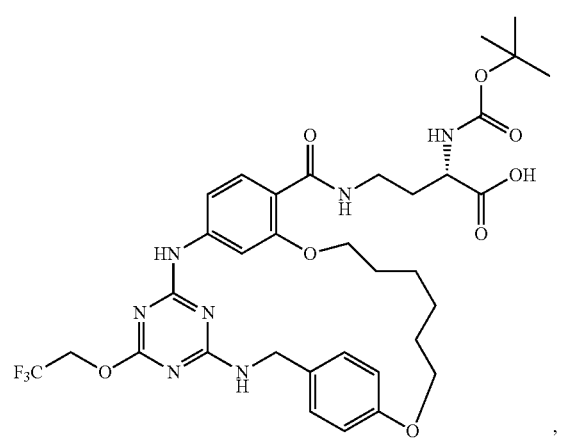
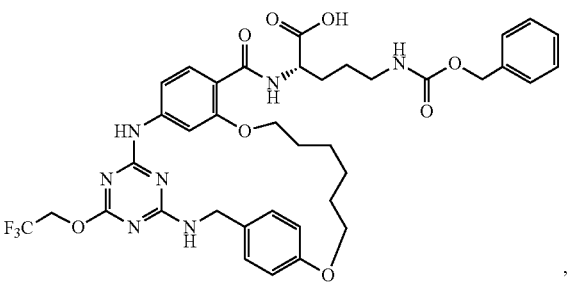
222
-continued 223
-continued
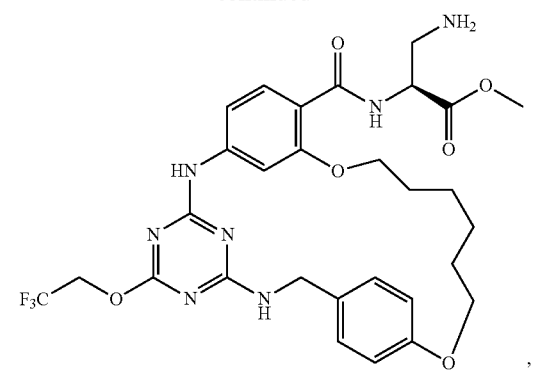
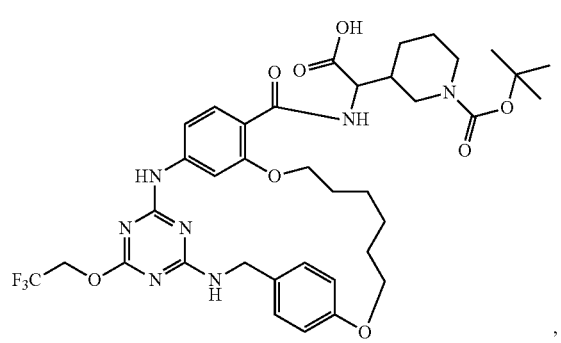
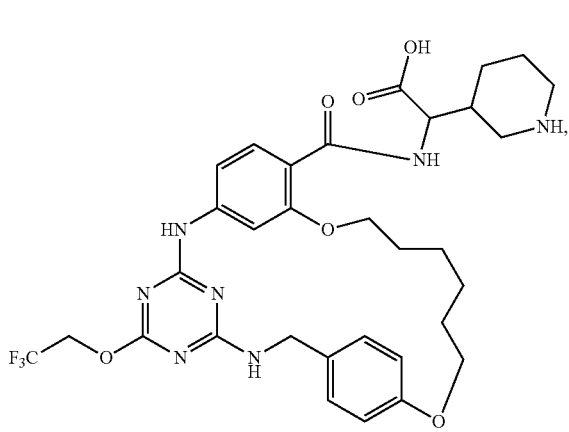
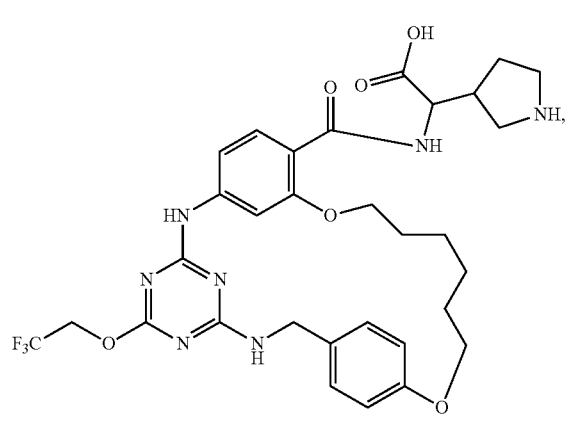
224
-continued
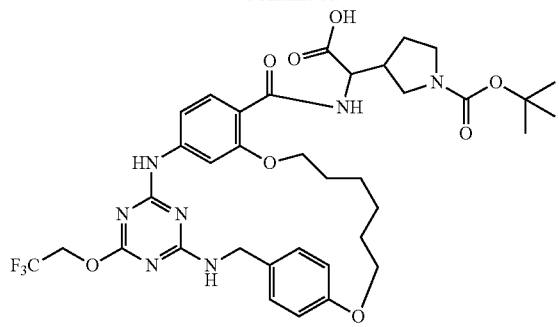
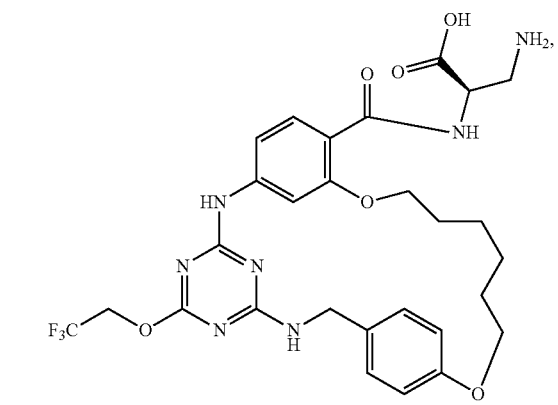
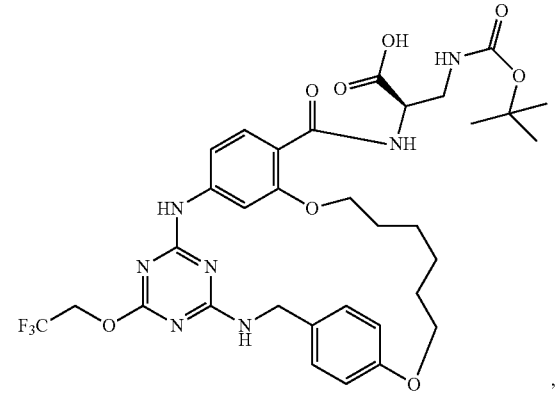
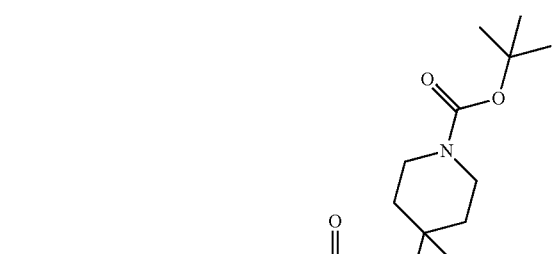
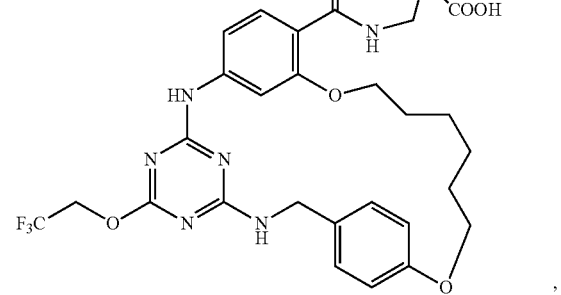

225
-continued
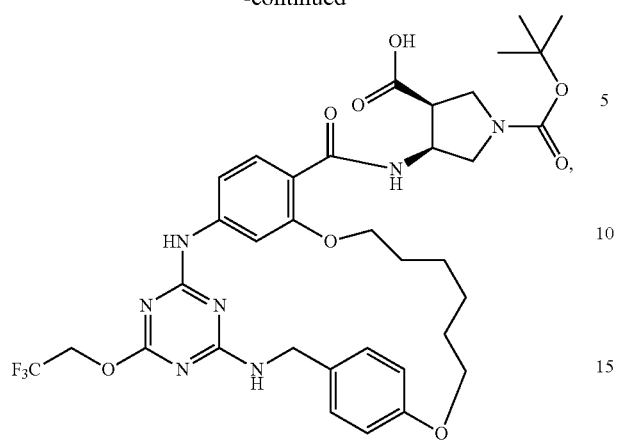
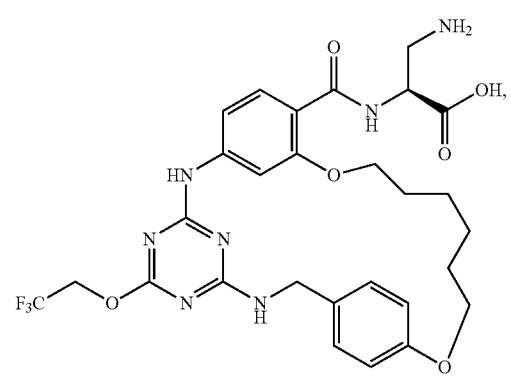
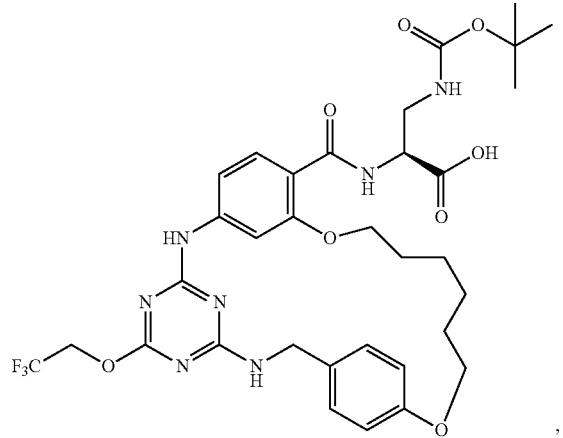
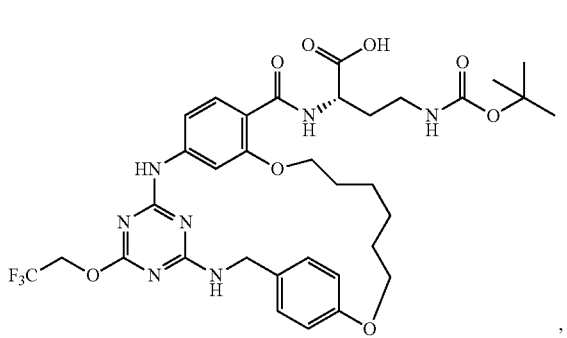
226
-continued
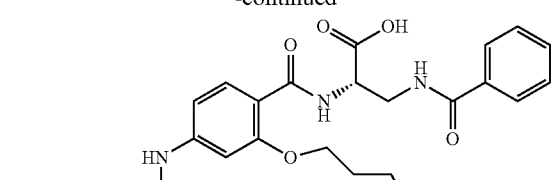
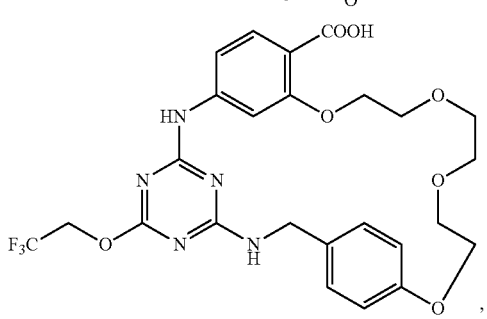
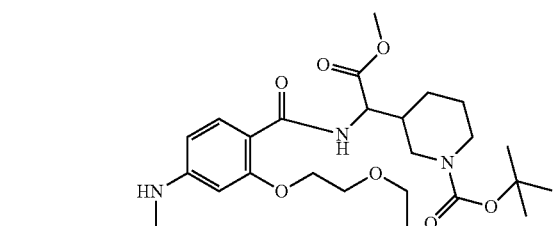
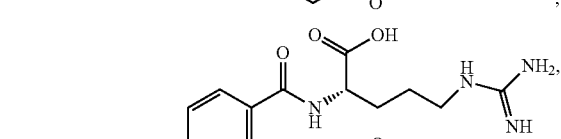
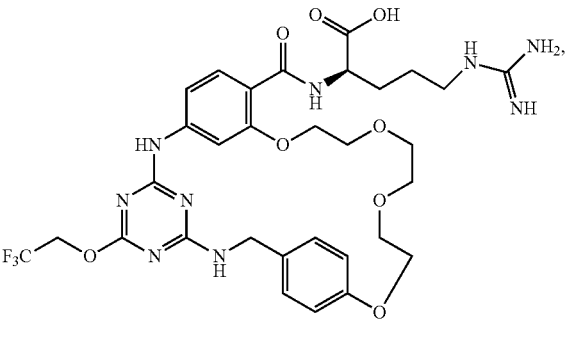

227
-continued
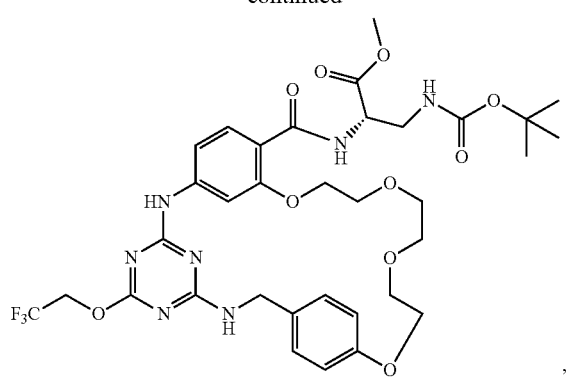
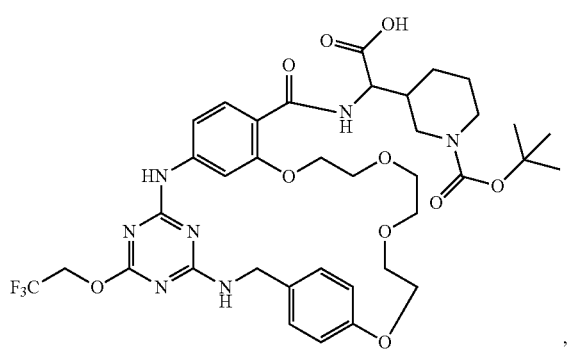
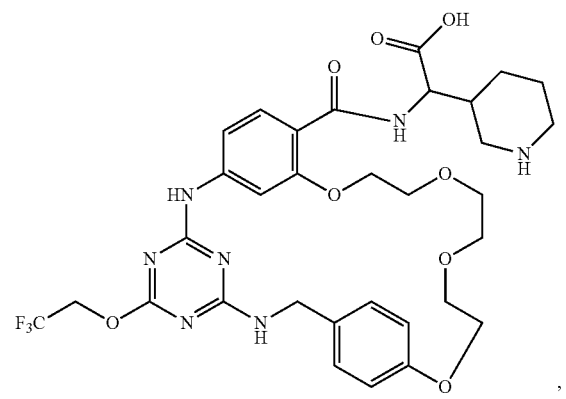
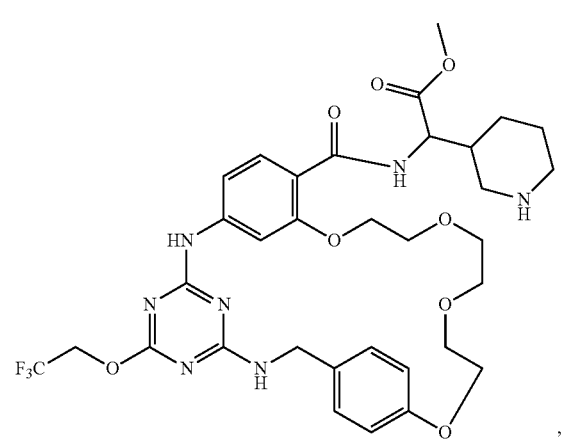
228
-continued
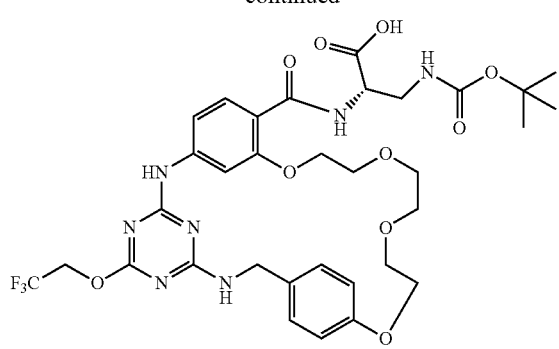
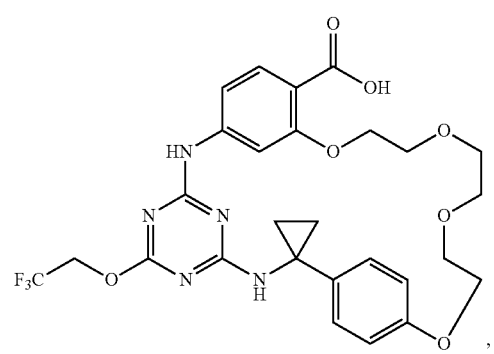
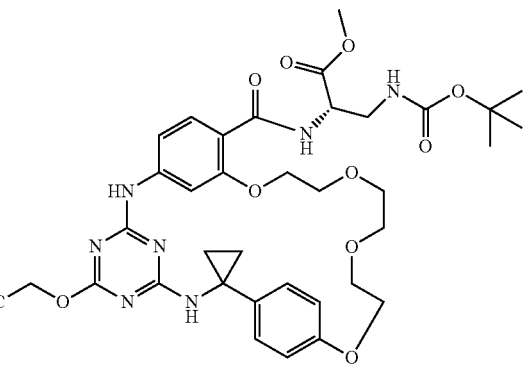
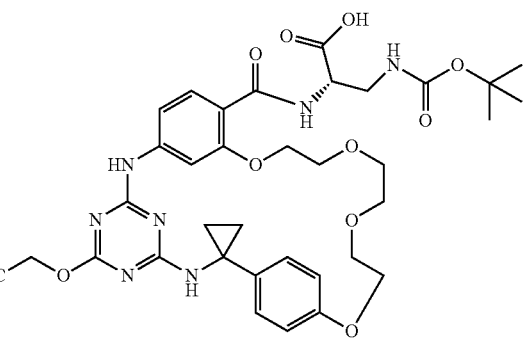

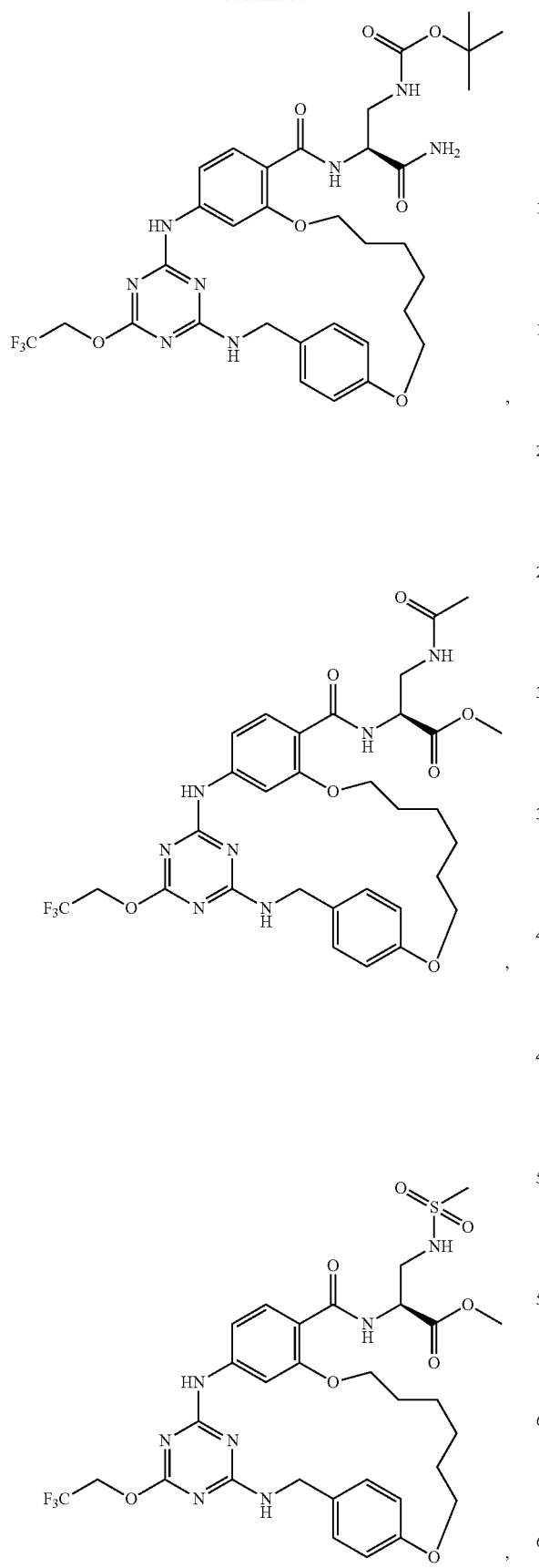
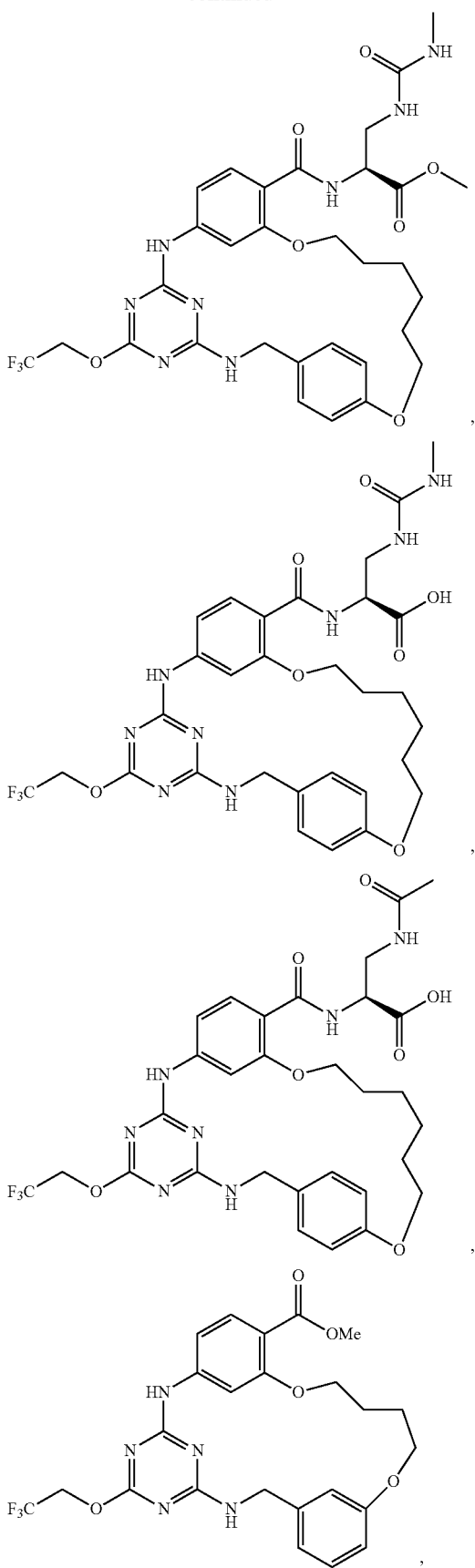

231
-continued
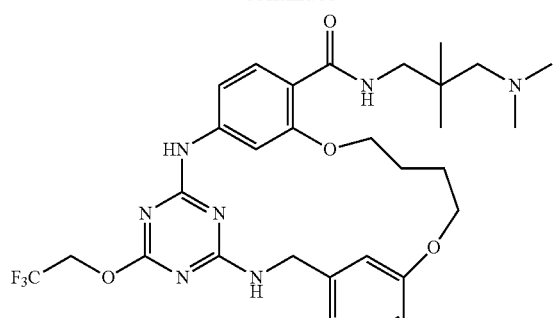
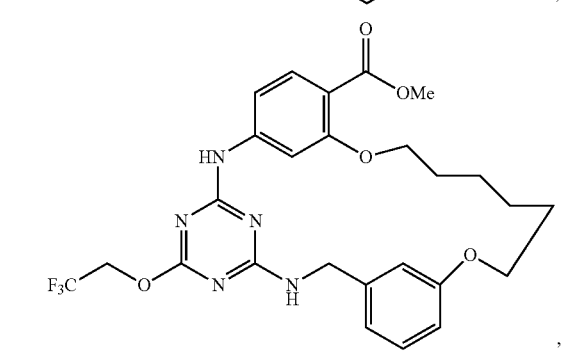
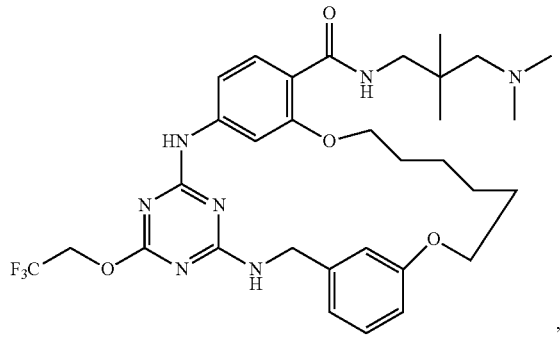
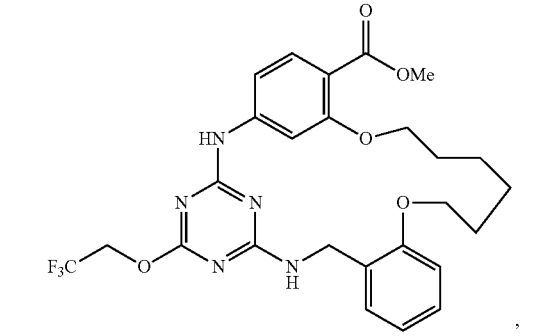
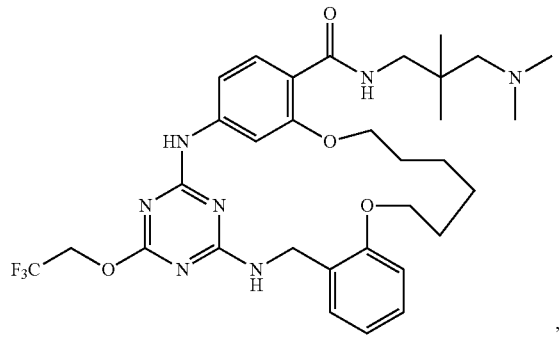
232
-continued
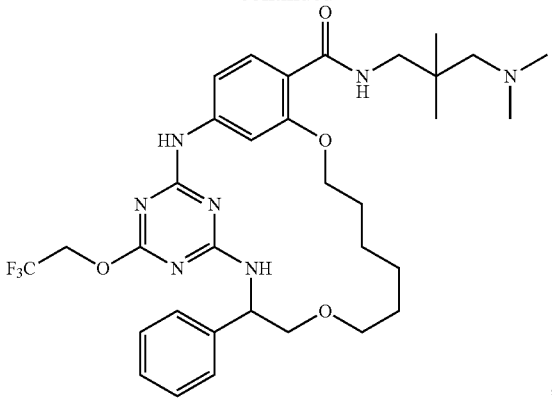
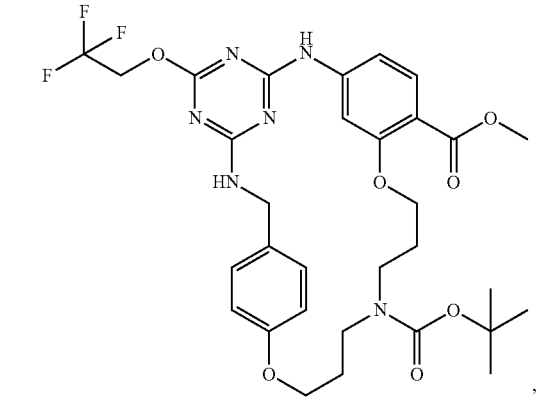
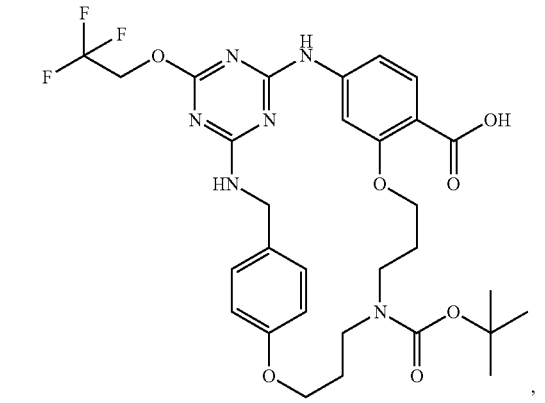
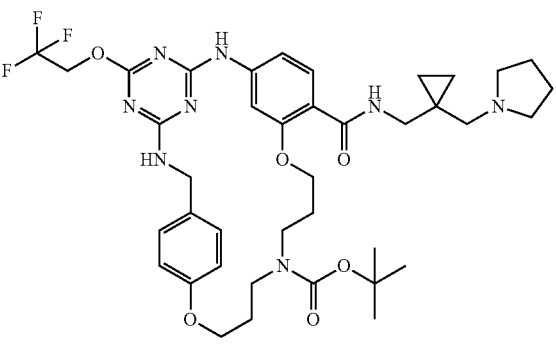

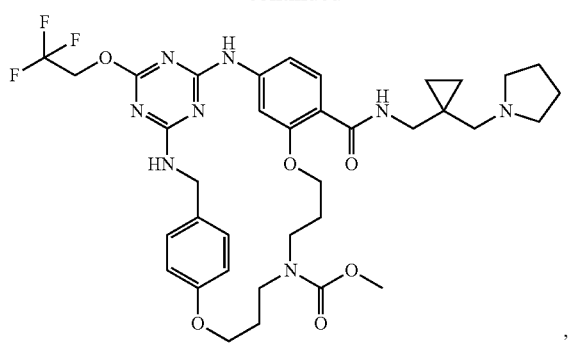
,
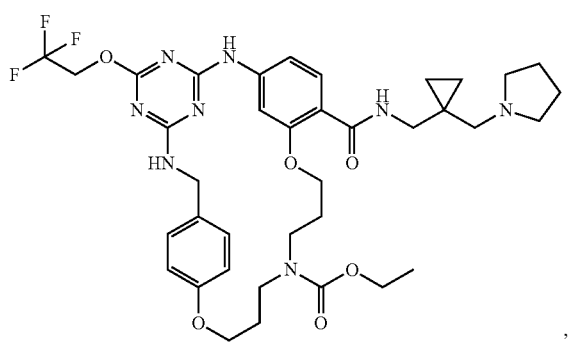
,
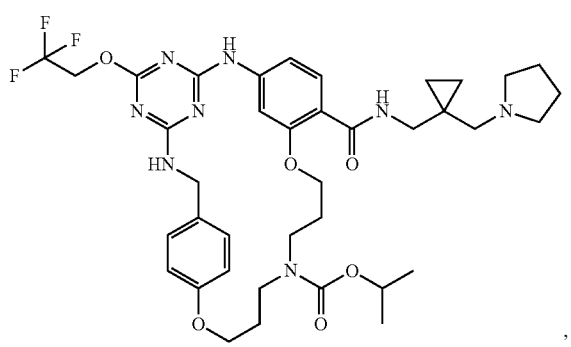
,
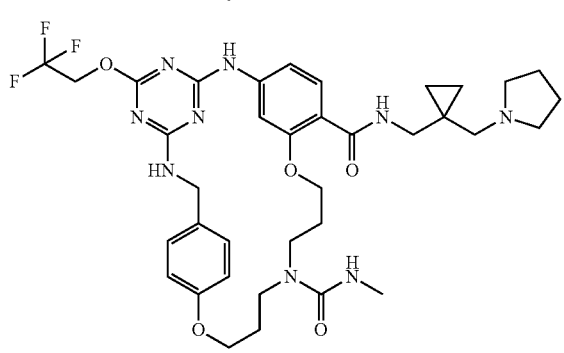
,
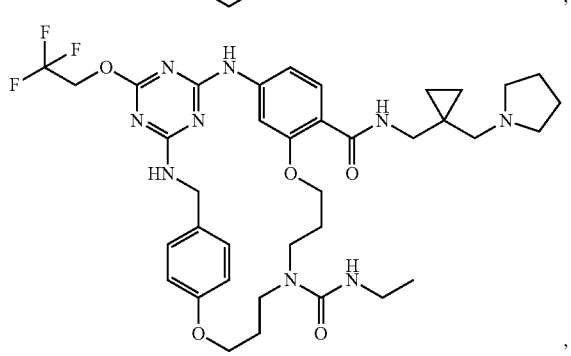
,
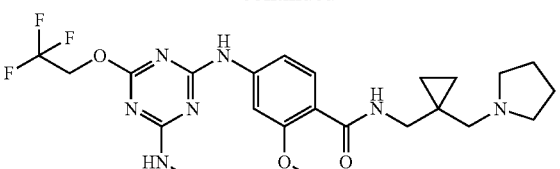
,
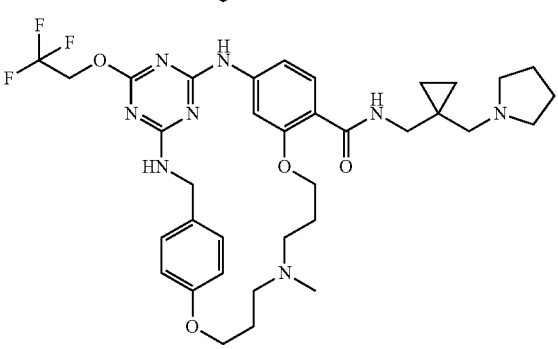
,
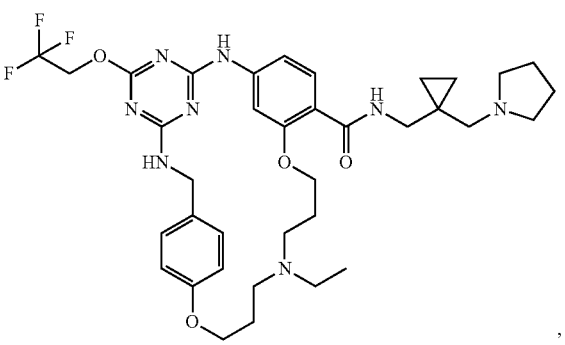
,
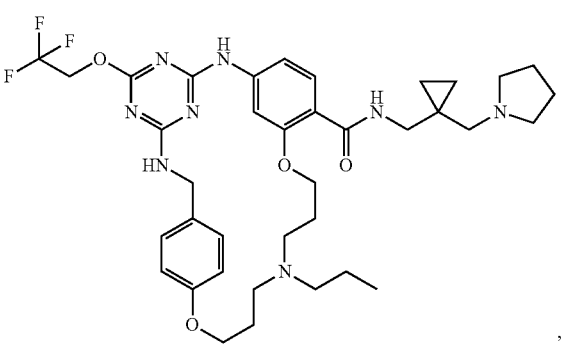
,
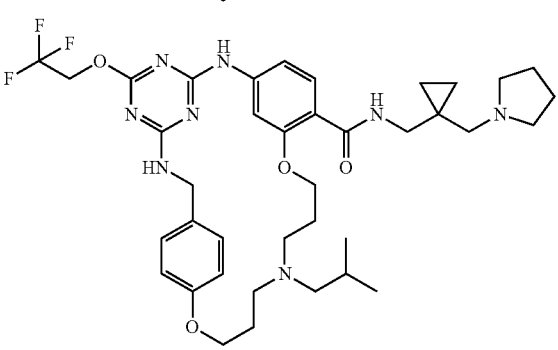
, 235
-continued
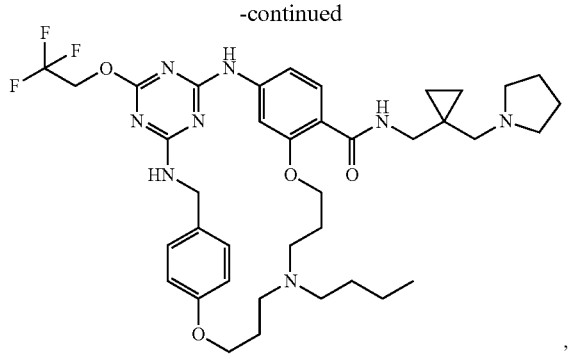
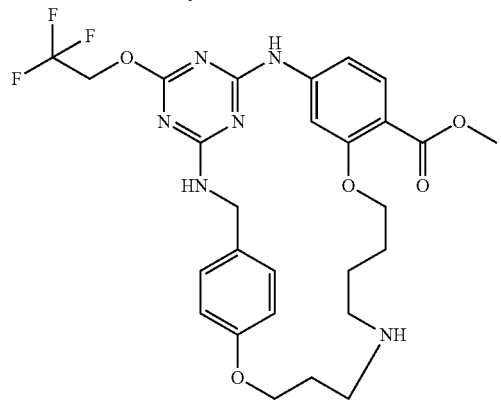
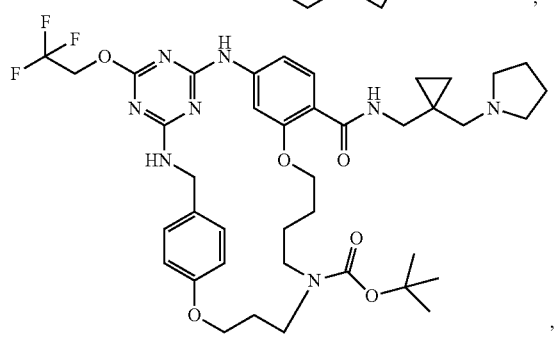
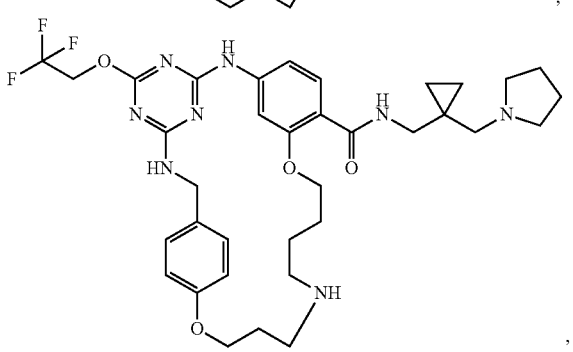
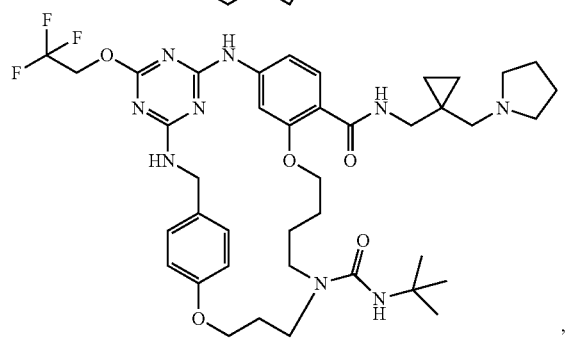
236
-continued
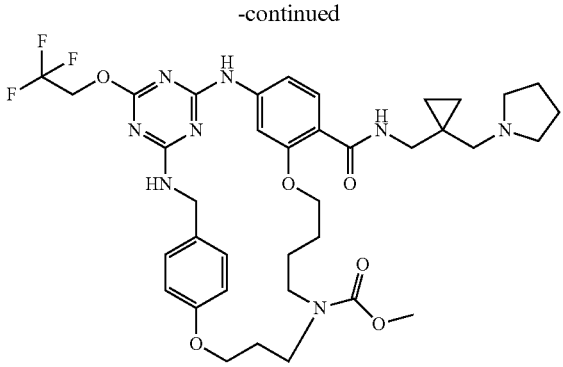
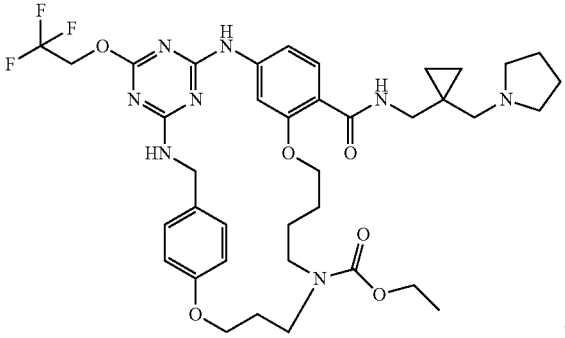
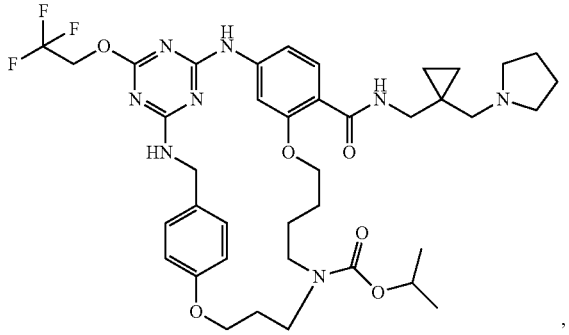
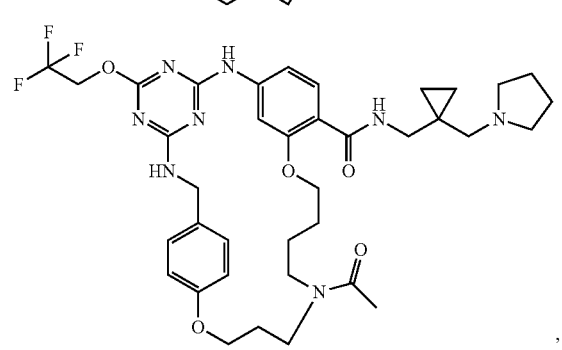
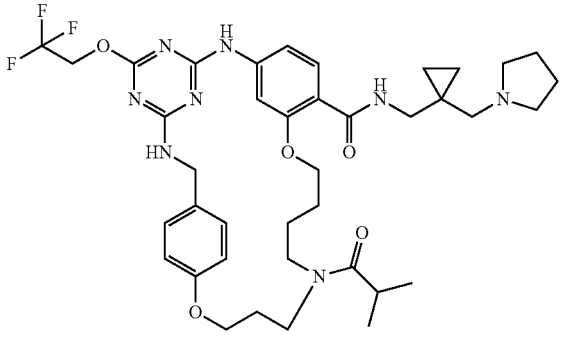

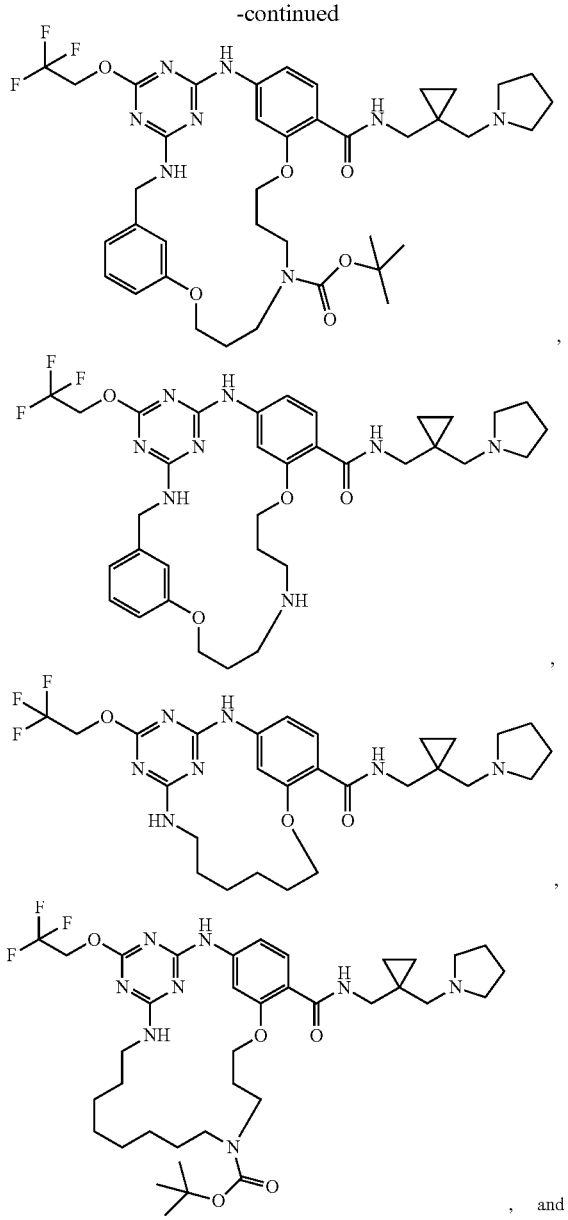

, and or a pharmaceutically acceptable salt thereof.

12. A composition comprising a compound of claim 1, or a pharmaceutically acceptable salt thereof, and a pharmaceutically acceptable carrier.

13. The composition of claim 12 further comprising at least one additional compound having therapeutic benefits for HCV wherein the compound is selected from the group consisting of interferons, cyclosporins, interleukins, HCV metalloprotease inhibitors, HCV serine protease inhibitors, HCV polymerase inhibitors, HCV helicase inhibitors, HCV NS4B protein inhibitors, HCV entry inhibitors, HCV assembly inhibitors, HCV egress inhibitors, HCV NS5A protein inhibitors, HCV NS5B protein inhibitors, and HCV replicon inhibitors.

14. A method of treating hepatitis C infection comprising administering a therapeutically effective amount of a compound of claim 1 to a patient.

15. The method of claim 14 further comprising administering at least one additional compound having therapeutic benefits for HCV wherein the compound is selected from the group consisting of interferons, cyclosporins, interleukins, HCV metalloprotease inhibitors, HCV serine protease inhibitors, HCV polymerase inhibitors, HCV helicase inhibitors, HCV NS4B protein inhibitors, HCV entry inhibitors, HCV assembly inhibitors, HCV egress inhibitors, HCV NS5A protein inhibitors, HCV NS5B protein inhibitors, and HCV replicon inhibitors.

* * * * *

UNITED STATES PATENT AND TRADEMARK OFFICE
CERTIFICATE OF CORRECTION

PATENT NO. : 8,741,884 B2  
APPLICATION NO. : 13/086704  
DATED : June 3, 2014  
INVENTOR(S) : Tao Wang et al.

Page 1 of 3

It is certified that error appears in the above-identified patent and that said Letters Patent is hereby corrected as shown below:

On the Title Page:

Item (75), Inventors:

Change "Samuel Gerritz, Gullford, CT (US);" to -- Samuel Gerritz, Guilford, CT (US); --.

Change "Eric Mull, Gullford, CT (US)" to -- Eric Mull, Guilford, CT (US) --.

Item (57), ABSTRACT:

Column 2, after " 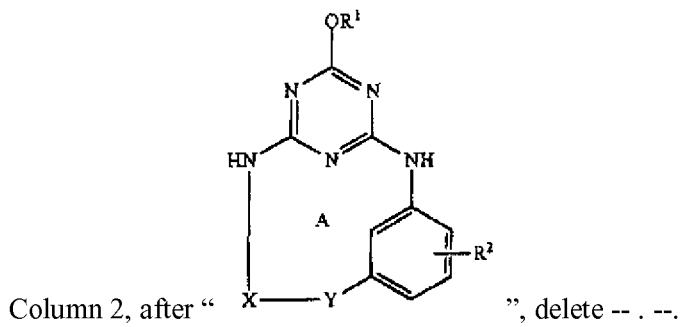 ", delete -- . --.

In the Specification:

Column 3, line 38, change "dialkyaminocarbonyl;" to -- dialkylaminocarbonyl; --.

Column 4, line 40, change "dialkyaminocarbonyl;" to -- dialkylaminocarbonyl; --.

Column 9, line 64, change "Imiqimod," to -- Imiquimod, --.

Column 9, line 64, change "5′-monophospate" to -- 5′-monophosphate --.

Signed and Sealed this  
Thirty-first Day of March, 2015

Michelle K. Lee  
*Director of the United States Patent and Trademark Office*

Column 10, line 46, change "Imiqimod," to -- Imiquimod, --.

Column 10, line 47, change "5'-monophospate" to -- 5'-monophosphate --.

In the Claims:

Claim 1:

Column 207, lines 26 and 27, change "dialkyaminocarbonyl;" to -- dialkylaminocarbonyl; --.

Column 207, line 55, change "bicylic" to -- bicyclic --.

Column 207, line 59, change "C(O)(N($R^{10}$)(R11))," to -- C(O)(N($R^{10}$)($R^{11}$)), --.

Column 207, line 60, change "$R^{11}$)),CON($R^{10}$)$SO_2R^{13}$,N($R^{10}$)($R^{11}$), N($R^{10}$)$COR^6$,N" to -- ($R^{11}$)), CON($R^{10}$)$SO_2R^{13}$, N($R^{10}$)($R^{11}$), N($R^{10}$)$COR^6$, N --.

Column 207, line 61, change "$CO_2R^6$,N" to -- $CO_2R^6$, N --.

Column 207, line 63, change "$R^{10}$is" to -- $R^{10}$ is --.

Column 208, line 10, change "(N$R^{12}$)$NR^4$;," to -- (N$R^{12}$)$NR^{4'}$, --.

Column 208, line 22, change "therof." to -- thereof. --.

Claim 2:

Column 208, line 31, change "alkylaminoearbonyl," to -- alkylaminocarbonyl, --.

Column 208, lines 31 and 32, change "dialkyaminocarbonyl;" to -- dialkylaminocarbonyl; --.

Column 208, line 44, change "$CO_2R^6$,)CON" to -- $CO_2R^6$, CON --.

Column 208, line 47, change "bicylic" to -- bicyclic --.

Column 208, line 49, change "$CO_2R^6$,)CON" to -- $CO_2R^6$, CON --.

Column 208, line 51, change "$R^9$ is $CO_2R^6$,C(=N$R^{12}$)(N($R^{10}$)($R^{11}$)), CON($R^{10}$$SO_2R^{13}$,)" to -- $R^9$ is $CO_2R^6$, C(=N$R^{12}$)(N($R^{10}$)($R^{11}$)), CON($R^{10}$)$SO_2R^{13}$, --.

Column 208, line 53, change "$R^{10}$is" to -- $R^{10}$ is --.

Column 209, line 13, change "therof." to -- thereof. --.

In the Claims:

Claim 3:

Column 209, line 20, change "therof." to -- thereof. --.

Claim 4:

Column 209, line 27, change "therof." to -- thereof. --.

Claim 6:

Column 209, line 36, change "$CO_2R^6$,)CON" to -- $CO_2R^6$, CON --.

Claim 7:

Column 209, line 40, change "bicylic" to -- bicyclic --.

Claim 11:

Column 209, line 49, change "claim" to -- claim 1 --.